(12) United States Patent
Nicolau et al.

(10) Patent No.: US 12,016,886 B2
(45) Date of Patent: *Jun. 25, 2024

(54) MICROVASCULAR ENDOTHELIAL CELL COMPRISING A NUCLEIC ACID ENCODING AN ANTI-TDP-43 FAB

(71) Applicant: ALSaTECH, Inc., Boston, MA (US)

(72) Inventors: Claude Nicolau, Boston, MA (US); Claudine Kieda, Boston, MA (US); Reynald Thinard, Boston, MA (US); Ruth Greferath, Boston, MA (US); Melanie Chevalier, Boston, MA (US)

(73) Assignee: ALSaTECH, Inc., Boston, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/046,734

(22) Filed: Oct. 14, 2022

(65) Prior Publication Data
US 2023/0248780 A1 Aug. 10, 2023

Related U.S. Application Data

(63) Continuation of application No. 17/290,608, filed as application No. PCT/US2019/059989 on Nov. 6, 2019.

(60) Provisional application No. 62/896,627, filed on Sep. 6, 2019, provisional application No. 62/847,586, filed on May 14, 2019, provisional application No. 62/843,755, filed on May 6, 2019, provisional application No. 62/773,659, filed on Nov. 30, 2018, provisional application No. 62/756,417, filed on Nov. 6, 2018.

(51) Int. Cl.
| | |
|---|---|
| *C12N 5/071* | (2010.01) |
| *A61K 35/44* | (2015.01) |
| *A61K 39/00* | (2006.01) |
| *A61K 39/395* | (2006.01) |
| *C07K 16/00* | (2006.01) |
| *C07K 16/18* | (2006.01) |
| *C12N 5/07* | (2010.01) |
| *C12N 5/16* | (2006.01) |
| *C12N 15/00* | (2006.01) |
| *C12N 15/09* | (2006.01) |
| *C12N 15/85* | (2006.01) |

(52) U.S. Cl.
CPC ............ *A61K 35/44* (2013.01); *C07K 16/18* (2013.01); *C12N 5/0691* (2013.01); *C12N 15/85* (2013.01); *C07K 2317/50* (2013.01); *C07K 2317/54* (2013.01); *C07K 2317/55* (2013.01); *C07K 2317/565* (2013.01); *C07K 2317/76* (2013.01); *C07K 2319/01* (2013.01); *C07K 2319/02* (2013.01)

(58) Field of Classification Search
CPC .......... A61P 25/00; A61P 25/28; A61P 25/14; A61P 21/00; A61K 48/00; A61K 35/28; C07K 16/18; C12N 5/0623; C12N 5/0602; C12N 15/86; C12N 15/85

See application file for complete search history.

(56) References Cited

U.S. PATENT DOCUMENTS

| | | | |
|---|---|---|---|
| 5,273,743 A | 12/1993 | Ahlem et al. |
| 5,527,814 A | 6/1996 | Louvel |
| 5,837,242 A | 11/1998 | Holliger et al. |
| 5,837,821 A | 11/1998 | Wu |
| 6,294,654 B1 | 9/2001 | Bogen et al. |
| 6,303,341 B1 | 10/2001 | Hiatt et al. |
| 6,432,992 B1 | 8/2002 | Aubourg et al. |
| 6,551,592 B2 | 4/2003 | Lindhofer et al. |
| 6,838,254 B1 | 1/2005 | Hamers et al. |
| 7,087,411 B2 | 8/2006 | Daly et al. |
| 7,150,872 B2 | 12/2006 | Whitlow et al. |
| 7,235,641 B2 | 6/2007 | Kufer et al. |
| 7,772,375 B2 | 8/2010 | Greferath et al. |
| 7,807,171 B2 | 10/2010 | Tosi et al. |
| 7,807,175 B2 | 10/2010 | Pfeifer et al. |
| 7,892,544 B2 | 2/2011 | Pfeifer et al. |
| 8,048,420 B2 | 11/2011 | Pfeifer et al. |
| 8,124,353 B2 | 2/2012 | Pfeifer et al. |
| 8,246,954 B2 | 8/2012 | Pfeifer et al. |
| 8,409,580 B2 | 4/2013 | Tosi et al. |
| 8,603,487 B2 | 12/2013 | Pfeifer et al. |
| 8,613,923 B2 | 12/2013 | Pfeifer et al. |
| 8,647,631 B2 | 2/2014 | Pfeifer et al. |
| 8,663,650 B2 | 3/2014 | Nicolau et al. |
| 8,673,940 B2 | 3/2014 | Froestl et al. |
| 8,796,439 B2 | 8/2014 | Pfeifer et al. |
| 8,916,590 B2 | 12/2014 | Kroth et al. |

(Continued)

FOREIGN PATENT DOCUMENTS

| | | | |
|---|---|---|---|
| EP | 2152872 B1 | 9/2010 |
| EP | 1763364 B1 | 4/2012 |

(Continued)

OTHER PUBLICATIONS

Burgess et al. J of Cell Bio. 1990, 111:2129-2138.*
Pawson et al. 2003, Science 300:445-452.*
Alaoui-Ismaili et al., Cytokine Growth Factor Rev. 2009; 20:501-507.*
Guo et al., PNAS 2004; 101:9205-9210.*
Bernas, et al., "Establishment of primary cultures of human brain microvascular endothelial cells to provide an in vitro cellular model of the blood-brain barrier," Natural Protocols, vol. 5, No. 7, pp. 1265-1272, 2010.
International Search Report & Written Opinion, PCT Application No. PCT/US19/59989, dated Mar. 10, 2020, 17 pages.

(Continued)

*Primary Examiner* — Chang-Yu Wang
(74) *Attorney, Agent, or Firm* — Morgan, Lewis & Bockius LLP

(57) ABSTRACT

The present invention relates, in part, to cell-based gene therapies, including those targeting, by way of non-limiting example, TDP43 and Aβ aggregates, for the use in neurodegenerative disorders, including without limitation Amyotrophic Lateral Sclerosis (ALS) and Alzheimer's Disease, respectively.

10 Claims, 26 Drawing Sheets

Specification includes a Sequence Listing.

(56) References Cited

U.S. PATENT DOCUMENTS

| | | | |
|---|---|---|---|
| 8,926,983 B2 | 1/2015 | Nicolau et al. | |
| 9,146,244 B2 | 9/2015 | Pfeifer et al. | |
| 9,175,094 B2 | 11/2015 | Pfeifer et al. | |
| 9,221,812 B2 | 12/2015 | Kroth et al. | |
| 9,221,900 B2 | 12/2015 | Pfeifer et al. | |
| 9,228,173 B2 | 1/2016 | Kieda et al. | |
| 9,241,988 B2 | 1/2016 | Shaw et al. | |
| 9,289,488 B2 | 3/2016 | Hickman et al. | |
| 9,304,138 B2 | 4/2016 | Pfeifer et al. | |
| 9,314,486 B2 * | 4/2016 | Guha | A61K 35/407 |
| 9,403,902 B2 | 8/2016 | Pfeifer et al. | |
| 9,518,078 B2 | 12/2016 | Shaw et al. | |
| 9,540,434 B2 | 1/2017 | Pfeifer et al. | |
| 9,585,956 B2 | 3/2017 | Pfeifer et al. | |
| 9,598,485 B2 | 3/2017 | Ayalon et al. | |
| 9,631,117 B2 | 4/2017 | Sommer et al. | |
| 9,631,178 B2 | 4/2017 | Kieda et al. | |
| 9,657,091 B2 | 5/2017 | Pfeifer et al. | |
| 9,687,447 B2 | 6/2017 | Reis et al. | |
| 9,701,660 B2 | 7/2017 | Kroth et al. | |
| 9,902,940 B2 * | 2/2018 | Shusta | C12N 5/069 |
| 9,975,946 B2 | 5/2018 | Nicolau et al. | |
| 9,993,564 B2 * | 6/2018 | Freskgard | A61K 38/10 |
| 10,066,010 B2 | 9/2018 | Pfeifer et al. | |
| 10,100,104 B2 | 10/2018 | Pfeifer et al. | |
| 10,112,990 B2 | 10/2018 | Adolfsson et al. | |
| 10,143,744 B2 | 12/2018 | Shaw et al. | |
| 2003/0088074 A1 | 5/2003 | Hamers et al. | |
| 2004/0101905 A1 | 5/2004 | Brekke et al. | |
| 2004/0146505 A1 | 7/2004 | Durrant et al. | |
| 2004/0253238 A1 | 12/2004 | Bogen et al. | |
| 2005/0033031 A1 | 2/2005 | Couto | |
| 2005/0043519 A1 | 2/2005 | Dooley et al. | |
| 2005/0079170 A1 | 4/2005 | Le Gall et al. | |
| 2005/0089519 A1 | 4/2005 | Kipriyanov et al. | |
| 2006/0280734 A1 | 12/2006 | Winter et al. | |
| 2007/0004909 A1 | 1/2007 | Johnson et al. | |
| 2008/0095767 A1 | 4/2008 | Jennings et al. | |
| 2008/0181890 A1 | 7/2008 | Lazar et al. | |
| 2008/0227958 A1 | 9/2008 | Thompson et al. | |
| 2009/0148438 A1 | 6/2009 | Nuttal et al. | |
| 2009/0298195 A1 | 12/2009 | Rüker et al. | |
| 2010/0105874 A1 | 4/2010 | Schuurman et al. | |
| 2010/0316602 A1 | 12/2010 | Zardi et al. | |
| 2017/0035938 A1 | 2/2017 | Guha et al. | |
| 2017/0065638 A1 * | 3/2017 | Fraser | A61P 25/00 |
| 2017/0073430 A1 * | 3/2017 | Boontanrart | A61K 47/6871 |
| 2017/0128581 A1 * | 5/2017 | Freskgard | C07K 16/28 |
| 2019/0153471 A1 * | 5/2019 | Paul | C12N 15/86 |
| 2019/0225699 A1 * | 7/2019 | Lannfelt | C07K 16/2881 |
| 2022/0000935 A1 * | 1/2022 | Nicolau | A61P 25/28 |

FOREIGN PATENT DOCUMENTS

| | | | |
|---|---|---|---|
| EP | 1959991 B1 | 3/2013 | |
| EP | 2046833 B1 | 8/2013 | |
| EP | 2238166 B1 | 11/2013 | |
| EP | 2361638 B1 | 1/2014 | |
| EP | 2170389 B1 | 10/2014 | |
| EP | 2465533 B1 | 3/2015 | |
| EP | 2170953 B1 | 7/2015 | |
| EP | 2625198 B1 | 7/2015 | |
| EP | 2380588 B1 | 8/2015 | |
| EP | 1651257 B1 | 2/2016 | |
| EP | 2108644 B1 | 7/2016 | |
| EP | 2413957 B1 | 7/2016 | |
| EP | 2764022 B1 | 8/2016 | |
| EP | 2205631 B1 | 11/2016 | |
| EP | 2205632 B1 | 11/2016 | |
| EP | 2316478 B1 | 4/2017 | |
| EP | 2598882 B1 | 7/2017 | |
| EP | 2074145 B1 | 8/2017 | |
| EP | 2527366 B1 | 8/2017 | |
| EP | 2468770 B1 | 12/2017 | |
| EP | 2488513 B1 | 12/2017 | |
| EP | 2586795 B1 | 5/2018 | |
| EP | 2808032 B1 | 8/2018 | |
| EP | 2758071 B1 | 11/2018 | |
| EP | 3135689 B1 | 12/2018 | |
| WO | WO 2005/081872 A2 | 9/2005 | |
| WO | WO 2009/117531 A1 | 9/2009 | |
| WO | WO-2010005567 A2 * | 1/2010 | A61K 31/337 |
| WO | WO 2010/063785 A2 | 6/2010 | |
| WO | WO-2011028811 A2 * | 3/2011 | A61K 45/06 |
| WO | WO-2011050262 A2 * | 4/2011 | C07K 16/22 |
| WO | WO-2011088215 A2 * | 7/2011 | C07K 16/28 |
| WO | WO-2014047426 A1 * | 3/2014 | C07K 16/28 |
| WO | WO-2015134627 A1 * | 9/2015 | A61K 39/39558 |
| WO | WO-2015164392 A2 * | 10/2015 | A61K 47/48646 |
| WO | WO-2016007775 A1 * | 1/2016 | A61K 31/497 |
| WO | WO 2017/079831 A1 | 5/2017 | |
| WO | WO-2017218707 A2 * | 12/2017 | A61P 35/00 |

OTHER PUBLICATIONS

Kaiser, et al., "Liposome-Mediated High-Efficiency Transfection of Human Endothelial Cells," J Vasc Res, vol. 38, pp. 133-143, 2001.

Rafii, et al., "Isolation and Characterization of Human Bone Marrow Microvascular Endothelial Cells: Hematopoietic Progenitor Cell Adhesion," Blood, vol. 84, No. 1, pp. 10-19, Jul. 1, 1994.

Yockell-Lelièvre, et al., "Efficient Transfection of Endothelial Cells by a Double-Pulse Electroporation Method," DNA and Cell Biology, vol. 28, No. 11, pp. 561-566, 2009.

Alving, et al., "Liposomes containing lipid A: an effective, safe, generic adjuvant system for synthetic vaccines," Expert Review of Vaccines, vol. 11, No. 6, pp. 733-744, Jun. 2012.

Arai, et al., "TDP-43 is a component of ubiquitin-positive tau-negative inclusions in frontotemporal lobar degeneration and amyotrophic lateral sclerosis," Biochem. Biophys. Comm. vol. 351, pp. 602-611, 2006.

Bosco, et al., "Wild-type and mutant SOD1 share an aberrant conformation and a common pathogenic pathway in ALS," Nat Neurosci, vol. 13, No. 11, pp. 1396-1403, Nov. 2010.

Chandra, et al., "A Broken α-Helix in Folded α-Synuclein," The Journal of Biological Chemistry, vol. 278, No. 17, pp. 15313-15318, Apr. 25, 2003.

Chia, et al., "Superoxide Dismutase 1 and tgSOD1$^{G93A}$ Mouse Spinal Cord Seed Fibrils, Suggesting a Propagative Cell Death Mechanism in Amyotrophic Lateral Sclerosis," PLOS One, vol. 5, No. 5, pp. e10627, May 2010.

Collet, et al., "Hypoxia-shaped vascular niche for cancer stem cells," Contemp. Oncol. (Pozn.). 19(1A): A39-A43, 2015.

Deffar, et al., "Nanobodies—the new concept in antibody engineering," African Journal of Biotechnology, vol. 8, No. 12, pp. 2645-2652, Jun. 17, 2009.

Gatouillat, et al., "Immunization with liposome-anchored pegylated peptides modulates doxorubicin sensitivity in P-glycoprotein-expressing P388 cells," Cancer Letters, vol. 257, pp. 165-171, 2007.

Gilks, et al., "Stress Granule Assembly Is Mediated by Prion-like Aggregation of TIA-1," Molecular Biology of the Cell, vol. 15, pp. 5383-5398, Dec. 2004.

Grad, et al., "Intermolecular transmission of superoxide dismutase 1 misfolding in living cells," PNAS, vol. 108, No. 39, pp. 16398-16403, Sep. 27, 2011.

Guilliams, et al., "Nanobodies Raised against Monomeric α-Synuclein Distinguish between Fibrils at Different Maturation Stages," J. Mol. Biol., vol. 425, pp. 2397-2411, 2013.

Harmsen, et al., "Properties, production, and applications of camelid single-domain antibody fragments," Appl. Microbiol Biotechnol, vol. 77, pp. 13-22, 2007.

Hickman, et al., "Sequence-independent Control of Peptide Conformation in Liposomal Vaccines for Targeting Protein Misfolding Diseases," The Journal of Biological Chemistry, vol. 286, No. 16, pp. 13966-13976, Apr. 22, 2011.

Higham, et al., "Processing of synthetic pro-islet amyloid polypeptide (proIAPP) 'amylin' by recombinant prohormone convertase enzymes, PC2 and PC3, in vitro," Eur. J. Biochem., vol. 267, pp. 4998-5004, 2000.

(56) References Cited

OTHER PUBLICATIONS

Ilieva, et al., "Non-cell autonomous toxicity in neurodegenerative disorders: ALS and beyond," J. Cell. Biol., vol. 187, No. 6, pp. 761-772, 2009.
Jaikaran, et al., "Islet amyloid and type 2 diabetes; from molecular misfolding to islet pathophysiology," Biochimica et Biophysica Acta, vol. 1537, pp. 179-203, 2001.
Kabashi, et al., "*TARDBP* mutations in individuals with sporadic and familial amyotrophic lateral sclerosis," Nature Genetics, vol. 40, pp. 572-574, 2008.
Kerman, et al., "Amyotrophic lateral sclerosis is a non-amyloid disease in which extensive misfolding of $SOD_1$ is unique to the familial form," Acta Neuropathologica, vol. 119, pp. 335-344, 2010.
Klimkiewicz, et al., "A 3D model of tumour angiogenic microenvironment to monitor hypoxia effects on cell interactions and cancer stem cell selection," Cancer Letters, vol. 396, pp. 10-20, 2017.
Laiger-Tourenne, et al., "TDP-43 and FUS/TLS: emerging roles in RNA processing and neurodegeneration," Human Molecular Genetics, vol. 19, No. R1, pp. R46-R64, 2010.
Lim, et al., "ALS-Causing Mutations Significantly Perturb the Self-Assembly and Interaction with Nucleic Acid of the Intrinsically Disordered Prion-Like Domain of TDP-43," PLOS Biology, Jan. 6, 2016.
Mandelkow, et al., "Biochemistry and Cell Biology of Tau Protein in Neurofibrillary Degeneration," Cold Spring Harb Perspect Med, 2012, 2:006247, 25 pages.
Marzban, et al., "Islet amyloid polypeptide and type 2 diabetes," Experimental Gerontology, vol. 38, No. 4, pp. 347-351, Apr. 2003.
Münch, et al., "Prion-like propagation of mutant superoxide dismutase-1 misfolding in neuronal cells," PNAS, vol. 108, No. 9, pp. 3548-3553, Mar. 1, 2011.
Muhs, et al., "Liposomal vaccines with conformation-specific amyloid peptide antigens define immune response and efficacy in APP transgenic mice," PNAS, vol. 104, No. 23, pp. 9810-9815, Jun. 5, 2007.
Neumann, et al., "Ubiquitinated TDP-43 in Frontotemporal Lobar Degeneration and Amyotrophic Lateral Sclerosis,".
Nicolau, et al., "A liposome-based therapeutic vaccine against B-amyloid plaques on the pancreas of transgenic NORBA mice," PNAS, vol. 99, No. 4, pp. 2332-2337, Feb. 19, 2002.
Pawlak-Robin, et al., "Inhibition of multidrug resistance by immunization with synthetic P-glycoprotein-derived peptides," European Journal of Cancer, vol. 40, No. 4, pp. 606-613, Mar. 2004.
Perrin, et al., "Induction of autoantibodies to murine P-glycoprotein: Consequences on drug sensitivity in MDR cancer cells and on the expression of *mdr* genes in organs," Biochemical and Biophysical Research Communications, vol. 358, No. 1, pp. 325-330, Jun. 22, 2007.
Polymenidou, et al., "The Seeds of Neurodegeneration: Prion-like Spreading in ALS," Cell, vol. 143, No. 3, pp. 498-508, Oct. 28, 2011.
Polymenidou, et al., "Prion-like spread of protein aggregates in neurodegeneration," J. Exp. Med, vol. 209, No. 5, pp. 889-893, 2012.
Prudencio, et al., "Variation in aggregation propensities among ALS-associated variants of SOD1: Correlation to human disease," Human Molecular Genetics, vol. 18, No. 17, pp. 3217-3226, 2009.
Rosen, et al., "Mutations in Cu/Zn superoxide dismutase gene are associated with familial amyotrophic lateral sclerosis," Nature, vol. 362, pp. 59-62, 1993.
Sreedharan, et al., "TDP-43 Mutations in Familial and Sporadic Amyotrophic Lateral Sclerosis," Science, vol. 319, No. 5870, pp. 1668-1672, Mar. 21, 2008.
Stefanis, "α-Synuclein in Parkinson's Disease," Cold Spring Harb Perspect Med, 2012, 4:a009399, 23 pages.
Tosi, et al., "Immune Response against the Murine MDRI Protein Induced by Vaccination with Synthetic Lipopeptides in Liposomes," Biochemical and Biophysical Research Communications, vol. 212, No. 2, pp. 494-500, Jul. 17, 1995.
Vance, et al., "Mutations in FUS, an RNA Processing Protein, Cause Familial Amyotrophic Lateral Sclerosis Type 6," Science, vol. 323, No. 5918, pp. 1208-1211, Feb. 27, 2009.
Watson, et al., "Role of lipid structure in the humoral immune response in mice to covalent lipid-peptides from the membrane proximal region of HIV-1 gp41," Vaccine, vol. 27, No. 34, pp. 4672-4683, Jul. 23, 2009.
Weksler, et al., "The hCMEC/D3 cell line as a model of the human blood brain barrier," Fluids and Barriers of the CNS, 10:16, 10 pages, 2013.
Wegorzewska and Baloh, "TDP-43-based animal models of neurodegeneration: new insights into ALS pathology and pathophysiology." *Neurodegener Dis.* vol. 8, No. 4, 2011: pp. 262-274.

\* cited by examiner

MICROVASCULAR ENDOTHELIAL CELL COMPRISING A NUCLEIC ACID ENCODING AN ANTI-TDP-43 FAB

CROSS-REFERENCE TO RELATED APPLICATIONS

This application is a continuation of U.S. application Ser. No. 17/290,608, filed Apr. 30, 2021, which is a U.S. National Stage of International Application PCT/US2019/059989 filed Nov. 6, 2019, which claims priority to and the benefit of U.S. Provisional Patent Application Nos. 62/756,417, filed on Nov. 6, 2018; 62/773,659, filed on Nov. 30, 2018; 62/843,755, filed on May 6, 2019; 62/847,586, filed on May 14, 2019; and 62/896,627, filed on Sep. 6, 2019, the entire contents of which are herein incorporated by reference.

FIELD

The present invention relates to, in part, cell-based gene therapies for various disorders, including neurodegenerative disorders, including, without limitation, Amyotrophic Lateral Sclerosis (ALS) and Alzheimer's disease.

DESCRIPTION OF THE TEXT FILE SUBMITTED ELECTRONICALLY

The contents of the text file submitted electronically herewith are incorporated herein by reference in their entirety: A computer readable format copy of the Sequence Listing (filename: ALS-007C1_ST26.xml; date recorded: Oct. 14, 2022; file size: 207,738 bytes).

BACKGROUND

Diseases of the brain and central nervous system (CNS) can have permanent and devastating consequences on the physical and social well-being of the affected individual. In some cases, highly invasive surgery is required to correct the source of the problem or improve the symptoms of disease. Alternatively, or in addition, medication may be used to treat the cause or symptoms of disease.

Methods for effective administration of medicines to and/or past the blood brain barrier (BBB) and often onwards into the brain, are needed. To date, the focus has been on receptor-mediated ligand targeting; however, this is hindered by a lack of receptors which are exclusively expressed at the BBB. Delivery of biologic agents, e.g., antibodies, across the BBB continues to be a challenge. For instance, the humanized anti-VEGF monoclonal antibody bevacizumab (AVASTIN) has also been developed as a targeted treatment of brain cancer. However, a randomized, double-blind, placebo-controlled clinical trials showed no overall improvement to patient survival rates following this treatment regime (Gilbert, et al. 'A Randomized Trial of Bevacizumab for Newly Diagnosed Glioblastoma' N. Engl. J. Med. 2014, 699-708), perhaps due to poor penetration of the antibody across the BBB. Accordingly, there is a need for improved delivery of agents, especially biologic agents, across and/or past the BBB.

Protein aggregations that result from abnormal protein folding form different deposits called amyloid which is associated with different diseases including but not limited to neurodegenerative disorders and Type II diabetes mellitus.

Neurodegenerative disorders, such as Parkinson's, Huntington's and Alzheimer's diseases, fronto-temporal lobar degeneration (FTLD) and Amyotrophic Lateral Sclerosis (ALS) are associated with the accumulation of misfolded proteins both inside and outside of neuronal and glial cells in the central nervous system. These misfolded protein aggregates are pathological hallmarks of these diseases. The major component of these aggregates is characteristic for each neurodegenerative disease, e.g. α-synuclein for Parkinson, Huntingtin for Huntington, Aβ for Alzheimer disease. Although the major protein component of the pathological aggregation may be unique for each of the diseases, several proteins misfold and accumulate in multiple diseases. The most glaring example is TDP43, which aggregates in ALS, FTLD and many other conditions. Another example is Tau proteins which stabilize microtubules in the neurons. Defective Tau proteins are discovered and associated with Alzheimer's and Parkinson's diseases. Further, beta amyloid is associated with Alzheimer's disease.

Type II diabetes mellitus is associated with a decrease in insulin secretion as a result of β-cells failure. Islet amyloid polypeptide (IAPP) is co-localized with insulin in the islet β-cells to play a role in regulating glucose levels by suppressing food intake and gastric emptying. In Type II diabetes, IAPP aggregates to form amyloid fibrils which are toxic to β-cells.

While there is some understanding in the field of therapeutics antibodies about the role of aggregation in disease progression, there is a paucity of safe and effective therapies for various neurodegenerative disorders and type II diabetes mellitus.

SUMMARY

Accordingly, the present invention relates to, in some aspects, therapies involving cell-based gene agents which effectively deliver therapeutic agents across the BBB. In some aspects, the present invention relates to therapies involving cell-based gene agents which effectively deliver therapeutic agents to and/or past the BBB, for example to the brain parenchyma and/or microvasculature. The present invention relates to, in some aspects, therapies involving cell-based gene therapies comprising nucleic acid vectors encoding antibodies against components of the aggregates. For example, the present invention contemplates a cell (e.g., a microvascular endothelial cell), or precursor thereof, engineered to release a therapeutic protein or peptide (e.g., a soluble protein or peptide), including, without limitation, an antibody or antibody fragment, at a site of therapeutic action.

Such therapies may solubilize the intra- or extra-cellular protein aggregates and inhibit the spreading of the disease. In some aspects, the present invention provides for a method for treating or preventing a neurodegenerative disease (e.g., Parkinson's disease, Huntington's disease, Alzheimer's disease, fronto-temporal lobar degeneration (FTLD) and Amyotrophic Lateral Sclerosis (ALS)), comprising administering to a subject a cell, or precursor thereof, engineered to release a therapeutic protein or peptide, including, without limitation, an antibody or antibody fragment, at a site of therapeutic action. In some embodiments, the microvascular endothelial cell is derived from bone marrow of the patient or subject. In some embodiments, the microvascular endothelial cell is from the central nervous system (CNS), optionally the brain. In further embodiments, the site of therapeutic action is selected from, but not limited to, the brain, the CNS, the heart, the liver, and the pancreas. In some embodiments, the microvascular endothelial cell is derived from the subject having the neurodegenerative disorder in need of treatment.

In some aspects, the present invention relates to compositions and methods involving cell-based gene therapies comprising nucleic acid vectors encoding antibodies against components of disease-related aggregates. Such compositions and methods may solubilize the intra- or extra-cellular protein aggregates and inhibit the spreading of the disease once released at the therapeutic site of action. Such compositions and methods cross the BBB (e.g. better BBB crossing than antibodies delivered via standard methods, e.g., intravenously). Compositions of the present invention may also be delivered to and/or past the BBB.

In some aspects, the present invention provides delivery (e.g., to, across, and/or past the BBB) of a protein or peptide, including, without limitation, an antibody or antibody fragment, including, but not limited to, a conformation-sensitive antibody or antibody fragment that is directed against one or more of mutated TDP43, beta-amyloid (Aβ), SOD-1, FUS/TLS, α-synuclein, Tau protein, and IAPP, including peptide fragments thereof. In various embodiments, the agent of the invention targets protein aggregates that comprise one or more of mutated and/or misfolded TDP43 and beta-amyloid (Aβ) proteins. In some embodiments, the agents of the invention are conformation-sensitive antibodies directed against the mutated TDP43 and beta-amyloid (Aβ) protein aggregates. In some embodiments, the agents of the invention are conformation-sensitive antibodies directed against the mutated TDP43, beta-amyloid (Aβ), SOD-1, FUS/TLS, α-synuclein, Tau protein, and IAPP protein aggregates, including peptide fragments thereof.

In some aspects, the present invention provides a method of constructing an expression vector encoding said sequences. In some embodiments, the vector is based on the pUC high copy derived from pBR322. In further embodiments, the vector comprises a Synapsin promoter that promotes expression in neurons. In still further embodiments, the vector comprises a CAG promoter that promotes expression in endothelial cells. In some embodiments, the vector comprises a peptide used for neuronal targeting (e.g., directed against ApoE4). In further embodiments, the expression vectors of the present invention comprise an amino acid sequence that expresses insulin. In some embodiments, the insulin sequence promotes the export of the expressed antibodies.

In some aspects, the present invention provides for transfection of the autologous microvascular endothelial cells (e.g., autologous brain microvascular endothelial cells or microvascular endothelial cells derived from bone marrow, or precursors thereof) with any one of the aforementioned nucleic acid expression vectors that encode the therapeutic protein or peptide, including, without limitation, an antibody or antibody fragment. In some embodiments, the transfection is performed via electroporation. In some embodiments, transfection involves the use of a cationic lipid, including but not limited to, lipofectine and lipofectamine.

In some embodiments, the present invention provides for making a microvascular endothelial cell that is suitable for delivery of protein or peptide or antibody or antibody fragment agents across the BBB. In some embodiments, the present invention provides for making a microvascular endothelial cell that is suitable for delivery of protein or peptide or antibody or antibody fragment agents to and/or past the BBB.

In some aspects, the present invention relates to a method for delivering a protein or peptide, including, without limitation, an antibody or antibody fragment, across the BBB. In further aspects, the present invention relates to a method for delivering a protein or peptide, including, without limitation, an antibody or antibody fragment, to and/or past the BBB. In some aspects, the present invention relates to a method for delivering a protein or peptide, including, without limitation, an antibody or antibody fragment, across the BBB (or to and/or past the BBB) and cause an about 2-fold, or about a 3-fold, or about a 4-fold, or about a 5-fold, or about a 10-fold, or about a 30-fold, or about a 100-fold, or about a 300-fold, or about a 500-fold, or about a 1,000-fold increase in crossing the BBB, relative to a protein or peptide, including, without limitation, an antibody or antibody fragment, not delivered using the present methods (e.g., without a endothelial cell delivery, e.g. upon administration of a "naked" antibody or antibody fragment). In embodiments, the protein or peptide, including, without limitation, the antibody or antibody fragment, crosses the BBB by either a paracellular pathway or a transcellular pathway.

In some aspects, the present invention relates to a method delivering a protein or peptide, including, without limitation, an antibody or antibody fragment, e.g. across one or more brain microvascular endothelial cells, pericytes, astrocytes, tight junctions, neurons, and basal membrane.

In some aspects, the present invention relates to a method of treating a neurodegenerative disorder and/or Type 2 diabetes mellitus by administering a therapeutically effective amount of an agent of the invention, e.g. the autologous transfected cells, to a patient in need thereof. Such administration may be one or more of the agents of the invention targeting mutated TDP43, beta-amyloid (Aβ), SOD-1, FUS/TLS, α-synuclein, Tau protein, and IAPP (e.g. a cocktail of antibodies). In some embodiments, such administration comprises autologous microvascular endothelial cells that are transfected with a nucleic acid vector encoding one or more antibodies directed against TDP43, beta-amyloid (Aβ), SOD-1, FUS/TLS, α-synuclein, Tau protein, and IAPP. In other embodiments, the invention includes vectors that encode one or more antibodies directed against TDP43, beta-amyloid (Aβ), SOD-1, FUS/TLS, α-synuclein, Tau protein, and IAPP.

In some aspects, the invention provides for pharmaceutical compositions comprising cell-based gene therapies comprising autologous cells transfected with nucleic acid vectors encoding conformation-sensitive antibodies directed against the mutated TDP43, beta-amyloid (Aβ), SOD-1, FUS/TLS, α-synuclein, Tau protein, and IAPP protein aggregates, in a pharmaceutically or physiologically accepted carrier.

In some aspects, the present invention relates to a method of treating a neurodegenerative disorder by administering an effective amount of an agent (e.g., autologous transfected cells comprising nucleic acid vectors encoding conformation-sensitive antibodies directed against the mutated TDP43, beta-amyloid (Aβ), SOD-1, FUS/TLS, α-synuclein, Tau protein, and IAPP protein aggregates) of the invention to a patient in need thereof by using his own endothelial cells. Indeed, the present invention contemplates, in some embodiments, the use of autologous transfected microvascular endothelial cells for the treatment of a neurodegenerative disorder by reintroduction at the BBB via IA or IV injection.

In some embodiments, the agent of the invention is administered to the patient via inferior alveolar injection or intravenous injection. In some embodiments, the transfected cells are delivered to and/or past the blood brain barrier (BBB) of said patients in need thereof. In further embodiments, the transfected cells are early precursors such that they exhibit homing to and/or past the BBB. In some embodiments, the cells are administered so that they are allowed to cross the BBB. In further embodiments, the transfected cells insert into the apical surface of the BBB and release proteins, peptides, antibodies, and/or antigen presenting fragments to the basolateral side of the BBB. In such embodiments, the proteins, peptides, antibodies, and/or antigen presenting fragments are delivered to the brain parenchyma and/or microvasculature. In some embodiments, the present invention provides for the use of organ-specific and/or early progenitors of endothelial cells in order to transport cells comprising vectors encoding therapeutic proteins or peptides, including, without limitation, antibodies or antibody fragments into the brain. In further embodiments, the present invention provides for the use of homing properties of endothelial cells (e.g., precursors) to transfer agents of the invention in an organo-specific manner.

In specific embodiments, the present methods of making or treatment relate to the transfection of microvascular endothelial cells with nucleic acids (optionally codon optimized) encoding antibodies (or Fab fragments) directed against TDP43 and beta-amyloid (Aβ), e.g. as defined by SEQ ID NOs: 13 and 14 or SEQ ID NOs: 94 and 31.

In specific embodiments, the present invention provides for treatment of ALS by delivering to a subject a microvascular endothelial cell having a nucleic acid (optionally codon optimized) encoding an antibody (or Fab fragment) directed against TDP43, e.g. as defined by SEQ ID NOs: 13 and 14.

In specific embodiments, the present invention provides for treatment of Alzheimer's disease by delivering to a subject a microvascular endothelial cell having a nucleic acid (optionally codon optimized) encoding an antibody (or Fab fragment) directed against Aβ, e.g. as defined by SEQ ID NOs: 94 and 31.

In some embodiments, the present invention can be used to repair the BBB, e.g., in diseases like Alzheimer Disease (AD) and Amyotrophic Lateral Sclerosis (ALS). In other embodiments, the present invention allows for the repair of BBB as well as release of antibodies or antibody fragments by the BBB without damaging the BBB and its functions.

In some embodiments, the present invention relates to the repair of cellular damage in tumors, diabetes II, heart attack, myocardial infarction, stroke, respiratory insufficiency, etc.

In some embodiments, the present invention is used for repair of angiogenesis in retina, repair of wounds caused by a deficient blood supply (diabetes foot), repair of myocardial tissue after heart attack, vessel normalization in case of pathological tumor angiogenesis, skin diseases, etc.

Other aspects and embodiments of the invention will be apparent from the following detailed description.

DESCRIPTION OF THE DRAWINGS

FIG. 4A depicts fluorescence imaging at 5 hours, and FIG. 4B depicts fluorescence imaging at 12 hours.

FIG. 1a shows TDP43 and FIG. 1b shows A8.

FIG. 9A shows the solubilization of TDP-43 aggregates with anti-TDP-43 antigen-binding fragments (Fab) expressed by vector in human cells (HEK293 cell line), as compared to a control group where no Fab was administered and a control group where an irrelevant antibody was administered. FIG. 9B shows the solubilization of β-Amyloid aggregates with anti-β-Amyloid antigen-binding fragments (Fab) expressed by vector in human cells (HEK293 cell line), as compared to a control group where no Fab was administered and a control group where an irrelevant antibody was administered.

DETAILED DESCRIPTION

Figure 1:
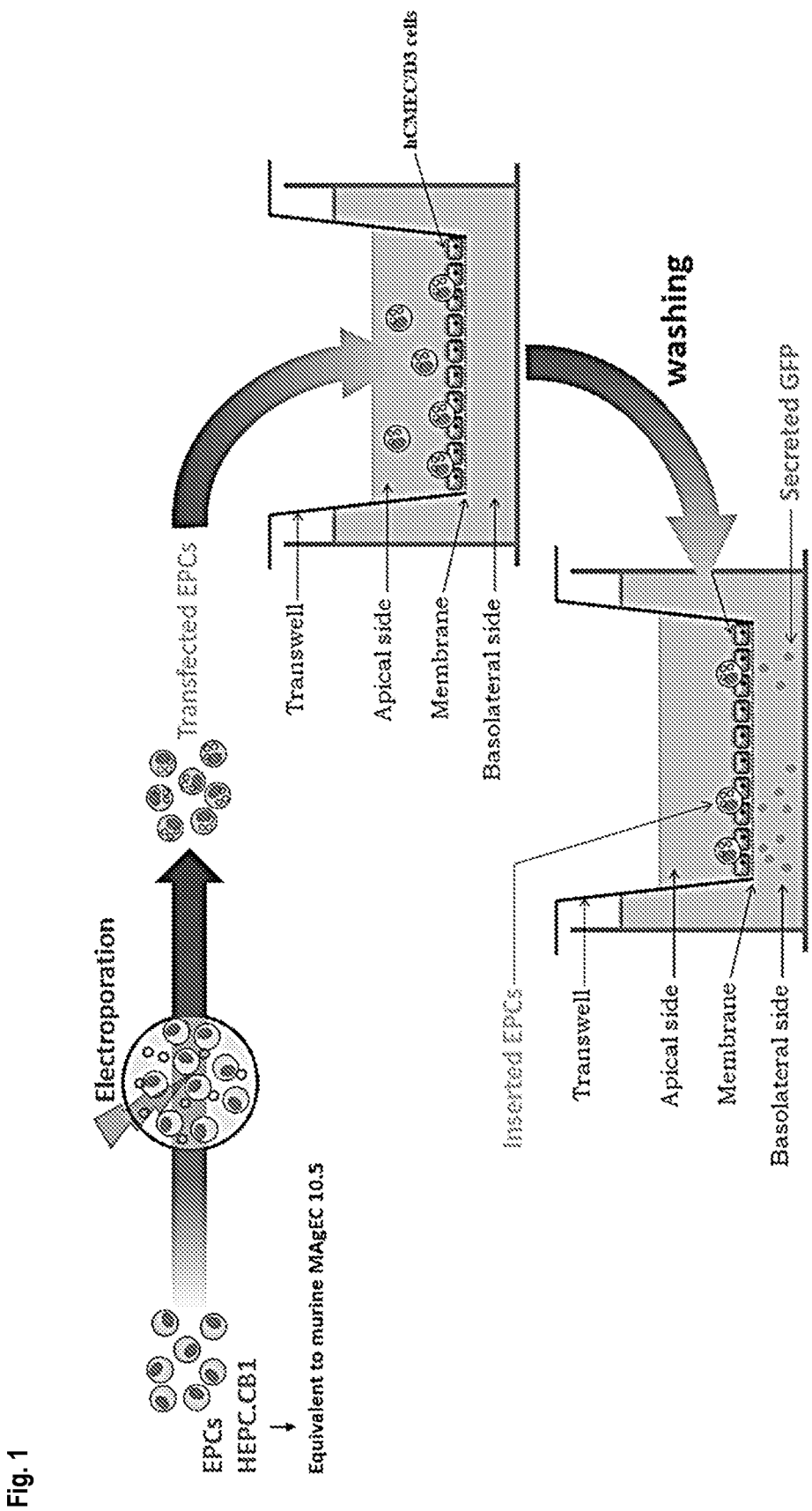
FIG. 1 depicts a schematic of the insertion of transfected cells in an in vitro model of the human Blood Brain Barrier (BBB) and export of GFP by the transfected cells.

The present invention is based, in part, on the discovery that proteins or peptides, including, without limitation, antibodies directed against one or more of mutated protein aggregates associated with various neurodegenerative diseases can be delivered to the brain via microvascular endothelial cells (e.g., from the CNS) comprising nucleic acid vectors encoding such proteins or antibodies. In some embodiments, the microvascular endothelial cell, or precursor thereof, is engineered to release a therapeutic protein or peptide, including, without limitation, an antibody or antibody fragment, at a site of therapeutic action (e.g., a neuron, the CNS, or the brain).

In certain aspects, the present invention provides for the use of microvascular endothelial cells (e.g., from the CNS or the brain) to deliver therapeutic proteins or peptides, including, without limitation, antibodies, or fragments thereof, to therapeutic sites of action (e.g., the blood brain barrier and neurons). Microvascular endothelial cells transfected ex vivo with nucleic acid vectors encoding such proteins, including therapeutic antibodies, can be delivered to and/or past the blood brain barrier (BBB), which acts as a highly specialized structural and biochemical barrier that regulates the entry of blood-borne molecules into brain, and preserves ionic homeostasis within the brain microenvironment. Indeed, BBB properties are primarily determined by junctional complexes between the cerebral endothelial cells. In some embodiments, the endothelial cells, transfected ex vivo are collected from the patient's blood.

In addition, the present invention provides for neuronal targeting via a targeting element, including, but not limited to, an additional peptide directed against ApoE4. The present invention further contemplates the use of homing properties of microvascular endothelial cells (or precursors thereof) to transfer molecules in an organospecific manner. In further embodiments, the expression vectors of the present invention comprise an amino acid sequence that expresses insulin. In such embodiments, the insulin sequence promotes the export of the expressed antibodies. In some embodiments, administration of the aforementioned cell-based therapies occurs via inferior alveolar (IA) and/or intravenous (IV) injection in order to allow the cells to cross the BBB.

In some aspects, the present invention provides for antibodies directed against one or more of mutated SOD-1, TDP43 and FUS/TLS protein aggregates are useful in treating ALS by, for example, solubilizing the protein aggregates and preventing their spreading to motor neurons. In some aspects, the present invention provides for antibodies directed against mutated beta-amyloid (Aβ) protein aggregates are useful in treating Alzheimer's disease by, for example, solubilizing the protein aggregates and interaction with amyloid oligomers.

The present invention is also based, in part, on the discovery that antibodies directed against one or more of the amyloid protein of TDP43, beta-amyloid (Aβ), SOD-1, FUS/TLS, α-synuclein, Tau protein, and IAPP, protein aggregates are useful in treating ALS by, for example, solubilizing the protein aggregates and preventing their spreading to motor neurons. Similarly, antibodies directed against one or more of the amyloid protein of IAPP protein aggregates is useful in treating type II diabetes mellitus.

In various aspects, the present agent of the invention is a cell, for example a microvascular endothelial cell, or precursor thereof, engineered to release a therapeutic protein or peptide, including, without limitation, an antibody or antibody fragment, at a site of therapeutic action. In various embodiments, the therapeutic protein or peptide, including, without limitation, the antibody or antibody fragment, is directed against one or more mutated protein selected from TDP43, beta-amyloid (Aβ), SOD-1, FUS/TLS, α-synuclein, Tau protein, and IAPP. Accordingly, the present invention provides for methods of treating and/or preventing one or more neurodegenerative disorders selected from Parkinson's disease, Huntington's disease, Alzheimer's disease, frontotemporal lobar degeneration (FTLD) and Amyotrophic Lateral Sclerosis (ALS).

Microvascular Endothelial Cells

The present invention provides for the use of microvascular endothelial cells (or progenitors/precursors thereof) as vehicles for transporting and delivering therapeutic proteins or peptides, including, without limitation, antibodies, to sites of action, such as, but not limited to, the brain, the neuron, and the CNS. The microvascular endothelial cells can be derived from the bone marrow, brain, the CNS, the heart, the liver, the pancreas, etc. Certain properties of such microvascular endothelial cells allow for organospecific delivery of the molecules of the present invention.

Brain microvascular endothelial cells (BMEC), the major component of the blood-brain barrier, limit the passage of soluble and cellular substances from the blood into the brain. BMEC have unique features to distinguish themselves from those of peripheral endothelial cells, such as 1) intercellular tight junctions that display high electrical resistance and slow paracellular flux, 2) the absence of fenestrae and a reduced level of pinocytic activity, and 3) asymmetrically-localized enzymes and carrier-mediated transport systems. Similar to peripheral endothelial cells, BMEC express, or can be induced to express, cell adhesion molecules on their surface that regulate the extravasation of leukocytes into the brain. BMEC have been widely used for studying the molecular and cellular properties of blood-brain barrier because of their unique functions.

The present invention also includes cells that are precursors of endothelial cells, and in some embodiments, does not include embryonic stem cells, as described in U.S. Pat. No. 9,631,117, which is hereby incorporated by reference in its entirety. In some embodiments, the cells of the present invention include lines of isolated human cells that are precursors of endothelial cells and established cell lines of isolated cells that are precursors of endothelial cells. These cells include isolated human endothelial cell precursor cells, and murine endothelial cell precursor cells. In some embodiments, the cells are immortalized cells or established cell lines, i.e. immortalized, stable, nontumorigenic cell lines whose characteristics are identical from one generation to another. The present invention also relates to an isolated human endothelial cell precursor cell, other than embryonic stem cells, comprising the clusters of differentiation (CD) 133, 13, 271, 90 202b, 309, 146, 105 and 143; and not comprising the clusters of differentiation CD31 and CD45.

In some embodiments, the cells include cells deposited under the Budapest Treaty at the National Collection of Cultures of Microorganisms (Collection Nationale de Cultures de Microorganismes, CNCM), Institut Pasteur, 25 rue du Docteur Roux, 75724 Paris cedex 15, France. These are, for example, isolated human cells that are endothelial cell precursors other than embryonic stem cells deposited at the Collection Nationale de Cultures de Microorganismes (CNCM), Institut Pasteur, 25 rue du Docteur Roux, 75724 Paris cedex 15, France on Aug. 18, 2009 under CNCM numbers No. 1-4220 (HucPEC 55.1) and No. 1-4221 (HucPEC 55.2).

In some embodiments, the cells include isolated human cells that are endothelial cell precursors isolated from cord blood. The endothelial cell precursors are selected from HEPC.CB1 and HEPC.CB2. See Paprocka, et al. "CD133 positive progenitor endothelial cell lines from human cord blood," Cytometry A. 2011 August; 79(8):594-602. doi: 10.1002/cyto.a.21092, the entire contents of which are hereby incorporated in their entirety.

In other embodiments, the cells of the present invention include isolated murine cells that are endothelial cell precursors. In particular, the cells can be isolated murine cell that is a precursor of endothelial cells, other than embryonic stem cells, deposited at the Collection Nationale de Cultures de Microorganismes (CNCM), Institut Pasteur, rue du Docteur Roux, 75724 Paris cedex 15, France on Aug. 18, 2009 under CNCM numbers No. 1-4222 (MAgEC 10.5) and No. 1-4223 (MagEC 11.5).

The present invention includes isolated cells that are capable of targeting pathological sites as well as regenerating new endothelial tissues at the targeted sites. In some embodiments, the cells according to the invention, are capable of specifically targeting tumors and/or injured tissues. Thus, in some embodiments, the cells of the invention can supply therapeutic molecules and/or genes at pathological sites.

In some aspects, the present agent of the invention is a cell, for example, a microvascular endothelial cell, or precursor thereof, engineered to release a therapeutic protein or peptide, including, without limitation, an antibody or antibody fragment, at a site of therapeutic action. In some aspects, the present agent of the invention is a cell, for example, a microvascular endothelial cell, or precursor thereof, engineered to release a therapeutic protein or peptide, including, without limitation, an antibody or antibody fragment in spinal cord motor neurons or glial cells.

In various embodiments, the site of therapeutic action is one or more of the CNS, brain, spinal cord, glial cells, neurons in the hippocampus and habenular nuclei, and astrocytes. In various embodiments, the pathological site is one or more of the CNS, brain, spinal cord, glial cells, neurons in the hippocampus and habenular nuclei, and astrocytes.

The engineered cell comprises, in some embodiments, a nucleic acid expression vector having one or more nucleic acid sequences selected from SEQ ID NOs:1-12 or a variant thereof (e.g. one or more nucleic acid sequences having about 90%, or about 93%, or about 95%, or about 97%, or about 98%, or about 99% sequence identity with one of SEQ ID NOs:1-6). In various embodiments, the DNA sequences encode variable heavy and variable light chain domains. For example, the DNA sequences can encode, for each chain, a variable domain, a signal peptide, and/or a constant domain.

The engineered cell comprises, in some embodiments, a nucleic acid expression vector having one or more amino acid sequences selected from SEQ ID NOs: 13 and 14.

The engineered cell comprises, in some embodiments, a nucleic acid expression vector having one or more amino acid sequences selected from SEQ ID NOs: 94 and 31.

The engineered cell comprises, in some embodiments, a nucleic acid expression vector of any one of SEQ ID NOs: 83-93 or a variant thereof (e.g. one or more nucleic acid sequences having about 90%, or about 93%, or about 95%, or about 97%, or about 98%, or about 99% sequence identity with one of SEQ ID NOs: 83-93). In some embodiments, the cell comprises a vector of any one of FIGS. 10-23.

In some embodiments, the DNA sequence encoding a variable heavy chain of the anti-TDP43 antibody of the present invention has at least 65%, at least 70%, at least 75%, at least 80%, at least 85%, at least 90%, at least 95%, at least 96%, at least 97%, at least 98%, or at least 99% sequence identity to SEQ ID NO: 1:

(SEQ ID NO: 1)
CAGGTTCAGCTGCAGCAGTCTGGAGCTGAGCTGGCGAGGCCTGGGGC

TTCAGTGAAGCTGTCCTGCAAGGCTTCTGGCTACACCTTCACAAGCTAT

GGTATAAGCTGGGTGAGGCAGAGAACTGGACAGGGCCTTGAGTGGATT

GGAGAGATTTATCCTAGACGTGGTAATACTTACTACAATGAGAAGTTCA

AGGGCAAGGCCACACTGACTGCATACAAATCCTCCGGCACAGCGTACA

TGGAGCTCCGCAGCCTGACATCTGAGGACTCTGCGGTCTTTTTCTGTG

CAAGAGGGGGTATCTACTATGGTAACTTATTTGACTACTGGGGCCAAGG

CACCACTCTCACAGTCTCCTCA.

In some embodiments, the DNA sequence encoding a signal peptide of the variable heavy chain of the anti-TDP43 antibody of the present invention has at least 65%, at least 70%, at least 75%, at least 80%, at least 85%, at least 90%, at least 95%, at least 96%, at least 97%, at least 98%, or at least 99% sequence identity to SEQ ID NO: 2:

(SEQ ID NO: 2)
ATGGAATGGATCTGGATCTTTCTCTTCATCCTGTCAGGAACTGCAGGTG

TCCAATCC.

In some embodiments, the DNA sequence encoding a constant domain of the variable heavy chain of the anti-TDP43 antibody of the present invention has at least 65%, at least 70%, at least 75%, at least 80%, at least 85%, at least 90%, at least 95%, at least 96%, at least 97%, at least 98%, or at least 99% sequence identity to SEQ ID NO: 3:

(SEQ ID NO: 3)
GCCAAAACAACACCCCCATCAGTCTATCCACTGGCCCCTGGGTGTGGA

GATACAACTGGTTCCTCTGTGACTCTGGGATGCCTGGTCAAGGGCTAC

TTCCCTGAGTCAGTGACTGTGACTTGGAACTCTGGATCCCTGTCCAGCA

GTGTGCACACCTTCCCAGCTCTCCTGCAGTCTGGACTCTACACTATGAG

CAGCTCAGTGACTGTCCCCTCCAGCACCTGGCCAAGTCAGACCGTCAC

CTGCAGCGTTGCTCACCCAGCCAGCAGCACCACGGTGGACAAAAAACT

-continued

TGAGCCCAGCGGGCCCATTTCAACAATCAACCCCTGTCCTCCATGCAA

GGAGTGTCACAAATGCCCAGCTCCTAACCTCGAGGGTGGACCATCCGT

CTTCATCTTCCCTCCAAATATCAAGGATGTACTCATGATCTCCCTGACA

CCCAAGGTCACGTGTGTGGTGGTGGATGTGAGCGAGGATGACCCAGAC

GTCCGGATCAGCTGGTTTGTGAACAACGTGGAAGTACACACAGCTCAG

ACACAAACCCATAGAGAGGATTACAACAGTACTATCCGGGTGGTCAGT

GCCCTCCCCATCCAGCACCAGGACTGGATGAGTGGCAAGGAGTTCAAA

TGCAAGGTCAACAACAAAGACCTCCCATCACCCATCGAGAGAACCATCT

CAAAAATTAAAGGGCTAGTCAGAGCTCCACAAGTATACATCTTGCCGCC

ACCAGCAGAGCAGTTGTCCAGGAAAGATGTCAGTCTCACTTGCCTGGT

CGTGGGCTTCAACCCTGGAGACATCAGTGTGGAGTGGACCAGCAATGG

GCATACAGAGGAGAACTACAAGGACACCGCACCAGTCCTGGACTCTGA

CGGTTCTTACTTCATATACAGCAAGCTCGATATAAAAACAAGCAAGTGG

GAGAAAACAGATTCCTTCTCATGCAACGTGAGACACGAGGGTCTGAAAA

ATTACTACCTGAAGAAGACCATCTCCCGGTCTCCGGGTAAA.

In some embodiments, the DNA sequence encoding a variable light chain of the anti-TDP43 antibody of the present invention has at least 65%, at least 70%, at least 75%, at least 80%, at least 85%, at least 90%, at least 95%, at least 96%, at least 97%, at least 98%, or at least 99% sequence identity to SEQ ID NO: 4:

(SEQ ID NO: 4)
CAGGCTGTTGTGACTCAGGAATCTGCACTCACCACATCACCTGGTGAAA

CAGTCACACTCACTTGTCGCTCAAGTACTGGGGCTGTTACAACTAGTAA

CTATGCCAACTGGGTCCAAGAAAAACCAGATCATTTATTCACTGGTCTA

ATAGGTGGTACCAACAACCGAGCTCCAGGTGTTCCTGCCAGATTCTCA

GGCTCCCTGATTGGAGACAAGGCTGCCCTCACCATCACAGGGGCACAG

ACTGAGGATGAGGCAATATATTTCTGTGCTCTATGGTTCAGCAACCACT

GGGTGTTCGGTGGAGGAACCAAACTGACTGTCCTAGGC.

In some embodiments, the DNA sequence encoding a signal peptide of the variable light chain of the anti-TDP43 antibody of the present invention has at least 65%, at least 70%, at least 75%, at least 80%, at least 85%, at least 90%, at least 95%, at least 96%, at least 97%, at least 98%, or at least 99% sequence identity to SEQ ID NO: 5:

(SEQ ID NO: 5)
ATGGCCTGGATTTCACTTATACTCTCTCTCCTGGCTCTCAGCTCAGGGG

CCATTTCC.

In some embodiments, the DNA sequence encoding a constant domain of the variable light chain of the anti-TDP43 antibody of the present invention has at least 65%, at least 70%, at least 75%, at least 80%, at least 85%, at least 90%, at least 95%, at least 96%, at least 97%, at least 98%, or at least 99% sequence identity to SEQ ID NO: 6:

(SEQ ID NO: 6)
CAGCCCAAGTCTTCGCCATCAGTCACCCTGTTTCCACCTTCCTCTGAAG

AGCTCGAGACTAACAAGGCCACACTGGTGTGTACGATCACTGATTTCTA

CCCAGGTGTGGTGACAGTGGACTGGAAGGTAGATGGTACCCCTGTCAC

TCAGGGTATGGAGACAACCCAGCCTTCCAAACAGAGCAACAACAAGTA

CATGGCTAGCAGCTACCTGACCCTGACAGCAAGAGCATGGGAAAGGCA

TAGCAGTTACAGCTGCCAGGTCACTCATGAAGGTCACACTGTGGAGAA

GAGTTTGTCCCGTGCTGACTGTTCC.

In some embodiments, the DNA sequence encoding a variable heavy chain of the beta-amyloid antibody of the present invention has at least 65%, at least 70%, at least 75%, at least 80%, at least 85%, at least 90%, at least 95%, at least 96%, at least 97%, at least 98%, or at least 99% sequence identity to SEQ ID NO: 7:

(SEQ ID NO: 7)
CAGGTTCAGCTGCAGCAGTCTGGGGCTGAGCTGGTGAAGCCTGGGGC

CTCAGTGAAGATTTCCTGCAAAGCTTCTGGCTACGCATTCAGTAACTAC

TGGATGAACTGGGTGAAGCAGAGGCCTGGAAAGGGTCTTGAGTGGATT

GGACAGATTTATCCTGGAGATGGTGATACTAACTACAACGGAAAGTTCA

AGGGCAAGGCCACACTGACTGCAGACAAATCCTCCAGCACAGCCTACA

TGCAGCTCAGCAGCCTGACCTCTGAGGACTCTGCGGTCTATTTCTGTG

CAAGAGGTGACTACTGGGGCCAAGGCACCACTCTCACAGTCTCCTCA.

In some embodiments, the DNA sequence encoding a variable light chain of the beta-amyloid antibody of the present invention has at least 65%, at least 70%, at least 75%, at least 80%, at least 85%, at least 90%, at least 95%, at least 96%, at least 97%, at least 98%, or at least 99% sequence identity to SEQ ID NO: 8:

(SEQ ID NO: 8)
GACATTGTGATGACACAGTCTCCATCCTCCCTGGCTATGTCAGTAGGA

CAGAAGGTCACTATGAGCTGCAAGTCCAGTCAGAGCCTTTTAAATAGTA

GCAATCAAAAGAACTATTTGGCCTGGTACCAGCAGAAACCAGGACAGT

CTCCTAAACTTCTGGTATACTTTGCATCCACTAGGGAATCTGGGGTCCC

TGATCGCTTCATAGGCAGTGGATCTGGGACAGATTTCACTCTTACCATC

AGCAGTGTGCAGGCTGAAGACCTGGCAGATTACTTCTGTCAGCAACAT

TATAACACTCCGCTCACGTTCGGTGCTGGGACCAAGCTGGAGCTGAAA.

In some embodiments, the DNA sequence encoding a constant heavy chain of the beta-amyloid antibody of the present invention has at least 65%, at least 70%, at least 75%, at least 80%, at least 85%, at least 90%, at least 95%, at least 96%, at least 97%, at least 98%, or at least 99% sequence identity to SEQ ID NO: 9:

(SEQ ID NO: 9)
GAGAGTCAGTCCTTCCCAAATGTCTTCCCCCTCGTCTCCTGCGAGAGC

CCCCTGTCTGATAAGAATCTGGTGGCCATGGGCTGCCTGGCCCGGGAC

TTCCTGCCCAGCACCATTTCCTTCACCTGGAACTACCAGAACAACACT

-continued

```
GAAGTCATCCAGGGTATCAGAACCTTCCCAACACTGAGGACAGGGGGC

AAGTACCTAGCCACCTCGCAGGTGTTGCTGTCTCCCAAGAGCATCCTT

GAAGGTTCAGATGAATACCTGGTATGCAAAATCCACTACGGAGGCAAA

AACAAAGATCTGCATGTGCCCATTCCAGCTGTCGCAGAGATGAACCCC

AATGTAAATGTGTTCGTCCCACCACGGGATGGCTTCTCTGGCCCTGCA

CCACGCAAGTCTAAACTCATCTGCGAGGCCACGAACTTCACTCCAAAA

CCGATCACAGTATCCTGGCTAAAGGATGGGAAGCTCGTGGAATCTGGC

TTCACCACAGATCCGGTGACCATCGAGAACAAAGGATCCACACCCCAA

ACCTACAAGGTCATAAGCACACTTACCATCTCTGAAATCGACTGGCTGA

ACCTGAATGTGTACACCTGCCGTGTGGATCACAGGGGTCTCACCTTCT

TGAAGAACGTGTCCTCCACATGTGCTGCCAGTCCCTCCACAGACATCC

TAACCTTCACCATCCCCCCCTCCTTTGCCGACATCTTCCTCAGCAAGTC

CGCTAACCTGACCTGTCTGGTCTCAAACCTGGCAACCTATGAAACCCT

GAATATCTCCTGGGCTTCTCAAAGTGGTGAACCACTGGAAACCAAAATT

AAAATCATGGAAAGCCATCCCAATGGCACCTTCAGTGCTAAGGGTGTG

GCTAGTGTTTGTGTGGAAGACTGGAATAACAGGAAGGAATTTGTGTGTA

CTGTGACTCACAGGGATCTGCCTTCACCACAGAAGAAATTCATCTCAAA

ACCCAATGAGGTGCACAAACATCCACCTGCTGTGTACCTGCTGCCACC

AGCTCGTGAGCAACTGAACCTGAGGGAGTCAGCCACAGTCACCTGCCT

GGTGAAGGGCTTCTCTCCTGCAGACATCAGTGTGCAGTGGCTTCAGAG

AGGGCAACTCTTGCCCCAAGAGAAGTATGTGACCAGTGCCCCGATGCC

AGAGCCTGGGGCCCCAGGCTTCTACTTTACCCACAGCATCCTGACTGT

GACAGAGGAGGAATGGAACTCCGGAGAGACCTATACCTGTGTTGTAGG

CCACGAGGCCCTGCCACACCTGGTGACCGAGAGGACCGTGGACAAGT

CCACTGGTAAACCCACACTGTACAATGTCTCCCTGATCATGTCTGACAC

AGGCGGCACCTGCTAT.
```

In some embodiments, the DNA sequence encoding a constant light chain the beta-amyloid antibody of the present invention has at least 65%, at least 70%, at least 75%, at least 80%, at least 85%, at least 90%, at least 95%, at least 96%, at least 97%, at least 98%, or at least 99% sequence identity to SEQ ID NO: 10:

```
                                     (SEQ ID NO: 10)
CGGGCTGATGCTGCACCAACTGTATCCATCTTCCCACCATCCAGTGAG

CAGTTAACATCTGGAGGTGCCTCAGTCGTGTGCTTCTTGAACAACTTCT

ACCCCAAAGACATCAATGTCAAGTGGAAGATTGATGGCAGTGAACGAC

AAAATGGCGTCCTGAACAGTTGGACTGATCAGGACAGCAAAGACAGCA

CCTACAGCATGAGCAGCACCCTCACGTTGACCAAGGACGAGTATGAAC

GACATAACAGCTATACCTGTGAGGCCACTCACAAGACATCAACTTCACC

CATTGTCAAGAGCTTCAACAGGAATGAGTGT.
```

In some embodiments, the DNA sequence encoding a signal peptide of the heavy chain of the beta-amyloid antibody of the present invention has at least 65%, at least 70%, at least 75%, at least 80%, at least 85%, at least 90%, at least 95%, at least 96%, at least 97%, at least 98%, or at least 99% sequence identity to SEQ ID NO: 11:

```
                                     (SEQ ID NO: 11)
ATGGAATGGCCTTTGATCTTTCTCTTCCTCCTGTCAGGAACTGCAGGTG

TCCAATCC.
```

In some embodiments, the DNA sequence encoding a signal peptide of the light chain of the beta-amyloid antibody of the present invention has at least 65%, at least 70%, at least 75%, at least 80%, at least 85%, at least 90%, at least 95%, at least 96%, at least 97%, at least 98%, or at least 99% sequence identity to SEQ ID NO: 12:

```
                                     (SEQ ID NO: 12)
ATGGAATCACAGACCCAGGTCCTCATGTTTCTTCTGCTCTGGGTATCTGGT

GCCTGTGCA.
```

Therapeutic Proteins or Peptides, Including Antibodies or Fragments Thereof

In embodiments, the therapeutic proteins or peptides find use in a gene replacement therapy, e.g. delivery of a wild type protein or peptide to a subject bearing a mutant form of the protein or peptide, which is associated with a disease. For instance, the present endothelial cells can be transfected or transformed with a vector, e.g. those described herein, being a wild type or otherwise non-defective protein or peptide and such cell can be delivered to a subject bearing a mutant form of the protein or peptide, which is associated with a disease. In embodiments, the therapeutic protein or peptide is selected from nerve growth factor (NGF, e.g. without limitation for use in treating Alzheimer's), apolipoprotein E (ApoE, e.g. ApoE1, ApoE2, ApoE3, and ApoE4, e.g. without limitation for use in treating Alzheimer's), survival motor neuron 1 (SMN1, e.g. without limitation for use in treating SMA), almitoyl-protein thioesterase 1 (PPT1 e.g., without limitation for use in treating CLN1 disease), CLN3/battenin (e.g., without limitation for use in treating CLN3 disease), CLN6 (e.g., without limitation for use in treating CLN6 disease), CLN8 (e.g., without limitation for use in treating CLN8 disease), huntingtin (e.g., without limitation for use in treating Huntington's Disease), ASAP (e.g., without limitation for use in treating Canavan disease), neurturin, GDNF, BDNF, CDNF, VEGF-A (e.g., without limitation for use in treating Parkinson's), MECP2 (e.g., without limitation for use in treating Rett Syndrome), beta-galactosidase (β-galactosidase, e.g., without limitation for use in treating GM-1 gangliosidoses), aromatic L-amino acid decarboxylase (AADC, e.g., without limitation for use in treating Parkinson's Disease), SOD-1 (e.g., without limitation for use in treating ALS), TDP43 (e.g., without limitation for use in treating ALS), beta-amyloid (Aβ, e.g. without limitation for use in treating Alzheimer's disease), FUS/TLS (e.g., without limitation for use in treating ALS), α-synuclein (e.g., without limitation for use in treating Parkinson's), Tau protein (e.g. without limitation for use in treating Alzheimer's disease), and IAPP (e.g. without limitation for use in treating Alzheimer's disease).

In some aspects, the present agent of the invention is a protein or peptide, including, without limitation, an antibody, or fragment thereof (e.g., Fab fragment), that is directed against one or more of mutated TDP43, beta-amyloid (Aβ), SOD-1, FUS/TLS, α-synuclein, Tau protein, and IAPP, optionally in the context of protein aggregates. In various embodiments, the agent of the invention targets protein aggregates that comprise one or more of mutated TDP43, beta-amyloid (Aβ), SOD-1, FUS/TLS, α-synuclein, Tau protein, and IAPP proteins. In some embodiments, the agents of the invention are conformation-sensitive antibodies directed against the mutated TDP43, beta-amyloid (Aβ), SOD-1, FUS/TLS, α-synuclein, Tau protein, and IAPP protein aggregates. In various embodiments the present antibodies solubilize the intra- or extra-cellular protein aggregates and therefore prevent or reduce their spreading.

In some aspects, the present invention agent of the invention is an antibody, or fragment thereof (e.g., Fab fragment), that is directed against one or more of mutated TDP43, beta-amyloid (Aβ), SOD-1, FUS/TLS, α-synuclein, Tau protein, and IAPP, optionally in the context of protein aggregates. In various embodiments, the agent of the invention targets protein aggregates that comprise one or more of mutated TDP43, beta-amyloid (Aβ), SOD-1, FUS/TLS, α-synuclein, Tau protein, and IAPP. In some embodiments, the agents of the invention are conformation-sensitive antibodies directed against the mutated TDP43, beta-amyloid (Aβ), SOD-1, FUS/TLS, α-synuclein, Tau protein, and IAPP protein aggregates.

In some embodiments, the present invention provides for an antibody, or Fab, directed against wild type or mutant TDP43, or peptide fragment. In various embodiments, the antibody, or Fab, comprises a heavy chain and/or a light chain, which are identified based on the sequence of the constant domain (e.g., mouse IgG1, rat kappa, etc.). The antibody, or Fab, can comprise, for each chain, a variable domain, a signal peptide, and/or a constant domain. In some embodiments, the antibody, or Fab, of the present invention comprises a variable heavy domain that comprises a peptide having an amino acid sequence at least 65%, at least 70%, at least 75%, at least 80%, at least 85%, at least 90%, at least 95%, at least 96%, at least 97%, at least 98%, or at least 99% identical to SEQ ID NO: 13:

(SEQ ID NO: 13)
QVQLQQSGAELARPGASVKLSCKASGYTFTSYGISWVRQRTGQGLEWIGEI

YPRRGNTYYNEKFKGKATLTAYKSSGTAYMELRSLTSEDSAVFFCARGGIY

YGNLFDYWGQGTTLTVSS.

In some embodiments, the antibody, or Fab, of the present invention comprises a variable light domain that comprises a peptide having an amino acid sequence at least 65%, at least 70%, at least 75%, at least 80%, at least 85%, at least 90%, at least 95%, at least 96%, at least 97%, at least 98%, or at least 99% identical to SEQ ID NO: 14:

(SEQ ID NO: 14)
QAVVTQESALTTSPGETVTLTCRSSTGAVTTSNYANWVQEKPDHLFTGLIG

GTNNRAPGVPARFSGSLIGDKAALTITGAQTEDEAIYFCALWFSNHWVFGG

GTKLTVLG.

In various embodiments, the antibody, or Fab, of the present invention comprises a constant domain that comprises a peptide having an amino acid sequence at least 65%, at least 70%, at least 75%, at least 80%, at least 85%, at least 90%, at least 95%, at least 96%, at least 97%, at least 98%, or at least 99% identical to SEQ ID NO: 15 and/or SEQ ID NO: 16:

SEQ ID NO: 15
AKTTPPSVYPLAPGCGDTTGSSVTLGCLVKGYFPESVTVTWNSGSLSSSV

HTFPALLQSGLYTMSSSVTVPSSTWPSQTVTCSVAHPASSTTVDKKLEPS

GPISTINPCPPCKECHKCPAPNLEGGPSVFIFPPNIKDVLMISLTPKVTC

VVVDVSEDDPDVRISWFVNNVEVHTAQTQTHREDYNSTIRVVSALPIQHQ

DWMSGKEFKCKVNNKDLPSPIERTISKIKGLVRAPQVYILPPPAEQLSRK

DVSLTCLVVGFNPGDISVEWTSNGHTEENYKDTAPVLDSDGSYFIYSKLD

IKTSKWEKTDSFSCNVRHEGLKNYYLKKTISRSPGK;
and/or

SEQ ID NO: 16
QPKSSPSVTLFPPSSEELETNKATLVCTITDFYPGVVTVDWKVDGTPVTQ

GMETTQPSKQSNNKYMASSYLTLTARAWERHSSYSCQVTHEGHTVEKSLS

RADCS.

In some embodiments, the antibody, or Fab, of the present invention comprises a signal peptide comprising a peptide having amino acid sequence identity to SEQ ID NO: 17 and/or SEQ ID NO: 18: MEWIWIFLFILSGTAGVQS (SEQ ID NO: 17), and/or MAWISLILSLLALSSGAIS (SEQ ID NO: 18). In various embodiments, the signal peptide comprises an amino acid sequence having one or more amino acid mutations. In various embodiments, the signal peptide comprises an amino acid sequence having one, or two, or three, or four, or five, or six, or seven, or eight, or nine, or ten amino acid mutations. In some embodiments, the one or more amino acid mutations may be independently selected from substitutions, insertions, deletions, and truncations. In some embodiments, the amino acid mutations are amino acid substitutions, and may include conservative and/or non-conservative substitutions.

In further embodiments, the present invention contemplates an antibody, or Fab, comprising one or more complementarity-determining regions (CDR) for the variable heavy and/or variable light domains. In some embodiments, the CDRs are presented in Kabat definition. In various embodiments, the CDR comprises an amino acid sequence having one or more amino acid mutations. In various embodiments, the CDR comprises an amino acid sequence having one, or two, or three, or four, or five, or six, or seven, or eight, or nine, or ten amino acid mutations. In some embodiments, the one or more amino acid mutations may be independently selected from substitutions, insertions, deletions, and truncations. In some embodiments, the amino acid mutations are amino acid substitutions, and may include conservative and/or non-conservative substitutions. In further embodiments, the variable heavy domain comprises a CDR1 having an amino acid sequence of SEQ ID NO: 19. In further embodiments, the variable heavy domain comprises a CDR2 having an amino acid sequence of SEQ ID NO: 20. In still further embodiments, the variable heavy domain comprises a CDR3 having an amino acid sequence of SEQ ID NO: 21. In some embodiments, the antibody, or Fab, of the present invention comprises CDR1: SYGIS (SEQ ID NO: 19); CDR2: EIYPRRGNTYYNEKFKG (SEQ ID NO: 20); and/or CDR3: GGIYYGNLFDY (SEQ ID NO: 21). In some embodiments, the variable light domain comprises a CDR1 having an amino acid sequence of SEQ ID NO: 22. In further embodiments, the variable heavy domain comprises a CDR2 having an amino acid sequence of SEQ ID NO: 23. In still further embodiments, the variable heavy domain comprises a CDR3 having an amino acid sequence of SEQ ID NO: 24.

In some embodiments, the antibody, or Fab, of the present invention comprises CDR1: RSSTGAVTTSNYAN (SEQ ID NO: 22); CDR2: GTNNRAP (SEQ ID NO: 23); and/or CDR3: ALWFSNHWV (SEQ ID NO: 24).

Amyotrophic Lateral Sclerosis (ALS)

ALS is a neurodegenerative condition that targets primarily motor neurons, resulting in progressive paralysis and death within a few years from onset. Just like Alzheimer's, Parkinson's and other neurodegenerative disease, a proportion (~10%) of ALS is dominantly inherited, with the remaining 90% (referred to as sporadic) of unknown origin. The identification in 1993 of mutation in the gene encoding superoxide dismutase 1 (SOD-1) as the first or second most common form of inherited ALS, and subsequent generation of transgenic mice expressing ALS-causing mutants in SOD1, initiated the molecular era of deciphering disease mechanism. A flurry of approaches established that non-cell autonomous disease depends on one or more toxic properties of mutant SOD-1. The latter drives disease initiation when synthesized within motor neurons while its synthesis by glial neighbors provokes rapid disease advance. Along with prion-infected mice, the ALS-linked mutant SOD-1 mice are among the most faithful model of neuro-degeneration, recapitulating the selective progressive loss of motor neurons that leads to the paralysis characteristic of human ALS.

In both inherited and sporadic ALS, affected neurons and glial cells contain abnormal proteinaceous accumulations, often labeled by anti-ubiquitin antibodies. The major protein component of these accumulations in familial cases with SOD-1 mutations, and in mutant sporadic disease has recently been challenged. This controversy notwithstanding, over the past five years it has been established that a main component of proteinaceous cytoplasmic inclusions in essentially all sporadic ALS cases is the RNA/DNA-binding protein TDP43, accompanied by its nuclear depletion. Moreover, mutations in TDP43 are causes of inherited ALS and rare instances of FTLD.

Affected neurons of patients with TDP43 mutations also develop cytoplasmic TDP43-positive inclusions and nuclear loss, implying that abnormal localization and aggregation of TDP43 could represent a first mechanistic link between sporadic ALS and an inherited form caused by a known mutation. Furthermore, ALS-causing mutations were identified in a gene encoding another RNA/DNA-binding protein, called FUS/TLS for fused in sarcoma or translocated in liposarcoma. FUS-mutant mediated disease is also accompanied by FUS/TLS-containing cytoplasmic inclusions and disturbed subcellular localization. Unresolved is whether pathogenesis in TDP43- or FUS/TLS-mediated disease results from a loss of nuclear function of either protein, from a gain of toxic property(ies) associated (or not) with the cytoplasmic inclusions, or—perhaps most likely, from a combination of all possibilities.

SOD-1 is a small 153-amino acid protein, which in its native state occurs as a remarkably stable dimmer that is highly resistant to proteolytic degradation. ALS-associated point mutations occur in almost every position (>140 mutations are known) with each leading to destabilization and eventually accumulation of misfolded species within affected cells of the nervous system. In vitro studies with purified SOD-1 have shown that both the wild-type and several mutant versions of the protein spontaneously fibrillize under denaturing conditions with propensity to aggregate that is enhanced in the mutants.

In various embodiments, present agents are raised against and/or target a peptide. In various embodiments, peptide refers to a series of residues, typically L-amino acids, connected one to the other typically by peptide bonds between the α-amino and carboxyl groups of adjacent amino acids. The term includes modified peptides and synthetic peptide analogues. In various embodiments, the peptide epitope of the invention comprises a sequence as set out in any of the preceding statements of the invention and consists of 6 to 18 amino acids. In various embodiments, the peptide consists of 8, 9, 10, 11, 12, 13, 14, 15, 16, 17 or 18 amino acids. For example, the peptide epitope may comprise a sequence of 8 to 12 amino acids or 8 to 10 amino acids. It is understood by those in the art that other fragments of proteins and peptides disclosed herein, such as amino-truncated, carboxy-truncated, or internal deletions, or any combination of these, as well as conservative variants of these peptides, may be employed in this invention.

In various embodiments, the present agents target a mutated protein comprising one or more mutations of Table 1, optionally in the context of a protein aggregate. For instance, the present agents may be an antibody targeting a protein bearing one or more mutations of Table 1, optionally in the context of a protein aggregate.

In various embodiments, the present agents target a mutated protein comprising one or more mutations of Table 1, optionally in the context of a protein aggregate. For instance, the present agents may be conformation-specific antibodies targeting a protein bearing one or more mutations of Table 1, optionally in the context of a protein aggregate.

In various embodiments, the present agents target mutated SOD-1, optionally in the context of a protein aggregate. In some embodiments, the mutated SOD-1 comprises the A4V mutation. In some embodiments, the mutated SOD-1 comprises an SOD-1 mutation of Table 1.

Mutations of TAR DNA binding protein 43 (TDP43) cause a dominant form of ALS. The normal role of the TDP43 protein includes binding to RNA, the genetic messenger molecule. Mutations in the TDP43 gene cause the TDP43 protein to mislocalize in motor neurons, away from the nucleus where it is normally found, and into the cytoplasm, where it aggregates into clumps that can be seen under the microscope. Even in ALS not caused by TDP43 mutations, the protein is found in these aggregates, suggesting it may play a pivotal role in many forms of ALS.

In various embodiments, the present agents target mutated TDP43, optionally in the context of a protein aggregate. In various embodiments, the present agents target mutated ALS10 (TARDBP). Mutations of TARDBP include: p.Gly298Ser, p.Ala315Thr, p.Ala382Thr, p.Met337Val, p.Gly348Cys, p.Gly287Ser, p.Gly294Val, and p.Ala382Thr.

The human TDP43 protein is made of 414 amino acids and is encoded by the TARDBP gene. The amino acid sequence of human TDP43 is shown by SEQ ID NO: 25.

```
                                        SEQ ID NO.: 25
MSEYIRVTEDENDEPIEIPSEDDGTVLLSTVTAQFPGACGLRYRNPVSQC

MRGVRLVEGILHAPDAGWGNLVYVVNYPKDNKRKMDETDASSAVKVKRAV

QKTSDLIVLGLPWKTTEQDLKEYFSTFGEVLMVQVKKDLKTGHSKGFGFV

RFTEYETQVKVMSQRHMIDGRWCDCKLPNSKQSQDEPLRSRKVFVGRCTE

DMTEDELREFFSQYGDVMDVFIPKPFRAFAFVTFADDQIAQSLCGEDLII

KGISVHISNAEPKHNSNRQLERSGRFGGNPGGFGNQGGFGNSRGGGAGLG

NNQGSNMGGGMNFGAFSINPAMMAAAQAALQSSWGMMGMLASQQNQSGPS

GNNQNQGNMQREPNQAFGSGNNSYSGSNSGAAIGWGSASNAGSGSGFNGG

FGSSMDSKSSGWGM
```

In various embodiments, the present antibodies are directed to/or raised against a peptide comprising part of wild type or mutant TDP43, including stretches of amino acids of SEQ ID NO: 25.

In various embodiments, the present agents of conformation-sensitive antibodies target the following peptide sequences of amyloid TDP43, including but not limited to SEQ ID NOs: 26-28.

(311-344)
SEQ ID NO: 26
MNFGAFSINPAMMAAAQAALQSSWGMMGMLASQQ (311-320)
SEQ ID NO: 27
MNFGAFSINP (246-25)
SEQ ID NO: 28
EDLIIKGISV

In various embodiments, the present antibodies are directed to/or raised against a peptide comprising part or all of the amino acids of SEQ ID NOs: 26-28.

In some embodiments, the present invention provides for an antibody, or Fab, directed against wild type or mutant TDP43, or peptide fragment. In various embodiments, the antibody, or Fab, comprises a heavy chain and/or a light chain, which are identified based on the sequence of the constant domain (e.g., mouse IgG1, rat kappa, etc.). The antibody, or Fab, can comprise, for each chain, a variable domain, a signal peptide, and/or a constant domain. In some embodiments, the antibody, or Fab, of the present invention comprises a variable heavy domain that comprises a peptide having an amino acid sequence at least 65%, at least 70%, at least 75%, at least 80%, at least 85%, at least 90%, at least 95%, at least 96%, at least 97%, at least 98%, or at least 99% identical to SEQ ID NO: 13.

In some embodiments, the antibody, or Fab, of the present invention comprises a variable light domain that comprises a peptide having an amino acid sequence at least 65%, at least 70%, at least 75%, at least 80%, at least 85%, at least 90%, at least 95%, at least 96%, at least 97%, at least 98%, or at least 99% identical to SEQ ID NO: 14.

In various embodiments, the antibody, or Fab, of the present invention comprises a constant domain that comprises a peptide having an amino acid sequence at least 65%, at least 70%, at least 75%, at least 80%, at least 85%, at least 90%, at least 95%, at least 96%, at least 97%, at least 98%, or at least 99% identical to SEQ ID NO: 15 and/or SEQ ID NO: 16.

In some embodiments, the antibody, or Fab, of the present invention comprises a signal peptide comprising a peptide having amino acid sequence identity to SEQ ID NO: 17 and/or SEQ ID NO: 18: MEWIWIFLFILSGTAGVQS (SEQ ID NO: 17), and/or MAWISLILSLLALSSGAIS (SEQ ID NO: 18). In various embodiments, the signal peptide comprises an amino acid sequence having one or more amino acid mutations. In various embodiments, the signal peptide comprises an amino acid sequence having one, or two, or three, or four, or five, or six, or seven, or eight, or nine, or ten amino acid mutations. In some embodiments, the one or more amino acid mutations may be independently selected from substitutions, insertions, deletions, and truncations. In some embodiments, the amino acid mutations are amino acid substitutions, and may include conservative and/or non-conservative substitutions.

In further embodiments, the present invention contemplates an antibody, or Fab, comprising one or more complementarity-determining regions (CDR) for the variable heavy and/or variable light domains. In some embodiments, the CDRs are presented in Kabat definition. In various embodiments, the CDR comprises an amino acid sequence having one or more amino acid mutations. In various embodiments, the CDR comprises an amino acid sequence having one, or two, or three, or four, or five, or six, or seven, or eight, or nine, or ten amino acid mutations. In some embodiments, the one or more amino acid mutations may be independently selected from substitutions, insertions, deletions, and truncations. In some embodiments, the amino acid mutations are amino acid substitutions, and may include conservative and/or non-conservative substitutions. In further embodiments, the variable heavy domain comprises a CDR1 having an amino acid sequence of SEQ ID NO: 19. In further embodiments, the variable heavy domain comprises a CDR2 having an amino acid sequence of SEQ ID NO: 20. In still further embodiments, the variable heavy domain comprises a CDR3 having an amino acid sequence of SEQ ID NO: 21. In some embodiments, the antibody, or Fab, of the present invention comprises CDR1: SYGIS (SEQ ID NO: 19); CDR2: EIYPRRGNTYYNEKFKG (SEQ ID NO: 20); and/or CDR3: GGIYYGNLFDY (SEQ ID NO: 21). In some embodiments, the variable light domain comprises a CDR1 having an amino acid sequence of SEQ ID NO: 22. In further embodiments, the variable heavy domain comprises a CDR2 having an amino acid sequence of SEQ ID NO: 23. In still further embodiments, the variable heavy domain comprises a CDR3 having an amino acid sequence of SEQ ID NO: 24. In some embodiments, the antibody, or Fab, of the present invention comprises CDR1: RSSTGAVTTSNYAN (SEQ ID NO: 22); CDR2: GTNNRAP (SEQ ID NO: 23); and/or CDR3: ALWFSNHWV (SEQ ID NO: 24). Fused in sarcoma/Translocated in sarcoma (FUS/TLS) is inherited in a dominant manner. It is also an RNA binding protein, and may play a similar normal role in the cell as TDP43. FUS and TDP43 may in fact interact as part of their normal function.

In various embodiments, any FUS/TLS mutations described in Science 27 Feb. 2009: vol. 323 no. 5918 1205-1208, the entire contents of which are hereby incorporated by reference, may be targeted by the present agents.

In various embodiments, the following mutations in the fused in sarcoma/translated in liposarcoma (FUS/TLS) gene on chromosome 16 may be present (base numbering begins with the start codon; amino acid numbering begins with the methionine start codon):

| | Mutation | | |
|---|---|---|---|
| ID | Amino acid | Base pair | Exon |
| F577 | H517Q | C1551G* | 15 |
| F55 | R521G | C1561G | 15 |
| F213 | insGG | insGAGGTG523 | 5 |
| MTL 10 | delGG | delGAGGTG523 | 5 |
| MTL 7 | R244C | C730T | 6 |
| F360 | R514S, G515C | G1542T, G1543T | 15 |
| NUFMS9900 | R518K | G1553A | 15 |
| F072 | R521C | C1561T | 15 |
| F080 | R521C | C1561T | 15 |
| F085 | R521C | C1561T | 15 |
| F002 | R521G | C1561G | 15 |
| F136 | R521G | C1561G | 15 |
| F067 | R521H | G1562A | 15 |
| F287 | R522G | A1564G | 15 |

-continued

| | Mutation | | |
|---|---|---|---|
| ID | Amino acid | Base pair | Exon |
| F597 | R524T | G1571C | 15 |
| F346 | R524S | G1572C | 15 |
| F568 | P525L | C1574T | 15 |

In various embodiments, the present agents target mutated FUS/TLS, optionally in the context of a protein aggregate. In various embodiments, the present antibodies are directed to/or raised against a peptide comprising part of wild type or mutant FUS/TLS.

In various embodiments, the present agents target Ubiquilin-2, including mutants thereof. Ubiquilin-2 resides on the X chromosome. The normal function of the protein is to help degrade damaged or defective proteins in the cell. It is likely that mutations in the gene interfere with this function, and may lead to accumulation of harmful material within the cell. In various embodiments, the present antibodies are directed to/or raised against a peptide comprising part of wild type or mutant ubiquilin-2.

In various embodiments, the present agents are directed to/or raised against a protein bearing mutations in one or more of the following illustrative ALS-related mutations, including peptide fragments thereof:

| Locus Name (Gene) | Protein Name |
|---|---|
| ALS1 (SOD1) | Superoxide dismutase (Cu—Zn) |
| ALS3 (18q21) | |
| ALS4 (SETX) | Probable helicase senataxin |
| ALS6 (FUS/TLS) | RNA-binding protein FUS |
| ALS7 (20p13) | |
| ALS8 (VAPB) | Vesicle-associated membrane protein-associated protein B/C |
| ALS9 (ANG) | Angiogenin |
| ALS10 (TARDBP) | TAR DNA-binding protein 43 |
| ALS11 (FIG. 4) | Polyphosphoinositide phosphatase |
| ALS/FTD (C9orf72) | Uncharacterized protein C9orf72 |
| ALS/FTD (CHCHD10) | Coiled-coil-helix-coiled-coil-helix domain-containing protein 10, mitochondrial |
| ALS-FTD (17q) | Unknown |
| ALS14 (VCP) | Transitional endoplasmic reticulum ATPase |

BBB Delivery

In some aspects, therapies involving cell-based gene agents which effectively deliver therapeutic agents across the BBB are provided. In some aspects, therapies involving cell-based gene agents which effectively deliver therapeutic agents to and/or past the BBB are provided.

In some aspects, the present invention relates to a method of delivering an antibody or antibody fragment across the BBB. In some aspects, the present invention relates to a method delivering an antibody or antibody fragment across the BBB and cause an about 2-fold, or about a 3-fold, or about a 4-fold, or about a 5-fold, or about a 10-fold, or about a 30-fold, or about a 100-fold, or about a 300-fold, or about a 500-fold, or about a 1,000-fold increase in crossing the BBB, relative to an antibody or antibody fragment not delivered using the present methods (e.g. without a endothelial cell delivery, e.g. upon administration of a "naked" antibody or antibody fragment). In embodiments, the antibody or antibody fragment crosses the BBB by either a paracellular pathway or a transcellular pathway.

In some aspects, the present invention relates to a method delivering an antibody or antibody fragment, e.g. across one or more brain microvascular endothelial cells, pericytes, astrocytes, tight junctions, neurons, and basal membrane.

In embodiments, the present invention provides delivery of an antibody or antibody fragment, e.g. across the BBB, including, but not limited to, an antibody or antibody fragment that is directed against one or more of mutated TDP43, beta-amyloid (Aβ), SOD-1, FUS/TLS, α-synuclein, Tau protein, and IAPP, including peptide fragments thereof, inclusive of a Fab having SEQ ID NOs: 13 and 14 and/or CDRs of SEQ ID NOs: 19-24 and/or SEQ ID NOs: 94 and 31 and/or CDRs of SEQ ID NOs: 36-38 and 39-41.

In some embodiments, the use of autologous transfected microvascular endothelial cells for the treatment of a neurodegenerative disorder by reintroduction at and/or past the BBB via IA or IV injection.

In some embodiments, the agent of the invention is administered to the patient via inferior alveolar injection or intravenous injection. In some embodiments, the transfected cells are delivered to the blood brain barrier (BBB) of said patients in need thereof. In further embodiments, the transfected cells are early precursors such that they exhibit homing to and/or past the BBB. In some embodiments, the cells are administered so that they are allowed to cross the BBB. In some embodiments, the present invention provides for the use of organ-specific and/or early progenitors of endothelial cells in order to transport cells comprising vectors encoding therapeutic antibodies or antibody fragments into the brain. In further embodiments, the present invention provides for the use of homing properties of endothelial cells (e.g., precursors) to transfer agents of the invention in an organo-specific manner.

In such embodiments, the insulin sequence promotes the export of the expressed antibodies. In some embodiments, administration of the aforementioned cell-based therapies occurs via inferior alveolar (IA) and/or intravenous (IV) injection in order to allow the cells to cross the BBB.

In various embodiments, the present cells, administered peripherally, cross the blood brain barrier and cause substantial release of therapeutic antibodies or antibody fragments. In embodiments, this effect is obtained without the need of using blood-brain barrier disrupting agents. Hyperthermia, mannitol, bradykinin and NS1619 are illustrative blood-brain barrier disrupting agents.

Accordingly, in a particular embodiment, the invention relates to use or method as described herein, comprising peripheral administration of the present cells, wherein no blood-brain barrier disrupting agent is implemented. Furthermore, the invention relates to a use or method as described herein, wherein no mannitol is injected to the subject.

Alternatively, in embodiments, the invention relates to a use or method as described herein, further comprising disruption of the blood-brain barrier with a blood-brain barrier disrupting agent or process, to further increase the crossing of the cells or therapeutic antibodies implemented in the present invention through the blood-brain barrier.

Alzheimer's Disease

Proteinaceous deposits (called amyloid) appear as neurofibrillary tangles, amyloid plaque cores, and amyloid of the congophilic angiopathy in Alzheimer's disease. Beta-amyloid (Aβ) peptide naturally occurs as a series of peptides which are 39 to 43 amino acids long, with the shorter, more soluble forms being present in cerebrovascular deposits and the longer forms being found primarily in senile plaques. F. Prelli, et al. Journal of Neurochemistry, 51:648-651 (1988). Indeed, beta-amyloid is a small piece of a larger protein called "amyloid precursor protein" (APP). When APP is activated to do its normal job, it is cut by other proteins into separate, smaller sections that stay inside and outside of cells. In some circumstances, APP is cut in such a way to produce beta-amyloid.

In turn, beta-amyloid can accumulate in stages into microscopic amyloid plaques that are considered a hallmark of a brain affected by Alzheimer's disease. The pieces first form small oligomer clusters, then fibril chains of clusters, followed by beta-sheet mats of fibrils. The final stage is plaques, which contain clumps of beta-sheets and other substances. Without wishing to be bound by any one theory, it is believed that these stages of beta-amyloid aggregation disrupt cell-to-cell communication and activate immune cells, which trigger inflammation and ultimately destroy the brain cells.

The primary structure of the 42 amino acid residue long, beta-amyloid peptide is SEQ ID NO: 29:

```
                                    (SEQ ID NO: 29)
DAEFRHDSGYEVHHQKLVFFAEDVGSNKGAIIGLMVGGVVIA.
```

In various embodiments, the present agents of conformation-sensitive antibodies target beta-amyloid, optionally in the context of a protein aggregate. In various embodiments, the present antibodies are directed to/or raised against a peptide comprising part of wild type or mutant beta-amyloid, including stretches of amino acids of SEQ ID NO: 29. In further embodiments, the antibody or antibody fragment is directed to/or raised against a peptide comprising amino acids 1-16 of SEQ ID NO: 29.

In various embodiments, the present agents of conformation-sensitive antibodies target the following peptide sequence of beta-amyloid (Aβ) peptide, including but not limited to SEQ ID NO: 30.

SEQ ID NO: 30 (1-16):
DAEFRHDSGYEVHHQK

In various embodiments, the present antibodies are directed to/or raised against a peptide comprising part or all of the amino acids of SEQ ID NO: 30. In some embodiments, the present antibodies are directed to/or raised against an epitope present in SEQ ID NO: 30.

In some embodiments, the present invention provides for an antibody, or Fab, directed against wild type or mutant beta-amyloid (Aβ) peptide, or peptide fragment. In various embodiments, the antibody, or Fab, comprises a heavy chain and/or a light chain, which are identified based on the sequence of the constant domain (e.g., mouse IgG1, rat kappa, etc.). The antibody, or Fab, can comprise, for each chain, a variable domain, a signal peptide, and/or a constant domain. In some embodiments, the antibody, or Fab, of the present invention comprises a variable heavy domain that comprises a peptide having an amino acid sequence at least 65%, at least 70%, at least 75%, at least 80%, at least 85%, at least 90%, at least 95%, at least 96%, at least 97%, at least 98%, or at least 99% identical to SEQ ID NO: 94:

```
                                    (SEQ ID NO: 94)
QVQLQQSGAELVKPGASVKISCKASGYAFSNYWMNWVKQRPGKGLEWIGQI

YPGDGDTNYNGKFKGKATLTADKSSSTAYMQLSSLTSEDSAVYFCARGDY

WGQGTTLTVSS.
```

In some embodiments, the antibody, or Fab, of the present invention comprises a variable light domain that comprises a peptide having an amino acid sequence at least 65%, at least 70%, at least 75%, at least 80%, at least 85%, at least 90%, at least 95%, at least 96%, at least 97%, at least 98%, or at least 99% identical to SEQ ID NO: 31:

```
                                    (SEQ ID NO: 31)
DIVMTQSPSSLAMSVGQKVTMSCKSSQSLLNSSNQKNYLAWYQQKPGQSPK

LLVYFASTRESGVPDRFIGSGSGTDFTLTISSVQAEDLADYFCQQHYNTPL

TFGAGTKLELK.
```

In various embodiments, the antibody, or Fab, of the present invention comprises a constant domain that comprises a peptide having an amino acid sequence at least 65%, at least 70%, at least 75%, at least 80%, at least 85%, at least 90%, at least 95%, at least 96%, at least 97%, at least 98%, or at least 99% identical to SEQ ID NO: 32 and/or SEQ ID NO: 33:

```
(Heavy Chain)
                                         SEQ ID NO: 32
ESQSFPNVFPLVSCESPLSDKNLVAMGCLARDFLPSTISFTWNYQNNTEV

IQGIRTFPTLRTGGKYLATSQVLLSPKSILEGSDEYLVCKIHYGGKNKDL

HVPIPAVAEMNPNVNVFVPPRDGFSGPAPRKSKLICEATNFTPKPITVSW

LKDGKLVESGFTTDPVTIENKGSTPQTYKVISTLTISEIDWLNLNVYTCR

VDHRGLTFLKNVSSTCAASPSTDILTFTIPPSFADIFLSKSANLTCLVSN

LATYETLNISWASQSGEPLETKIKIMESHPNGTFSAKGVASVCVEDWNNR

KEFVCTVTHRDLPSPQKKFISKPNEVHKHPPAVYLLPPAREQLNLRESAT

VTCLVKGFSPADISVQWLQRGQLLPQEKYVTSAPMPEPGAPGFYFTHSIL

TVTEEEWNSGETYTCVVGHEALPHLVTERTVDKSTGKPTLYNVSLIMSDT

GGTCY;
and/or (Light Chain)
                                         SEQ ID NO: 33
RADAAPTVSIFPPSSEQLTSGGASVVCFLNNFYPKDINVKWKIDGSERQN

GVLNSWTDQDSKDSTYSMSSTLTLTKDEYERHNSYTCEATHKTSTSPIVK

SFNRNEC.
```

In some embodiments, the antibody, or Fab, of the present invention comprises a signal peptide comprising a peptide having amino acid sequence identity to SEQ ID NO: 34 and/or SEQ ID NO: 35: MEWPLIFLFLLSGTAGVQS (SEQ ID NO: 34), and/or MESQTQVLMFLLLWVSGACA (SEQ ID NO: 35). In various embodiments, the signal peptide comprises an amino acid sequence having one or more amino acid mutations. In various embodiments, the signal peptide comprises an amino acid sequence having one, or two, or three, or four, or five, or six, or seven, or eight, or nine, or ten amino acid mutations. In some embodiments, the one or more amino acid mutations may be independently selected from substitutions, insertions, deletions, and truncations. In some embodiments, the amino acid mutations are amino acid substitutions, and may include conservative and/or non-conservative substitutions.

In further embodiments, the present invention contemplates an antibody, or Fab, comprising one or more complementarity-determining regions (CDR) for the variable heavy and/or variable light domains. In some embodiments, the CDRs are presented in Kabat definition. In various embodiments, the CDR comprises an amino acid sequence having one or more amino acid mutations. In various embodiments, the CDR comprises an amino acid sequence having one, or two, or three, or four, or five, or six, or seven, or eight, or nine, or ten amino acid mutations.

In some embodiments, the one or more amino acid mutations may be independently selected from substitutions, insertions, deletions, and truncations. In some embodiments, the amino acid mutations are amino acid substitutions, and may include conservative and/or non-conservative substitutions.

In further embodiments, the variable heavy domain comprises a CDR1 having an amino acid sequence of SEQ ID NO: 36. In further embodiments, the variable heavy domain comprises a CDR2 having an amino acid sequence of SEQ ID NO: 37. In still further embodiments, the variable heavy domain comprises a CDR3 having an amino acid sequence of SEQ ID NO: 38. In some embodiments, the antibody, or Fab, of the present invention comprises CDR1: NYWMN (SEQ ID NO: 36); CDR2: QIYPGDGDTNYNGKFKG (SEQ ID NO: 37); and/or CDR3: GDY (SEQ ID NO: 38).

In some embodiments, the variable light domain comprises a CDR1 having an amino acid sequence of SEQ ID NO: 39. In further embodiments, the variable heavy domain comprises a CDR2 having an amino acid sequence of SEQ ID NO: 40. In still further embodiments, the variable heavy domain comprises a CDR3 having an amino acid sequence of SEQ ID NO: 41. In some embodiments, the antibody, or Fab, of the present invention comprises CDR1: KSSQSLLNSSNQKNYLA (SEQ ID NO: 39); CDR2: FASTRES (SEQ ID NO: 40); and/or CDR3: QQHYNTPLT (SEQ ID NO: 41).

In some embodiments, the antibody, or Fab, of the present invention comprises a variable heavy domain that comprises a peptide having an amino acid sequence at least 65%, at least 70%, at least 75%, at least 80%, at least 85%, at least 90%, at least 95%, at least 96%, at least 97%, at least 98%, or at least 99% identical to SEQ ID NO: 42:

(SEQ ID NO: 42)
QVQLQQSGAELARPGASVKLSCKASGYTFTSYGIRWVKQRTGQGLEWIGEI

XPRSGNTYYNEKFKGKATVTADKSSSTAYMELRSLTSEDSAVYFCARSIYY

GRPYYFDYWGQGTTLTVSS.

In some embodiments, the antibody, or Fab, of the present invention comprises a variable light domain that comprises a peptide having an amino acid sequence at least 65%, at least 70%, at least 75%, at least 80%, at least 85%, at least 90%, at least 95%, at least 96%, at least 97%, at least 98%, or at least 99% identical to SEQ ID NO: 43:

(SEQ ID NO: 43)
DIVMTQSQLFMSTSDRVSVTCKASQNVAVGTNVAWYQQKPGQSPKALIYSA

SYRYSGVPDRFTGSGSGTDFTLTISNVQSEDLAEYFCQQYNSYPLTFGAGT

KLELK.

In further embodiments, the variable heavy domain comprises a CDR1 having an amino acid sequence of GYTFTSYGIR (SEQ ID NO: 44). In further embodiments, the variable heavy domain comprises a CDR2 having an amino acid sequence of EIXPRSGNTYYNEKFK (SEQ ID NO: 45). In still further embodiments, the variable heavy domain comprises a CDR3 having an amino acid sequence of SIYYGRPYYFDY (SEQ ID NO: 46).

In some embodiments, the variable light domain comprises a CDR1 having an amino acid sequence of KASQNVATNVA (SEQ ID NO: 47). In further embodiments, the variable light domain comprises a CDR2 having an amino acid sequence of SASYRYS (SEQ ID NO: 48). In still further embodiments, the variable light domain comprises a CDR3 having an amino acid sequence of QQYNSYPLT (SEQ ID NO: 49).

In some embodiments, the antibody, or Fab, of the present invention comprises a variable heavy domain that comprises a peptide having an amino acid sequence at least 65%, at least 70%, at least 75%, at least 80%, at least 85%, at least 90%, at least 95%, at least 96%, at least 97%, at least 98%, or at least 99% identical to SEQ ID NO: 50:

(SEQ ID NO: 50)
QVQLQQSDAELVKPGASVKISCKVSGYTFTDHTIHWMKQRPEQGLEWIGYI

YPRDGSTKYNEKFKGKATLTADKSSSTAYMQLNSLTSEDSAVYFCARDYGY

AFDYWGQGTTLTVSS.

In some embodiments, the antibody, or Fab, of the present invention comprises a variable heavy domain that comprises a peptide having an amino acid sequence at least 65%, at least 70%, at least 75%, at least 80%, at least 85%, at least 90%, at least 95%, at least 96%, at least 97%, at least 98%, or at least 99% identical to SEQ ID NO: 51:

(SEQ ID NO: 51)
QVQLQQSDAELVKPGASVKISCKVSGYTFTDHTIHWMKQRPEQGLEWIGYI

YPRDGSTKYNEKFKGKATLTADKSSSTAYMQLNSLTSEDSAVYFCARDYGY

AFDYWGQGTTLTVSS.

In some embodiments, the antibody, or Fab, of the present invention comprises a variable light domain that comprises a peptide having an amino acid sequence at least 65%, at least 70%, at least 75%, at least 80%, at least 85%, at least 90%, at least 95%, at least 96%, at least 97%, at least 98%, or at least 99% identical to SEQ ID NO: 52:

(SEQ ID NO: 52)
QAVVTQESALTTSPGGTVILTCRSSTGAVTTSNYANWVQEKPDHLFTGLIG

GTSNRAPGVPVRFSGSLIGDKAALTITGAQTEDDAMYFCALWYSTHYVFGG

GTKVTVL.

In some embodiments, the antibody, or Fab, of the present invention comprises a variable light domain that comprises a peptide having an amino acid sequence at least 65%, at least 70%, at least 75%, at least 80%, at least 85%, at least 90%, at least 95%, at least 96%, at least 97%, at least 98%, or at least 99% identical to SEQ ID NO: 53:

(SEQ ID NO: 53)
QAVVTQESALTTSPGGTVILTCRSSTGAVTTSNYANWVQEKPDHLFTGLI

GGTSNRAPGVPVRFSGSLIGDKAALTITGAQTEDDAMYFCALWYSTHYVF

GGGTKVTVL.

In some embodiments, the variable heavy domain comprises a CDR1 having an amino acid sequence of GYTFTDHTIH (SEQ ID NO: 54). In further embodiments, the variable heavy domain comprises a CDR2 having an amino acid sequence of YIYPRDGSTKYNEKFK (SEQ ID NO: 55). In still further embodiments, the variable heavy domain comprises a CDR3 having an amino acid sequence of DYGYAFDY (SEQ ID NO: 56).

In further embodiments, the variable light domain comprises a CDR1 having an amino acid sequence of RSSTGAVTTSNYAN (SEQ ID NO: 57). In further embodiments, the variable light domain comprises a CDR2 having an amino acid sequence of GTSNRAP (SEQ ID NO: 58). In still further embodiments, the variable light domain comprises a CDR3 having an amino acid sequence of ALWYSTHYV (SEQ ID NO: 59).

In some embodiments, the antibody, or Fab, of the present invention comprises a variable heavy domain that comprises a peptide having an amino acid sequence at least 65%, at least 70%, at least 75%, at least 80%, at least 85%, at least 90%, at least 95%, at least 96%, at least 97%, at least 98%, or at least 99% identical to SEQ ID NO: 60:

(SEQ ID NO: 60)
QVQLQQSGAELARPGASVKLSCKASGYTFTSYGIRWVKQRTGQGLEWIGE

IXPRSGNTYYNEKFKGKATVTADKSSSTAYMELRSLTSEDSAVYFCARSI

YYGRPYYFDYWGQGTTLTVSS.

In some embodiments, the antibody, or Fab, of the present invention comprises a variable light domain that comprises a peptide having an amino acid sequence at least 65%, at least 70%, at least 75%, at least 80%, at least 85%, at least 90%, at least 95%, at least 96%, at least 97%, at least 98%, or at least 99% identical to SEQ ID NO: 61:

(SEQ ID NO: 61)
DIVMTQSQLFMSTSVGDRVSVTCKASQNVATNVAWYQQKPGQSPKALIYS

ASYRYSGVPDRFTGSGSGTDFTLTISNVQSEDLAEYFCQQYNSYPLTFGA

GTKLELK.

In some embodiments, the antibody, or Fab, of the present invention comprises a variable heavy domain that comprises a peptide having an amino acid sequence at least 65%, at least 70%, at least 75%, at least 80%, at least 85%, at least 90%, at least 95%, at least 96%, at least 97%, at least 98%, or at least 99% identical to SEQ ID NO: 62:

(SEQ ID NO: 62)
QVQLQQSDAELVKPGASVKISCKVSGYTFTDHTIHWMKQRPEQGLEWIGY

IYPRDGSTKYNEKFKGKATLTADKSSSTAYMQLNSLTSEDSAVYFCARDY

GYAFDYWGQGTTTVSS.

In some embodiments, the antibody, or Fab, of the present invention comprises a variable light domain that comprises a peptide having an amino acid sequence at least 65%, at least 70%, at least 75%, at least 80%, at least 85%, at least 90%, at least 95%, at least 96%, at least 97%, at least 98%, or at least 99% identical to SEQ ID NO: 63:

(SEQ ID NO: 63)
QAVVTQESALTTSPGGTVILTCRSSTGAVTTSNYANWVQEKPDHLFTGLI

GGTSNRAPGVPVRFSGSLIGDKAALTITGAQTEDDAMYFCALWYSTHYVF

GGGTKVTVL.

In some embodiments, the antibody, or Fab, of the present invention comprises a variable heavy domain that comprises a peptide having an amino acid sequence at least 65%, at least 70%, at least 75%, at least 80%, at least 85%, at least 90%, at least 95%, at least 96%, at least 97%, at least 98%, or at least 99% identical to SEQ ID NO: 64:

(SEQ ID NO: 64)
QVQLQQSDAELVKPGASVKISCKVSGYTFTDHTIHWMKQRPEQGLEWIGY

IYPRDGSTKYNEKFKGKATLTADKSSSTAYMQLNSLTSEDSAVYFCARDY

GYAFDYWGQGTTLTVSS

In some embodiments, the antibody, or Fab, of the present invention comprises a variable light domain that comprises a peptide having an amino acid sequence at least 65%, at least 70%, at least 75%, at least 80%, at least 85%, at least 90%, at least 95%, at least 96%, at least 97%, at least 98%, or at least 99% identical to SEQ ID NO: 65:

(SEQ ID NO: 65)
QAVVTQESALTTSPGGTVILTCRSSTGAVTTSNYANWVQEKPDHLFTGLI

GGTSNRAPGVPVRFSGSLIGDKAALTITGAQTEDDAMYFCALWYSTHYVF

GGGTKVTVL

In some embodiments, the antibody, or Fab, of the present invention comprises a variable heavy domain that comprises a peptide having an amino acid sequence at least 65%, at least 70%, at least 75%, at least 80%, at least 85%, at least 90%, at least 95%, at least 96%, at least 97%, at least 98%, or at least 99% identical to SEQ ID NO: 66:

(SEQ ID NO: 66)
EVQLVESGGGLVQPGGSLRLSCAASGFTFSSYGMSWVRQAPGKGLELVAS

INSNGGSTYYPDSVKGRFTISRDNAKNSLYLQMNSLRAEDTAVYYCASGD

YWGQGTTVTVSS

In some embodiments, the antibody, or Fab, of the present invention comprises a variable light domain that comprises a peptide having an amino acid sequence at least 65%, at least 70%, at least 75%, at least 80%, at least 85%, at least 90%, at least 95%, at least 96%, at least 97%, at least 98%, or at least 99% identical to SEQ ID NO: 67:

(SEQ ID NO: 67)
DIVMTQSPLSLPVTPGEPASISCRSSQSLVYSNGDTYLHWYLQKPGQSPQ

LLIYKVSNRFSGVPDRFSGSGSGTDFTLKISRVEAEDVGVYYCSQSTHVP

WTFGQGTKVEIK.

In some embodiments, the variable heavy domain comprises a CDR1 having an amino acid sequence of GFTFSSYGMS (SEQ ID NO: 68). In further embodiments, the variable heavy domain comprises a CDR2 having an amino acid sequence of SINSNGGSTYYPDSVK (SEQ ID NO: 69). In still further embodiments, the variable heavy domain comprises a CDR3 having an amino acid sequence of GDY (SEQ ID NO: 70).

In further embodiments, the variable light domain comprises a CDR1 having an amino acid sequence of RSSQSLVYSNGDTYLH (SEQ ID NO: 71). In further embodiments, the variable light domain comprises a CDR2 having an amino acid sequence of KVSNRFS (SEQ ID NO: 72). In still further embodiments, the variable light domain comprises a CDR3 having an amino acid sequence of SQSTHVPWT (SEQ ID NO: 73). In still further embodiments, the variable light domain comprises a CDR having an amino acid sequence of RVSNRFS (SEQ ID NO: 74) or KVSSRFS (SEQ ID NO: 75).

Parkinson's Disease

Lewy bodies are the hallmark of Parkinson's disease which is mainly composed of alpha-synuclein. Alpha-synuclein plays a role in the development of rare familial and more common sporadic cases of Parkinson's disease. In familial Parkinson's disease, the expression levels of alpha-synuclein gene is increased or an abnormal form of the protein is found which are toxic to brain cells and result in neuron dysfunction. Alpha-synuclein is the primary structural component of Lewy bodies, suggesting that protein aggregation plays a role in sporadic Parkinson's disease. To treat Parkinson's disease, therapies that reduce alpha-synuclein gene expression or block its aggregation should be developed.

Alpha-synuclein is abundant in the human brain at the neurons tips in specialized structures called presynaptic terminals. Presynaptic terminals release chemical messengers, neurotransmitters, from synaptic vesicles. The release of neurotransmitters relays signals between neurons and is critical for normal brain function. So, alpha-Synuclein is a presynaptic neuronal protein that is thought that its abnormal soluble oligomeric conformations, L a protofibrils, are the toxic species that mediate disruption of cellular homeostasis and neuronal death, through effects on various intracellular targets, including synaptic function. Furthermore, secreted Alpha-synuclein may exert deleterious effects on neighboring cells, including seeding of aggregation, thus possibly contributing to disease propagation.

The human alpha-synuclein protein is made of 140 amino acids and is encoded by the SNCA gene. The amino acid sequence of human alpha-synuclein is shown by SEQ ID NO.: 76.

```
                                            SEQ ID NO: 76
SNCAMDVFMKGLSKAKEGVVAAAEKTKQGVAEAAGKTKEGVLYVGSKTKE

GVVHGVATVAEKTKEQVTNVGGAVVTGVTAVAQKTVEGAGSIAAATGFVK

KDQLGKEGYQDYEPEA
```

In various embodiments, the present antibodies are directed to/or raised against a peptide comprising part of wild type or mutant SCNA, including stretches of amino acids of SEQ ID NO: 76.

In various embodiments, the present agents of conformation-sensitive antibodies target mutated alpha-synuclein, optionally in the context of a protein aggregate. In various embodiments, the present agents of conformation-sensitive antibodies target the following peptide sequences of alpha-synuclein, including but not limited to SEQ ID NO.: 77.

```
                                    SEQ ID NO: 77 (60-95)
          KEQVTNVGGAVVTGVTAVAQKTVEGAGSIAAATGFV
```

In various embodiments, the present antibodies are directed to/or raised against a peptide comprising part or all of amino acids of SEQ ID NO: 77.

Tau proteins (Tubulin-binding protein) are proteins that function in stabilizing microtubules. Tau proteins are abundant in nerve cells and when become defective or fail to stabilize microtubules, pathologies of the nervous system can develop such as Alzheimer's disease or Parkinson's disease. Tau proteins are mainly active in the distal portions of axons where they stabilize microtubules as well as providing flexibility. Together with tubulin, Tau proteins stabilize microtubules and aid the assembly of tubulin in the microtubules. Hyper-phosphorylation of tau proteins can cause the helical and straight filaments to tangle (referred to as neurofibrillary tangles) which contribute to the pathology of Alzheimer's disease or Parkinson's disease.

Human Tau is encoded on chromosome 17q21 and the protein occurs mainly in the axons of the CNS and consists largely of six isoforms generated by alternative splicing (27). In various embodiments, any mutations of different Tau isoforms described in Cold Spring Harbor Perspectives in Medicine 2012; 2:a006247, the entire contents of which are hereby incorporated by reference, may be targeted by the present agents of conformation-sensitive antibodies.

The human Tau protein is made of 863 amino acids and is encoded by the MAPT gene. The amino acid sequence of human Tau protein is shown by SEQ ID NO.: 78.

```
                                                  SEQ ID NO: 78
MAEPRQEFEVMEDHAGTYGLGDRKDQGGYTMHQDQEGDTDAGLKESPLQT

PTEDGSEEPGSETSDAKSTPTAEDVTAPLVDEGAPGKQAAAQPHTEIPEG

TTAEEAGIGDTPSLEDEAAGHVTQEPESGKVVQEGFLREPGPPGLSHQLM

SGMPGAPLLPEGPREATRQPSGTGPEDTEGGRHAPELLKHQLLGDLHQEG

PPLKGAGGKERPGSKEEVDEDRDVDESSPQDSPPSKASPAQDGRPPQTAA

REATSIPGFPAEGAIPLPVDFLSKVSTEIPASEPDGPSVGRAKGQDAPLE

FTFHVEITPNVQKEQAHSEEHLGRAAFPGAPGEGPEARGPSLGEDTKEAD

LPEPSEKQPAAAPRGKPVSRVPQLKARMVSKSKDGTGSDDKKAKTSTRSS

AKTLKNRPCLSPKHPTPGSSDPLIQPSSPAVCPEPPSSPKYVSSVTSRTG

SSGAKEMKLKGADGKTKIATPRGAAPPGQKGQANATRIPAKTPPAPKTPP

SSGEPPKSGDRSGYSSPGSPGTPGSRSRTPSLPTPPTREPKKVAVVRTPP

KSPSSAKSRLQTAPVPMPDLKNVKSKIGSTENLKHQPGGGKVQIINKKLD

LSNVQSKCGSKDNIKHVPGGGSVQIVYKPVDLSKVTSKCGSLGNIHHKPG

GGQVEVKSEKLDFKDRVQSKIGSLDNITHVPGGGNKKIETHKLTFRENAK

AKTDHGAEIVYKSPVVSGDTSPRHLSNVSSTGSIDMVDSPQLATLADEVS

ASLAKQGL
```

In various embodiments, the present agents of conformation-sensitive antibodies target mutated Tau protein, optionally in the context of a protein aggregate. In various embodiments, the present antibodies are directed to/or raised against a peptide comprising part of wild type or mutant tau, including stretches of amino acids of SEQ ID NO: 78.

In various embodiments, the present agents of conformation-sensitive antibodies target the following peptide sequences of Tau protein, including but not limited to SEQ ID NOs: 79-80.

```
                                    SEQ ID NO: 79 (275-305)
              VSTEIPASEPDGPSVGRAKGQDAPLEFTFHV

SEQ ID NO: 80 (306-336)
              EITPNVQKEQAHSEEHLGRAAFPGAPGEGPE
```

In various embodiments, the present antibodies are directed to/or raised against a peptide comprising part or all of amino acids of SEQ ID NO: 79 or 80.

Type II Diabetes

There are two major types of diabetes in man, both of which result in a disturbance of the normally tight control of glucose homeostasis affected by insulin secreted from pancreatic islets. Insulin-dependent (Type 1) diabetes is an autoimmune disease resulting in destruction of insulin-secreting cells and the requirement for insulin replacement therapy. Type 2 diabetes is a multifactorial disease with genetic and environmental components; it is characterized by a progressive decrease in the regulation of blood glucose levels. Amyloid is formed only in type 2 diabetic subjects since destruction of the islet β-cells in type 1 diabetes removes the source of IAPP.

Type 2 diabetes is associated with a decrease in insulin secretion and increasing hyperglycemia as a result of β-cell failure. A correlation between β-cell failure in type 2 diabetes and the formation of pancreatic islet amyloid deposits is established. IAPP (amylin), the major component of islet amyloid, is co-secreted with insulin from β-cell and aggregates to form amyloid fibrils that are toxic to 8-cells.

Conversion from soluble monomer IAPP to 8-sheet fibrils involves changes in the molecular conformation, cellular biochemistry and diabetes-related factors. In humans, the level of production of IAPP is important but is not the main factor in islet amyloidosis. Animal models of islet amyloidosis suggest that diabetes is induced by the deposits whereas in man, fibril formation appears to result from diabetes-associated islet dysfunction. Islet secretory failure results from progressive amyloidosis which provides a target for new therapeutic interventions.

Human IAPP protein is expressed from IAPP gene and is processed from an 89-residue coding sequence (SEQ ID NO.: 81). Proislet amyloid polypeptide (proIAPP, proamylin, proislet protein) is produced in the pancreatic beta cells (β-cells) as a 67 amino acid, 7404 Dalton pro-peptide and undergoes post-translational modifications including protease cleavage to produce amylin.

```
                                           SEQ ID NO.: 81
MGILKLQVFLIVLSVALNHLKATPIESHQVEKRKCNTATCATQRLANFLV

HSSNNFGAILSSTNVGSNTYGKRNAVEVLKREPLNYLPL
```

In various embodiments, the present antibodies are directed to/or raised against a peptide comprising part of wild type or mutant IAPP, including stretches of amino acids of SEQ ID NO: 81.

In various embodiments, the present agents of conformation-sensitive antibodies target mutated IAPP protein, optionally in the context of a protein aggregate. In various embodiments, the present agents of conformation-sensitive antibodies target the following peptide sequences of IAPP protein, including but not limited to SEQ ID NO.: 82.

```
                                    SEQ ID NO.: 82 (34-70)
        KCNTATCATQRLANFLVHSSNNFGAILSSTNVGSNTY
```

In various embodiments, the present antibodies are directed to/or raised against a peptide comprising part or all of amino acids of SEQ ID NO: 82.

In some embodiments, the present invention relates to an anti-amyloid therapeutic vaccine and solubilizing monoclonal antibody. The present invention also includes antigenic peptide fragments modified so as to increase their antigenicity. For example, antigenic moieties and adjuvants may be attached to or admixed with the peptide. Examples of antigenic moieties and adjuvants include, but are not limited to, lipophilic muramyl dipeptide derivatives, nonionic block polymers, aluminum hydroxide or aluminum phosphate adjuvant, and mixtures thereof. It is also to be understood that the supramolecular antigenic construct compositions of the present invention can further comprise additional adjuvants including, but not limited to, keyhole limpet hemocyanin (KLH), bovine serum albumin (BSA) and other adjuvants such as, for example, lipid A, alum, calcium phosphate, interleukin 1, and/or microcapsules of polysaccharides and proteins, but particularly a detoxified lipid A, such as monophosphoryl or diphosphoryl lipid A, or alum, further preservatives, diluents, emulsifiers, stabilizers, and other components that are known and used in vaccines of the prior art. Moreover, any adjuvant system known in the art can be used in the composition of the present invention. Such adjuvants include, but are not limited to, Freund's incomplete adjuvant, Freund's complete adjuvant, polydispersed β-(1,4) linked acetylated mannan ("Acemannan"), TITERMAX® (polyoxyethylene-polyoxypropylene copolymer adjuvants from CytRx Corporation), modified lipid adjuvants from Chiron Corporation, saponin derivative adjuvants from Cambridge Biotech, killed *Bordetella pertussis*, the lipopolysaccharide (LPS) of gram-negative bacteria, large polymeric anions such as dextran sulfate, and inorganic gels such as alum, aluminum hydroxide, or aluminum phosphate.

In various embodiments, the agents of the invention, e.g. transfected cells comprising conformation-sensitive antibodies, are capable of substantially solubilizing aggregates that are linked to disease, e.g. ALS. In some embodiments, the solubilization is in vivo. In some embodiments, the solubilization is in vitro. In various embodiments, the agents cause about 90% solubilization, or about 80% solubilization, or about 70% solubilization, or about 60% solubilization, or about 50% solubilization, or about 40% solubilization, or about 30% solubilization, or about 25% solubilization.

Further, in some embodiments, the agents of the invention target the toxic form of the aggregate conformation. Since alone the β-sheet conformation of Aβ is cytotoxic, the antigenic construct elicits antibodies displaying a higher affinity for Aβ in that conformation, as compared to the affinity for the alpha-helix or random coil conformation of the amyloid target. Synthetic peptide, immunogens that mimic the conformation of a target epitope of pathological relevance offer the possibility to precisely control the immune response specificity.

In some embodiments of the present invention, the peptide of interest is added to phospholipids to give a peptide/phospholipid ratio of about 1:100. In other aspects, the peptide/phospholipid ratio is about 1:50, about 1:150, about 1:200, about 1:250, or about 1:300.

The term "antibody," as used herein, is intended to refer to immunoglobulin molecules comprised of four polypeptide chains, two heavy (H) chains and two light (L) chains inter-connected by disulfide bonds capable of binding one or more antigens (e.g. bi-specific or multi-specific antibodies). Each heavy chain is comprised of a heavy chain variable region (abbreviated herein as HCVR or $V_H$) and a heavy chain constant region. The heavy chain constant region is comprised of three domains, $CH_1$, $CH_2$ and $CH_3$. Each light chain is comprised of a light chain variable region (abbreviated herein as LCVR or $V_L$) and a light chain constant region. The light chain constant region is comprised of one domain, CL. The $V_H$ and $V_L$ regions can be further subdivided into regions of hypervariability, termed complementarity determining regions (CDRs), interspersed with regions that are more conserved, termed framework regions (FR). Each variable region ($V_H$ or $V_L$) contains 3 CDRs, designated CDR1, CDR2 and CDR3. Each variable region also contains 4 framework sub-regions, designated FR1, FR2, FR3 and FR4. The term antibody includes all types of antibodies, including, for example, IgA, IgG, IgD, IgE and IgM, and their respective subclasses (isotypes), e.g., IgG-1, IgG-2, IgG-3, and IgG-4; IgA-1 and IgA-2. The term "antibody" as used herein is also intended to refer to antibody fragments and antigen-binding fragments.

In certain embodiments, the agent is an antibody. The antibody may be polyclonal or monoclonal; intact or truncated (e.g., F(ab')$_2$, Fab, Fv); bispecific or multispecific; xenogeneic, allogeneic, syngeneic, or modified forms thereof (e.g., a chimeric antibody or a humanized antibody). In an embodiment, the agent is a monoclonal antibody. The monoclonal antibody may be a non-human mammal-derived monoclonal antibody, a recombinant chimeric monoclonal antibody, a recombinant humanized monoclonal antibody, or a human monoclonal antibody. In certain embodiments, the antibody further comprises an Fc region of an immunoglobulin (e.g. IgA, IgG, IgE, IgD or IgM) which may interact with Fc receptors and activate an immune response.

A variety of suitable antibody formats are known in the art, such as, bispecific IgG-like formats (e.g., chimeric antibodies, humanized antibodies, human antibodies, single chain antibodies, heterodimers of antibody heavy chains and/or light chains, antigen-binding fragments of any of the foregoing (e.g., a Fv fragment (e.g., single chain Fv (scFv), a disulfide bonded Fv), a Fab fragment, a Fab' fragment, a F(ab')$_2$ fragment), a single variable domain (e.g., $V_H$, $V_L$, $V_{HH}$, a dAb, and modified versions of any of the foregoing (e.g., modified by the covalent attachment of polyalkylene glycol (e.g., polyethylene glycol, polypropylene glycol, polybutylene glycol) or other suitable polymer).

Further, smaller immunoglobulin molecules have been constructed and are possible formats for the present agents. A single-chain variable antibody fragment (scFv) comprises an antibody heavy chain variable domain joined via a short peptide to an antibody light chain variable domain (Huston et al., Proc. Natl. Acad. Sci. USA, 1988, 85: 5879-83). Because of the small size of scFv molecules, they exhibit more effective penetration into tissues than whole immunoglobulin. Alternatively, it has been proposed that fusion of a scFv to another molecule, such as a toxin, could take advantage of the specific antigen-binding activity and the small size of a scFv to deliver the toxin to a target tissue. See Chaudary et al., Nature 1989, 339:394; Batra et al., Mol. Cell. Biol. 1991, 11:2200. Conjugation or fusion of toxins to scFvs has thus been offered as an alternative strategy to provide potent, antigen-specific molecules.

Antibodies that are agents of the present invention and/or suitable for practicing the methods described herein can be, for example, monoclonal, polyclonal, bispecific, multispecific, and can include, but are not limited to, human, humanized or chimeric antibodies, comprising single chain antibodies, Fab fragments, F(ab') fragments, fragments produced by a Fab expression library, and/or binding fragments of any of the above. Antibodies also refer to immunoglobulin molecules and immunologically active portions of immunoglobulin molecules, i.e., molecules that contain at least two antigen or target binding sites against at least two targets described herein. The immunoglobulin molecules described herein can be of any type (e.g., IgG, IgE, IgM, IgD, IgA and IgY), class (e.g., IgGl, IgG2, IgG3, IgG4, IgA1 and IgA2) or subclass of immunoglobulin molecule, as is understood by one of skill in the art. In addition, antibodies (e.g. mono-specific, bi-specific, and/or multi-specific) suitable for practicing the methods of the invention described herein can be, for example, Probodies (e.g. capped or masked prodrug antibodies (e.g. Cytomix)); Diabodies; "BITEs"; TandAbs; Flexibodies; Camelid Antibodies; dAbs; Immunobodies; Triomabs; Troybodies; Pepbodies; Vaccibodies; SigA plAntibodies; SMIPs; NARs; IgNARs; XmABs; syn-humanisation antibodies; minibodies; RabMAbs; Fcabs; mAb2 antibodies; Sympress antibodies; UniBodies; DuoBodies; or Vascular Targeting antibodies, as described in US Patent Nos. or Patent Publication Nos. U.S. Pat. No. 7,150,872, US 2007/004909, U.S. Pat. Nos. 5,837, 242, 7,235,641, US 2005/089519, US 2005/079170, U.S. Pat. No. 6,838,254, US 2003/088074, US 2006/280734, US 2004/146505, U.S. Pat. Nos. 5,273,743, 6,551,592, 6,294, 654, US 2004/101905, US 2004/253238, U.S. Pat. No. 6,303,341, US 2008/227958, US 2005/043519, US 2009/ 148438, US 2008/0181890, US 2008/095767, U.S. Pat. No. 5,837,821, WO 2009/117531, US 2005/033031, US 2009/ 298195, US 2009/298195, European Patent Publication EP 2152872, WO 2010/063785, US 2010/105874, U.S. Pat. No. 7,087,411 and/or US 2010/316602. See also, Storz Mabs. 2011 May-June; 3(3): 310-317.

In some embodiments of the invention described herein, the antibody is an antibody fragment. As used herein, the term "antibody fragment" or "antigen-binding fragment" refers to a protein fragment that comprises only a portion of an intact antibody, generally including an antigen binding site of the intact antibody and thus retaining the ability to bind antigen. Examples of antibody fragments include: (i) the Fab fragment, having $V_L$, $C_L$, $V_H$ and $C_H1$ domains; (ii) the Fab' fragment, which is a Fab fragment having one or more cysteine residues at the C-terminus of the $C_H1$ domain; (iii) the Fd fragment having $V_H$ and $C_H1$ domains; (iv) the Fd' fragment having $V_H$ and $C_H1$ domains and one or more cysteine residues at the C-terminus of the CH1 domain; (v) the Fv fragment having the $V_L$ and $V_H$ domains of a single arm of an antibody; (vi) the dAb fragment (Ward et al., Nature 341, 544-546 (1989)) which consists of a $V_H$ domain; (vii) isolated CDR regions; (viii) F(ab')$_2$ fragments, a bivalent fragment including two Fab' fragments linked by a disulphide bridge at the hinge region; (ix) single chain antibody molecules (e.g. single chain Fv; scFv) (Bird et al., Science 242:423-426 (1988); and Huston et al, PNAS (USA) 85:5879-5883 (1988)); (x)"diabodies" with two antigen binding sites, comprising a heavy chain variable domain ($V_H$) connected to a light chain variable domain ($V_L$) in the same polypeptide chain (see, e.g., EP 404,097; WO 93/11161; and Hollinger et al., Proc. Natl. Acad. Sci. USA, 90:6444-6448 (1993)); (xi) "linear antibodies" comprising a pair of tandem Fd segments ($V_H$-$C_h1$-$V_H$-$C_h1$) which, together with complementary light chain polypeptides, form a pair of antigen binding regions (Zapata et al., Protein Eng. 8(10): 1057-1062 (1995); and U.S. Pat. No. 5,641,870).

Repair

The main obstacle to brain delivery of drugs, proteins, oligonucleotides, etc. is constituted by the blood brain barrier. The BBB is practically impermeable. In some embodiments, the present invention can be used to repair the BBB, e.g., in diseases like Alzheimer Disease (AD) and Amyotrophic Lateral Sclerosis (ALS). In other embodiments, the present invention allows for the repair of BBB as well as release of antibodies or antibody fragments by the BBB without damaging the BBB and its functions.

In some embodiments, the present invention relates to the repair of cellular damage in tumors, diabetes II, heart attack, myocardial infarction, stroke, respiratory insufficiency, etc. The cellular vehicles described herein (e.g., EPCs) are therapeutic tools when they are modified by transfection with genes encoding therapeutic proteins, peptides, antibodies, antibody fragments, etc.

In some embodiments, the present invention can be used for repair of angiogenesis in retina, repair of wounds caused by a deficient blood supply (diabetes foot), repair of myocardial tissue after heart attack, vessel normalization in case of pathological tumor angiogenesis, skin diseases, etc.

Vectors

This invention also provides nucleic acid constructs that encode one or more antibodies or portions thereof and, optionally, allow for expression of the antibodies or portions thereof in prokaryotic and eukaryotic cells. For example, this invention provides vectors (e.g., DNA- or RNA-based vectors, including replication vectors or expression vectors) containing nucleotide sequences that encode one or more antibodies directed against (or antibody that specifically binds to) TDP43, beta-amyloid (Aβ), SOD-1, FUS/TLS, α-synuclein, Tau protein, and IAPP. In other embodiments, this invention provides vectors containing nucleotide sequences that encode a portion of one or more antibodies directed against (or antibody that specifically binds to) TDP43, beta-amyloid (Aβ), SOD-1, FUS/TLS, α-synuclein, Tau protein, and IAPP. For example, in one embodiment, one vector encodes a heavy chain or portions thereof and another vector encodes the light chain of the antibody or portions thereof.

In one embodiment, the vector includes the whole antibody or Fab portion of the antibody and is transfected into a host cell to express the whole antibody or the Fab portion of the antibody. In another embodiment, two or more vectors are transfected in to the host cell where a first vector encodes for a first portion of the antibody (e.g., the heavy chain) and a second vector encodes for a second portion of the antibody (e.g., the light chain). Such two or more vectors may be, in one example, cotransfected into the host cell.

Figure 5A:
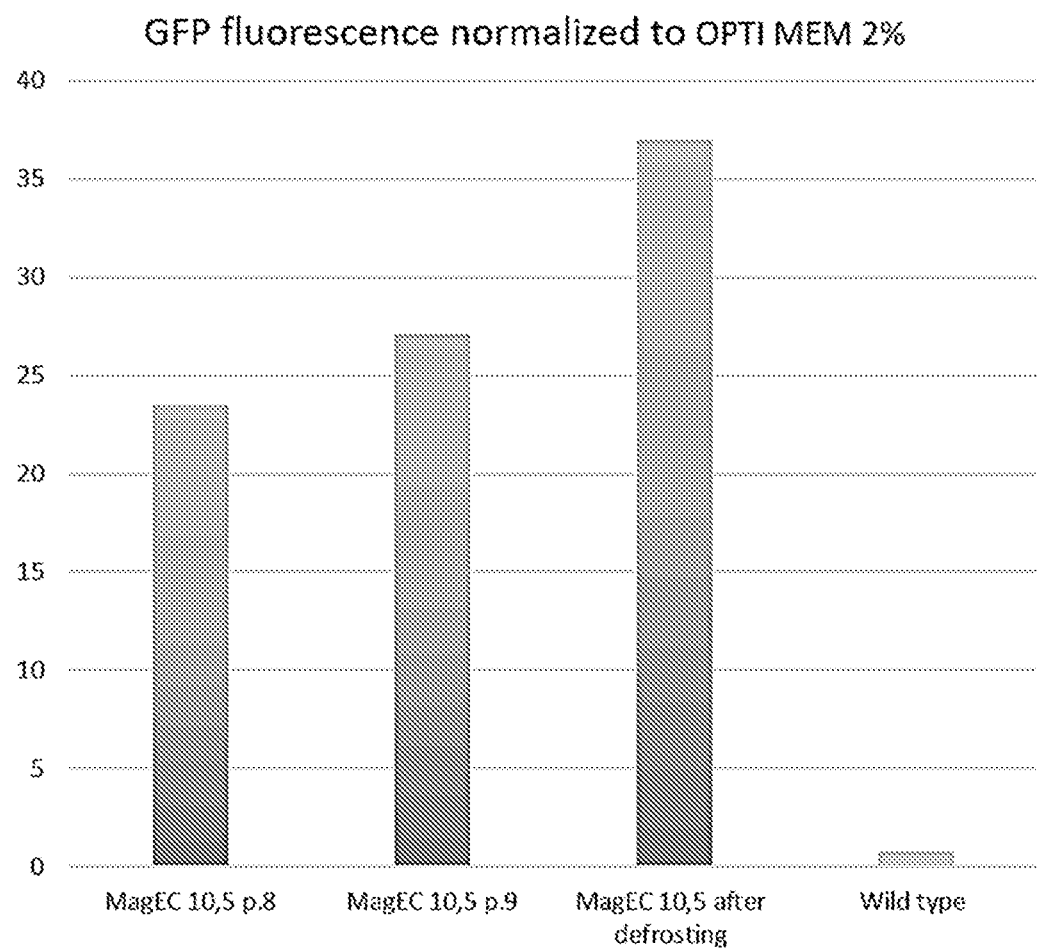
FIG. 5A-C depicts the results of using flow cytometry to measure GFP expression by EPCs transfected with a vector over time, where MAgEC 10.5 p.8 is synonymous with MAgEC 10.5 cells after 8 passages and MAgEC 10.5 p.9 is synonymous with MAgEC 10.5 cells after 9 passages. A wild-type control where cells were not transfected with a vector showed little to no GFP expression.
Figure 5B:
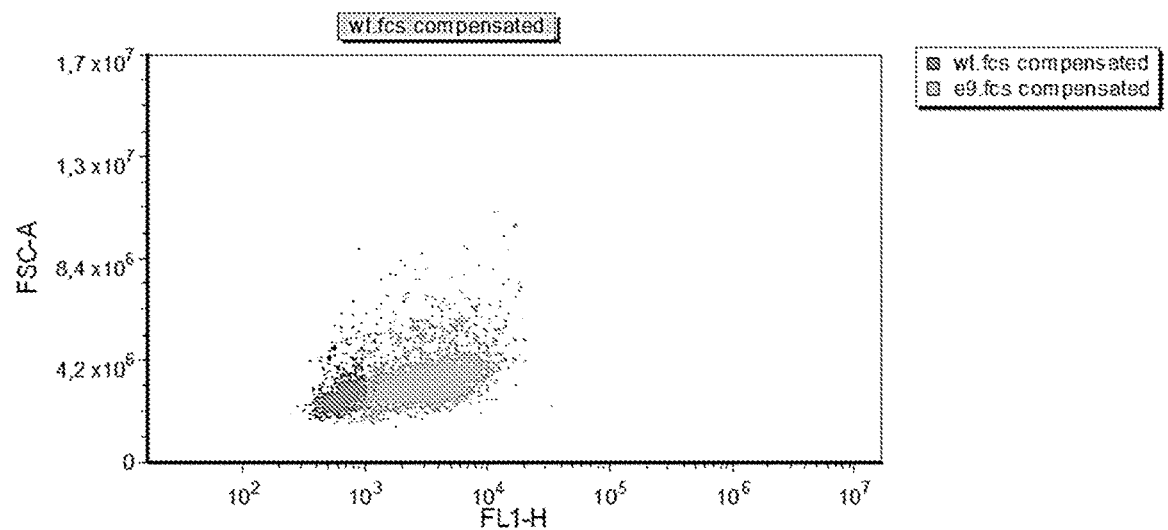
Figure 5C:
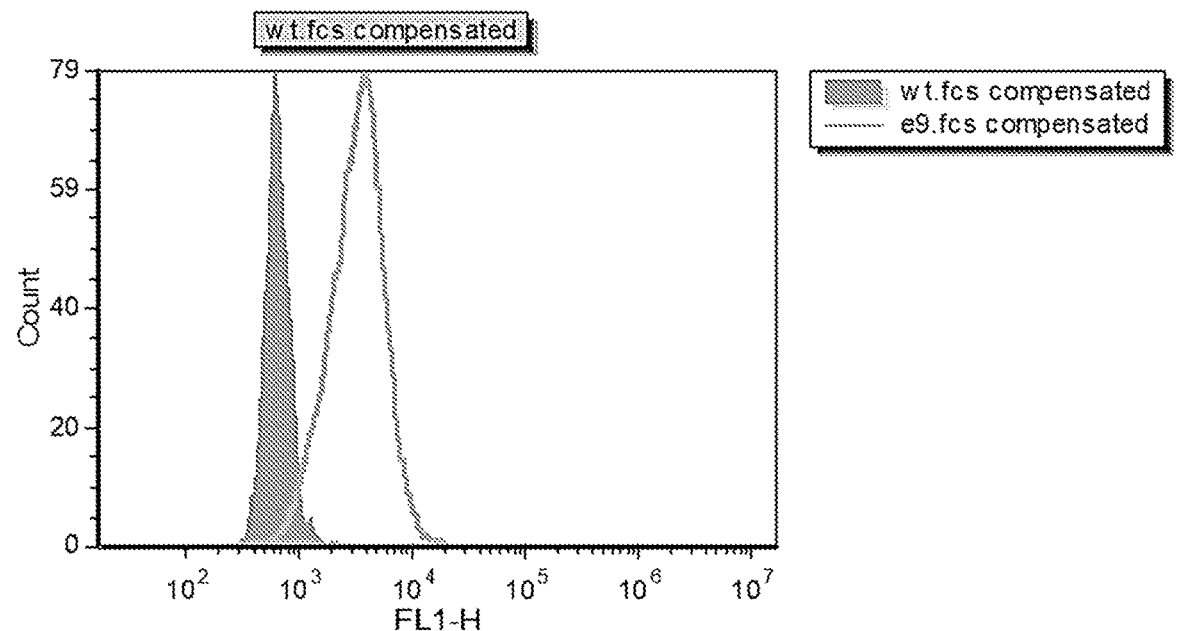
Figure 6:
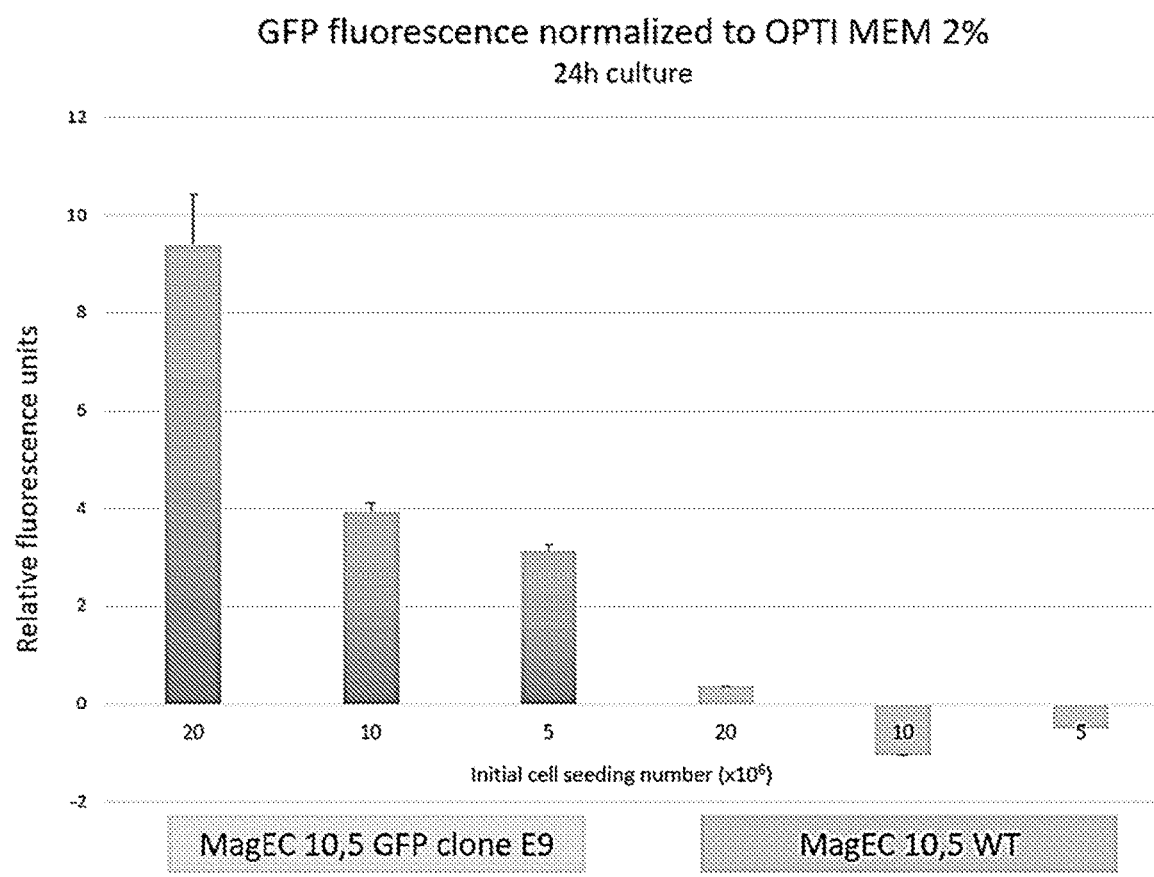
FIG. 6 depicts GFP secretion as a function of cell number.
Figure 7A:
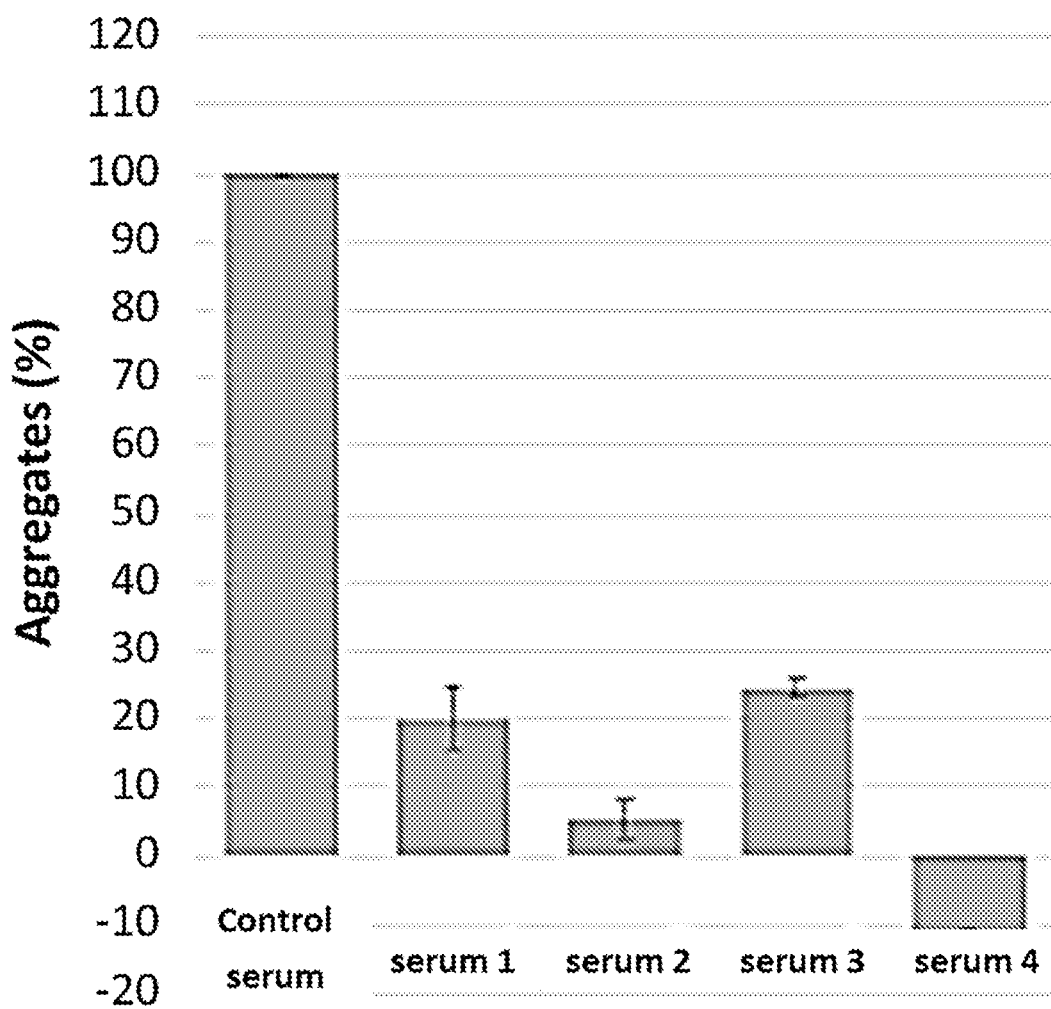
FIG. 7A-B depicts the percentage of aggregated protein in the presence of anti-sera of immunized C57BL/6 mice compared to sera of non-immunized mouse (control) measuring the ThT fluorescence emission.
Figure 7B:
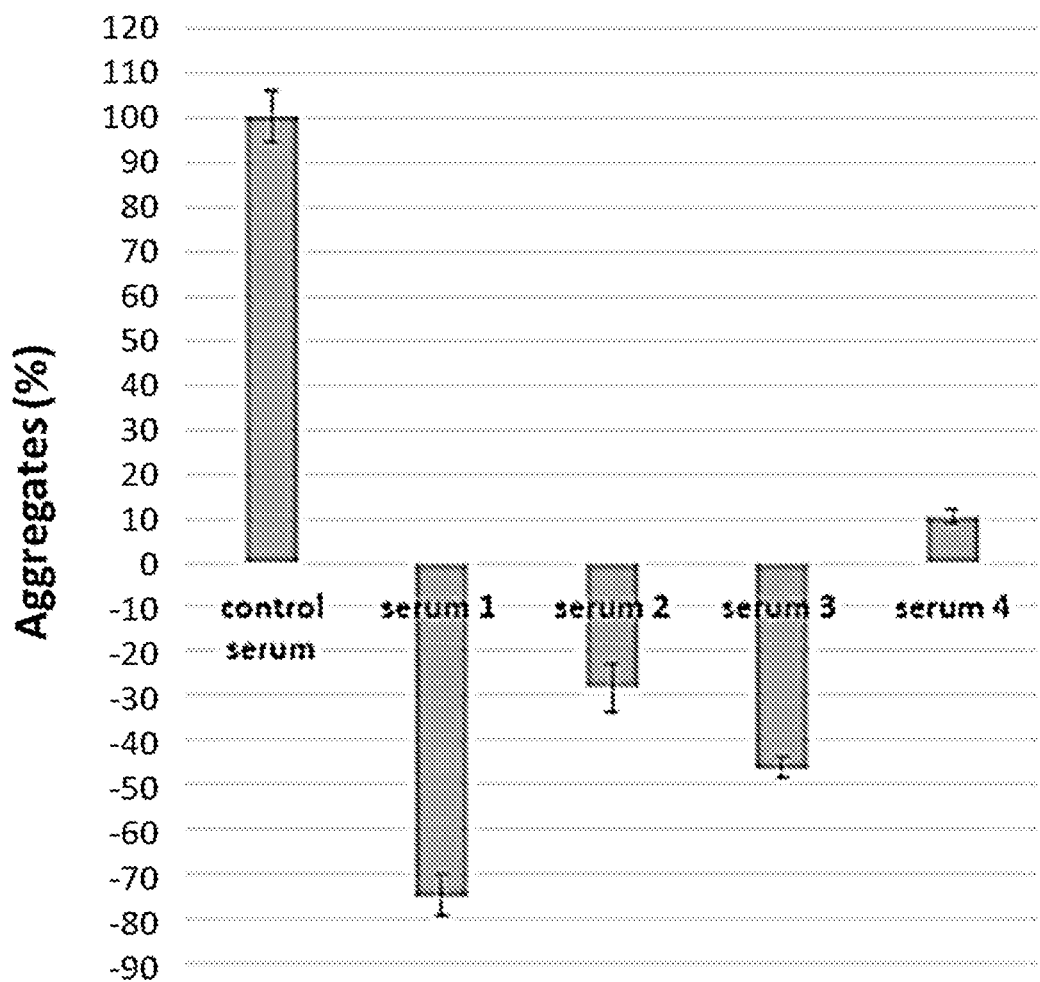
Figure 8:
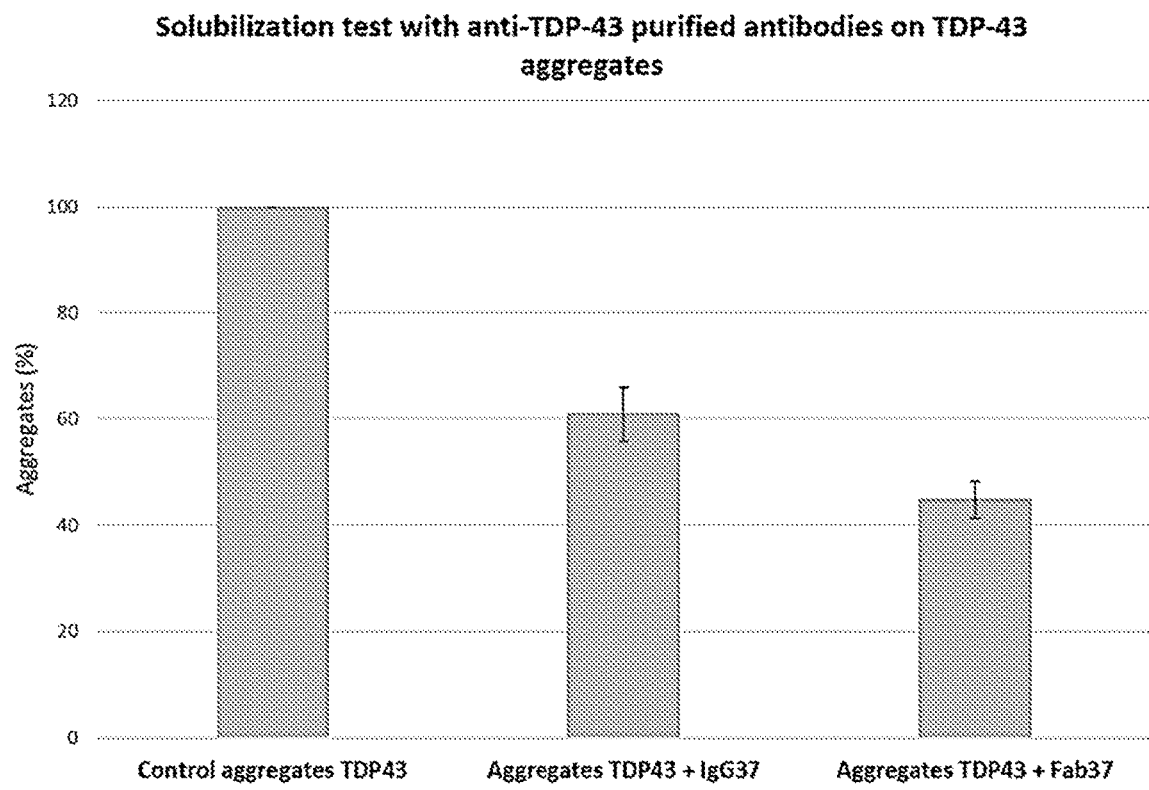
FIG. 8 shows the solubilization of TDP-43 aggregates with purified anti-TDP-43 antibodies (both IgG and Fab) in mice.
Figure 10:
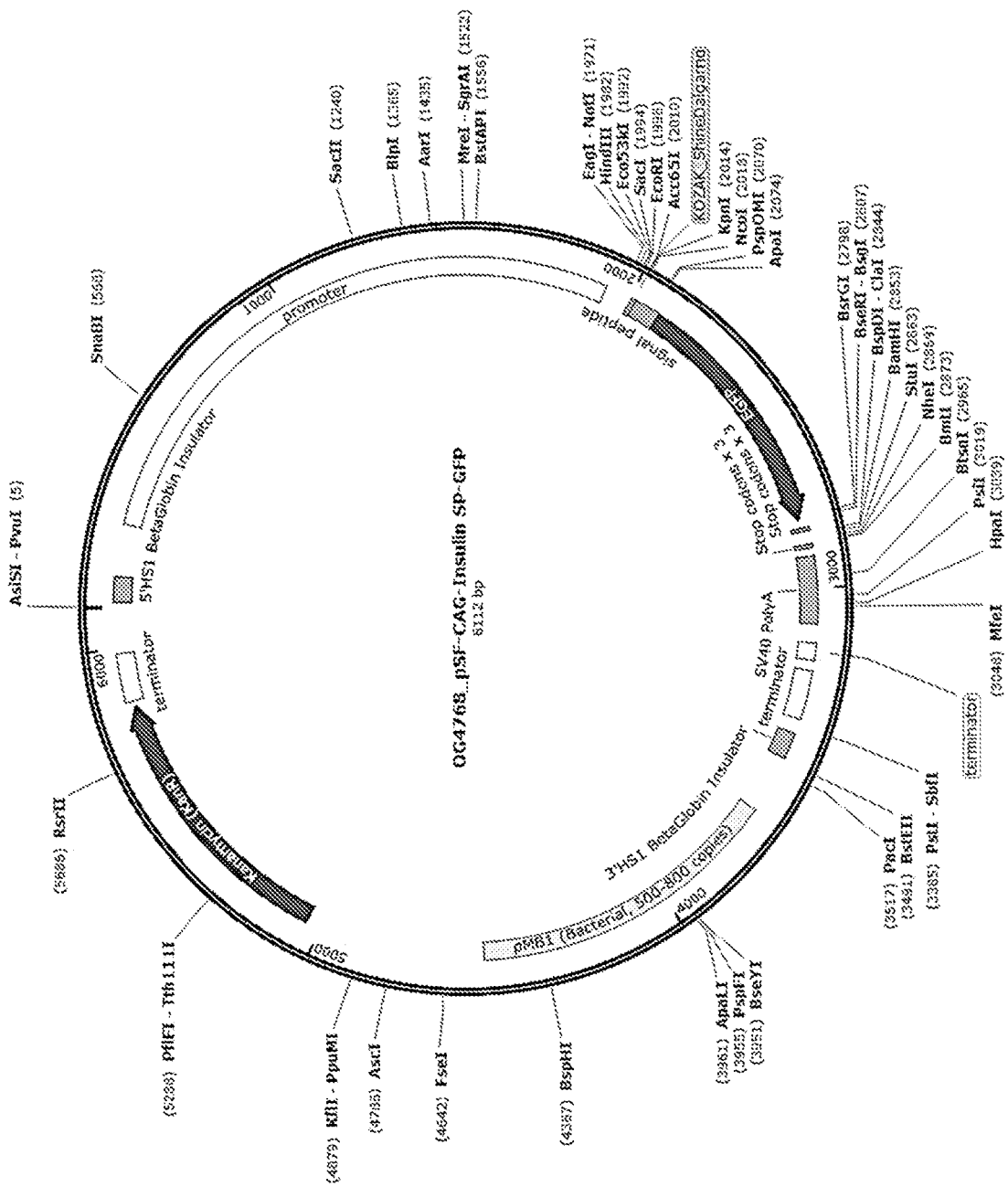
FIG. 10 depicts a map of the OG4768_pSF-CAG-Insulin SP-GFP vector.
Figure 11:
FIG. 11 depicts a map of the OG503_pSF-Synapsin-Insulin SP-GFP vector.
Figure 12:
FIG. 12 depicts a map of the Q7226 pSF-CAG Prom Insulin SP-EGFP Hygro vector.
Figure 13:
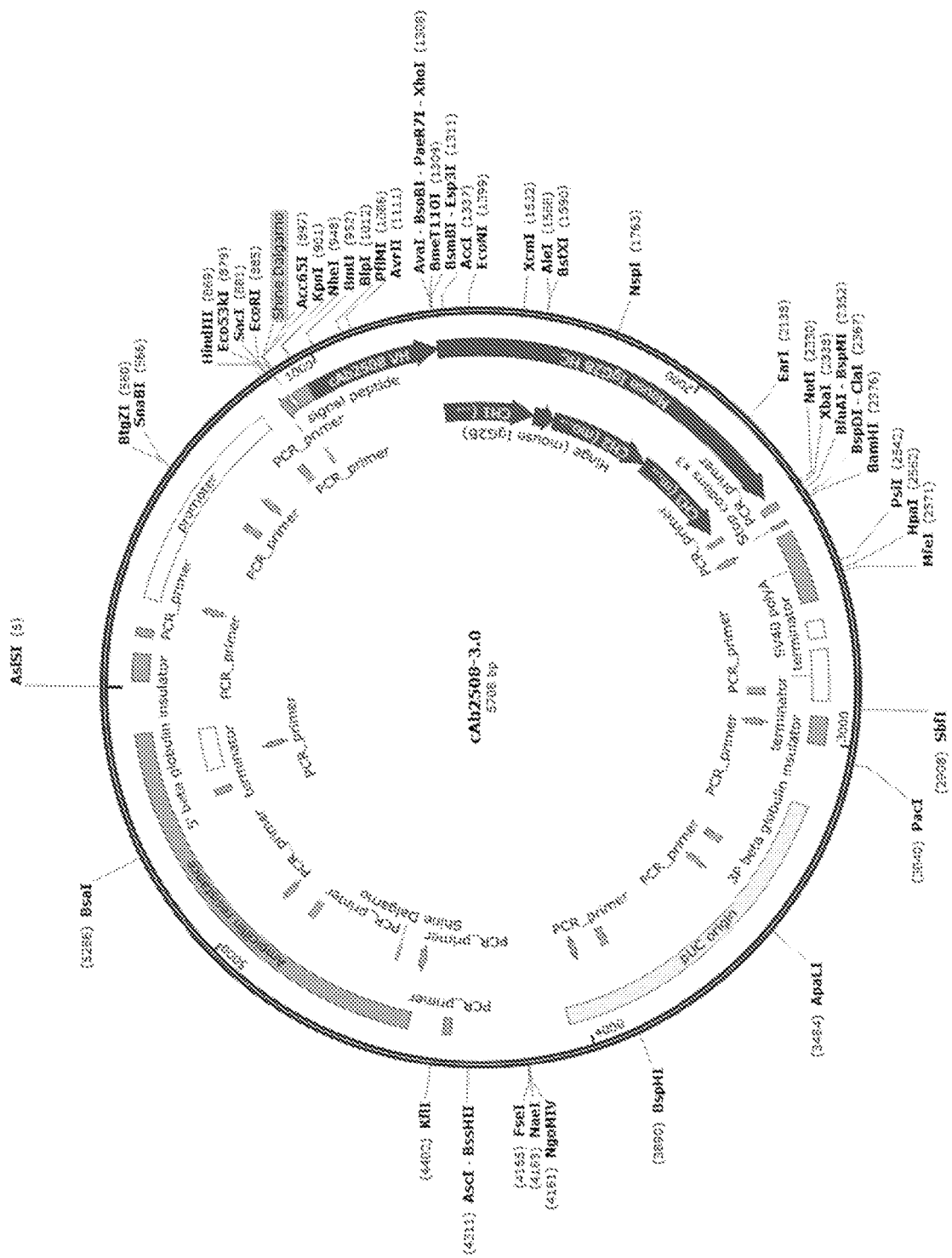
FIG. 13 depicts a map of the cAb2508-3.0 vector (SEQ ID NO: 84) expressing antiTDP43 Fab antibody fragment having a nucleotide sequence encoding the heavy chain and the light chain.
Figure 14:
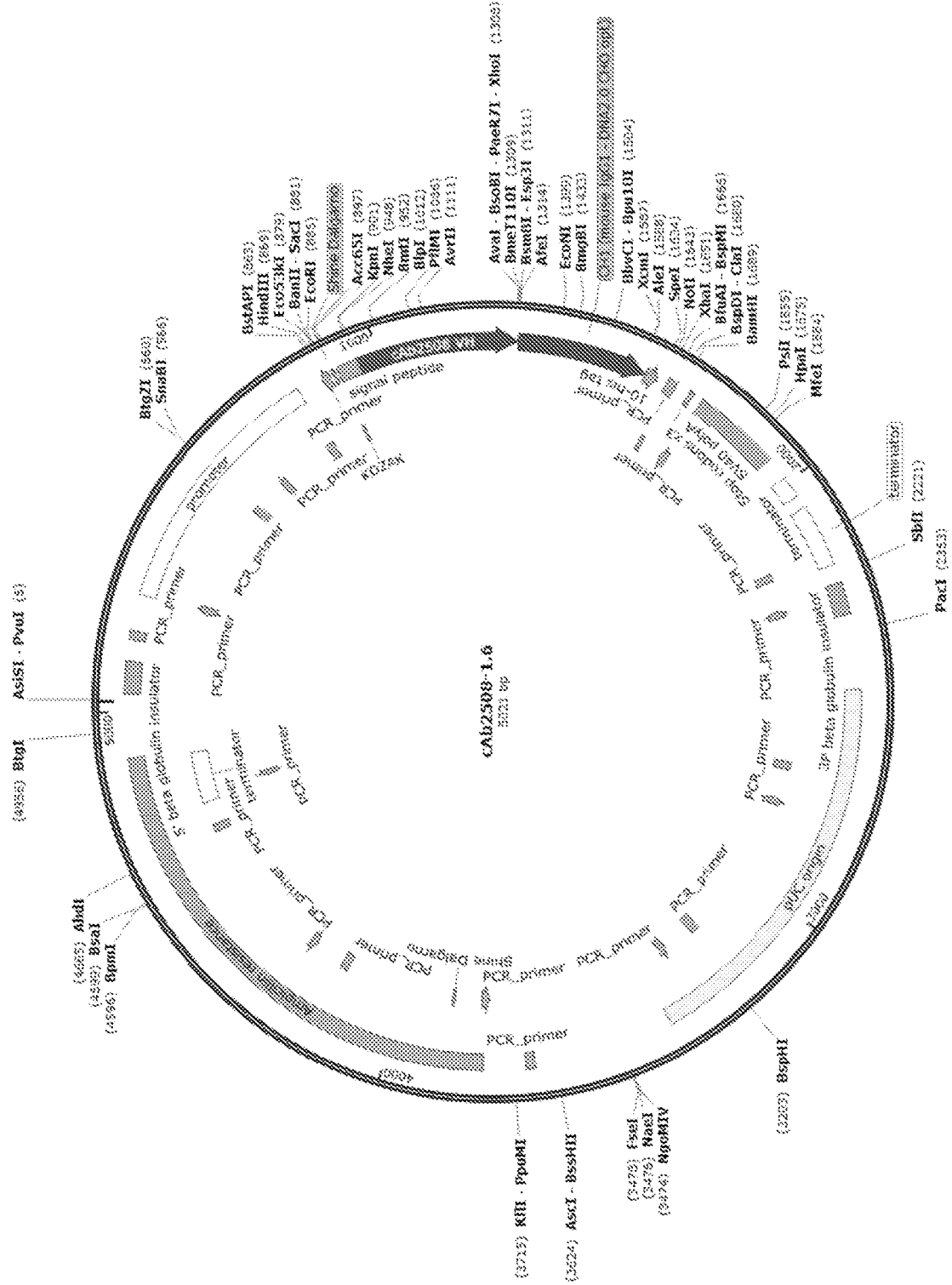
FIG. 14 depicts a map of the cAb2508-1.6 vector (SEQ ID NO: 83) expressing portions of antiTDP43 Fab antibody fragment having a nucleotide sequence encoding the heavy chain.
Figure 15:
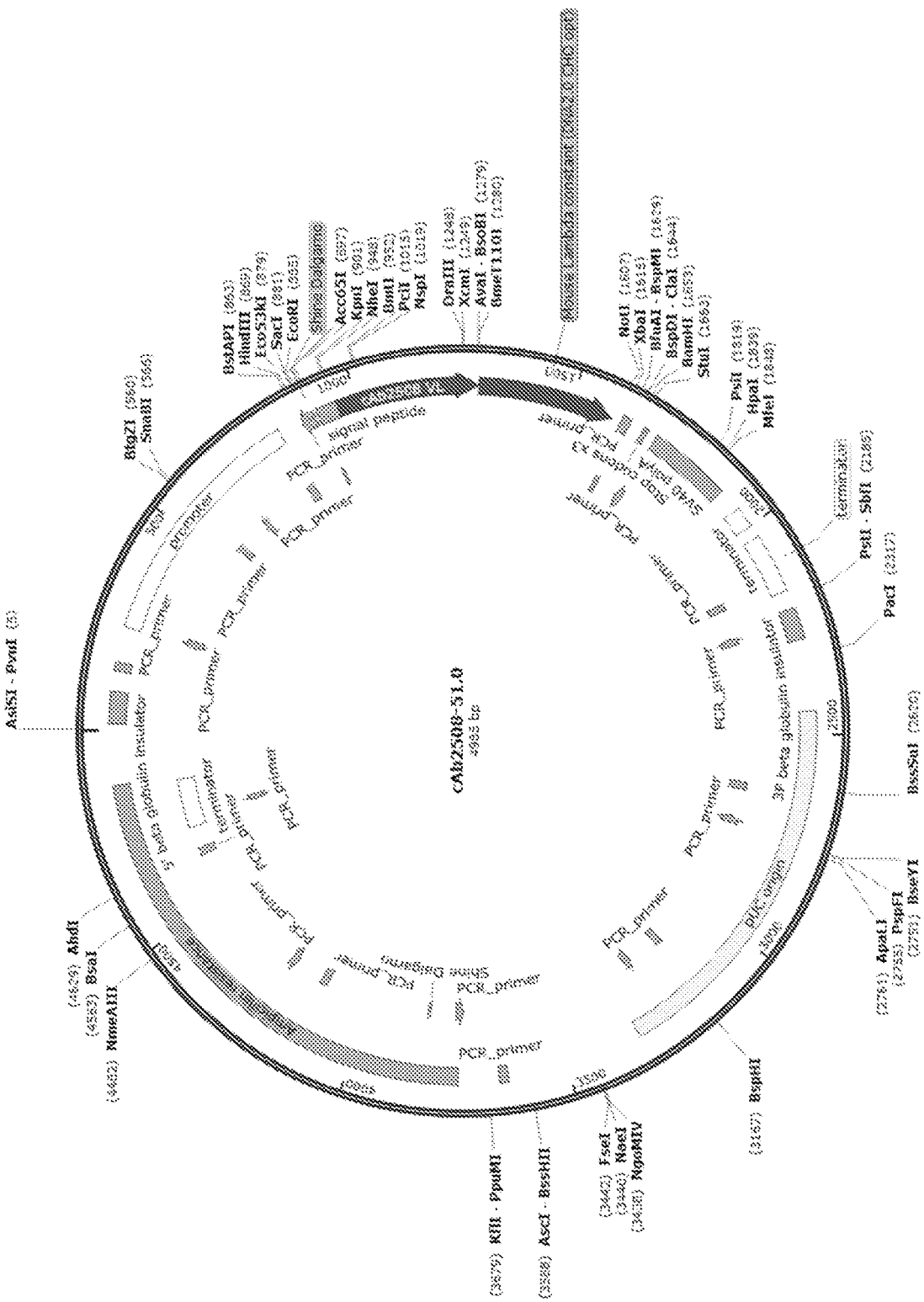
FIG. 15 depicts a map of the cAb2508-51.0 vector (SEQ ID NO: 85) expressing portions of antiTDP43 Fab antibody fragment having a nucleotide sequence encoding the light chain.
Figure 16:
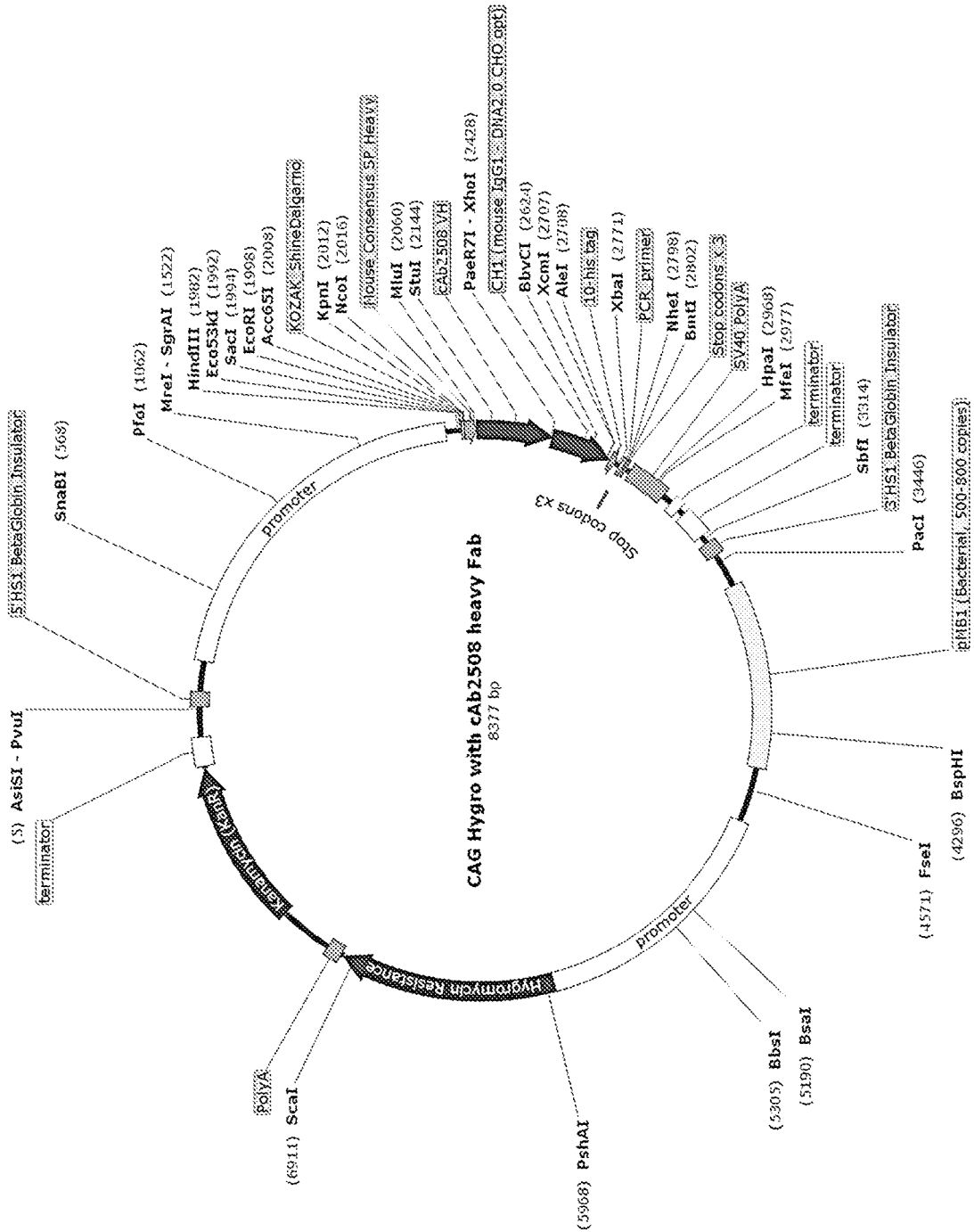
FIG. 16 depicts a map of the CAG Hygro with cAb2508 Heavy Fab vector (SEQ ID NO: 86) expressing portions of antiTDP43 Fab antibody fragment having a nucleotide sequence encoding the heavy chain.
Figure 17:
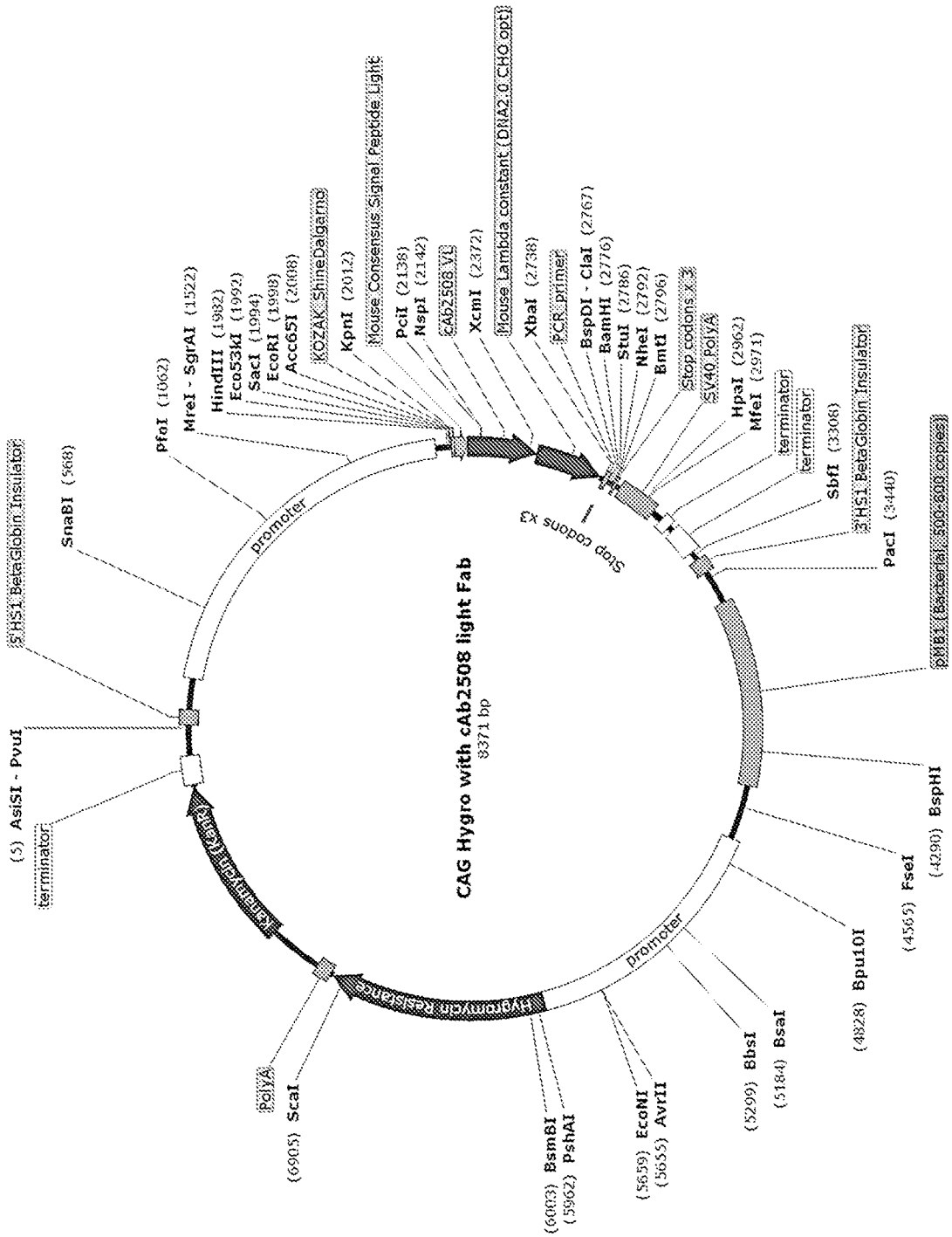
FIG. 17 depicts a map of the CAG hygro with cAb2508 Light Fab vector (SEQ ID NO: 87) expressing portions of antiTDP43 Fab antibody fragment having a nucleotide sequence encoding the light chain.
Figure 18:
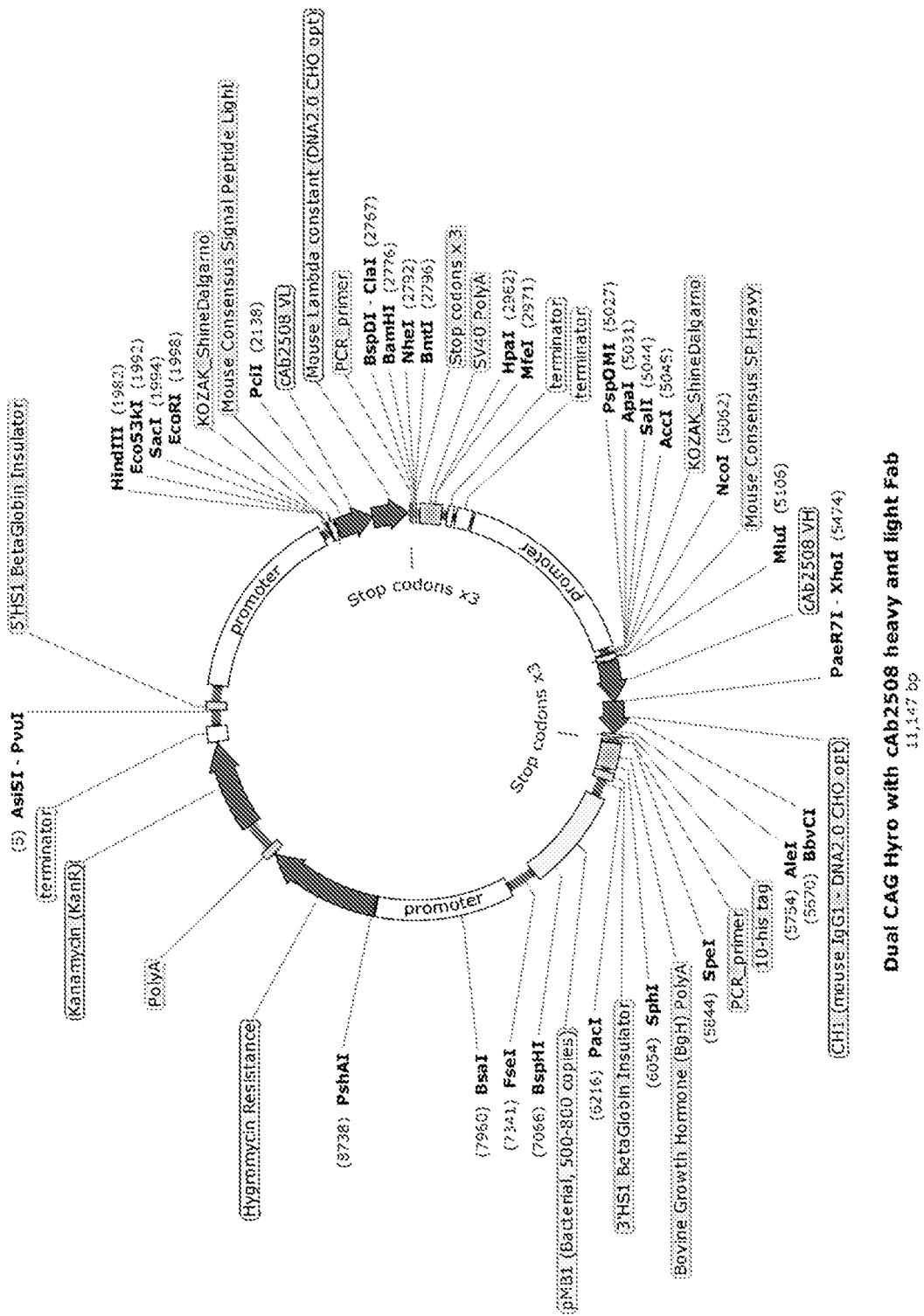
FIG. 18 depicts a map of the Dual CAG Hygro cAb2508 heavy and light Fab vector (SEQ ID NO: 88) expressing antiTDP43 Fab antibody fragment having a nucleotide sequences encoding the heavy chain and the light chain.
Figure 19:
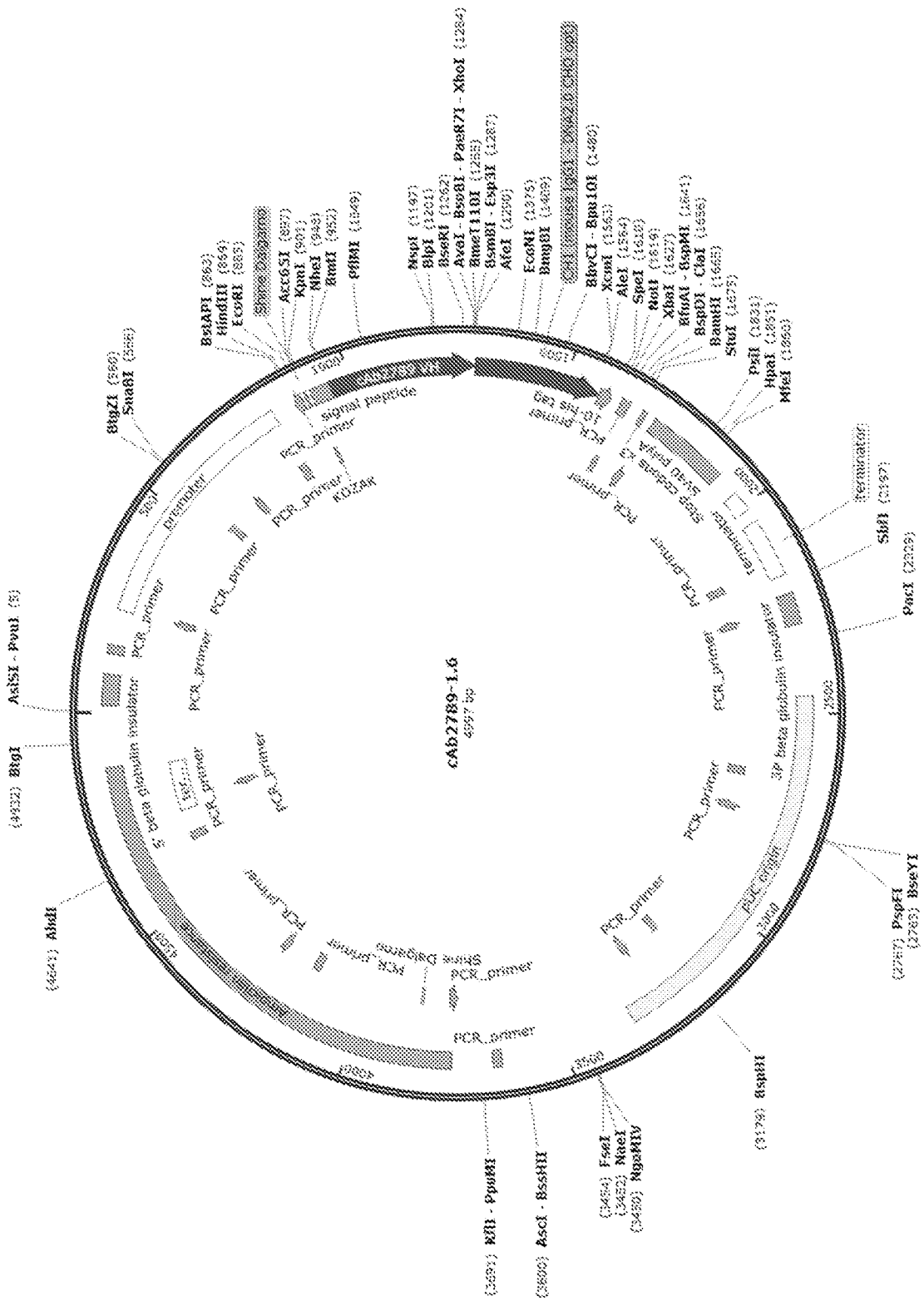
FIG. 19 depicts a map of the cAb2789-1.6 vector (SEQ ID NO: 89) expressing portion of anti-8 Amyloid Fab antibody fragment having a nucleotide sequence encoding the heavy chain.
Figure 20:
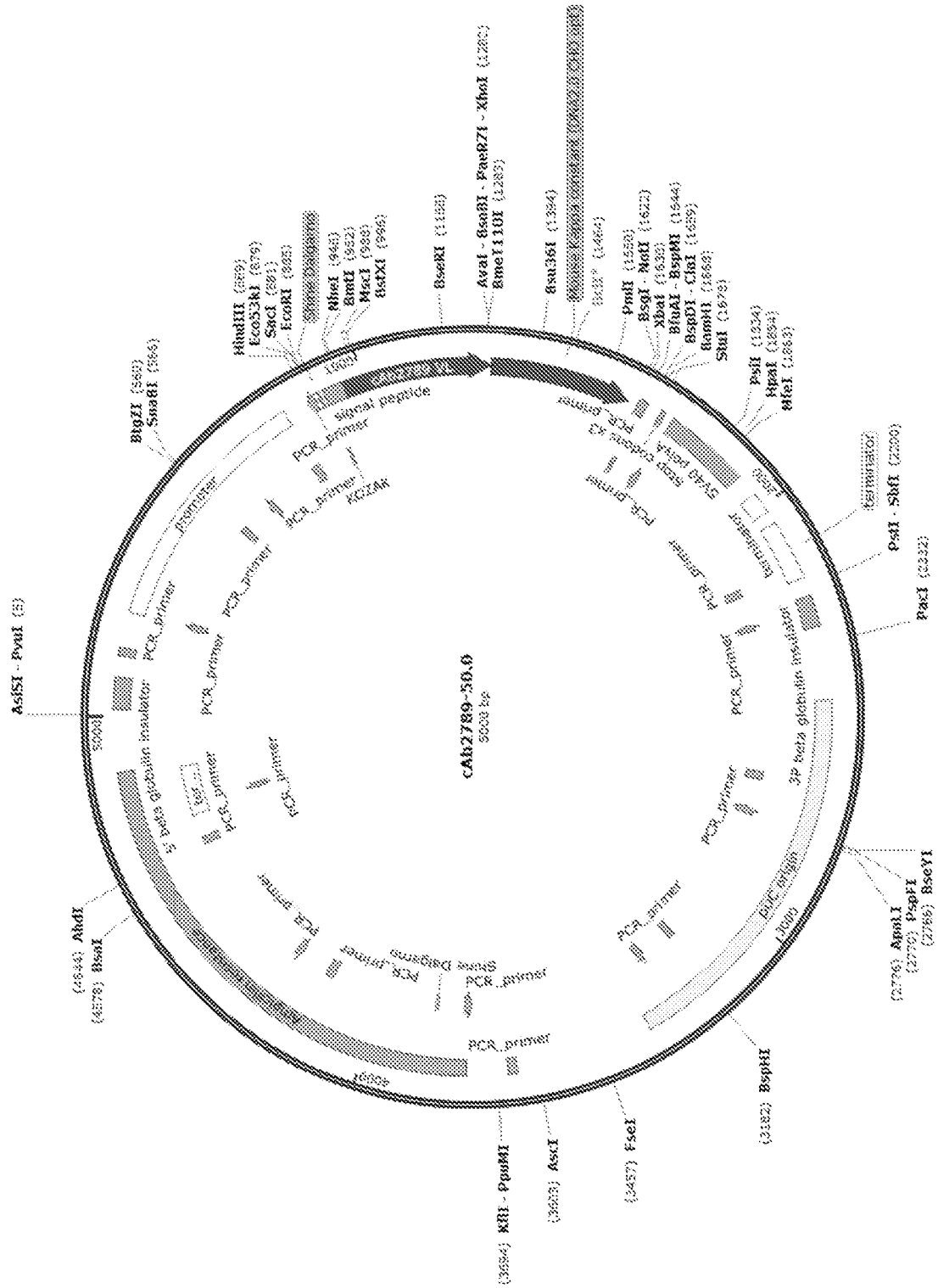
FIG. 20 depicts a map of the cAb2789-50.0 vector (SEQ ID NO: 90) expressing portion of anti-8 Amyloid Fab antibody fragment having a nucleotide sequence encoding the light chain.
Figure 21:
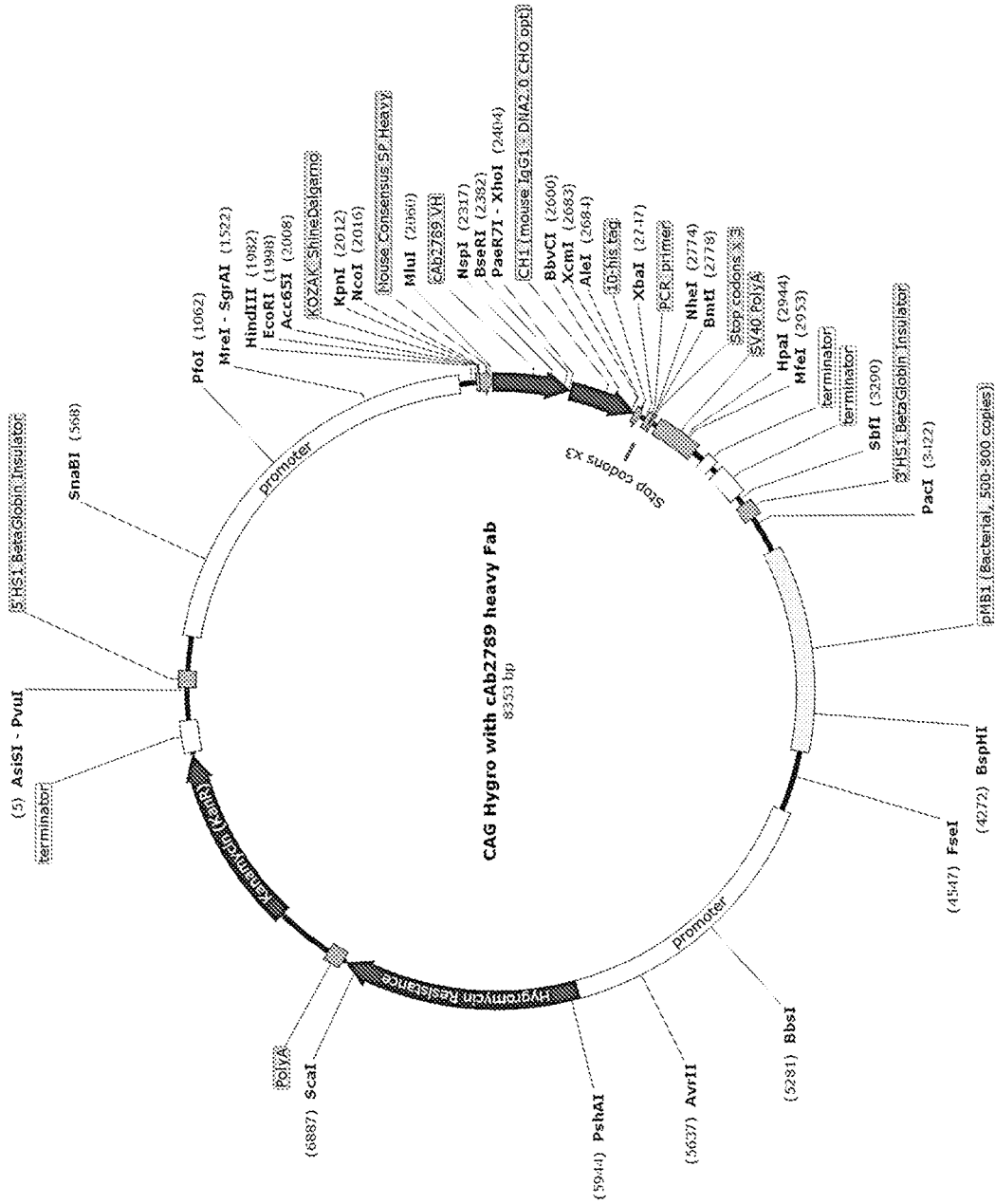
FIG. 21 depicts a map of the CAG Hygro cAb2789 Heavy Fab vector (SEQ ID NO: 91) expressing portion of anti-8 Amyloid Fab antibody fragment having a nucleotide sequence encoding the heavy chain.
Figure 22:
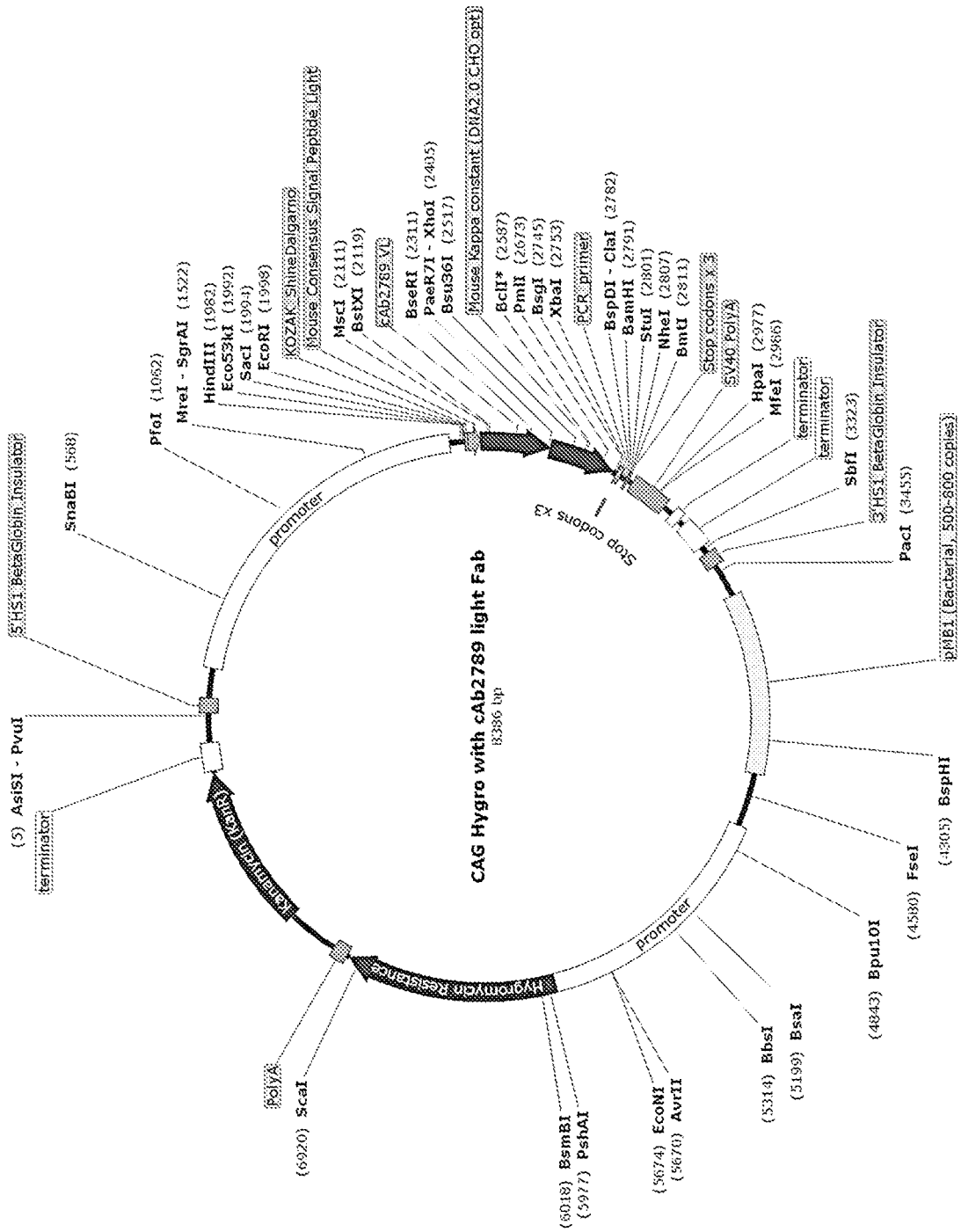
FIG. 22 depicts a map of the CAG Hygro cAb2789 Light Fab vector (SEQ ID NO: 92) expressing portion of anti-8 Amyloid Fab antibody fragment having a nucleotide sequence encoding the light chain.
Figure 23:
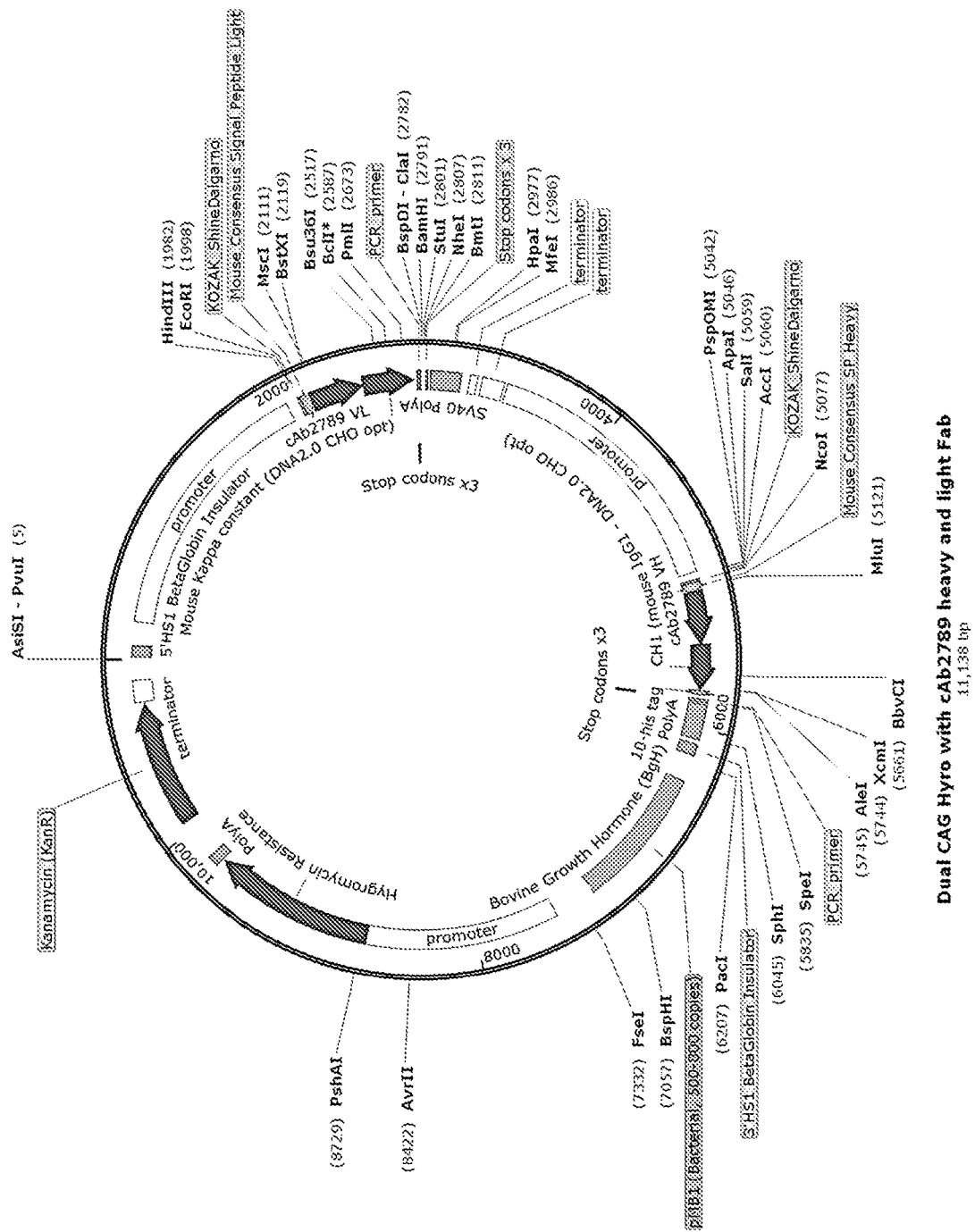
FIG. 23 depicts a map of the CAG Hygro cAb2789 Heavy and Light Fab vector (SEQ ID NO: 93) expressing anti-8 Amyloid Fab antibody fragment having a nucleotide sequence encoding the heavy and the light chains.

The vectors provided herein contain a nucleotide sequence that encodes an antibody or a portion thereof. Examples of vectors of the invention are described in FIGS. 2 to 14 which show the map of the vector. In addition, sequences of exemplary vectors are provided in SEQ ID NOs: 83 to 93. FIGS. 4-6 show first generation vectors expressing anti-TDP43 antibody or a portion thereof. FIGS. 7-9 show second generation vectors expressing anti-TDP43 antibody or a portion thereof. FIGS. 10 and 11 show first generation vectors expressing anti-beta amyloid antibody or a portion thereof. FIGS. 12-14 show second generation vectors expressing anti-beta amyloid antibody or a portion thereof.

In addition, this invention provides methods for making the vectors described herein, as well as methods for introducing the vectors into appropriate host cells for expression of the encoded antibodies. In general, the methods provided herein include constructing nucleic acid sequences encoding an antibody, cloning the sequences encoding the antibody into an expression vector. The expression vector can be introduced into host cells or incorporated into virus particles, either of which can be administered to a subject.

cDNA or DNA sequences encoding antibodies disclosed herein can be obtained (and, if desired, modified) using conventional DNA cloning and mutagenesis methods, DNA amplification methods, and/or synthetic methods. In general, a sequence encoding an antibody can be inserted into a cloning vector for genetic modification and replication purposes prior to expression. Each coding sequence can be operably linked to a regulatory element, such as a promoter, for purposes of expressing the encoded protein in suitable host cells in vitro and in vivo.

Expression vectors can be introduced into host cells for producing antibodies disclosed herein. There are a variety of techniques available for introducing nucleic acids into viable cells. Techniques suitable for the transfer of nucleic acid into mammalian cells in vitro include the use of liposomes, electroporation, microinjection, cell fusion, polymer-based systems, DEAE-dextran, viral transduction, the calcium phosphate precipitation method, etc. For in vivo gene transfer, a number of techniques and reagents may also be used, including liposomes; natural polymer-based delivery vehicles, such as chitosan and gelatin; viral vectors are also suitable for in vivo transduction. Where liposomes are employed, proteins which bind to a cell surface membrane protein associated with endocytosis may be used for targeting and/or to facilitate uptake, e.g., capsid proteins or fragments thereof tropic for a particular cell type, antibodies for proteins which undergo internalization in cycling, proteins that target intracellular localization and enhance intracellular half-life. The technique of receptor-mediated endocytosis is described, for example, by Wu et al., J. Biol. Chem. 262, 4429-4432 (1987); and Wagner et al, Proc. Natl. Acad. Sci. USA 87, 3410-3414 (1990).

Where appropriate, gene delivery agents such as, e.g., integration sequences can also be employed. Numerous integration sequences are known in the art (see, e.g., Nunes-Duby et al., Nucleic Acids Res. 26:391-406, 1998; Sadwoski, J. Bacteriol., 165:341-357, 1986; Bestor, Cell, 122 (3):322-325, 2005; Plasterk et al., TIG 15:326-332, 1999; Kootstra et al., Ann. Rev. Pharm. Toxicol., 43:413-439, 2003). These include recombinases and transposases. Examples include Cre (Sternberg and Hamilton, J. Mol. Biol., 150:467-486, 1981), lambda (Nash, Nature, 247, 543-545, 1974), Fip (Broach, et al, Cell, 29:227-234, 1982), R (Matsuzaki, et al., J. Bacteriology, 172:610-618, 1990), cpC31 (see, e.g., Groth et al., J. Mol. Biol. 335:667-678, 2004), sleeping beauty, transposases of the mariner family (Plasterk et al., supra), and components for integrating viruses such as AAV, retroviruses, and antiviruses having components that provide for virus integration such as the LTR sequences of retroviruses or lentivirus and the ITR sequences of AAV (Kootstra et al, Ann. Rev. Pharm. Toxicol., 43:413-439, 2003).

Both prokaryotic and eukaryotic vectors can be used for expression of antibodies disclosed herein. Prokaryotic vectors include constructs based on E. coli sequences (see, e.g., Makrides, Microbiol Rev 1996, 60:512-538). Non-limiting examples of regulatory regions that can be used for expression in E. coli include lac, trp, Ipp, phoA, recA, tac, T3, T7 and $\lambda P_L$. Non-limiting examples of prokaryotic expression vectors may include the λgt vector series such as λgt11 (Huynh et al., in "DNA Cloning Techniques, Vol. I: A Practical Approach," 1984, (D. Glover, ed.), pp. 49-78, IRL Press, Oxford), and the pET vector series (Studier et al., Methods Enzymol 1990, 185:60-89). Prokaryotic host-vector systems cannot perform much of the post-translational processing of mammalian cells, however. Thus, eukaryotic host-vector systems may be particularly useful.

A variety of regulatory regions can be used for expression of the antibodies disclosed herein in mammalian host cells. For example, the SV40 early and late promoters, the cytomegalovirus (CMV) immediate early promoter, and the Rous sarcoma virus long terminal repeat (RSV-LTR) promoter can be used. Inducible promoters that may be useful in mammalian cells include, without limitation, promoters associated with the metallothionein II gene, mouse mammary tumor virus glucocorticoid responsive long terminal repeats (MMTV-LTR), the β-interferon gene, and the hsp70 gene (see, Williams et al., Cancer Res 1989, 49:2735-42; and Taylor et al., Mol Cell Biol 1990, 10:165-75).

In an embodiment, the present invention contemplates the use of inducible promoters capable of effecting high level of expression transiently in response to a cue. Illustrative inducible expression control regions include those comprising an inducible promoter that is stimulated with a cue such as a small molecule chemical compound. Particular examples can be found, for example, in U.S. Pat. Nos. 5,989,910, 5,935,934, 6,015,709, and 6,004,941, each of which is incorporated herein by reference in its entirety.

An expression vector can also include transcription enhancer elements, such as those found in SV40 virus, Hepatitis B virus, cytomegalovirus, immunoglobulin genes, metallothionein, and β-actin (see, Bittner et al., *Meth Enzymol* 1987, 153:516-544; and Gorman, *Curr Op Biotechnol* 1990, 1:36-47). In addition, an expression vector can contain sequences that permit maintenance and replication of the vector in more than one type of host cell, or integration of the vector into the host chromosome. Such sequences include, without limitation, to replication origins, autonomously replicating sequences (ARS), centromere DNA, and telomere DNA.

In addition, an expression vector can contain one or more selectable or screenable marker genes for initially isolating, identifying, or tracking host cells that contain DNA encoding antibodies as described herein. For long term, stable expression in mammalian cells can be useful. A number of selection systems can be used for mammalian cells. For example, the Herpes simplex virus thymidine kinase (Wigler et al., *Cell* 1977, 11:223), hypoxanthine-guanine phosphoribosyltransferase (Szybalski and Szybalski, *Proc Natl Acad Sci USA* 1962, 48:2026), and adenine phosphoribosyltransferase (Lowy et al., *Cell* 1980, 22:817) genes can be employed in tk⁻, hgprt⁻, or aprt⁻ cells, respectively. In addition, antimetabolite resistance can be used as the basis of selection for dihydrofolate reductase (dhfr), which confers resistance to methotrexate (Wigler et al., *Proc Natl Acad Sci USA* 1980, 77:3567; O'Hare et al., *Proc Natl Aced Sci USA* 1981, 78:1527); gpt, which confers resistance to mycophenolic acid (Mulligan and Berg, *Proc Natl Acad Sci USA* 1981, 78:2072); neomycin phosphotransferase (neo), which confers resistance to the aminoglycoside G-418 (Colberre-Garapin et al., *J Mol Biol* 1981, 150:1); and hygromycin phosphotransferase (hyg), which confers resistance to hygromycin (Santerre et al., *Gene* 1984, 30:147). Other selectable markers known in the art, such as, Kanamycin resistance, ampicillin resistance, histidinol and Zeocin™ (phyleomycin D1 selectable marker, Invitrogen, Inc) also can be used.

A number of viral-based expression systems also can be used with mammalian cells to produce the antibody disclosed herein. Vectors using DNA virus backbones have been derived from simian virus 40 (SV40) (Hamer et al., *Cell* 1979, 17:725), adenovirus (Van Doren et al., *Mol Cell Biol* 1984, 4:1653), adeno-associated virus (McLaughlin et al., *J Virol* 1988, 62:1963), and bovine papillomas virus (Zinn et al., *Proc Natl Aced Sci USA* 1982, 79:4897). When an adenovirus is used as an expression vector, the donor DNA sequence may be ligated to an adenovirus transcription/translation control complex, e.g., the late promoter and tripartite leader sequence. Nucleotide sequence encoding the antibodies disclosed herein may then be inserted in the adenovirus genome by in vitro or in vivo recombination. Insertion in a non-essential region of the viral genome (e.g., region E1 or E3) can result in a recombinant virus that is viable and capable of expressing heterologous products in infected hosts. (See, e.g., Logan and Shenk, *Proc Natl Acad Sci USA* 1984, 81:3655-3659).

Bovine papillomavirus (BPV) can infect many higher vertebrates, including man, and its DNA replicates as an episome. A number of shuttle vectors have been developed for recombinant gene expression which exist as stable, multicopy (20-300 copies/cell) extrachromosomal elements in mammalian cells. Typically, these vectors contain a segment of BPV DNA (the entire genome or a 69% transforming fragment), a promoter with a broad host range, a polyadenylation signal, splice signals, a selectable marker, and "poisonless" plasmid sequences that allow the vector to be propagated in *E. coli*. Following construction and amplification in bacteria, the expression gene constructs are transfected into cultured mammalian cells by, for example, calcium phosphate coprecipitation. For those host cells that do not manifest a transformed phenotype, selection of transformants is achieved by use of a dominant selectable marker, such as histidinol and G418 resistance.

Alternatively, the vaccinia 7.5K promoter can be used. (See, e.g., Mackett et al., *Proc Natl Acad Sci USA* 1982, 79:7415-7419; Mackett et al., *J Virol* 1984, 49:857-864; and Panicali et al., *Proc Natl Aced Sci USA* 1982, 79:4927-4931.) In cases where a human host cell is used, vectors based on the Epstein-Barr virus (EBV) origin (OriP) and EBV nuclear antigen 1 (EBNA-1; a trans-acting replication factor) can be used. Such vectors can be used with a broad range of human host cells, e.g., EBO-pCD (Spickofsky et al., *DNA Prot Eng Tech* 1990, 2:14-18); pDR2 and λDR2 (available from Clontech Laboratories).

Retroviruses, such as Moloney murine leukemia virus, can be used since most of the viral gene sequence can be removed and replaced with exogenous coding sequence while the missing viral functions can be supplied in trans. In contrast to transfection, retroviruses can efficiently infect and transfer genes to a wide range of cell types including, for example, primary hematopoietic cells. Moreover, the host range for infection by a retroviral vector can be manipulated by the choice of envelope used for vector packaging.

For example, a retroviral vector can comprise a 5' long terminal repeat (LTR), a 3' LTR, a packaging signal, a bacterial origin of replication, and a selectable marker. The antibody coding sequence, for example, can be inserted into a position between the 5' LTR and 3' LTR, such that transcription from the 5' LTR promoter transcribes the cloned DNA. The 5' LTR contains a promoter (e.g., an LTR promoter), an R region, a U5 region, and a primer binding site, in that order. Nucleotide sequences of these LTR elements are well known in the art. A heterologous promoter as well as multiple drug selection markers also can be included in the expression vector to facilitate selection of infected cells. See, McLauchlin et al., *Prog Nucleic Acid Res Mol Biol* 1990, 38:91-135; Morgenstern et al., *Nucleic Acid Res* 1990, 18:3587-3596; Choulika et al., *J Virol* 1996, 70:1792-1798; Boesen et al., *Biotherapy* 1994, 6:291-302; Salmons and Gunzberg, *Human Gene Ther* 1993, 4:129-141; and Grossman and Wilson, *Curr Opin Genet Devel* 1993, 3:110-114.

Any of the cloning and expression vectors described herein may be synthesized and assembled from known DNA sequences using techniques that are known in the art. The regulatory regions and enhancer elements can be of a variety of origins, both natural and synthetic. Some vectors and host cells may be obtained commercially. Non-limiting examples of useful vectors are described in Appendix 5 of *Current Protocols in Molecular Biology,* 1988, ed. Ausubel et al., Greene Publish. Assoc. & Wiley Interscience, which is incorporated herein by reference; and the catalogs of commercial suppliers such as Clontech Laboratories, Stratagene Inc., and Invitrogen, Inc.

In some embodiments, the nucleotide sequences in the vectors that express an antibody may be codon optimized, for example the codons may be optimized for human use. In some embodiments the nucleotide sequences may be mutated to abrogate the normal in vivo function of the encoded proteins or codon optimized for human use.

As regards codon optimization, the nucleic acid molecules have a nucleotide sequence that encodes the antibodies of the invention and can be designed to employ codons that are used in the genes of the subject in which the antibody is to be produced. Many viruses, including HIV and other lentiviruses, use a large number of rare codons and, by altering these codons to correspond to codons commonly used in the desired subject, enhanced expression of the antibodies can be achieved. The codons used are "humanized" codons, i.e., the codons are those that appear frequently in highly expressed human genes (Andre et al., J. Virol. 72:1497-1503, 1998). Such codon usage provides for efficient expression of the transgenic antibodies in human cells. Any suitable method of codon optimization may be used. Such methods, and the selection of such methods, are well known to those of skill in the art.

Administration

The invention is based, in part, on the finding that the peripheral administration of the present cells allows for effective delivery of therapeutic agents (inclusive of, without limitation, the Fabs described herein) across the BBB. The invention is based, in part, on the finding that the peripheral administration of the present cells allows for effective delivery of therapeutic agents (inclusive of, without limitation, the Fabs described herein) to and/or past the BBB. Such peripheral administration includes, in some embodiments, any administration route which does not imply direct injection into the brain. More particularly, in some embodiments, peripheral administration comprises systemic injections, such as intramuscular (i.m.), intravenous (i.v.), intraperitoneal (i.p.), intra-arterial, sub-cutaneous or transdermic injections. Peripheral administration also includes oral administration, delivery using implants, or administration by instillation through the respiratory system, e.g., using sprays, aerosols or any other appropriate formulations.

Pharmaceutical Compositions and Formulation

The present invention further provides pharmaceutical compositions of the contemplated therapeutic agents, and a pharmaceutically acceptable carrier or excipient. As one skilled in the art will recognize, the agents described herein may be made up, together or separately, in any suitable form appropriate for the desired use and route of administration. As used herein the term "pharmaceutically acceptable" means approved by a regulatory agency of the Federal or a state government or listed in the U.S. Pharmacopeia or other generally recognized pharmacopeia for use in animals, and more particularly in humans. Examples of suitable dosage forms include, for example, oral, parenteral, and intravenous dosage forms.

Suitable dosage forms for oral use include, for example, solid dosage forms such as tablets, dispersible powders, granules, and capsules. In such dosage forms, the active agent is mixed with at least one inert, pharmaceutically acceptable excipient or carrier such as sodium citrate, dicalcium phosphate, etc., and/or a) fillers or extenders such as starches, lactose, sucrose, glucose, mannitol, silicic acid, microcrystalline cellulose, etc.; b) binders such as, for example, carboxymethylcellulose, alginates, gelatin, polyvinylpyrrolidone, sucrose, acacia, etc.; c) humectants such as glycerol, etc.; d) disintegrating agents such as agar-agar, calcium carbonate, potato or tapioca starch, alginic acid, certain silicates, sodium carbonate, cross-linked polymers such as crospovidone (cross-linked polyvinylpyrrolidone), croscarmellose sodium (cross-linked sodium carboxymethylcellulose), sodium starch glycolate, etc.; e) solution retarding agents such as paraffin, etc.; f) absorption accelerators such as quaternary ammonium compounds, etc.; g) wetting agents such as, for example, cetyl alcohol and glycerol monostearate, etc.; h) absorbents such as kaolin and bentonite clay, etc.; and i) lubricants such as talc, calcium stearate, magnesium stearate, solid polyethylene glycols, sodium lauryl sulfate, glyceryl behenate, etc., and mixtures of such excipients. One of skill in the art will recognize that particular excipients may have two or more functions in the oral dosage form. In the case of an oral dosage form, for example, a capsule or a tablet, the dosage form may also comprise buffering agents.

The solid oral dosage forms can be prepared by any conventional method known in the art, for example granulation (e.g., wet or dry granulation) of the active agent with one or more suitable excipients. Alternatively, the active agent can be layered onto an inert core (e.g., a nonpareil/sugar sphere or silica sphere) using conventional methods such as fluidized bed or pan coating, or extruded and spheronized using methods known in the art, into active agent-containing beads. Such beads can then be incorporated into tablets or capsules using conventional methods.

The solid dosage forms of capsules, tablets, granules, active agent-containing beads can be prepared with coatings, such as enteric coatings, reverse enteric coatings, extended release coatings, pulsatile release coatings, etc. and other coatings, or combinations of coatings, well known in the art. Optionally, the dosage forms may release the active ingredient(s) only, or preferentially, in a certain part of the intestinal tract, for example, in a delayed manner.

Liquid dosage forms for oral administration include pharmaceutically acceptable emulsions, solutions, suspensions, syrups and elixirs. In addition to the active agents, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethyl formamide, oils (in particular, cottonseed, groundnut, corn, germ, olive, castor, and sesame oils), glycerol, tetrahydrofurfuryl alcohol, polyethylene glycols and fatty acid esters of sorbitan, etc., and mixtures thereof.

Besides inert diluents, the oral compositions can also include adjuvants such as sweetening, flavoring, and perfuming agents.

Suspensions, in addition to the active agents, may contain suspending agents such as, for example, ethoxylated isostearyl alcohols, polyoxyethylene sorbitol and sorbitan esters, microcrystalline cellulose, aluminum metahydroxide, bentonite, agar-agar, tragacanth, etc., and mixtures thereof.

Dosage forms suitable for parenteral administration (e.g. intravenous, intramuscular, intraperitoneal, subcutaneous and intra-articular injection and infusion) include, for example, solutions, suspensions, dispersions, emulsions, and the like. They may also be manufactured in the form of sterile solid compositions (e.g. lyophilized composition), which can be dissolved or suspended in sterile injectable medium immediately before use. They may contain, for example, suspending or dispersing agents known in the art.

The formulations comprising the therapeutic agents of the present invention may conveniently be presented in unit dosage forms and may be prepared by any of the methods well known in the art of pharmacy. Such methods generally include the step of bringing the therapeutic agents into association with a carrier, which constitutes one or more accessory ingredients. Typically, the formulations are prepared by uniformly and intimately bringing the therapeutic agent into association with a liquid carrier, a finely divided solid carrier, or both, and then, if necessary, shaping the product into dosage forms of the desired formulation (e.g., wet or dry granulation, powder blends, etc., followed by tableting using conventional methods known in the art).

It will be appreciated that the actual dose of the therapeutic agents to be administered according to the present invention will vary according to the particular agent, the particular dosage form, and the mode of administration. Many factors that may modify the action of the agents described herein (e.g., body weight, gender, diet, time of administration, route of administration, rate of excretion, condition of the subject, drug combinations, genetic disposition and reaction sensitivities) can be taken into account by those skilled in the art. Administration can be carried out continuously or in one or more discrete doses within the maximum tolerated dose. Optimal administration rates for a given set of conditions can be ascertained by those skilled in the art using conventional dosage administration tests.

The desired dose of the therapeutic agents may be presented as one dose or two or more sub-doses administered at appropriate intervals throughout the dosing period (e.g., about one hour, about one day, about one week, etc).

In accordance with certain embodiments of the invention, the therapeutic agents may be administered, for example, more than once daily, about once per day, about every other day, about every third day, or about once a week.

The agents of the present invention may be administered by any appropriate route, for example, parenterally or non-parenterally. In an embodiment, the present agent may be administered parenterally, including for example, intravenous, intramuscular, intraperitoneal, subcutaneous and intra-articular injection and infusion, among others.

Additional Agents and Administration

In some embodiments, the present agents may be used alone or in combination with one or more additional agent(s) for simultaneous, separate or sequential use.

For instance, when used in the context of ALS, an additional agent may be Riluzole (e.g. RILUTEK, see, e.g., U.S. Pat. Nos. 5,527,814 and 6,432,992, the contents of which are hereby incorporated by reference). In some embodiments, the additional agent is one or more of an anti-Nogo-A antibody, GM604 (GENERVON), fingolimod (e.g. GILENYA), Dexpramipexole (BIOGEN), ceftriaxone, CK2017357 (TIRASEMTIV, CYTOKINETICS), NP001 (NEURALTUS PHARMACEUTICALS), lithium, selegiline hydrochloride (ELDEPRYL), GF-1 (rhIGF-1, or IGF-1), or derivatives thereof. In some embodiments, the additional agent is one that targets one or more neurotrophic factors, e.g. NGF, BDNF, CNTF, and MNTF.

Further, in the context of type 2 diabetes, an additional agent may be insulin and/or any non-insulin diabetes agents (e.g. selected from metformin (e.g. GLUCOPHAGE, GLUMETZA); sulfonylureas (e.g. glyburide (e.g. DIABETA, GLYNASE), glipizide (e.g. GLUCOTROL) and glimepiride (e.g. AMARYL)); thiazolidinediones (e.g. rosiglitazone (e.g. AVANDIA) and pioglitazone (e.g. ACTOS)); DPP-4 inhibitors (e.g. sitagliptin (e.g. JANUVIA), saxagliptin (e.g. ONGLYZA) and linagliptin (e.g. TRADJENTA)); GLP-1 receptor agonists (e.g. exenatide (e.g. BYETTA) and liraglutide (e.g. VICTOZA)); and SGLT2 inhibitors (e.g. canagliflozin (e.g. NVOKANA) and dapagliflozin (e.g. FARXIGA))) and/or insulin may be used in treatment. For example, certain patients may be able to manage diabetes with diet and exercise alone (e.g. along with glucose monitoring). However, often this is not the case and therapeutic agents are needed. A first line of treatment may be a non-insulin diabetes agent (e.g. selected from metformin (e.g. GLUCOPHAGE, GLUMETZA); sulfonylureas (e.g. glyburide (e.g. DIABETA, GLYNASE), glipizide (e.g. GLUCOTROL) and glimepiride (e.g. AMARYL)); thiazolidinediones (e.g. rosiglitazone (e.g. AVANDIA) and pioglitazone (e.g. ACTOS)); DPP-4 inhibitors (e.g. sitagliptin (e.g. JANUVIA), saxagliptin (e.g. ONGLYZA) and linagliptin (e.g. TRADJENTA)); GLP-1 receptor agonists (e.g. exenatide (e.g. BYETTA) and liraglutide (e.g. VICTOZA)); and SGLT2 inhibitors (e.g. canagliflozin (e.g. NVOKANA) and dapagliflozin (e.g. FARXIGA)).

Co-administration of the agents described herein with an additional agent can be simultaneous or sequential. Further, the present invention contemplates co-formulation of one or more agents of the invention with one or more additional agent(s).

In some embodiments, the agents described herein and an additional agent is administered to a subject simultaneously. The term "simultaneously" as used herein, means that agents described herein and an additional agent are administered with a time separation of no more than about 60 minutes, such as no more than about 30 minutes, no more than about 20 minutes, no more than about 10 minutes, no more than about 5 minutes, or no more than about 1 minute. Administration of the agents described herein and an additional agent can be by simultaneous administration of a single formulation (e.g., a formulation comprising the agents described herein and an additional agent) or of separate formulations (e.g., a first formulation including the agents described herein and a second formulation including an additional agent).

Co-administration does not require the therapeutic agents to be administered simultaneously, if the timing of their administration is such that the pharmacological activities of the agents described herein and an additional agent overlap in time, thereby exerting a combined therapeutic effect. For example, the agents described herein and an additional agent can be administered sequentially. The term "sequentially" as used herein means that the agents described herein and an additional agent are administered with a time separation of more than about 60 minutes. For example, the time between the sequential administration of the agents described herein and an additional agent can be more than about 60 minutes, more than about 2 hours, more than about 4 hours, more than about 8 hours, more than about 10 hours, more than about 12 hours, more than about 24 hours, more than about 36 hours, more than about 48 hours, more than about 72 hours, more than about 96 hours, or more than about 1 week apart. The optimal administration times will depend on the rates of metabolism, excretion, and/or the pharmacodynamic activity or toxicity of the agents described herein and an additional agent being administered. Either the agents described herein or an additional agent can be administered first.

Methods of measuring or monitoring the immune effect induced by the present agents are well known in the art. These methods include, but are not limited to, flow cytometry (including, for example, fluorescent activating cell sorting (FACS)), solid phase enzyme-linked immunosorbent assay (ELISA), western blotting (including in cell western), immunofluorescent staining, microengraving (see Han Q et al. Lab Chip. 2010; 10(11):1391-1400), immunofluorescent staining of incorporated bromodeoxyuridine (BrdU) or 7-aminoactinomycin D (7-AAD); ELISPOT Assays; mRNA analysis; quantitative RT-PCR; TaqMan Q-PCR; histology; laser capture microdissection; and bioluminescent imaging.

In accordance with certain embodiments of the invention, the agent agents described herein and an additional agent may each be administered, for example, more than once daily, about once per day, about every other day, about every third day, or about once a week, or once every 2 or 3 weeks.

Co-administration also does not require the therapeutic agents to be administered to the subject by the same route of administration. Rather, each therapeutic agent can be administered by any appropriate route, for example, parenterally or non-parenterally.

Methods of Treatment/Patient Selection

In some embodiments, the neurodegenerative disease that is treated by the present agents is selected from MS (including without limitation the subtypes described herein), Alzheimer's. disease (including, without limitation, Early-onset Alzheimer's, Late-onset Alzheimer's, and Familial Alzheimer's disease (FAD), Parkinson's disease and parkinsonism (including, without limitation, Idiopathic Parkinson's disease, Vascular parkinsonism, Drug-induced parkinsonism, Dementia with Lewy bodies, Inherited Parkinson's, Juvenile Parkinson's), Huntington's disease, Amyotrophic lateral sclerosis (ALS, including, without limitation, Sporadic ALS, Familial ALS, Western Pacific ALS, Juvenile ALS, Hiramaya Disease).

In some embodiments, the disease is one characterized by amyloid plaque formation including secondary amyloidosis and age-related amyloidosis including, but not limited to, neurological disorders such as Alzheimer's Disease (AD), including diseases or conditions characterized by a loss of cognitive memory capacity such as, for example, mild cognitive impairment (MCI), Lewy body dementia, Down's syndrome, hereditary cerebral hemorrhage with amyloidosis (Dutch type); the Guam Parkinson-Dementia complex; as well as other diseases which are based on or associated with amyloid-like proteins such as progressive supranuclear palsy, multiple sclerosis; Creutzfeld Jacob disease, Parkinson's disease, HIV-related dementia, ALS (amyotropic lateral sclerosis), Adult Onset Diabetes; senile cardiac amyloidosis; endocrine tumors, and others, including macular degeneration, but particularly a disease or condition In a specific embodiment, the disease being treated by the present agents is ALS, including, without limitation, Sporadic ALS, Familial ALS, Western Pacific ALS, Juvenile ALS, Hiramaya Disease.

In a specific embodiment, the disease being treated by the present agents is one or more of familial ALS, Motor neuropathy with pyramidal features, Finkel type SMA or SMA IV, TARDBP-related amyotrophic lateral sclerosis, C9orf72-related FTD/ALS, and CHCHD10-related ALS/FTD.

In various embodiments, the present agents find use in a method of treatment in which neurodegeneration is halted or slowed relative to an untreated state. In various embodiments, the present agents reduce or eliminate the spreading of aggregates described herein. In various embodiments, the present agents reduce or eliminate the progression of the neurodegenerative disease.

In various embodiments, the present agents reduce or eliminate the progression of ALS. In some embodiments, the present agents extend one or more of: survival, time to tracheostomy and time to mechanical ventilation. In various embodiments, the present agents improve or reduce the severity of various symptoms of ALS, including without limitation: Early symptoms of ALS often include increasing muscle weakness, especially involving the arms and legs, speech, swallowing or breathing. In some embodiments, the present agents find use in a method that delays onset of ALS or ALS symptom(s) in a patient at risk for ALS. In some embodiments, the present agents find use in a method that slows progression of ALS or ALS symptom(s) in a patient having ALS. In some embodiments, the present agents find use in a method that causes regression of ALS. In some embodiments, the present agents increase swallowing volume in a patient having ALS.

In various embodiments, the present agents improve a patient's ALS as measured via the Amyotrophic Lateral Sclerosis Functional Rating Scale (ALSFRS, see, e.g., *Arch Neurol.* 1996 February; 53(2):141-7, the entire contents of which are hereby incorporated by reference). In various embodiments, the present agents cause an increase in scoring in any of the following parameters in the ALSFRS: (1) speech, (2) salivation, (3) swallowing, (4) handwriting, (5) cutting food and handling utensils (with or without gastrostomy), (6) dressing and hygiene, (7) turning in bed and adjusting bed clothes, (8) walking, (9) climbing stairs, and (10) breathing. In various embodiments, each parameter, which is scored between 0 (worst) and 4 (best) is improved. For instance, the agents might increase the scoring of any parameter to a score of 4, or 3, or 2, or 1, relative to untreated measures.

In some embodiments, the present agents increase forced vital capacity (FVC) as described in, for example, J Neurol Neurosurg Psychiatry. 2006 March; 77(3): 390-392, the entire contents of which are hereby incorporated by reference).

In some embodiments, the present agents increase FVC above about 75% to, e.g. to about 80%, or about 85%, or about 90%, or about 95%, or about 100%.

In some embodiments, the present agents increase Appel ALS (AALS) score. The Appel ALS Scale consists of 5 subscales (Bulbar Function, Respiratory Function, Overall Muscle Strength, Upper Extremity, and Lower Extremity Function) with scores ranging from 30 (Normal) to 164 (Maximal Dysfunction). Patients with a baseline AALS score of between 40 and 80 may be patients of the present invention.

In some embodiments, the present invention relates to the treatment of tumors, heart attack, myocardial infarction, stroke, respiratory insufficiency, etc.

In some embodiments, the present invention relates to the treatment of angiogenesis in retina, repair of wounds caused by a deficient blood supply (diabetes foot), repair of myocardial tissue after heart attack, vessel normalization in case of pathological tumor angiogenesis, skin diseases, etc.

In some embodiments, the present invention relates to the treatment of type 2 diabetes (or "type 2 diabetes mellitus" or "noninsulin-dependent diabetes mellitus (NIDDM)" or "adult-onset diabetes"). In some embodiments, the present invention relates to the treatment of an inappropriate increase in blood glucose levels, which generates chronic complications as it affects large and small vessels and nerves. In some embodiments, the present invention relates to the treatment of insulin resistance.

As used herein, the terms "subject" and "patient" refer to any animal, such as a mammal. The term "mammal" as used herein refers to any mammal classified as a mammal, including humans, non-human primates, apes, pigs, cows, goats, sheep, horses, dogs, cats and those mammals employed in scientific research commonly known in the art, for example, mice, rats, hamsters, rabbits, guinea-pigs, and ferrets. In one embodiment of the invention, the mammal is a human.

This invention is further illustrated by the following non-limiting examples.

EXAMPLES

Example 1: Insertion of Transfected Cells in an In-Vitro Model of the Human Blood Brain Barrier (BBB) and Export of GFP by the Transfected Cells The purpose of this experiment was to assess the ability of the EPCs to integrate into the BBB.

Specifically, the BBB was set up by coating cell culture inserts with 1:20 collagen for 1 hour at 37° C., followed by seeding with $2\times10^5$ hCMEC/D3 cells in OptiMEM. 500 µl of Optimem was pipetted into a receiver well (i.e., the basolateral side), and the BBB was then incubated for 72 hours at 37° C./5% $CO_2$ in order to allow for monolayer formation. On Day 4, the medium was removed and replaced with HEPC.CB1 pl.CAG.GFP cells. The experimental groups were split into (1) a positive control (n=3) of HEPC.CB1 pl.CAG.GFP only (GFP-EPCs); and (2) a BBB experimental group (n=3) of hCMEC.D3 (BBB)+HEPC.CB1 pl.CAG.GFP cells. Specifically, the HEPC.CB1 cells were suspended in OptiMEM to $1.2\times10^7$/ml, and finally a 200 µl cell suspension was combined with 1800 µl OptiMEM to $10^6$ cells/ml ($2\times10^5$ cells/200 µl). Medium was then removed from upper and lower wells, and 200 µl of the cell suspension as transferred to the upper well. 500 µl of Optimem was added to the lower well and the BBB was allowed to incubated for 48 hours @ 37° C./5% $CO_2$. On Day 6, 300 µl of medium was pipetted from the receiver well (i.e., the basolateral side) into a black 96-well plate. GFP was then quantified using Lumistar (BMG Biotech).

The results showed that when the GFP-EPCs were added to BBB (hCMEC/D3), they insert into the apical and basolateral side, and 37% to 73% of the GFP is found on the basolateral side, suggesting than the GFP-EPCs can integrate into the BBB and release the GFP (the native permeability of this BBB model for 20 kDa protein (similar to GFP) is less than 5%.

Human endothelial precursor cells (HEPC.CB1, the equivalent of murine MAgEC 10.5 cells) were isolated and electroporated. A model of the human blood brain barrier (BBB) was constructed based upon work of Weksler B., Ignacio A Romero and Pierre-Olivier Couraud (2013) Fluids and Barriers of the CNS 2013, 10:16, using a human CMEC/D3 cell line. Injection of $4.5\times10^9$ transfected cells (where the overall cells produced at least 4.5 mg Fab/day) were added to the constituted BBB, incubated overnight with it then washed 3 times and the fluorescence emission of the BBB was assayed. The fluorescence of GFP expressed by the transfected cells, which was detected in the washed BBB, indicated insertion of these cells in the barrier. A schematic of the overall experiment is depicted in FIG. 1.

The electroporated cells (or those treated with cationic lipids) were cultured in cell culture inserts (Millicell®). At 6 hours, 24 hours, 48 hours after electroporation the cells were washed and the GFP fluorescence was measured. The supernatants in the medium on both sides of the BBB were measured as well and the intensity of fluorescence was quantitated after 48 hours. The fluorescence results indicated substantial export of the expressed GFP by the cells transfected.

Figure 2:
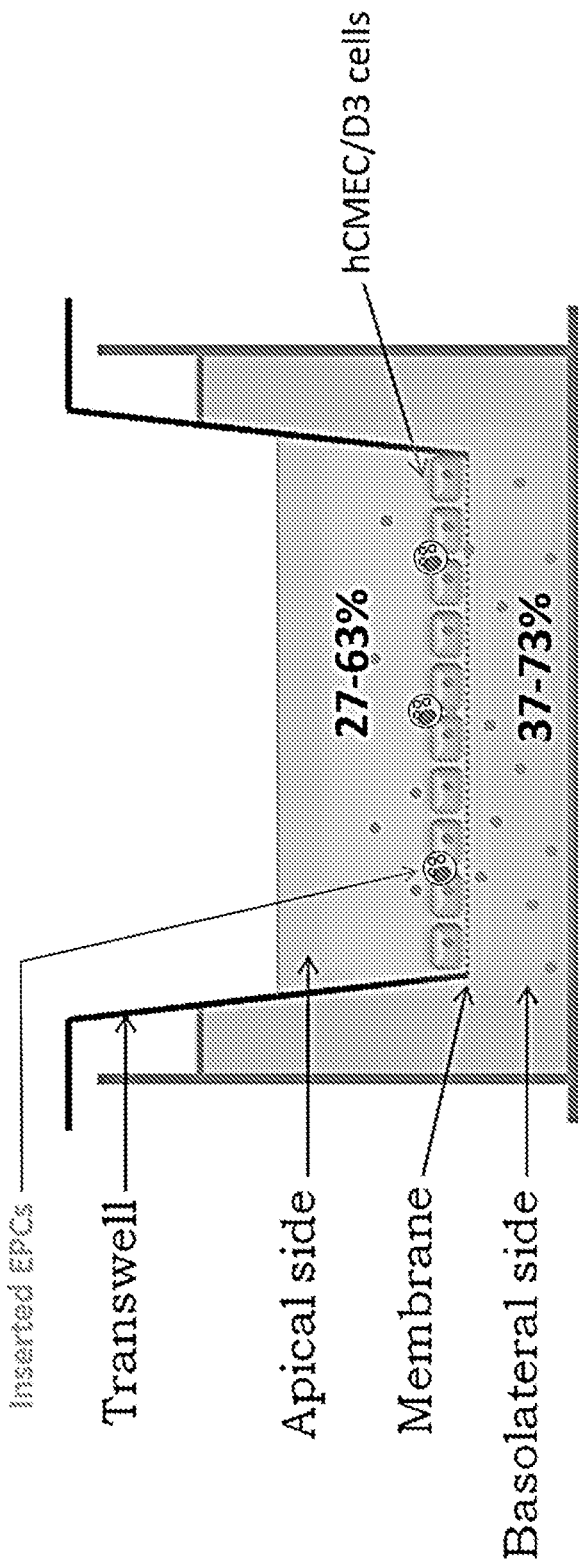
FIG. 2 shows that from 37% to 73% of the GFP expressed by the EPCs was expressed in the basolateral side of the BBB, while from 27%-63% GFP expression was found on the apical side of the BBB.

FIG. 2 shows that from 37% to 73% of the GFP expressed by the EPCs was expressed in the basolateral side of the BBB, while from 27%-63% GFP expression was found on the apical side of the BBB. Taking into account that 37% to 73% of expressed proteins were released from the EPCs inserted into the BBB compared to 0.21% upon systemic IV inoculation of intact antibodies, this experiment showed that a significant amount of antibodies and/or protein end up in the brain parenchyma and microvasculature using the EPCs as targeted carriers and producers of antibodies.

Example 2: Homing of the Transfected Cells to the Brain Microvasculature

Early precursors of brain microvascular endothelial cells and mature cells were transfected with vectors described in Example 5. The two types of transfected cells were inserted in the blood brain barrier in-vitro and GFP fluorescence was measured. Results showed that the insertion of precursor cells in BBB was significantly higher than that of mature cells, which was very weak.

Figure 3:
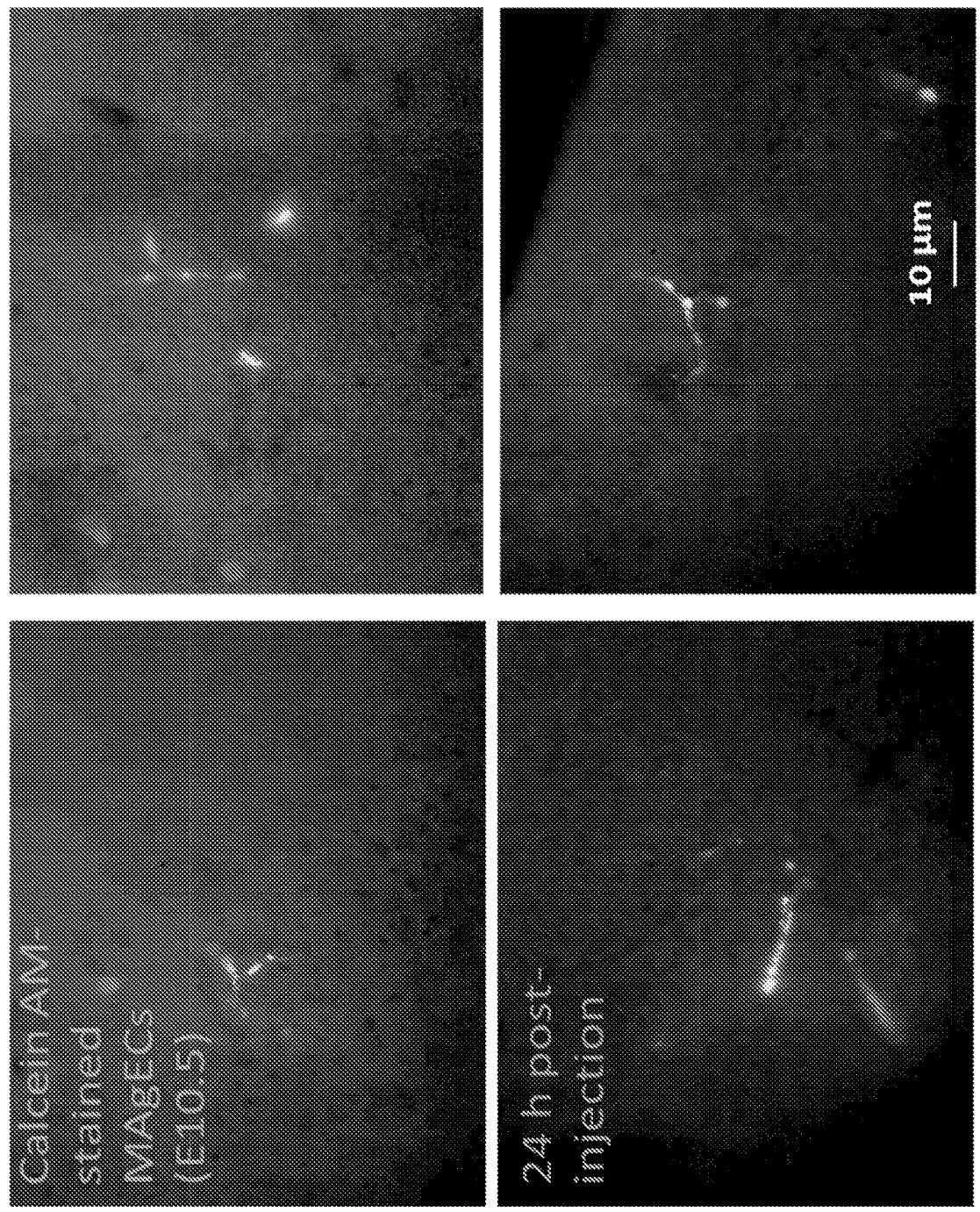
FIG. 3 depicts the fluorescence microscopy detection of GFP-MAgEC 10.5 in the mouse brain microvasculature.

To test whether MAgEC cells (E10.5) would adhere to vessel walls in vivo in the mouse brain and stay there for a prolonged period of time, $10^6$ MAgEC cells were injected into the right common carotid artery of the BALB/cx DSRed$^-$ mouse. 24 hours later, the brain was processed for sectioning and imaging. FIG. 3 depicts the fluorescence microscopy detection of GFP-MAgEC 10.5 in the mouse brain microvasculature. The results show that when the EPCs are co-cultured with mature endothelial cells (MBrMEC), it is observed that insertion of the EPCs into the BBB cooperates to create vessels.

Example 3: Homing of Transfected EPCs to the Blood Brain Barrier

Figures 4A, 4B:
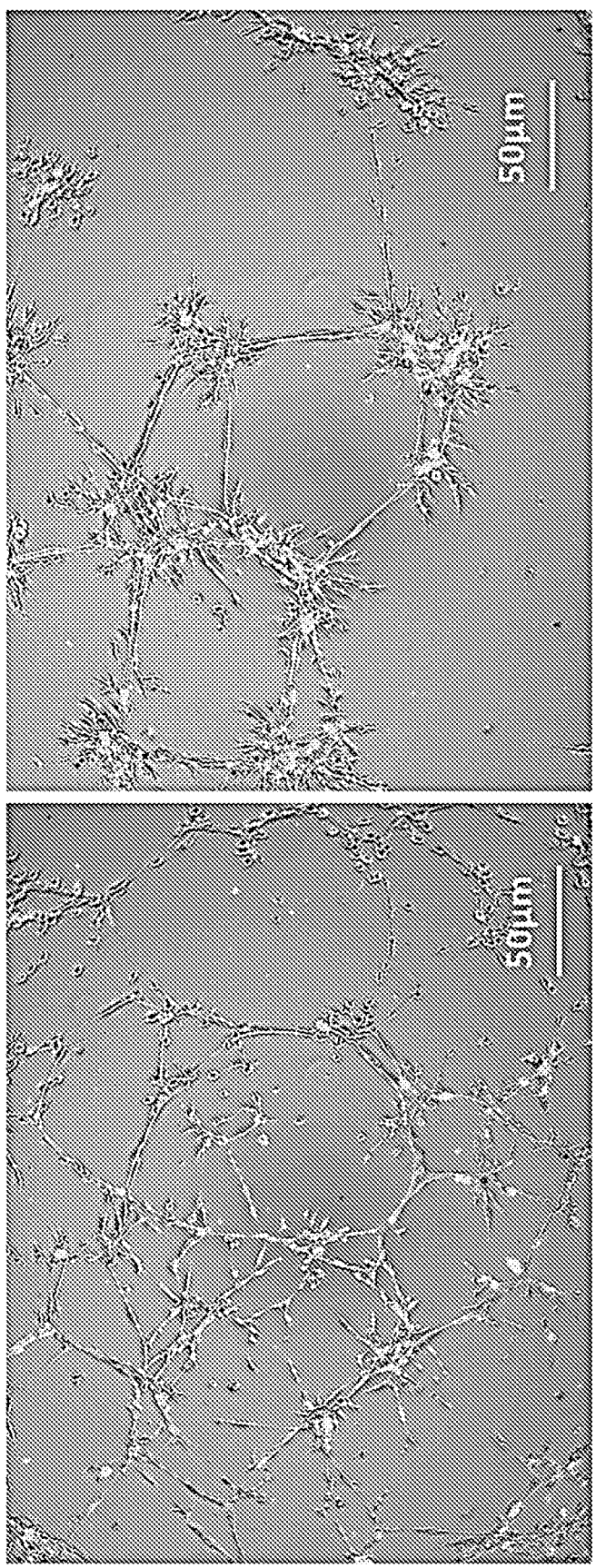
FIG. 4A-B shows cooperation in the angiogenesis process between the co-cultivated BBB (MBrMEC Hoescht-labelled) and the EPCs (GFP-MAgEC 10.5 cells) via co-localization of fluorescence signals.

The purpose of this experiment was to determine whether inserted transfected EPCs were incorporated in the angiogenesis network formed by the BBB cells (MBrMEC cells used as surrogate for BBB). In particular, the cells used were the MBrMEC, Hoescht-labelled beforehand, to create the BBB and the GFP transfected MAgEC10.5 as EPCs. To evaluate the angiogenesis and the interaction between EPCs and BBB, both cell types were seeded on Matrigel-coated wells or slides. The Matrigel matrix was diluted by two thirds in optiMEM (without FBS) at 4° C. Matrigel was allowed to polymerize at room temperature, and then the cells ($2.5\times10^4$ cells per milliliter) were seeded. Endothelial cell rearrangement and vessel formation was observed regularly under an inverted light contrast microscope at specific time points. Cooperation in the angiogenesis process between the co-cultivated BBB (MBrMEC Hoescht-labelled) and the EPCs (GFP-MAgEC 10.5 cells) was shown via co-localization of fluorescence signals, as depicted in FIG. 4A-B. FIG. 4A depicts fluorescence imaging at 5 hours, and FIG. 4B depicts fluorescence imaging at 12 hours. The imaging shows that while the MBrMEC are making tubes, the MAgEC 10.5 cells co-localize with the MBrMEC at the nodes. Indeed, the in vivo experiment on aged WT mice confirmed that the GFP-EPCs migrate to the brain (Homing) as shown on the fluorescence imaging.

Expression vectors were constructed for anti-TDP43 and anti-βamyloid, which are abundantly expressed even in non-specialized human cells and which retain their affinity for the antigens against which they were raised.

When injected in the carotid artery of mice, the homing of the transfected EPCs to the BBB was demonstrated, as well as their association with the BBB. Moreover, it was shown that, in an in vitro BBB model, greater than 70% of the produced proteins by the transfected EPCs are released in the basolateral compartment and only about 22% are left in the apical compartment. Compared with the very low BBB crossing of the intact IgG (0.21%) of the injected mAbs, they represent a potential significant advantage.

Example 4: Solubilization of TDP43 and Aβ Aggregates In Vitro

Antibodies were raised against Aβ and TDP43 in order to determine solubilization of the associated aggregated proteins. To determine the capacity of these antibodies to solubilize preformed TDP43 and Aβ aggregates, a disaggregation assay test of TDP43 and Aβ aggregates was performed. FIG. 7A shows that the antibodies were able to dissolve in-vitro aggregates of the TDP43 proteins. FIG. 7B shows that the antibodies were able to dissolve in-vitro aggregates of the Aβ proteins.

Specifically, reaction tubes containing 30 μg of $TDP43_{311-344}$/10 μl of PBS and 30 μg of $A\beta_{1-16}$/10 μl of PBS, pH 7.3, were incubated for 1 week at 37° C. Aggregation was measured by thioflavin T (ThT)-binding assay in which the dye's fluorescence emission intensity reflects the degree of TDP43 fibrillar aggregation. Disaggregation was followed after addition of various undiluted sera of immunized mice or purified antibodies to the preformed fibers (10 μl each). The reaction mixtures were incubated for 2 days at 37° C. An irrelevant control antibody (mouse IgG) was used at a final concentration of 1 mg/ml. Fluorescence (excitation: 450 nm; emission: 482 nm) was measured on Fluoromax3 (Horiba Fluoromax 4C fluorometer, Japan) after addition of 1 ml of ThT (3 NM in 50 mM sodium phosphate buffer, pH 6.0). Sera with ThT was used as controls to subtract the emission of the sera themselves from the emission of the reaction mixtures (aggregates+ThT±sera), so as to follow the emission of the aggregates only.

Maximum solubilization obtained with both proteins and with the corresponding anti-sera was 100%. FIG. 7A-B depicts the percentage of aggregated protein in the presence of anti-sera of immunized C57BL/6 mice compared to sera of non-immunized mouse (control) measuring the ThT fluorescence emission. FIG. 7A: TDP43 and FIG. 7B: Aβ.

FIG. 8 shows the solubilization of TDP-43 aggregates with purified anti-TDP-43 antibodies (both IgG and Fab) in mice. Specifically, the percentage of TDP-43 aggregates was reduced when anti-TDP-43 antibodies were administered as compared to the control group that was not administered anti-TDP-43 antibodies. The group that was administered the Fab anti-TDP-43 antibody exhibited the greater reduction in TDP-43 aggregates as compared to the control group.

Figure 9A:
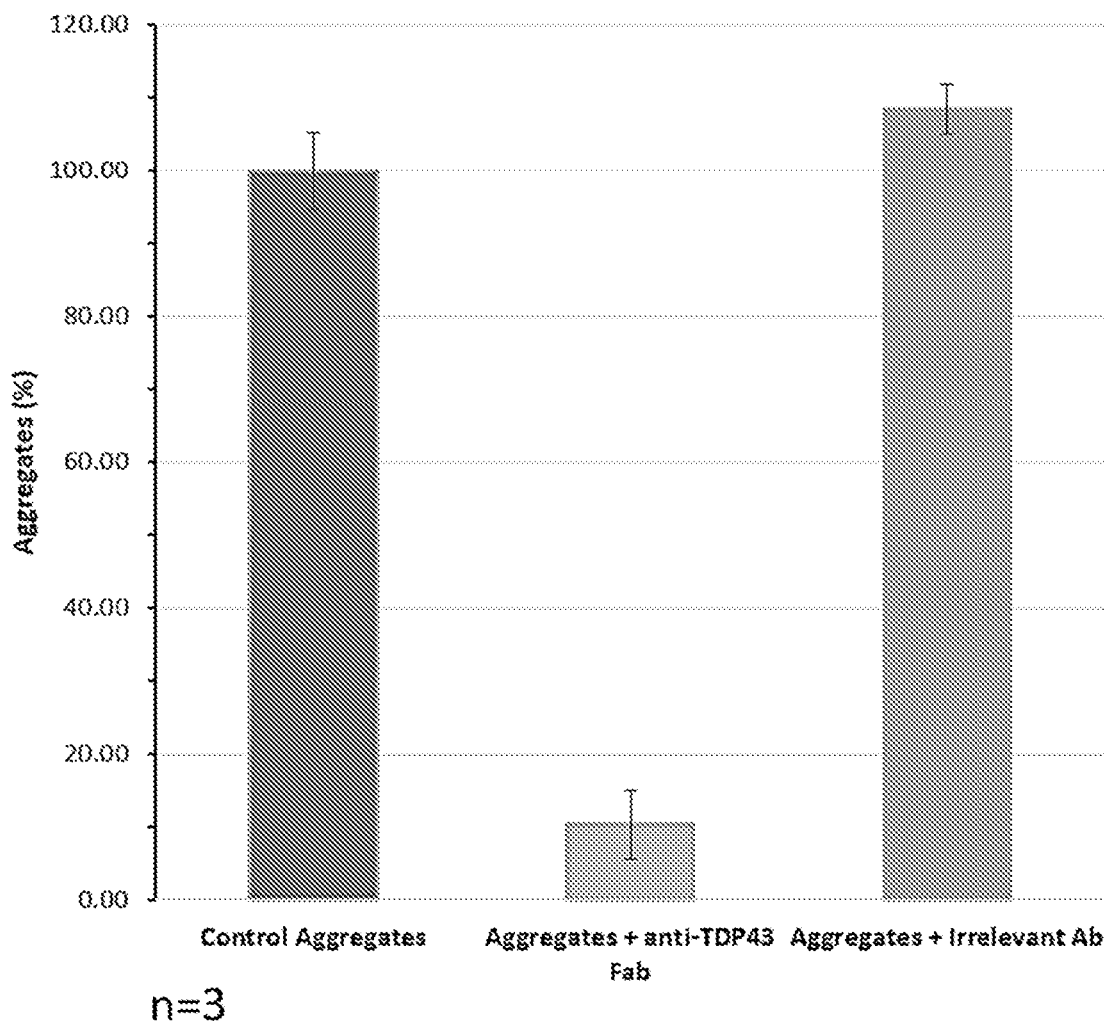
FIG. 9A-B shows the solubilization of TDP-43 and β-Amyloid aggregates.
Figure 9B:
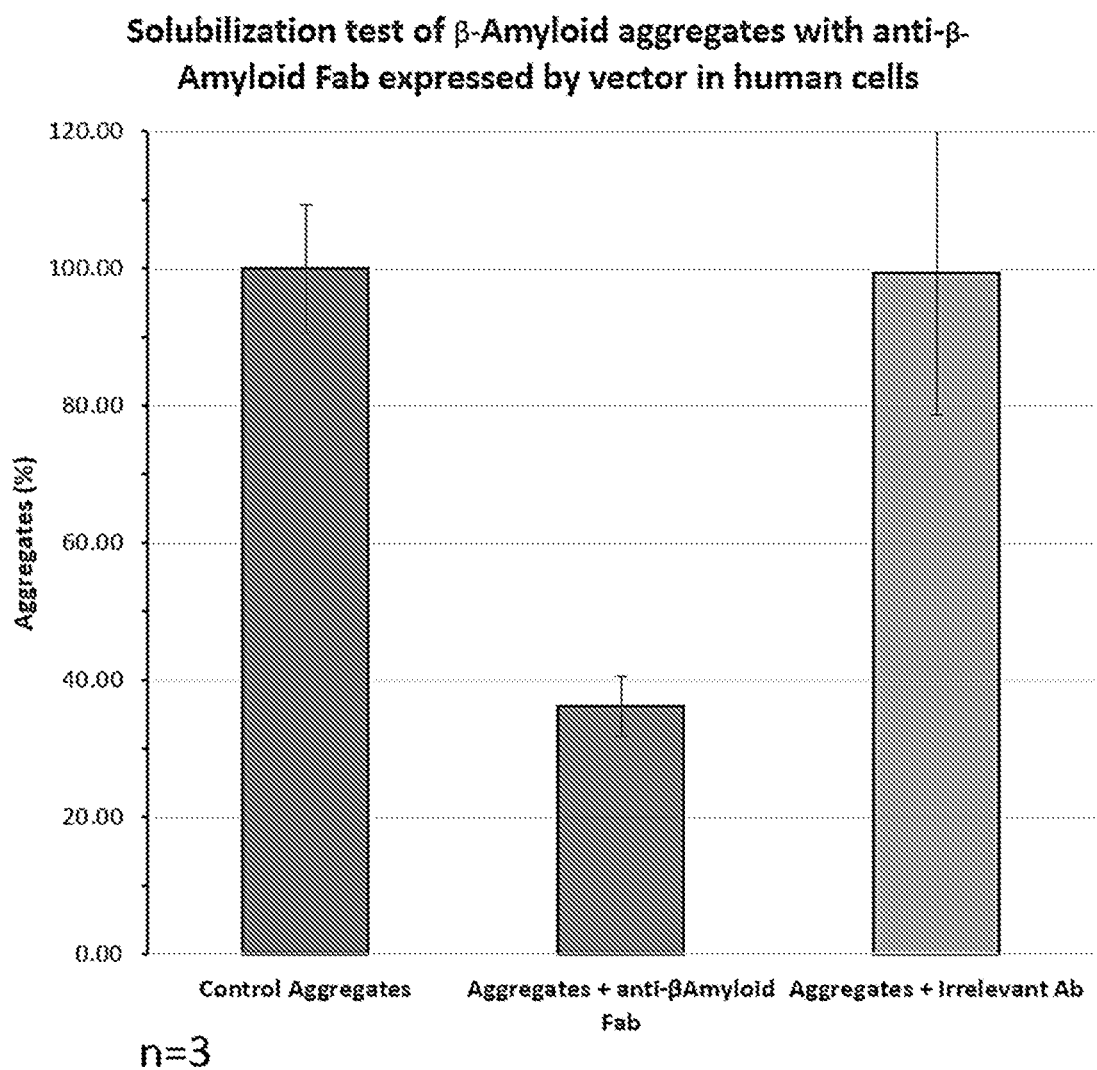

FIG. 9A shows the solubilization of TDP-43 aggregates with the inventive anti-TDP-43 antigen-binding fragments (Fab) expressed by vector in human cells (HEK293 cell line), as compared to a control group where no Fab was administered and a control group where an irrelevant antibody was administered. FIG. 9A depicts a reduction in the percentage of TDP-43 aggregates where anti-TDP-43 Fab was administered, as compared to the control groups. Accordingly, the data shows that the inventive anti-TDP-43 Fab, which was successfully expressed in human HEK cells, produced active Fab and the capacity of the anti-TDP-43 Fab to solubilize aggregates was about 90% of the aggregates. FIG. 9B shows the solubilization of β-Amyloid aggregates with the inventive anti-β-Amyloid antigen-binding fragments (Fab) expressed by vector in human cells (HEK293 cell line), as compared to a control group where no Fab was administered and a control group where an irrelevant antibody was administered. FIG. 9B depicts a reduction in the percentage of β-Amyloid aggregates where anti-β-Amyloid Fab was administered, as compared to the control groups. Accordingly, the data shows that the inventive anti-β-Amyloid Fab, which was successfully expressed in human HEK cells, produced active Fab and the capacity of the anti-β-Amyloid Fab to solubilize aggregates was about 64% of the aggregates.

Example 5: Preparation of Expression Vectors

Vectors were created express secreted GFP, anti-δ-Amyloid fragment antibody (Fab) and anti-TDP43 Fab. The backbone is the same for all, e.g., a CAG promoter to have a strong expression in Endothelial Progenitor Cells (EPCs); the Kanamycin for bacteria selection; and the Hygromycin for mammal cells selection. The GFP vector includes an insulin peptide signal to allow the secretion of the GFP from the EPCs. There are three vectors for the "anti-protein" vectors, one expressing the light chain of the Fab, one the heavy chain (including a 10-His tag) and one "Dual" expressing both chains (with His tag) with a dual CAG promoter.

The vectors used were based on the pUC high copy derived from pBR322. A Synapsin promoter is included to promote expression in neurons or a CAG promoter is included for their expression in endothelial cells. The protein expressed is the eGFP and a peptide signal from the insulin gene. In this way, the GFP expressed in neurons or endothelial cells was secreted, favored by the peptide signal. In the case of neuron targeting, a 14 aa peptide sequence X will be used. FIG. 10 depicts a map of the OG4768_pSF-CAG-Insulin SP-GFP vector. FIG. 11 depicts a map of the OG503_pSF-Synapsin-Insulin SP-GFP vector. FIG. 12 depicts a map of the Q7226 pSF-CAG Prom Insulin SP-EGFP Hygro vector.

GFP expression was measured over time using the plasmid GFP (i.e., Q7226 pSF-CAG Prom Insulin SP-EGFP Hygro) of FIG. 12. As depicted in FIG. 5A-C, flow cytometry was used to measure GFP expression by EPCs transfected with the vector over time, where MAgEC 10.5 p.8 is synonymous with MAgEC 10.5 cells after 8 passages and MAgEC 10.5 p.9 is synonymous with MAgEC 10.5 cells after 9 passages. A wild-type control where cells were not transfected with a vector showed little to no GFP expression. FIG. 6 depicts GFP secretion as a function of cell number. The GFP-EPCs clones created by stable lipotransfection that were characterized for long-term expression displayed strong GFP expression even after 9 passages.

Example 6: Transfection of Microvascular Endothelial Cells

Brain microvascular endothelial cells (and/or their precursors) collected from WT mice and transgenic mice for human Alzheimer 5xFAD are transfected with the vectors described in Example 5 either by electroporation or with the help of cationic lipids, e.g., lipofectine, lipofectamine. Expression is followed by measuring the fluorescence emission of GFP.

The 5xFAD transgenic mice overexpress mutant human APP (695) with four Familial Alzheimer's Disease (FAD)

mutations along with human PS1 harboring two FAD mutations. Both transgenes are regulated by the mouse Thy1 promoter to drive overexpression in the brain. 5×FAD mice recapitulate major features of Alzheimer's Disease amyloid pathology and may be a useful model of intraneuronal Abeta-42 induced neurodegeneration and amyloid plaque formation.

EQUIVALENTS

While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features hereinbefore set forth.

Those skilled in the art will recognize, or be able to ascertain, using no more than routine experimentation, numerous equivalents to the specific embodiments described specifically herein.

INCORPORATION BY REFERENCE

All patents and publications referenced herein are hereby incorporated by reference in their entireties.

The publications discussed herein are provided solely for their disclosure prior to the filing date of the present application. Nothing herein is to be construed as an admission that the present invention is not entitled to antedate such publication by virtue of prior invention.

As used herein, all headings are simply for organization and are not intended to limit the disclosure in any manner. The content of any individual section may be equally applicable to all sections.

REFERENCES

All of the following documents are incorporated by reference in their entireties.
1. Polymenidou, M. and D. W. Cleveland (2011) Cell 147, 498-508
2. Polymenidou, M. and D. W. Cleveland (2012) J. Exp. Med 209, 889-893
3. Lagier-Tourenne, C., Polymenidou, M. and Cleveland, D. W. (2010) Hum Mol Genet 19 (R1), R46-R64
4. Nicolau, C., Greferath, R, Balaban T. S. Lazarte J. E. and Hopkins R. L. (2002) Proc. Natl. Acad. Sci. USA 99, 2332-2337
5. Muhs, A., Hickman, D. T., Pihlgren, M., Chouard, N., Giriens, V., Meershman, C., Van de Auwera, I., Leuven, F. V., Sugawara, M., Weingartner, M. C., Bechinger Greferath, R., Kolonko, N., Nagel-Steger, L., Riesner, D., Brady R. O., Pfeifer, A. and Nicolau, C. (2007) Proc. Natl. Acad. Sci. USA 104, 9810-9815
6. Hickman, D. T., Lopez-Deber, M. P., Ndao, D. M., Silva, A. B., Nand, D., Pihlgren, M., Giriens, V., Madani, R., St-Pierre, A., Karastaneva, H., Nagel-Steger, L., Willbold, D., Riesner, D., Nicolau, C., Baldus, M., Pfeifer, A. and Muhs, A. (2011) J. Biol. Hem. 286, 13966-13976
7. Rosen, D. R., Siddique, T., Patterson, D., Figlewicz D., et al (1993) Nature 362, 59-62
8. Ilieva, H., Polymenidou, M., Cleveland, D. W. (2009) J. Cell Biol. 187, 761-772
9. Kerman, A., Liu, H. N., Croul, S., Bilbao, J. et al. (2010) Acta Neuropathol. 119, 335-344
10. Bosco, D. A., Morfini, G., Karabaca, Song, Y., et al (2010) Nature Neurosci 13, 1396-1403
11. Arai, T., Hasegawa, M., Akiyama, H., Ikeda, K. et al (2006) Biochem. Biophys. Comm. 351, 602-611
12. Newman, M., Sampather, D. N., Kwong, L. K., Trux, A. C. et al (2006) Science 314, 130-133
13. Gilks, N., Kederasha, N., Agodele, M., Sen, L. et al (2004) Mol. Biol. Cell 15, 5383-5398
14. Kabashi, E., Vidmanis, P. N., Dion, P., Spiegelman, D. et al (2008) Nat. Genet 40, 572-574
15. Sredharan, J., Blair I. P., Tripethi, V. B., Hu, X. et al (2008) Science 319, 1668-1672
16. Vance, C., Rogelj, B., Hortobagyi, T., DeVoss K. J. et al (2009) Science 323, 1208-1211
17. Chia, R., Tattum, M. H., Jones, S., Collings, I. J. et al (2010) PloS One 5, e10627
18. Grad, L. I., Guest, W. C., Yanai, A., Pokrikeusky, A. et al (2011) Proc. Natl. Acad. Sci USA 108, 16398-16403
19. Munch, C., O'Brien, J. and Bertolotti, A. (2011) Proc. Natl. Acad. Sci USA 108, 3548-3553
20. Prudencio, M., Hart P. J., Borchlt, D. R. and Anderson, P. M. (2009) Hum. Mol. Genet 18, 3217-3226
21a. Tosi, P. F., Rada, D., Nicolau C. (1995) Biochem. Biophys. Res. Comm. 212, 494-500
21b. Pawlack-Robin, C., Tosi, P. F., Perrin, J., Devy, L. et al (2004) Eur. J. Cancer 40, 606-613
22. Perrin, J., Gatocrillat, G., Balasse, El, Odot, J., Nicolau, C. et al (2007) Biochem. Biophys. Res. Comm. 3, 325-330
23. Gatouillat, G., Odot, E., Balasse, E. et al (2007) Cancer Lett. 257, 165-171.
24. Lim L., Wey Y., Lu Y., Song J. (2016) PLOS Biology
25. Chandra, S., et. Al. (2003) J. Biol. Chem. 278, 15313-18.
26. Leonidas Stefanis (2012) CSH Persp. Med. 4:a009399.
27. Mandelkow, E., et. Al. (2012) CSH Persp. Med. 2:a006247.
28. Marzban, L., et. Al. (2003) Exp. Geront. 38, 347-351.
29. Jaikaran, E., et. Al. (2001) Biochem. Bioph. Acta 1537, 179-203.
30. Higham, C., et. Al. (2000) Eur. J. Biochem. 267, 4998-5004.
31. Watson, D., et. Al. (2009) Vaccine 27, 4672-83.
32. Alving, C., et. Al. (2012) Expert Rev. Vacc. 11, 733-744.
33. Deffar, K., et. Al. (2009) J. Mol. Biol. 425, 2397-411.
34. Harmsen, M. and Haard, H. (2007) App. Micro. Biotech. 77, 13-22.
35. Guilliams, T., et. Al. (2013) J. Mol. Biol. 425, 2397-411.
36. Hickman et al. (2016) U.S. Pat. No. 9,289,488 B2
37. Weksler B., Ignacio A Romero and Pierre-Olivier Couraud (2013) Fluids and Barriers of the CNS 2013, 10:16
38. Klimkiewicz et al. (2017) Cancer Letters. 396, pages 10-20.
39. Collet et al. (2015) Contemp. Oncol. (Pozn.). 19(1A): A39-A43.
40. Kieda et al. (2016) U.S. Pat. No. 9,228,173 B2
41. Kieda et al. (2017) U.S. Pat. No. 9,631,178 B2

What is claimed is:

1. A composition comprising a nucleic acid encoding a Fab directed against TDP43, the anti-TDP43 Fab comprising:
   (i) a variable heavy domain (VH) comprising: the amino acid sequence of SEQ ID NO: 13 and complementarity-determining region (CDR) 1 having the amino acid sequence of SEQ ID NO: 19,
   CDR2 having the amino acid sequence of SEQ ID NO: 20, and
   CDR3 having the amino acid sequence of SEQ ID NO: 21; and
   (ii) a variable light domain (VL) comprising: the amino acid sequence of SEQ ID NO: 14 and
   CDR1 having the amino acid sequence of SEQ ID NO: 22,
   CDR2 having the amino acid sequence of SEQ ID NO: 23, and
   CDR3 having the amino acid sequence of SEQ ID NO: 24.

2. The composition of claim 1, wherein the anti-TDP43 Fab further comprises a signal peptide having the amino acid sequence of SEQ ID NO: 34 or SEQ ID NO: 35.

3. An expression vector comprising the nucleic acid of claim 1.

4. An isolated host cell comprising the expression vector of claim 3.

5. A pharmaceutical composition comprising the composition of claim 1 and a pharmaceutically acceptable carrier.

6. An isolated microvascular endothelial cell (MEC) comprising a nucleic acid encoding a Fab directed against TDP43, the anti-TDP-43 Fab comprising:
   (i) a variable heavy domain (VH) comprising: the amino acid sequence of SEQ ID NO:13 and complementarity-determining region (CDR) 1 having the amino acid sequence of SEQ ID NO:19, CDR2 having the amino acid sequence of SEQ ID NO:20, and CDR3 having the amino acid sequence of SEQ ID NO:21; and
   (ii) a variable light domain (VL) comprising: the amino acid sequence of SEQ ID NO:14 and CDR1 having the amino acid sequence of SEQ ID NO:22, CDR2 having the amino acid sequence of SEQ ID NO:23, and CDR3 having the amino acid sequence of SEQ ID NO:24.

7. The MEC of claim 6, wherein the MEC is a brain-derived MEC which homes to brain microvasculature and traffic and release the anti-TDP43 Fab past blood brain barrier (BBB).

8. The MEC of claim 6, wherein the MEC is autologous, and wherein the MEC is derived from bone marrow, brain, CNS, heart, liver, or pancreas.

9. The MEC of claim 6, wherein the nucleic acid comprises a CAG promoter that promotes expression in endothelial cells and/or an insulin sequence that promotes export of the anti-TDP43 Fab.

10. The MEC of claim 6, wherein the anti-TDP43 Fab comprises a signal peptide having the amino acid sequence of SEQ ID NO: 34 or SEQ ID NO: 35.

* * * * *

SEQUENCE LISTING

```
Sequence total quantity: 94
SEQ ID NO: 1              moltype = DNA   length = 360
FEATURE                   Location/Qualifiers
misc_feature              1..360
                          note = Synthetic polymer.
source                    1..360
                          mol_type = other DNA
                          organism = synthetic construct
SEQUENCE: 1
caggttcagc tgcagcagtc tggagctgag ctggcgaggc ctggggcttc agtgaagctg    60
tcctgcaagg cttctggcta caccttcaca agctatggta taagctgggt gaggcagaga   120
actggacagg gccttgagtg gattggagag atttatccta gacgtggtaa tacttactac   180
aatgagaagt tcaagggcaa ggccacactg actgcataca aatcctccgg cacagcgtac   240
atggagctcc gcagcctgac atctgaggac tctgcggtct ttttctgtgc aagagggggt   300
atctactatg gtaacttatt tgactactgg ggccaaggca ccactctcac agtctcctca   360

SEQ ID NO: 2              moltype = DNA   length = 57
FEATURE                   Location/Qualifiers
misc_feature              1..57
                          note = Synthetic polymer.
source                    1..57
                          mol_type = other DNA
                          organism = synthetic construct
SEQUENCE: 2
atggaatgga tctggatctt tctcttcatc ctgtcaggaa ctgcaggtgt ccaatcc        57

SEQ ID NO: 3              moltype = DNA   length = 1008
FEATURE                   Location/Qualifiers
misc_feature              1..1008
                          note = Synthetic polymer.
source                    1..1008
                          mol_type = other DNA
                          organism = synthetic construct
SEQUENCE: 3
gccaaaacaa caccccatc agtctatcca ctggcccctg ggtgtggaga tacaactggt     60
tcctctgtga ctctgggatg cctggtcaag ggctacttcc ctgagtcagt gactgtgact   120
tggaactctg gatccctgtc cagcagtgtg cacaccttcc cagctctcct gcagtctgga   180
ctctacacta tgagcagctc agtgactgtc ccctccagca cctggccaag tcagaccgtc   240
acctgcagcg ttgctcaccc agccagcagc accacgtgg acaaaaaact gagcccagc    300
gggcccattt caacaatcaa ccctgtcct ccatgacagg agtgtcacaa atgcccagct   360
cctaacctcg agggtggacc atccgtcttc atcttccctc caaatatcaa ggatgtactc   420
atgatctccc tgacacccaa ggtcacgtgt gtggtggtgg atgtgagcga ggatgaccca   480
gacgtccgga tcagctggtt tgtgaacaac gtggaagtac acacagctca gacacaaacc   540
catagaggga attacaacag tactatccgg gtggtcagc ccctccccat ccagccaccag   600
gactggatga gtggcaagga gttcaaatgc aaggtcaaca caaagacct cccatcaccc   660
atcgagagaa ccatctcaaa aattaaaggg ctagtcagag ctccacaagt atacatcttg   720
ccgccaccag cagagcagtt gtccaggaaa gatgtcagtc tcacttgcct ggtcgtgggc   780
ttcaaccctg gagacatcag tgtggagtgg accagcaatg ggcatacaga ggagaactac   840
aaggacaccg caccagtcct ggactctgac ggttcttact tcatatacag caagctcgat   900
ataaaaacaa gcaagtggga gaaaacagat tccttctcat gcaacgtgag acacgagggt   960
ctgaaaaatt actacctgaa gaagaccatc tcccggtctc cgggtaaa              1008

SEQ ID NO: 4              moltype = DNA   length = 330
FEATURE                   Location/Qualifiers
misc_feature              1..330
                          note = Synthetic polymer.
source                    1..330
                          mol_type = other DNA
                          organism = synthetic construct
SEQUENCE: 4
caggctgttg tgactcagga atctgcactc accacatcac ctggtgaaac agtcacactc     60
acttgtcgct caagtactgg ggctgttaca actagtaact atgccaactg ggtccaagaa   120
aaaccagatc atttattcac tggtctaata ggtggtacca caaccgagc tccaggtgtt    180
cctgccagat tctcaggctc cctgattgga gacaaggctg ccctcaccat cacagggca    240
cagactgagg atgaggcaat atatttctgt gctctatggt tcagcaacca ctgggtgttc   300
ggtggaggaa ccaaactgac tgtcctaggc                                    330

SEQ ID NO: 5              moltype = DNA   length = 57
FEATURE                   Location/Qualifiers
misc_feature              1..57
                          note = Synthetic polymer.
source                    1..57
                          mol_type = other DNA
                          organism = synthetic construct
SEQUENCE: 5
atggcctgga tttcacttat actctctctc ctggctctca gctcaggggc catttcc        57

SEQ ID NO: 6              moltype = DNA   length = 315
```

```
FEATURE                 Location/Qualifiers
misc_feature            1..315
                        note = Synthetic polymer.
source                  1..315
                        mol_type = other DNA
                        organism = synthetic construct
SEQUENCE: 6
cagcccaagt cttcgccatc agtcaccctg tttccacctt cctctgaaga gctcgagact      60
aacaaggcca cactggtgtg tacgatcact gatttctacc caggtgtggt gacagtggac     120
tggaaggtag atggtacccc tgtcactcag ggtatggaga caacccagcc ttccaaacag     180
agcaacaaca agtacatggc tagcagctac ctgaccctga cagcaagagc atgggaaagg     240
catagcagtt acagctgcca ggtcactcat gaaggtcaca ctgtggagaa gagtttgtcc     300
cgtgctgact gttcc                                                      315

SEQ ID NO: 7            moltype = DNA   length = 336
FEATURE                 Location/Qualifiers
misc_feature            1..336
                        note = Synthetic polymer.
source                  1..336
                        mol_type = other DNA
                        organism = synthetic construct
SEQUENCE: 7
caggttcagc tgcagcagtc tggggctgag ctggtgaagc ctggggcctc agtgaagatt      60
tcctgcaaag cttctggcta cgcattcagt aactactgga tgaactgggt gaagcagagg     120
cctggaaagg gtcttgagtg gattggacag atttatcctg agatggtgga tactaactac     180
aacgaaaagt tcaagggcaa ggccacactg actgcagaca atcctccag cacagcctac      240
atgcagtcag gcagcctgac ctctgaggac tctgcggtct atttctgtgc aagaggtgac     300
tactggggcc aaggcaccac tctcacagtc tcctca                               336

SEQ ID NO: 8            moltype = DNA   length = 339
FEATURE                 Location/Qualifiers
misc_feature            1..339
                        note = Synthetic polymer.
source                  1..339
                        mol_type = other DNA
                        organism = synthetic construct
SEQUENCE: 8
gacattgtga tgacacagtc tccatcctcc ctggctatgt cagtaggaca gaaggtcact      60
atgagctgca agtccagtca gagcctttta aatagtagca atcaaaagaa ctatttggcc     120
tggtaccagc agaaaccagg acagtctcct aaacttctgg tatactttgc atccactagg     180
gaatctgggg tccctgatcg cttcataggc agtggatctg ggacagattt cactcttacc     240
atcagcagtg tgcaggctga agacctggca gattacttct gtcagcaaca ttataacact     300
ccgctcacgt tcggtgctgg gaccaagctg gagctgaaa                            339

SEQ ID NO: 9            moltype = DNA   length = 1365
FEATURE                 Location/Qualifiers
misc_feature            1..1365
                        note = Synthetic polymer.
source                  1..1365
                        mol_type = other DNA
                        organism = synthetic construct
SEQUENCE: 9
gagagtcagt ccttcccaaa tgtcttcccc ctcgtctcct gcgagagccc cctgtctgat      60
aagaatctgg tggccatggg ctgcctggcc cggacttcc tgcccagcac catttccttc      120
acctggaact accagaacaa cactgaagtc atccaggta tcagaacctc cccaacactg      180
aggacagggg gcaagtacct agccacctg caggtgttgc tgtctcccaa gagcatcctc      240
gaaggttcag atgaatacct ggtatgcaaa atccactacg gaggcaaaaa caaagatctg     300
catgtgccca ttccagctgt cgcagagatg aaccccaatg taaatgtgtt cgtcccacca     360
cgggatggct tctctggccc tgcaccacgc aagtctaaac tcatctgcga ggccacgaac     420
ttcactccaa aaccgatcac agtatcctgg ctaaggatg ggaagctcgt ggaatcggc       480
ttcaccacag atccggtgac catcgagaac aaaggatcca cccccaaac ctacaaggtc      540
ataagcacac ttaccatctc tgaaatcgac tggctgaacc tgaatgtgta cacctgccgt     600
gtggatcaca ggggtctcac cttcttgaag aacgtgtcct ccacatgtgc tgccagtccc     660
tccacagaca tcctaacctt caccatcccc ccctccttg ccgacatctt cctcagcagg      720
tccgctaacc tgacctgtct ggtctcaaac ctgcaacct atgaaaccct gaatatctcc      780
tgggcttctc aaagtggtga accactgaa accaaaatta aaatcatgga agccatccc       840
aatggcacct tcagtgctaa gggtgtggct agtgtttgtg tggaagactg gaataacagg     900
aaggaattg tgtgtactgt gactcacagg gatctgcctt caccacagaa gaaattcatc      960
tcaaaccca atgaggtgca caaaatccca cctgctgtgt acctgctgcc accagctcgt     1020
gagcaactga acctgagga gtcagccaca gtcacctgcc tggtgaaggg cttctctcct     1080
gcagacatca gtgtgcagtg gcttcagaga gggcaactct tgcccaagaa gaagtatgtg     1140
accagtgccc cgatgccaga gcctgggcc ccaggcttct actttaccca cagcatcctg     1200
actgtgcagg aggaggaatg gaactccgga gagaccata cctgtgttgt aggccacgag     1260
gccctgccac acctggtgac cgagaggacc gtggacaagt ccactggtaa acccacactg    1320
tacaatgtct ccctgatcat gtctgacaca ggcggcacct gctat                    1365

SEQ ID NO: 10           moltype = DNA   length = 321
FEATURE                 Location/Qualifiers
misc_feature            1..321
```

```
                        note = Synthetic polymer.
source                  1..321
                        mol_type = other DNA
                        organism = synthetic construct
SEQUENCE: 10
cgggctgatg ctgcaccaac tgtatccatc ttcccaccat ccagtgagca gttaacatct   60
ggaggtgcct cagtcgtgtg cttcttgaac aacttctacc ccaaagacat caatgtcaag  120
tggaagattg atggcagtga acgacaaaat ggcgtcctga cagttggac tgatcaggac   180
agcaaagaca gcacctacag catgagcagc accctcacgt tgaccaagga cgagtatgaa  240
cgacataaca gctatacctg tgaggccact cacaagacat caacttcacc cattgtcaag  300
agcttcaaca ggaatgagtg t                                            321

SEQ ID NO: 11           moltype = DNA   length = 57
FEATURE                 Location/Qualifiers
misc_feature            1..57
                        note = Synthetic polymer.
source                  1..57
                        mol_type = other DNA
                        organism = synthetic construct
SEQUENCE: 11
atggaatggc ctttgatctt tctcttcctc ctgtcaggaa ctgcaggtgt ccaatcc      57

SEQ ID NO: 12           moltype = DNA   length = 60
FEATURE                 Location/Qualifiers
misc_feature            1..60
                        note = Synthetic polymer.
source                  1..60
                        mol_type = other DNA
                        organism = synthetic construct
SEQUENCE: 12
atggaatcac agacccaggt cctcatgttt cttctgctct gggtatctgg tgcctgtgca   60

SEQ ID NO: 13           moltype = AA    length = 120
FEATURE                 Location/Qualifiers
REGION                  1..120
                        note = Synthetic polymer.
source                  1..120
                        mol_type = protein
                        organism = synthetic construct
SEQUENCE: 13
QVQLQQSGAE LARPGASVKL SCKASGYTFT SYGISWVRQR TGQGLEWIGE IYPRRGNTYY   60
NEKFKGKATL TAYKSSGTAY MELRSLTSED SAVFFCARGG IYYGNLFDYW GQGTTLTVSS  120

SEQ ID NO: 14           moltype = AA    length = 110
FEATURE                 Location/Qualifiers
REGION                  1..110
                        note = Synthetic polymer.
source                  1..110
                        mol_type = protein
                        organism = synthetic construct
SEQUENCE: 14
QAVVTQESAL TTSPGETVTL TCRSSTGAVT TSNYANWVQE KPDHLFTGLI GGTNNRAPGV   60
PARFSGSLIG DKAALTITGA QTEDEAIYFC ALWFSNHWVF GGGTKLTVLG             110

SEQ ID NO: 15           moltype = AA    length = 336
FEATURE                 Location/Qualifiers
REGION                  1..336
                        note = Synthetic polymer.
source                  1..336
                        mol_type = protein
                        organism = synthetic construct
SEQUENCE: 15
AKTTPPSVYP LAPGCGDTTG SSVTLGCLVK GYFPESVTVT WNSGSLSSSV HTFPALLQSG   60
LYTMSSSVTV PSSTWPSQTV TCSVAHPASS TTVDKKLEPS GPISTINPCP PCKECHKCPA  120
PNLEGGPSVF IFPPNIKDVL MISLTPKVTC VVVDVSEDDP DVRISWFVNN VEVHTAQTQT  180
HREDYNSTIR VVSALPIQHQ DWMSGKEFKC KVNNKDLPSP IERTISKIKG LVRAPQVYIL  240
PPPAEQLSRK DVSLTCLVVG FNPGDISVEW TSNGHTEENY KDTAPVLDSD GSYFIYSKLD  300
IKTSKWEKTD SFSCNVRHEG LKNYYLKKTI SRSPGK                           336

SEQ ID NO: 16           moltype = AA    length = 105
FEATURE                 Location/Qualifiers
REGION                  1..105
                        note = Synthetic polymer.
source                  1..105
                        mol_type = protein
                        organism = synthetic construct
SEQUENCE: 16
QPKSSPSVTL FPPSSEELET NKATLVCTIT DFYPGVVTVD WKVDGTPVTQ GMETTQPSKQ   60
SNNKYMASSY LTLTARAWER HSSYSCQVTH EGHTVEKSLS RADCS                  105
```

```
SEQ ID NO: 17          moltype = AA   length = 19
FEATURE                Location/Qualifiers
REGION                 1..19
                       note = Synthetic polymer.
source                 1..19
                       mol_type = protein
                       organism = synthetic construct
SEQUENCE: 17
MEWIWIFLFI LSGTAGVQS                                                      19

SEQ ID NO: 18          moltype = AA   length = 19
FEATURE                Location/Qualifiers
REGION                 1..19
                       note = Synthetic polymer.
source                 1..19
                       mol_type = protein
                       organism = synthetic construct
SEQUENCE: 18
MAWISLILSL LALSSGAIS                                                      19

SEQ ID NO: 19          moltype = AA   length = 5
FEATURE                Location/Qualifiers
REGION                 1..5
                       note = Synthetic polymer.
source                 1..5
                       mol_type = protein
                       organism = synthetic construct
SEQUENCE: 19
SYGIS                                                                      5

SEQ ID NO: 20          moltype = AA   length = 17
FEATURE                Location/Qualifiers
REGION                 1..17
                       note = Synthetic polymer.
source                 1..17
                       mol_type = protein
                       organism = synthetic construct
SEQUENCE: 20
EIYPRRGNTY YNEKFKG                                                        17

SEQ ID NO: 21          moltype = AA   length = 11
FEATURE                Location/Qualifiers
REGION                 1..11
                       note = Synthetic polymer.
source                 1..11
                       mol_type = protein
                       organism = synthetic construct
SEQUENCE: 21
GGIYYGNLFD Y                                                              11

SEQ ID NO: 22          moltype = AA   length = 14
FEATURE                Location/Qualifiers
REGION                 1..14
                       note = Synthetic polymer.
source                 1..14
                       mol_type = protein
                       organism = synthetic construct
SEQUENCE: 22
RSSTGAVTTS NYAN                                                           14

SEQ ID NO: 23          moltype = AA   length = 7
FEATURE                Location/Qualifiers
REGION                 1..7
                       note = Synthetic polymer.
source                 1..7
                       mol_type = protein
                       organism = synthetic construct
SEQUENCE: 23
GTNNRAP                                                                    7

SEQ ID NO: 24          moltype = AA   length = 9
FEATURE                Location/Qualifiers
REGION                 1..9
                       note = Synthetic polymer.
source                 1..9
                       mol_type = protein
                       organism = synthetic construct
SEQUENCE: 24
```

ALWFSNHWV                                                                                  9

SEQ ID NO: 25           moltype = AA  length = 414
FEATURE                 Location/Qualifiers
REGION                  1..414
                        note = Synthetic polymer.
source                  1..414
                        mol_type = protein
                        organism = synthetic construct
SEQUENCE: 25
MSEYIRVTED ENDEPIEIPS EDDGTVLLST VTAQFPGACG LRYRNPVSQC MRGVRLVEGI    60
LHAPDAGWGN LVYVVNYPKD NKRKMDETDA SSAVKVKRAV QKTSDLIVLG LPWKTTEQDL   120
KEYFSTFGEV LMVQVKKDLK TGHSKGFGFV RFTEYETQVK VMSQRHMIDG RWCDCKLPNS   180
KQSQDEPLRS RKVFVGRCTE DMTEDELREF FSQYGDVMDV FIPKPFRAFA FVTFADDQIA   240
QSLCGEDLII KGISVHISNA EPKHNSNRQL ERSGRFGGNP GGFGNQGGFG NSRGGGAGLG   300
NNQGSNMGGG MNFGAFSINP AMMAAAQAAL QSSWGMMGML ASQQNQSGPS GNNQNQGNMQ   360
REPNQAFGSG NNSYSGSNSG AAIGWGSASN AGSGSGFNGG FGSSMDSKSS GWGM         414

SEQ ID NO: 26           moltype = AA  length = 34
FEATURE                 Location/Qualifiers
REGION                  1..34
                        note = Synthetic polymer.
source                  1..34
                        mol_type = protein
                        organism = synthetic construct
SEQUENCE: 26
MNFGAFSINP AMMAAAQAAL QSSWGMMGML ASQQ                                34

SEQ ID NO: 27           moltype = AA  length = 10
FEATURE                 Location/Qualifiers
REGION                  1..10
                        note = Synthetic polymer.
source                  1..10
                        mol_type = protein
                        organism = synthetic construct
SEQUENCE: 27
MNFGAFSINP                                                           10

SEQ ID NO: 28           moltype = AA  length = 10
FEATURE                 Location/Qualifiers
REGION                  1..10
                        note = Synthetic polymer.
source                  1..10
                        mol_type = protein
                        organism = synthetic construct
SEQUENCE: 28
EDLIIKGISV                                                           10

SEQ ID NO: 29           moltype = AA  length = 42
FEATURE                 Location/Qualifiers
REGION                  1..42
                        note = Synthetic polymer.
source                  1..42
                        mol_type = protein
                        organism = synthetic construct
SEQUENCE: 29
DAEFRHDSGY EVHHQKLVFF AEDVGSNKGA IIGLMVGGVV IA                       42

SEQ ID NO: 30           moltype = AA  length = 16
FEATURE                 Location/Qualifiers
REGION                  1..16
                        note = Synthetic polymer.
source                  1..16
                        mol_type = protein
                        organism = synthetic construct
SEQUENCE: 30
DAEFRHDSGY EVHHQK                                                    16

SEQ ID NO: 31           moltype = AA  length = 113
FEATURE                 Location/Qualifiers
REGION                  1..113
                        note = Synthetic polymer.
source                  1..113
                        mol_type = protein
                        organism = synthetic construct
SEQUENCE: 31
DIVMTQSPSS LAMSVGQKVT MSCKSSQSLL NSSNQKNYLA WYQQKPGQSP KLLVYFASTR    60
ESGVPDRFIG SGSGTDFTLT ISSVQAEDLA DYFCQQHYNT PLTFGAGTKL ELK          113

```
SEQ ID NO: 32            moltype = AA  length = 455
FEATURE                  Location/Qualifiers
REGION                   1..455
                         note = Synthetic polymer.
source                   1..455
                         mol_type = protein
                         organism = synthetic construct
SEQUENCE: 32
ESQSFPNVFP LVSCESPLSD KNLVAMGCLA RDFLPSTISF TWNYQNNTEV IQGIRTFPTL    60
RTGGKYLATS QVLLSPKSIL EGSDEYLVCK IHYGGKNKDL HVPIPAVAEM NPNVNVFVPP   120
RDGFSGPAPR KSKLICEATN FTPKPITVSW LKDGKLVESG FTTDPVTIEN KGSTPQTYKV   180
ISTLTISEID WLNLNVYTCR VDHRGLTFLK NVSSTCAASP STDILTFTIP PSFADIFLSK   240
SANLTCLVSN LATYETLNIS WASQSGEPLE TKIKIMESHP NGTFSAKGVA SVCVEDWNNR   300
KEFVCTVTHR DLPSPQKKFI SKPNEVHKHP PAVYLLPPAR EQLNLRESAT VTCLVKGFSP   360
ADISVQWLQR GQLLPQEKYV TSAPMPEPGA PGFYFTHSIL TVTEEEWNSG ETYTCVVGHE   420
ALPHLVTERT VDKSTGKPTL YNVSLIMSDT GGTCY                              455

SEQ ID NO: 33            moltype = AA  length = 107
FEATURE                  Location/Qualifiers
REGION                   1..107
                         note = Synthetic polymer.
source                   1..107
                         mol_type = protein
                         organism = synthetic construct
SEQUENCE: 33
RADAAPTVSI FPPSSEQLTS GGASVVCFLN NFYPKDINVK WKIDGSERQN GVLNSWTDQD    60
SKDSTYSMSS TLTLTKDEYE RHNSYTCEAT HKTSTSPIVK SFNRNEC                 107

SEQ ID NO: 34            moltype = AA  length = 19
FEATURE                  Location/Qualifiers
REGION                   1..19
                         note = Synthetic polymer.
source                   1..19
                         mol_type = protein
                         organism = synthetic construct
SEQUENCE: 34
MEWPLIFLFL LSGTAGVQS                                                 19

SEQ ID NO: 35            moltype = AA  length = 20
FEATURE                  Location/Qualifiers
REGION                   1..20
                         note = Synthetic polymer.
source                   1..20
                         mol_type = protein
                         organism = synthetic construct
SEQUENCE: 35
MESQTQVLMF LLLWVSGACA                                                20

SEQ ID NO: 36            moltype = AA  length = 5
FEATURE                  Location/Qualifiers
REGION                   1..5
                         note = Synthetic polymer.
source                   1..5
                         mol_type = protein
                         organism = synthetic construct
SEQUENCE: 36
NYWMN                                                                 5

SEQ ID NO: 37            moltype = AA  length = 17
FEATURE                  Location/Qualifiers
REGION                   1..17
                         note = Synthetic polymer.
source                   1..17
                         mol_type = protein
                         organism = synthetic construct
SEQUENCE: 37
QIYPGDGDTN YNGKFKG                                                   17

SEQ ID NO: 38            moltype =     length =
SEQUENCE: 38
000

SEQ ID NO: 39            moltype = AA  length = 17
FEATURE                  Location/Qualifiers
REGION                   1..17
                         note = Synthetic polymer.
source                   1..17
                         mol_type = protein
                         organism = synthetic construct
```

-continued

```
SEQUENCE: 39
KSSQSLLNSS NQKNYLA                                                              17

SEQ ID NO: 40           moltype = AA  length = 7
FEATURE                 Location/Qualifiers
REGION                  1..7
                        note = Synthetic polymer.
source                  1..7
                        mol_type = protein
                        organism = synthetic construct
SEQUENCE: 40
FASTRES                                                                          7

SEQ ID NO: 41           moltype = AA  length = 9
FEATURE                 Location/Qualifiers
REGION                  1..9
                        note = Synthetic polymer.
source                  1..9
                        mol_type = protein
                        organism = synthetic construct
SEQUENCE: 41
QQHYNTPLT                                                                        9

SEQ ID NO: 42           moltype = AA  length = 121
FEATURE                 Location/Qualifiers
REGION                  1..121
                        note = Synthetic polymer.
SITE                    52
                        note = misc_feature - Xaa can be any naturally occurring
                         amino acid
source                  1..121
                        mol_type = protein
                        organism = synthetic construct
SEQUENCE: 42
QVQLQQSGAE LARPGASVKL SCKASGYTFT SYGIRWVKQR TGQGLEWIGE IXPRSGNTYY                60
NEKFKGKATV TADKSSSTAY MELRSLTSED SAVYFCARSI YYGRPYYFDY WGQGTTLTVS               120
S                                                                              121

SEQ ID NO: 43           moltype = AA  length = 107
FEATURE                 Location/Qualifiers
REGION                  1..107
                        note = Synthetic polymer.
source                  1..107
                        mol_type = protein
                        organism = synthetic construct
SEQUENCE: 43
DIVMTQSQLF MSTSDRVSVT CKASQNVAVG TNVAWYQQKP GQSPKALIYS ASYRYSGVPD                60
RFTGSGSGTD FTLTISNVQS EDLAEYFCQQ YNSYPLTFGA GTKLELK                             107

SEQ ID NO: 44           moltype = AA  length = 10
FEATURE                 Location/Qualifiers
REGION                  1..10
                        note = Synthetic polymer.
source                  1..10
                        mol_type = protein
                        organism = synthetic construct
SEQUENCE: 44
GYTFTSYGIR                                                                      10

SEQ ID NO: 45           moltype = AA  length = 16
FEATURE                 Location/Qualifiers
REGION                  1..16
                        note = Synthetic polymer.
SITE                    3
                        note = misc_feature - Xaa can be any naturally occurring
                         amino acid
source                  1..16
                        mol_type = protein
                        organism = synthetic construct
SEQUENCE: 45
EIXPRSGNTY YNEKFK                                                               16

SEQ ID NO: 46           moltype = AA  length = 12
FEATURE                 Location/Qualifiers
REGION                  1..12
                        note = Synthetic polymer.
source                  1..12
                        mol_type = protein
                        organism = synthetic construct
```

```
SEQUENCE: 46
SIYYGRPYYF DY                                                                    12

SEQ ID NO: 47           moltype = AA  length = 11
FEATURE                 Location/Qualifiers
REGION                  1..11
                        note = Synthetic polymer.
source                  1..11
                        mol_type = protein
                        organism = synthetic construct
SEQUENCE: 47
KASQNVATNV A                                                                     11

SEQ ID NO: 48           moltype = AA  length = 7
FEATURE                 Location/Qualifiers
REGION                  1..7
                        note = Synthetic polymer.
source                  1..7
                        mol_type = protein
                        organism = synthetic construct
SEQUENCE: 48
SASYRYS                                                                          7

SEQ ID NO: 49           moltype = AA  length = 9
FEATURE                 Location/Qualifiers
REGION                  1..9
                        note = Synthetic polymer.
source                  1..9
                        mol_type = protein
                        organism = synthetic construct
SEQUENCE: 49
QQYNSYPLT                                                                        9

SEQ ID NO: 50           moltype = AA  length = 117
FEATURE                 Location/Qualifiers
REGION                  1..117
                        note = Synthetic polymer.
source                  1..117
                        mol_type = protein
                        organism = synthetic construct
SEQUENCE: 50
QVQLQQSDAE LVKPGASVKI SCKVSGYTFT DHTIHWMKQR PEQGLEWIGY IYPRDGSTKY                 60
NEKFKGKATL TADKSSSTAY MQLNSLTSED SAVYFCARDY GYAFDYWGQG TTLTVSS                    117

SEQ ID NO: 51           moltype = AA  length = 117
FEATURE                 Location/Qualifiers
REGION                  1..117
                        note = Synthetic polymer.
source                  1..117
                        mol_type = protein
                        organism = synthetic construct
SEQUENCE: 51
QVQLQQSDAE LVKPGASVKI SCKVSGYTFT DHTIHWMKQR PEQGLEWIGY IYPRDGSTKY                 60
NEKFKGKATL TADKSSSTAY MQLNSLTSED SAVYFCARDY GYAFDYWGQG TTLTVSS                    117

SEQ ID NO: 52           moltype = AA  length = 109
FEATURE                 Location/Qualifiers
REGION                  1..109
                        note = Synthetic polymer.
source                  1..109
                        mol_type = protein
                        organism = synthetic construct
SEQUENCE: 52
QAVVTQESAL TTSPGGTVIL TCRSSTGAVT TSNYANWVQE KPDHLFTGLI GGTSNRAPGV                 60
PVRFSGSLIG DKAALTITGA QTEDDAMYFC ALWYSTHYVF GGGTKVTVL                             109

SEQ ID NO: 53           moltype = AA  length = 109
FEATURE                 Location/Qualifiers
REGION                  1..109
                        note = Synthetic polymer.
source                  1..109
                        mol_type = protein
                        organism = synthetic construct
SEQUENCE: 53
QAVVTQESAL TTSPGGTVIL TCRSSTGAVT TSNYANWVQE KPDHLFTGLI GGTSNRAPGV                 60
PVRFSGSLIG DKAALTITGA QTEDDAMYFC ALWYSTHYVF GGGTKVTVL                             109

SEQ ID NO: 54           moltype = AA  length = 10
FEATURE                 Location/Qualifiers
```

```
REGION                   1..10
                         note = Synthetic polymer.
source                   1..10
                         mol_type = protein
                         organism = synthetic construct
SEQUENCE: 54
GYTFTDHTIH                                                                  10

SEQ ID NO: 55            moltype = AA  length = 16
FEATURE                  Location/Qualifiers
REGION                   1..16
                         note = Synthetic polymer.
source                   1..16
                         mol_type = protein
                         organism = synthetic construct
SEQUENCE: 55
YIYPRDGSTK YNEKFK                                                           16

SEQ ID NO: 56            moltype = AA  length = 8
FEATURE                  Location/Qualifiers
REGION                   1..8
                         note = Synthetic polymer.
source                   1..8
                         mol_type = protein
                         organism = synthetic construct
SEQUENCE: 56
DYGYAFDY                                                                    8

SEQ ID NO: 57            moltype = AA  length = 14
FEATURE                  Location/Qualifiers
REGION                   1..14
                         note = Synthetic polymer.
source                   1..14
                         mol_type = protein
                         organism = synthetic construct
SEQUENCE: 57
RSSTGAVTTS NYAN                                                             14

SEQ ID NO: 58            moltype = AA  length = 7
FEATURE                  Location/Qualifiers
REGION                   1..7
                         note = Synthetic polymer.
source                   1..7
                         mol_type = protein
                         organism = synthetic construct
SEQUENCE: 58
GTSNRAP                                                                     7

SEQ ID NO: 59            moltype = AA  length = 9
FEATURE                  Location/Qualifiers
REGION                   1..9
                         note = Synthetic polymer.
source                   1..9
                         mol_type = protein
                         organism = synthetic construct
SEQUENCE: 59
ALWYSTHYV                                                                   9

SEQ ID NO: 60            moltype = AA  length = 121
FEATURE                  Location/Qualifiers
REGION                   1..121
                         note = Synthetic polymer.
SITE                     52
                         note = misc_feature - Xaa can be any naturally occurring
                          amino acid
source                   1..121
                         mol_type = protein
                         organism = synthetic construct
SEQUENCE: 60
QVQLQQSGAE LARPGASVKL SCKASGYTFT SYGIRWVKQR TGQGLEWIGE IXPRSGNTYY            60
NEKFKGKATV TADKSSSTAY MELRSLTSED SAVYFCARSI YYGRPYYFDY WGQGTTLTVS            120
S                                                                           121

SEQ ID NO: 61            moltype = AA  length = 107
FEATURE                  Location/Qualifiers
REGION                   1..107
                         note = Synthetic polymer.
source                   1..107
                         mol_type = protein
```

```
                        organism = synthetic construct
SEQUENCE: 61
DIVMTQSQLF MSTSVGDRVS VTCKASQNVA TNVAWYQQKP GQSPKALIYS ASYRYSGVPD    60
RFTGSGSGTD FTLTISNVQS EDLAEYFCQQ YNSYPLTFGA GTKLELK                107

SEQ ID NO: 62           moltype = AA   length = 116
FEATURE                 Location/Qualifiers
REGION                  1..116
                        note = Synthetic polymer.
source                  1..116
                        mol_type = protein
                        organism = synthetic construct
SEQUENCE: 62
QVQLQQSDAE LVKPGASVKI SCKVSGYTFT DHTIHWMKQR PEQGLEWIGY IYPRDGSTKY    60
NEKFKGKATL TADKSSSTAY MQLNSLTSED SAVYFCARDY GYAFDYWGQG TTTVSS       116

SEQ ID NO: 63           moltype = AA   length = 109
FEATURE                 Location/Qualifiers
REGION                  1..109
                        note = Synthetic polymer.
source                  1..109
                        mol_type = protein
                        organism = synthetic construct
SEQUENCE: 63
QAVVTQESAL TTSPGGTVIL TCRSSTGAVT TSNYANWVQE KPDHLFTGLI GGTSNRAPGV    60
PVRFSGSLIG DKAALTITGA QTEDDAMYFC ALWYSTHYVF GGGTKVTVL               109

SEQ ID NO: 64           moltype = AA   length = 117
FEATURE                 Location/Qualifiers
REGION                  1..117
                        note = Synthetic polymer.
source                  1..117
                        mol_type = protein
                        organism = synthetic construct
SEQUENCE: 64
QVQLQQSDAE LVKPGASVKI SCKVSGYTFT DHTIHWMKQR PEQGLEWIGY IYPRDGSTKY    60
NEKFKGKATL TADKSSSTAY MQLNSLTSED SAVYFCARDY GYAFDYWGQG TTLTVSS      117

SEQ ID NO: 65           moltype = AA   length = 109
FEATURE                 Location/Qualifiers
REGION                  1..109
                        note = Synthetic polymer.
source                  1..109
                        mol_type = protein
                        organism = synthetic construct
SEQUENCE: 65
QAVVTQESAL TTSPGGTVIL TCRSSTGAVT TSNYANWVQE KPDHLFTGLI GGTSNRAPGV    60
PVRFSGSLIG DKAALTITGA QTEDDAMYFC ALWYSTHYVF GGGTKVTVL               109

SEQ ID NO: 66           moltype = AA   length = 112
FEATURE                 Location/Qualifiers
REGION                  1..112
                        note = Synthetic polymer.
source                  1..112
                        mol_type = protein
                        organism = synthetic construct
SEQUENCE: 66
EVQLVESGGG LVQPGGSLRL SCAASGFTFS SYGMSWVRQA PGKGLELVAS INSNGGSTYY    60
PDSVKGRFTI SRDNAKNSLY LQMNSLRAED TAVYYCASGD YWGQGTTVTV SS           112

SEQ ID NO: 67           moltype = AA   length = 112
FEATURE                 Location/Qualifiers
REGION                  1..112
                        note = Synthetic polymer.
source                  1..112
                        mol_type = protein
                        organism = synthetic construct
SEQUENCE: 67
DIVMTQSPLS LPVTPGEPAS ISCRSSQSLV YSNGDTYLHW YLQKPGQSPQ LLIYKVSNRF    60
SGVPDRFSGS GSGTDFTLKI SRVEAEDVGV YYCSQSTHVP WTFGQGTKVE IK           112

SEQ ID NO: 68           moltype = AA   length = 10
FEATURE                 Location/Qualifiers
REGION                  1..10
                        note = Synthetic polymer.
source                  1..10
                        mol_type = protein
                        organism = synthetic construct
SEQUENCE: 68
```

-continued

```
GFTFSSYGMS                                                       10

SEQ ID NO: 69           moltype = AA   length = 16
FEATURE                 Location/Qualifiers
REGION                  1..16
                        note = Synthetic polymer.
source                  1..16
                        mol_type = protein
                        organism = synthetic construct
SEQUENCE: 69
SINSNGGSTY YPDSVK                                                16

SEQ ID NO: 70           moltype =     length =
SEQUENCE: 70
000

SEQ ID NO: 71           moltype = AA   length = 16
FEATURE                 Location/Qualifiers
REGION                  1..16
                        note = Synthetic polymer.
source                  1..16
                        mol_type = protein
                        organism = synthetic construct
SEQUENCE: 71
RSSQSLVYSN GDTYLH                                                16

SEQ ID NO: 72           moltype = AA   length = 7
FEATURE                 Location/Qualifiers
REGION                  1..7
                        note = Synthetic polymer.
source                  1..7
                        mol_type = protein
                        organism = synthetic construct
SEQUENCE: 72
KVSNRFS                                                          7

SEQ ID NO: 73           moltype = AA   length = 9
FEATURE                 Location/Qualifiers
REGION                  1..9
                        note = Synthetic polymer.
source                  1..9
                        mol_type = protein
                        organism = synthetic construct
SEQUENCE: 73
SQSTHVPWT                                                        9

SEQ ID NO: 74           moltype = AA   length = 7
FEATURE                 Location/Qualifiers
REGION                  1..7
                        note = Synthetic polymer.
source                  1..7
                        mol_type = protein
                        organism = synthetic construct
SEQUENCE: 74
RVSNRFS                                                          7

SEQ ID NO: 75           moltype = AA   length = 7
FEATURE                 Location/Qualifiers
REGION                  1..7
                        note = Synthetic polymer.
source                  1..7
                        mol_type = protein
                        organism = synthetic construct
SEQUENCE: 75
KVSSRFS                                                          7

SEQ ID NO: 76           moltype = AA   length = 116
FEATURE                 Location/Qualifiers
REGION                  1..116
                        note = Synthetic polymer.
source                  1..116
                        mol_type = protein
                        organism = synthetic construct
SEQUENCE: 76
SNCAMDVFMK GLSKAKEGVV AAAEKTKQGV AEAAGKTKEG VLYVGSKTKE GVVHGVATVA   60
EKTKEQVTNV GGAVVTGVTA VAQKTVEGAG SIAAATGFVK KDQLGKEGYQ DYEPEA      116

SEQ ID NO: 77           moltype = AA   length = 36
FEATURE                 Location/Qualifiers
```

| | | | |
|---|---|---|---|
| REGION | 1..36 | | |
| | note = Synthetic polymer. | | |
| source | 1..36 | | |
| | mol_type = protein | | |
| | organism = synthetic construct | | |

SEQUENCE: 77
KEQVTNVGGA VVTGVTAVAQ KTVEGAGSIA AATGFV                               36

| | | |
|---|---|---|
| SEQ ID NO: 78 | moltype = AA  length = 758 | |
| FEATURE | Location/Qualifiers | |
| REGION | 1..758 | |
| | note = Synthetic polymer. | |
| source | 1..758 | |
| | mol_type = protein | |
| | organism = synthetic construct | |

SEQUENCE: 78
MAEPRQEFEV MEDHAGTYGL GDRKDQGGYT MHQDQEGDTD AGLKESPLQT PTEDGSEEPG   60
SETSDAKSTP TAEDVTAPLV DEGAPGKQAA AQPHTEIPEG TTAEEAGIGD TPSLEDEAAG  120
HVTQEPESGK VVQEGFLREP GPPGLSHQLM SGMPGAPLLP EGPREATRQP SGTGPEDTEG  180
GRHAPELLKH QLLGDLHQEG PPLKGAGGKE RPGSKEEVDE DRDVDESSPQ DSPPSKASPA  240
QDGRPPQTAA REATSIPGFP AEGAIPLPVD FLSKVSTEIP ASEPDGPSVG RAKGQDAPLE  300
FTFHVEITPN VQKEQAHSEE HLGRAAFPGA PGEGPEARGP SLGEDTKEAD LPEPSEKQPA  360
AAPRGKPVSR VPQLKARMVS KSKDGTGSDD KKAKTSTRSS AKTLKNRPCL SPKHPTPGSS  420
DPLIQPSSPA VCPEPPSSPK YVSSVTSRTG SSGAKEMKLK GADGKTKIAT PRGAAPPGQK  480
GQANATRIPA KTPPAPKTPP SSGEPPKSGD RSGYSSPGSP GTPGSRSRTP SLPTPPTREP  540
KKVAVVRTPP KSPSSAKSRL QTAPVPMPDL KNVKSKIGST ENLKHQPGGG KVQIINKKLD  600
LSNVQSKCGS KDNIKHVPGG GSVQIVYKPV DLSKVTSKCG SLGNIHHKPG GGQVEVKSEK  660
LDFKDRVQSK IGSLDNITHV PGGGNKKIET HKLTFRENAK AKTDHGAEIV YKSPVVSGDT  720
SPRHLSNVSS TGSIDMVDSP QLATLADEVS ASLAKQGL                          758

| | | |
|---|---|---|
| SEQ ID NO: 79 | moltype = AA  length = 31 | |
| FEATURE | Location/Qualifiers | |
| REGION | 1..31 | |
| | note = Synthetic polymer. | |
| source | 1..31 | |
| | mol_type = protein | |
| | organism = synthetic construct | |

SEQUENCE: 79
VSTEIPASEP DGPSVGRAKG QDAPLEFTFH V                                   31

| | | |
|---|---|---|
| SEQ ID NO: 80 | moltype = AA  length = 31 | |
| FEATURE | Location/Qualifiers | |
| REGION | 1..31 | |
| | note = Synthetic polymer. | |
| source | 1..31 | |
| | mol_type = protein | |
| | organism = synthetic construct | |

SEQUENCE: 80
EITPNVQKEQ AHSEEHLGRA AFPGAPGEGP E                                   31

| | | |
|---|---|---|
| SEQ ID NO: 81 | moltype = AA  length = 89 | |
| FEATURE | Location/Qualifiers | |
| REGION | 1..89 | |
| | note = Synthetic polymer. | |
| source | 1..89 | |
| | mol_type = protein | |
| | organism = synthetic construct | |

SEQUENCE: 81
MGILKLQVFL IVLSVALNHL KATPIESHQV EKRKCNTATC ATQRLANFLV HSSNNFGAIL   60
SSTNVGSNTY GKRNAVEVLK REPLNYLPL                                     89

| | | |
|---|---|---|
| SEQ ID NO: 82 | moltype = AA  length = 37 | |
| FEATURE | Location/Qualifiers | |
| REGION | 1..37 | |
| | note = Synthetic polymer. | |
| source | 1..37 | |
| | mol_type = protein | |
| | organism = synthetic construct | |

SEQUENCE: 82
KCNTATCATQ RLANFLVHSS NNFGAILSST NVGSNTY                             37

| | | |
|---|---|---|
| SEQ ID NO: 83 | moltype = DNA  length = 5021 | |
| FEATURE | Location/Qualifiers | |
| misc_feature | 1..5021 | |
| | note = Synthetic polymer. | |
| source | 1..5021 | |
| | mol_type = other DNA | |
| | organism = synthetic construct | |

SEQUENCE: 83

```
gcgatcgcgg ctcccgacat cttggaccat tagctccaca ggtatcttct tccctctagt   60
ggtcataaca gcagcttcag ctacctctca attcaaaaaa cccctcaaga cccgtttaga  120
ggccccaagg ggttatgcta tcaatcgttg cgttacacac acaaaaaacc aacacacatc  180
catcttcgat ggatagcgat tttattatct aactgctgat cgagtgtagc cagatctagt  240
aatcaattac ggggtcatta gttcatagcc catatatgga gttccgcgtt acataactta  300
cggtaaatgg cccgcctggc tgaccgccca acgaccccg cccattgacg tcaataatga   360
cgtatgttcc catagtaacg ccaataggga cttttccattg acgtcaatgg gtggagtatt  420
tacggtaaac tgcccacttg gcagtacatc aagtgtatca tatgccaagt acgccccta   480
ttgacgtcaa tgacggtaaa tggcccgcct ggcattatgc ccagtacatg accttatgg  540
actttcctac ttggcagtac atctacgtat tagtcatcgc tattaccatg ctgatgcggt  600
tttggcagta catcaatggg cgtggatagc ggtttgactc acggggattt ccaagtctcc  660
accccattga cgtcaatggg agtttgtttt ggcaccaaaa tcaacgggac tttccaaaat  720
gtcgtaacaa ctccgcccca ttgacgcaaa tgggcggtag gcgtgtacgg tgggaggtct  780
atataagcag agctggttta gtgaaccgtc agatcagatc tttgtcgatc ctaccatcca  840
ctcgacacac ccgccagcag ccgctgccaa gcttccgagc tctcgaattc aaaggaggta  900
cccaccatgc cgctgctgct actgctgccc ctgctgtggg caggggcgct agctcaagtg  960
cagctgcagc agagcggagc cgaactggct agacccgagg cctccgtgaa gctgagctgt 1020
aaggcctccg gctacacctt caccagctac ggcatcagct gggtgaggca aaggaccggc 1080
caaggactgg aatggatcgg cgagatctac cctaggaggg gcaacaccta ctacaacgag 1140
aagttcaagg gcaaggccac actgacagcc tacaagtcca gcggcacagc ctacatggag 1200
ctgagatctc tgaccagcga ggatagcgcc gtgttctttt gcgccagagg cggcatctac 1260
tacggcaatc tgttcgacta ctgggggcaa ggcaccacc tgacctctc gagcgctaag  1320
acgactccac cgtccgtgta cccgctcgcg ccaggttcgg ccgctcagac gaacagcatg 1380
gtgaccctcg gctgcctcgt gaagggttat ttcccagagc cggtgaccgt gacgtggaac 1440
tccggctcac tgtcatcggg cgtgcacact tttccagcag tgctgcagtc ggacctttac 1500
accctcagct cgtccgtcac cgtccccttca tcaacttggc ctagccagac cgtgacttgc 1560
aatgtcgccc accccggcgtc cagcactaag gtggacaaga agatccacca ccatcaccat 1620
caccatcacc atcactagtg agcggccgcg tctagacctg cactgactga ctgatacaat 1680
cgatttctgg atccgcaggc ctctcctagc ttgactgact gagatacagc gtaccttcag 1740
ctcacagaca tgataagata cattgacgag tttggacaaa ccacaactag aatgcagtga 1800
aaaaaatgct ttatttgtga aatttgtgat gctattgctt tatttgtaac cattataagc 1860
tgcaataaac aagttaacaa caacaattgc attcattta tgtttcaggt tcagggggag  1920
gtgtgggagg ttttttaaag caagtaaaac ctctacaaat gtggtattgg cccatctcta 1980
tcggtatcgt agcataaccc cttggggcct ctaaacgggt cttgaggggt tttttgtgcc 2040
cctccggccg gattgctatc taccggcatt ggcgcagaaa aaaatgcctg atgcgacgct 2100
gcgcgtctta tactcccaca tatgccagat tcagcaacgg atacggcttc ccaacttgc  2160
ccacttccat acgtgtcctc cttaccagaaa atttatcctt aaggtcgtca gctatcctgc 2220
aggcgatctc tcgatttcga tcaagacatt cctttaatgg tcttttctgg acaccactag 2280
gggtcagaag tagttcatca aactttcttc cctccctaat ctcattggtt accttgggct 2340
atcgaaactt aattaaccag tcaagtcagc tacttggcga gatcgacttg tctgggtttc 2400
gactacgctc agaattgcgt cagtcaagtt cgatctggtc cttgctattg cacccgttct 2460
ccgattacga gtttcattta aatcatgtga gcaaaaggcc agcaaaaggc caggaaccgt 2520
aaaaaggccg cgttgctggc gttttccat aggctccgcc cccctgacga gcatcacaaa  2580
aatcgacgct caagtcagag gtggcgaaac ccgacaggac tataaagata ccaggcgttt 2640
ccccctggaa gctccctcgt gcgctctcct gttccgaccc tgccgcttac cggatacctg 2700
tccgcctttc tcccttcggg aagcgtggcg ctttctcata gctcacgctg taggtatctc 2760
agttcggtgt aggtcgttcg ctccaagctg ggctgtgtgc acgaaccccc cgttcagccc 2820
gaccgctgcg ccttatccgg taactatcgt cttgagtcca acccggtaag acacgactta 2880
tcgccactgg cagcagccac tggtaacagg attagcagag cgaggtatgt aggcggtgct 2940
acagagttct tgaagtggtg gcctaactac ggctacacta agaacagt atttggtatc  3000
tgcgctctgc tgaagccagt taccttcgga aaaagagttg gtagctcttg atccggcaaa 3060
caaaccaccg ctggtagcgg tggtttttt gtttgcaagc agcagattac gcgcagaaaa 3120
aaaggatctc aagaagatcc tttgatcttt tctacgggt ctgacgctca gtggaacgaa  3180
aactcacgtt aagggatttt ggtcatgaga ttatcaaaaa ggatcttcac ctagatcctt 3240
ttaaattaaa aatgaagttt taaatcaatc taaagtatat atgagtaaac ttggtctgac 3300
agttaccaat gcttaatcag tgaggcacct atctcagcga tctgtctatt tcgttcatcc 3360
atagttgcat ttaaatttcc gaactctcca aggccctcgt cggaaaatct tcaaaccttt 3420
cgtccgatcc atcttgcagg ctacctctcg aacgaactat cgcaagtctc ttggccggcc 3480
ttgcgccttg gctattgctt ggcagcgcct atcgccaggt attactccaa tcccgaatat 3540
ccgagatcgg gatcacccca gagaagttca acctacatcc tcaatcccga tctatccgaa 3600
atccgaggaa tatcgaaatc ggggcgcgcc tggtgtaccg agaacgatcc tctcagtgcg 3660
agtctcgacg atccatatcg ttgcttggca gtcagccagt cggaatccag cttgggaccc 3720
aggaagtcca atcgtcagat attgtactca agcctggtca cggcagcgta ccgatctgtt 3780
taaacctaga tattgataqt ctgatccgtc aacgtataat cgatgtcctag ctttttqaaa 3840
catctatcaa gagacaggat cagcaggagg ctttcgcatg agtattcaac atttccgtgt 3900
cgcccttatt ccctttttg cggcattttg ccttcctgtt tttgctcacc cagaaacgct 3960
ggtgaaagta aaagatgctg aagatcagtt gggtgcgcga gtgggttaca tcgaactgga 4020
tctcaacagc ggtaagatcc ttgagagttt tcgccccgaa gaacgctttc caatgatgag 4080
cactttaaa gttctgctat gtggcgcggt attatcccgt attgacgccg ggcaagagca 4140
actcggtcgc cgcatacact attctcagaa tgacttggtt gagtattcac cagtcacaga 4200
aaagcatctt acgatggca tgacagtaag agaattatgc agtgctgcca taaccatgag 4260
tgataacact gcggccaact tacttctgac aacgattgga ggaccgaagg agctaaccgc 4320
ttttttgcac aacatggggg atcatgtaac tcgccttgat cgttgggaac cggagctgaa 4380
tgaagccata ccaaacgacg agcgtgacac cacgatgcct gtagcaatgg caacaacctt 4440
gcgtaaacta ttaactggcg aactacttac tctagcttcc cggcaacagt tgatagactg 4500
gatgggaggcg ataaagttg caggaccact tctgcgctcg gcccttccgg ctggctggtt 4560
tattgctgat aaatctggag ccggtgagcg tgggtctcgc ggtatcattg cagcactggg 4620
gccagatggt aagccctccc gtatcgtagt tatctacacg acgggggagtc aggcaactat 4680
ggatgaacga aatagacaga tcgctgagat aggtgcctca ctgattaagc attggtaacc 4740
```

```
gattctaggt gcattggcgc agaaaaaaat gcctgatgcg acgctgcgcg tcttatactc  4800
ccacatatgc cagattcagc aacggatacg gcttccccaa cttgcccact tccatacgtg  4860
tcctccttac cagaaattta tccttaagat cccgaatcgt ttaaactcga ctctggctct  4920
atcgaatctc cgtcgtttcg agcttacgcg aacagccgtg gcgctcattt gctcgtcggg  4980
catcgaatct cgtcagctat cgtcagctta cctttttggc a                     5021

SEQ ID NO: 84          moltype = DNA  length = 5708
FEATURE                Location/Qualifiers
misc_feature           1..5708
                       note = Synthetic polymer.
source                 1..5708
                       mol_type = other DNA
                       organism = synthetic construct
SEQUENCE: 84
gcgatcgcgg ctcccgacat cttggaccat tagctccaca ggtatcttct tccctctagt    60
ggtcataaca gcagcttcag ctacctctca attcaaaaaa cccctcaaga cccgtttaga   120
ggcccccaagg ggttatgcta tcaatcgttg cgttacacac acaaaaaacc aacacacatc   180
catcttcgat ggatagcgat tttattatct aactgctgat cgagtgtagc cagatctagt   240
aatcaattac ggggtcatta gttcatagcc catatatgga gttccgcgtt acataactta   300
cggtaaatgg cccgcctggc tgaccgccca acgaccccg cccattgacg tcaataatga    360
cgtatgttcc catagtaacg ccaatagga ctttccattg acgtcaatgg gtggagtatt    420
tacggtaaac tgcccacttg gcagtacatc aagtgtatca tatgccaagt acgccccta    480
ttgacgtcaa tgacggtaaa tggcccgcct ggcattatgc ccagtacatg acctatggg    540
actttcctac ttggcagtac atctacgtat tagtcatcgc tattaccatg ctgatgcggt   600
tttggcagta catcaatggg cgtggatagc ggtttgactc acggggattt ccaagtctcc   660
accccattga cgtcaatggg agtttgtttt ggcaccaaaa tcaacgggac tttccaaaat   720
gtcgtaacaa ctccgcccca ttgacgcaaa tgggcggtag gcgtgtacgg tgggaggtct   780
atataagcag agctggttta gtgaaccgtc agatcagatc tttgtcgatc ctaccatcca   840
ctcgacacac ccgccagcag ccgctgccaa gcttccgagc tctcgaattc aaaggaggta   900
cccaccatgg cgctgctgct actgctgccc ctgctgtggg cagggccgct agctcaagtg   960
cagctgcagc agagcggagc cgaactggct agacccggag cctccgtgaa gctgagctgt  1020
aaggcctccg gctacacctt caccagctac ggcatcagct gggtgaggca aaggaccggc  1080
caaggactga atggatcggc cgagatctac cctaggaggg gcaacaccta ctacaacgag  1140
aagttcaagg gcaaggccac actgacagcc tacaagtgca gcggcacagc ctacatggag  1200
ctgagatctc tgagcagcga ggatagcgcc gtgttctttt gcgccagagg cggcatctac  1260
tacggcaatc tgttcgacta ctgggggcaa ggcaccacac tgaccgtctc gagcgccaaa  1320
accacccctc catccgtcta ccctctgccc ccggctgcg cgacaccac tggatcatcc   1380
gtgacttccg gatgcctggt caagggatac ttcccggagc cggtcactgt gacctggaac  1440
tccggttcac tgtcatcatc cgtccacacc tttccggccc tgtcagtc gggcttgtac   1500
accatgagca gcagcgtgac cgtgccatcc tcgacctggc ctagccaaac cgtgacttgc  1560
tccgtggcac accctgcgtc gtccactact gtggacaaga agctggagcc gtccggacct  1620
atctccacca ttaaccctg cccgccctgc aaggaatgtc acaagtgtcc cgctcccaat   1680
cttgagggag ggcccagcgt gttcattttc cctcctaaca ttaaggatgt gctgatgatc  1740
tccctgactc ccaaagtgac atgcgtggtg gtggacgtgt cagaagatga cccggacgtc  1800
cagatcagct ggttcgtgaa caacgtggaa gtgcatacgg cgcagaccca gactcaccgc  1860
gaggactata acagcaccat cagggtcgtg tccaccctgc cgattcagca ccaggactgg  1920
atgtccggga aggagttcaa gtgcaaggtc aacaacaagg acctcccatc cccgatcgaa  1980
cggaccatct cgaagatcaa gggcctcgtg cgggcccctc aagtgtacac gctgccgcca  2040
ccggccgagc agctgtcgcg gaaggacgtg tcccttacct gtctcgtcgt gggttttaac  2100
cccgagata tttcggtgga gtggaccagc aacgccaca ccgaagagaa ctacaaggat    2160
accgccggg tgctggactc cgacgggtcc tacttcatct actccaagct gaatatgaaa  2220
acctctaagt ggggaaaagac tgatagcttc tcgtgcaacg tcagacatga aggcttgaag  2280
aactactacc tgaaaaagac tatctcccgc tcgcccggaa agtagtgagc ggccgcgtct  2340
agacctgcac tgactgactg atacaatcga tttctggatc cgcaggcctc tcctagcttg  2400
actgactgag atacagcgta ccttcagctc acagacatga taagatacat tgatgagttt  2460
ggacaaacca caactagaat gcagtgaaaa aaatgcttta tttgtgaaat ttgtgatgct  2520
attgctttat ttgtaaccat tataagctgc aataaacaag ttaacaacaa caattgcatt  2580
cattttatgt ttcaggttca ggggaggtg tgggaggttt tttaaagcaa gtaaaacctc    2640
tacaaatgtg gtattggccc atctctatcg gtatcgtaac ataacccctt gggccctcta  2700
aacgggtctt gagggggttt ttgtgcccct ccggccggat gctatctac cggcattggc   2760
gcagaaaaaa atgcctgatg cgacgctgcg cgtcttatac tcccacatat gccagattca  2820
gcaacggata cggcttcccc aacttgccca cttccatacg tgtcctcctt accagaaatt  2880
tatccttaag gtcgtcagct atcctgcagg cgatctctcg atttcgatca agacattcct  2940
ttaatggtct tttctggaca ccactagggg tcagaagtag ttcatcaaac tttcttccct  3000
ccctaatctc attggttacc ttgggctatc gaaacttaat taaccagtca agtcagctac  3060
ttggcgagat cgacttgtct ggggtttcgac tacgctcaga attgcgtcag tcaagttcga  3120
tctggtcctt gctattgcac ccgttctccg attacgagtt tcatttaaat catgtgagca  3180
aaaggccagc aaaaggccag gaaccgtaaa aaggccgcgt tgctgcgtt tttccatagg    3240
ctccgccccc ctgacgagca tcacaaaaat cgacgctcaa gtcagaggtg gcgaaacccg  3300
acaggactat aaagatacca ggcgtttccc cctggaagct ccctcgtgcg ctctcctgtt  3360
ccgaccctgc cgcttaccgg atacctgtcc gcctttctcc cttcgggaag cgtggcgctt  3420
tctcatagct cacgctgtag gtatctcagt tcggtgtagg tcgttcgctc caagctgggc  3480
tgtgtgcacg aaccccccgt tcagcccgac cgctgcgcct tatccggtaa ctatcgtctt  3540
gagtccaacc cggtaagaca cgacttatcg ccactggcag cagccactgg taacaggatt  3600
agcagagcga ggtatgtagg cggtgctaca gagttcttga agtggtggcc taactacggc  3660
tacactagaa gaacagtatt tggtatctgc gctctgctga agccagttac cttcggaaaa  3720
agagttggta gctcttgatc cggcaaacaa accaccgctg gtagcggtgg tttttttgtt  3780
tgcaagcagc agattacgcg cagaaaaaaa ggatctcaag aagatccttt gatcttttct  3840
acggggtctg acgctcagtg gaacgaaaac tcacgttaag gatttttggt catgagatta  3900
```

```
tcaaaaagga tcttcaccta gatccttta  aattaaaaat gaagttttaa atcaatctaa   3960
agtatatatg agtaaacttg gtctgacagt taccaatgct taatcagtga ggcacctatc   4020
tcagcgatct gtctatttcg ttcatccata gttgcattta aatttccgaa ctctccaagg   4080
ccctcgtcgg aaaatcttca aacctttcgt ccgatccatc ttgcaggcta cctctcgaac   4140
gaactatcgc aagtctcttg gccggccttg cgccttggct attgcttggc agcgcctatc   4200
gccaggtatt actccaatcc cgaatatccg agatcgggat caccccagag aagttcaacc   4260
tacatcctca atcccgatct atccgagatc cgaggaatat cgaaatcggg gcgcgcctgg   4320
tgtaccgaga acgatcctct cagtgcgagt ctcgacgatc catatcgttg cttggcagtc   4380
agccagtcga aatccagctt gggacccagg aagtccaatc gtcagatatt gtactcaagc   4440
ctggtcacgg cagcgtaccg atctgtttaa acctagatat tgatagtctg atcggtcaac   4500
gtataatcga gtcctagctt ttgcaaacat ctatcaagag acaggatcag caggaggctt   4560
tcgcatgagt attcaacatt tccgtgtcgc ccttattccc tttttgcgg cattttgcct   4620
tcctgttttt gctcacccag aaacgctggt gaaagtaaaa gatgctgaag atcagttggg   4680
tgcgcgagtg ggttacatcg aactggatct caacagcggt aagatccttg agagttttcg   4740
ccccgaagaa cgctttccaa tgatgagcac ttttaaagtt ctgctatgtg gcgcggtatt   4800
atcccgtatt gacgccgggc aagagcaact cggtcgccgc atacactatt ctcagaatga   4860
cttggttgag tattcaccag tcacagaaaa gcatcttacg gatggcatga cagtaagaga   4920
attatgcagt gctgccataa ccatgagtga taacactgcg gccaacttac ttctgacaac   4980
gattggagga ccgaaggagc taaccgcttt tttgcacaac atgggggatc atgtaactcg   5040
ccttgatcgt tgggaaccgg agctgaatga agccatacca aacgacgagc gtgacaccac   5100
gatgcctgta gcaatggcaa caaccttgcg taaactatta actggcgaac tacttactct   5160
agcttcccgg caacagttga tagactggat ggaggcggat aaagttgcag gaccacttct   5220
gcgctcggcc cttccggctg gctggtttat tgctgataaa tctggagccg gtgagcgtgg   5280
gtctcgcggt atcattgcag cactgggcc agatggtaag ccctcccgta tcgtagttat   5340
ctacacgacg ggagtcagg caactatgga tgaacgaaat agacagatcg ctgagatagg   5400
tgcctcactg attaagcatt ggtaaccgat tctaggtgca ttggcgcaga aaaaatgctg   5460
tgatgcgacg ctgcgcgtct tatactccca catatgccag attcagcaac ggatacggct   5520
tccccaactt gcccacttcc atacgtgtcc tccttaccag aaatttatcc ttaagatccc   5580
gaatcgttta aactcgactc tggctctatc gaatctccgt cgtttcgagc ttacgcgaac   5640
agccgtggcg ctcatttgct cgtcgggcat cgaatcctcg cagctatcgt cagcttacct   5700
ttttggca                                                           5708
```

SEQ ID NO: 85          moltype = DNA  length = 4985
FEATURE                Location/Qualifiers
misc_feature           1..4985
                       note = Synthetic polymer.
source                 1..4985
                       mol_type = other DNA
                       organism = synthetic construct
SEQUENCE: 85

```
gcgatcgcgg ctcccgacat cttggaccat tagctccaca ggtatcttct tccctctagt     60
ggtcataaca gcagcttcag ctacctctca attcaaaaaa cccctcaaga cccgtttaga    120
ggccccaagg ggttatgcta tcaatcgttg cgttacacac acaaaaaacc aacacacatc    180
catcttcgat ggatagcgat tttattatct aactgctgat cgagtgtagc cagatctagt    240
aatcaattac ggggtcatta gttcatagcc catatatgga gttccgcgtt acataactta    300
cggtaaatgg cccgcctggc tgaccgccca acgaccccg cccattgacg tcaataatga    360
cgtatgttcc catagtaacg ccaataggga cttttccatt acgtcaattg gtggagtatt    420
tacggtaaac tgcccacttg gcagtacatc aagtgtatca tatgccaagt acgccccta    480
ttgacgtcaa tgacggtaaa tggcccgcct ggcattatgc ccagtacatg accttatggg    540
actttcctac ttggcagtac atctacgtat tagtcatcgc tattaccatg ctgatgcggt    600
tttggcagta tcaatgggg cgtggatagc ggttgactc acggggatt ccaagtcc    660
accccattga cgtcaatggg agtttgtttt ggcaccaaaa tcaacgggac tttccaaaat    720
gtcgtaacaa ctccgcccca ttgacgcaaa tgggcggtag gcgtgtacgg tgggaggtct    780
atataagcag agctggttta gtgaaccgtc agatcagatc tttgtcgatc ctaccatcca    840
ctcgacacac ccgccagcag ccgctgccaa gcttccgagc tctcgaattc aaaggaggta    900
cccaccatgc cgctgctgct actgctgccc ctgctgtggg caggggcgct agctcaagcc    960
gtggtgaccc aagagtccgc tctgacaaca agccccggcg agacagtgac actgacatgt   1020
agaagcagca ccgagccgt gaccaccagc aactacgcca actgggtgca agagaagccc   1080
gaccatctgt ttaccggact gatcggaggc accaataaca gagccccgg cgtgcccgcc   1140
agatttagcg gctctctgat tggcgacaag gctgctctga ccatcaccgg agccccagacc   1200
gaggacgagg ccatctactt ctgcgctctg tggttcagca accactgggt gtttggcggc   1260
ggcaccaaac tgaccgtgct cgggcagcct aaaagctcgc cgtccgtgac cctctttcca   1320
ccatcatcgg aagagctgga aaccaacaag gctactctcg tctgcaccat cacggatttc   1380
taccccggag tggtcaccgt ggactggaaa gtggacagga cctccggtgt tcagggaatg   1440
gaaacgaccc aaccgtcaaa gcagtcgaac aataagtaca tggcctccag ctacctgacc   1500
ttgaccgcca gagcgtggga gcggcacagc tcctactcat gtcaagtcac tcacgaaggc   1560
catactgtg agaagagcct gtcccgcgca gattgctcgt agtgagcggc cgcgtctaga   1620
cctgcactg ctgactgata caatcgattt ctggatccgc aggcctctcc tagcttgact   1680
gactgagata cagcgtacct tcagctcaca gacatgtaaa gatacattga tgagtttgga   1740
caaaccacaa ctagaatgca gtgaaaaaa tgctttattt gtgaaatttg tgatgctatt   1800
gctttatttg taaccattat aagctgcaat aaacaagtta acaacaacaa ttgcattcat   1860
tttatgtttc aggttcaggg ggaggtgtgg gaggtttttt aaagcaagta aaacctctac   1920
aaatgtggta ttggcccatc tctatcgta tcgtagcata accccttggg gcctctaaac   1980
gggtcttgag gggttttttg tgccctccg ccggattgc tatctaccgg cattggcgca   2040
gaaaaaaatg cctgatgcga cgctgcgcgt cttatactcc cacatatgcc agattcagca   2100
acggatacgg cttcccccaac ttgcccactt ccatacgtgt cctccttacc agaaatttat   2160
ccttaaggtc gtcagctatc ctgcaggcga tctctcgatt cgatcaaga cattccttta   2220
atggtctttt ctggacacca ctaggggtca gaagtagttc atcaaacttt cttccctccc   2280
taatctcatt ggttaccttg ggctatcgaa acttaattaa ccagtcaagt cagctacttg   2340
```

```
gcgagatcga cttgtctggg tttcgactac gctcagaatt gcgtcagtca agttcgatct 2400
ggtccttgct attgcacccg ttctccgatt acgagtttca tttaaatcat gtgagcaaaa 2460
ggccagcaaa aggccaggaa ccgtaaaaag gccgcgttgc tggcgttttt ccataggctc 2520
cgcccccctg acgagcatca caaaaatcga cgctcaagtc agaggtggcg aaacccgaca 2580
ggactataaa gataccaggc gtttccccct ggaagctccc tcgtgcgctc tcctgttccg 2640
accctgccgc ttaccggata cctgtccgcc tttctccctt cgggaagcgt ggcgctttct 2700
catagctcac gctgtaggta tctcagttcg gtgtaggtcg ttcgctccaa gctgggctgt 2760
gtgcacgaac cccccgttca gcccgaccgc tgcgccttat ccggtaacta tcgtcttgag 2820
tccaacccgg taagacacga cttatcgcca ctggcagcag ccactggtaa caggattagc 2880
agagcgaggt atgtaggcgg tgctacagag ttcttgaagt ggtggcctaa ctacggctac 2940
actagaagaa cagtatttgg tatctgcgct ctgctgaagc cagttacctt cggaaaaaga 3000
gttggtagct cttgatccgg caaacaaacc accgctggta gcggtggttt ttttgtttgc 3060
aagcagcaga ttacgcgcag aaaaaaagga tctcaagaag atcctttgat cttttctacg 3120
gggtctgacg ctcagtggaa cgaaaactca cgttaaggga ttttggtcat gagattatca 3180
aaaaggatct tcacctagat ccttttaaat taaaaatgaa gttttaaatc aatctaaagt 3240
atatatgagt aaacttggtc tgacagttac caatgcttaa tcagtgaggc acctatctca 3300
gcgatctgtc tatttcgttc atccatagtt gcatttaaat ttcgaactc tccaaggccc 3360
tcgtcggaaa atcttcaaac ctttcgtccg atccatcttg caggctacct ctcgaacgaa 3420
ctatcgcaag tctcttggcc ggccttgcgc cttggctatt gcttggcagc gcctatcgcc 3480
aggtattact ccaatcccga atatccgaga tcgggatcac cccagagaag ttcaacctac 3540
atcctcaatc ccgatctatc cgagatccga ggaatatcga aatcggggcg cgcctggtgt 3600
accgaaaacg atcctctcag tgcgagtctc gacgatccat atcgttgctt ggcagtcagc 3660
cagtcggaat ccagcttggg acccaggaag tccaatcgtc agatattgta ctcaagcctg 3720
gtcacggcag cgtaccgatc tgtttaaacc tagatattga tagtctgatc ggtcaacgta 3780
taatcgagtc ctagcttttg caaacatcta tcaagagaca ggatcagcag gaggctttcg 3840
catgagtatt caacatttcc gtgtcgccct tattcccttt tttgcggcat tttgccttcc 3900
tgtttttgct cacccagaaa cgctggtgaa agtaaaagat gctgaagatc agttgggtgc 3960
gcgagtgggt tacatcgaac tggatctcaa cagcggtaag atccttgaga gttttcgccc 4020
cgaagaacgc tttccaatga tgagcacttt taaagttctg ctatgtggcg cggtattatc 4080
ccgtattgac gccgggcaag agcaactcgg tcgccgcata cactattctc agaatgactt 4140
ggttgagtat tcaccagtca cagaaaagca tcttacggat ggcatgacag taagagaatt 4200
atgcagtgct gccataacca tgagtgataa cactgcggcc aacttacttc tgacaacgat 4260
tggaggaccg aaggagctaa ccgcttttt gcacaacatg ggggatcatg taactcgcct 4320
tgatcgttgg gaaccggagc tgaatgaagc cataccaaac gacgagcgtg acaccacgat 4380
gcctgtagca atggcaacaa ccttgcgtaa actattaact ggcgaactac ttactctagc 4440
ttcccggcaa cagttgatag actggatgga ggcggataaa gttgcaggac cacttctgcg 4500
ctcggccctt ccggctggct ggtttattgc tgataaatct ggagccggtg agcgtgggtc 4560
tcgcggtatc attgcagcac tggggccaga tggtaagccc tcccgtatcg tagttatcta 4620
cacgacgggg agtcaggcaa ctatggatga acgaaataga cagatcgctg agataggtgc 4680
ctcactgatt aagcattggt aaccgattct aggtgcattg gcgcagaaaa aaatgcctga 4740
tgcgacgctg cgcgtcttat actcccacat atgccagatt cagcaacgga tacggcttcc 4800
ccaacttgcc cacttccata cgtgtcctcc ttaccagaaa tttatcctta agatcccgaa 4860
tcgtttaaac tcgactctgg ctctatcgaa tctccgtcgt ttcgagctta cgcgaacagc 4920
cgtggcgctc atttgctcgt cgggcatcga atctcgtcag ctatcgtcag cttacctttt 4980
tggca                                                             4985
```

SEQ ID NO: 86        moltype = DNA   length = 8377
FEATURE              Location/Qualifiers
misc_feature       1..8377
                      note = Synthetic polymer.
source               1..8377
                      mol_type = other DNA
                      organism = synthetic construct
SEQUENCE: 86

```
gcgatcgcgg ctcccgacat cttggaccat tagctccaca ggtatcttct tccctctagt 60
ggtcataaca gcagcttcag ctacctctca attcaaaaaa cccctcaaga cccgtttaga 120
ggccccaagg ggttatgcta tcaatcgttg cgttacacac acaaaaaacc aacacacatc 180
catcttcgat ggatagcgat tttattatct aactgctgat cgagtgtagc cagatctata 240
gtaatcaatt acggggtcat tagttcatag cccatatatg gagttccgcg ttacataact 300
tacggtaaat ggcccgcctg gctgaccgcc caacgacccc cgcccattga cgtcaataat 360
gacgtatgtt cccatagtaa cgccaatagg gactttccat tgacgtcaat gggtggacta 420
tttacggtaa actgcccact tggcagtaca tcaagtgtat catatgccaa gtacgccccc 480
tattgacgtc aatgacggta aatggcccgc ctggcattat gcccagtaca tgaccttatg 540
ggactttcct acttggcagt acatctacgt attagtcatc gctattacca tggtcgaggt 600
tgagccccac gttctgcttc actctcccca tctcccccc ctcccacc caatttgtg 660
atttattat ttttaatta ttttatgcag cgatgggggc ggggggggg gggcgcgcg 720
ccaggcgggg cggggcgggg cgaggggcgg ggcggggcga ggcggagagg tgcggcggca 780
gccaatcaga gcggcgcgct ccgaaagttt cctttatgg cgaggcggcg gcggcggcgg 840
ccctataaaa agcgaagcgc gcggcgggcg gagtcgctg cgttgccttc gccccgtgc 900
ccgctccgcg ccgcctcgcg ccgcccgccc cggctctgac tgaccgcgtt actcccacag 960
gtgagcgggc gggacggccc ttctccctcc gggctgtaat agcgcttggg tttaatgacg 1020
gctcgttttct tttctgtggc tgcgtgaaag ccttaaaggg ctccgggagg gcctttgtgc 1080
gggggggagc ggctcggggg gtgcgtgcgt gtgtgtgtgc gtggggagcg ccgcgtgcgg 1140
cccgcgctgc ccggcgctg tgagcgctgc gggcgcggcg cggggctttg tgcgctccgc 1200
gtgtgcgcga ggggagcgcg gccgggggc ggtgccccgc ggtgcggggg gctgcgagg 1260
ggaacaaagg ctgcgtgcgg ggtgtgtgcg tgggggggtg agcagggggt gtgggcgcgg 1320
cggtcgggct gtaacccccc cctggcaccc cctcccga gttgctgagc acggcccggc 1380
ttcgggtgcg ggctccgtg cggggcgtgg cgcggggctc gccgtgccgg gcgggggtg 1440
gcggcaggtg ggggtgccgg gcggggcggg gccgcctcgg gccgggggag gctcggggga 1500
```

```
ggggcgcggc ggccccggag cgccggcggc tgtcgaggcg cggcgagccg cagccattgc   1560
cttttatggt aatcgtgcga gagggcgcag ggacttcctt tgtcccaaat ctggcggagc   1620
cgaaatctgg gaggcgccgc cgcacccct ctagcgggcg cgggcgaagc ggtgcggcgc    1680
cggcaggaag gaaatgggcg gggagggcct tcgtgcgtcg ccgcgccgcc gtccccttct   1740
ccatctccag cctcggggct gccgcaggg gacggctgcc ttcgggggg acggggcagg     1800
gcggggttcg gcttctggcg tgtgaccggc ggctttagag cctctgctaa ccatgttcat   1860
gccttcttct ttttcctaca gctcctgggc aacgtgctgg ttgttgtgct gtctcatcat   1920
tttggcaaag atctttgtcg atcctaccat ccactcgaca cacccgccag cggccgctgc   1980
caagcttccg agctctcgaa ttcaggaggt acccaccagg ggttggagcc tcatcttgtg   2040
cttccttgtc gctgttgcta cgcgtgtcca ctcccaagtg cagctgcagc agagcggagc   2100
cgaactggct agaccggag cctccgtgaa gctgagctgt aaggcctccg gctacacctt    2160
caccagctac ggcatcagct gggtgaggca aaggaccggc caaggactgg aatggatcgg   2220
cgagatctac cctaggaggg gcaacaccta ctacaacgaa aagttcaagg gcaaggccac   2280
actgacagcc tacaagtcca gcggcacagc ctacatggag ctgagatctc tgaccagcga   2340
ggatagcgcc gtgttctttt gcgccagagg cggcatctac tacggcaatc tgttcgacta   2400
ctgggggcca aggcaccacac tgaccgtctc gagcgctaag acgactccac cgtccgtgta   2460
cccgctcgcg ccaggttcgg ccgctcagac gaacagcatg gtgaccctcg gctgcctcgt   2520
gaagggttat ttcccagagc cggtgaccgt gacgtggaac tccggctcac tgtcatcggg   2580
cgtgcacact tttccagcag tgctgcagtc ggacctttac accctcagct cgtccgtcac   2640
cgtcccttca tcaacttggc ctagccagac cgtgacttgc aatgtcgccc acccggcgtc   2700
cagcactaag gtggacaaga agatccacca ccatcaccat caccatcacc atcactagag   2760
agcggccgcg tctagacctg cactgactga ctgatacgct agcttgactg actgagatac   2820
agcgtacctt cagctcacag acatgataag atacattgat gagtttggac aaaccacaac   2880
tagaatgcag tgaaaaaaat gctttatttg tgaaatttgt gatgctattg ctttatttgt   2940
aaccattata agctgcaata aacaagttaa caacaacaat tgcattcatt ttatgtttca   3000
ggttcagggg gaggtgtggg aggttttttta aagcaagtaa aacctctaca aatgtggtat   3060
tggcccatct ctatcggtat cgtagcataa ccccttgggg cctctaaacg ggtcttgagg   3120
ggttttttgt gccctcggg ccggattgct atctaccggc attggcgcag aaaaaaaatgc    3180
ctgatgcgac gctgcgcgtc ttatactccc acatatgcca gattcagcaa cggatacggc   3240
ttcccaaact tgcccacttc catacgtgtc ctccttacca gaatttatc cttaaggtcg    3300
tcagctatcc tgcaggcgat ctctcgattt cgatcaagac attcctttaa tggtcttttc   3360
tggacaccac taggggtcag aagtagttca tcaaactttc ttccctcct aatctcattg    3420
gttaccttgg gctatcgaaa cttaattaac cagtcaagtc agctacttgg cgagatcgac   3480
ttgtctgggt ttcgactacg ctcagaattg cgtcagtcaa gttcgatctg gtccttgcta   3540
ttgcaccccgt tctccgatta cgagtttcat ttaaatcatg tgacaaaag gccagcaaaa   3600
ggccaggaac cgtaaaaagg ccgcgttgct ggcgttttc cataggctcc gcccccctga    3660
cgagcatcac aaaaatcgac gctcaagtca gaggtggcga aacccgacag gactataaag   3720
ataccaggcg tttccccctg gaagctccct cgtgcgctct cctgttccga cctgccgct    3780
taccggatac ctgtccgcct ttctcccttc gggaagcgtg gcgctttctc atagctcacg   3840
ctgtaggtat ctcagttcgg tgtaggtcgt tcgctccaag ctgggctgtg tgcacgaacc   3900
ccccgttcag cccgaccgct gcgccttatc cggtaactat cgtcttgagt ccaacccggt   3960
aagacacgac ttatcgccac tggcagcagc cactggtaac aggattagca gagcgaggta   4020
tgtaggcggt gctacagagt tcttgaagtg gtggcctaac tacggctaca ctagaagaac   4080
agtatttggt atctgcgctc tgctgaagcc agttaccttc ggaaaaagag ttggtagctc   4140
ttgatccggc aaacaaacca ccgctggtag cggtggtttt tttgtttgca agcagcagat   4200
tacgcgcaga aaaaaaggat ctcaagaaga tcctttgatc ttttctacgg ggtctgacgc   4260
tcagtggaac gaaaactcac gttaagggat tttggtcatg agattatcaa aaaggatctt   4320
cacctagatc cttttaaatt aaaaatgaag ttttaaatca atctaaagta tatatgagta   4380
aacttggtct gacagttacc aatgcttaat cagtgaggca cctatctcag cgatctgtct   4440
atttcgttca tccatagttg catttaaatt tccgaactct ccaaggccct cgtcggaaaa   4500
tcttcaaacc tttcgtccga tccatcttgc aggctacctc tgaacgaac tatcgcaagt   4560
ctcttggccg gccttgcgcc ttggctattg cttggcagcg cctatcgcca ggtattactc   4620
caatcccgaa tatccgagat cgggatcacc cgagagaagt tcaacctaca tcctcaatcc   4680
cgatctatcc gagatccgag gaatatcgaa atcgggcgc gcctggctc cgcgccgggt    4740
tttggcgcct cccgcgggcg ccccctcgt cacggccggc gctgccacgt cagacgaagg    4800
gcgcaggagc gtcctgatcc ttccgccgg acgctcagga cagcggcccg ctgctcataa   4860
gactcggcct tagaacccca gtatcagcag aaggacattt taggacggga cttgggtgac   4920
tctagggcac tggttttctt tccagagagc ggaacaggcg aggaaagta gtcccttctc    4980
ggcgattctg cggagggatc tccgtgggc ggtgaagcc gatgattata taaggacgcg    5040
ccgggtgtgg cacagctagt tccgtcgcag ccgggatttg ggtcgcggtt cttgtttgtg   5100
gatcgctgtg atcgtcactt ggtgagtagc gggctgctgg gctggccggg gctttcgtgg   5160
ccgccgggcc gctcggtggg acggaagcgt gtggagagac cgccaagggc tgtagtctgg   5220
gtccgcgagc aaggttgccc tgaactgggg gttggggga gcgcagcaaa atggcggctg   5280
ttcccgagtc ttgaatgaac gacgcttgtg aggcgggtcg tgaggtcagt gaaacaagt    5340
gggggcatg gtgggcggca agaacccaag gtcttgagcc cttcgctaat gcgggaaagc   5400
tcttattcgg gtgagatggg ctgggcacca tctgggaacc ctgacgtgaa gtttgtcact   5460
gactggagaa ctcggtttgt cgtctgttgc gggggcggca gttatggcgg tgccgttggg   5520
cagtgcaccc gtacctttgg gagcgcgcgc cctcgtcgtg tcgtgacgtc acccgttctg   5580
ttggcttata atgcagggtg gggccacctg tcggtaggc ttttctcctg                5640
cgcaggacgc agggttcggg cctagggtag gctctcctga atcgacaggc gccggacctc   5700
tggtgagggg agggataagt gaggcgtcag ttttcttggt cggttttatg tacctatctt   5760
cttaagtagc tgaagctccg gttttgaact atgcgctcgg ggttggcgag tgtgttttgt   5820
gaagtttttt aggcacctttt tgaaatgtaa tcatttgggt caatatgtaa ttttcagtgt   5880
tagacttgta aattgtccgc taaattctgg cgtttttgt agacaacatg                5940
ggtaaaaagc ctgaactcac cgcgacgtct gtcgagaagt ttctgatcga aaagttcgac   6000
agcgtctccg acctgatgca gctctcggag gcgaagaat ctcgtgcttt cagcttcgat    6060
gtaggagggc gtggatatgt cctgcgggta aatagctgcg ccgatggttt ctacaaagat   6120
cgttatgttt atcggcactt tgcatccgcc gcgctcccga ttccgaagt gcttgacatt   6180
ggggagttca gcgagagcct gacctattgc atctcccgcc gtgcacaggg tgtcacgttg   6240
```

```
caagacctgc ctgaaaccga actgcccgct gttctgcagc cggtcgcgga ggcaatggat   6300
gccatcgctg ccgccgatct tagccagacg agcgggttcg gcccattcgg accgcaagga   6360
atcggtcaat acactacatg gcgtgatttc atatgcgcga ttgctgatcc ccatgtgtat   6420
cactggcaaa ctgtgatgga cgacaccgtc agtgcgtccg tcgcgcaggc tctcgatgag   6480
ctgatgcttt gggccgagga ctgccccgaa gtccggcacc tcgtgcacgc ggatttcggc   6540
tccaacaatg tcctgacgga caatggccgc ataacagcgg tcattgactg gagcgaggcg   6600
atgttcgggg attcccaata cgaggtcgcc aacatcttct tctggaggcc gtggttggct   6660
tgtatggagc agcagacgcg ctacttcgag cggaggcatc cggagcttgc aggatcgccc   6720
cggctccggg cgtatatgct ccgcattggt ctttgaccaac tctatcagag cttggttgac   6780
ggcaatttcg atgatgcagc ttgggcgcag ggtcgatgcg acgcaatcgt ccgatccgga   6840
gccgggactg tcgggcgtac acaaatcgcc cgcagaagcg ccgccgtctg gaccgatggc   6900
tgtgtagaag tactcgccga tagtggaaac cgacgcccca gcactcgtcc gagggcaaag   6960
gaataagcta gtatgtaagc ctagtcttag ataataaaat cgctatccat cgaagatgga   7020
tgtgtgttgg ttttttgtgt gtgtaacgct aggcgcgcct ggtgtaccga gaacgatcct   7080
ctcagtgcga gtctcgacga tccatatcgt tgcttggcag tcagccagtc ggaatccagc   7140
tttgggaccca ggaagtccaa tcgtcagata ttgtactcaa gcctggtcac ggcagcgtac   7200
cgatctgttt aaacctagat attgatagtc tgatcggtca acgtataatc gagtcctagc   7260
ttttgcaaac atctatcaag agacaggatc agcaggaggc tttcgcatga ttgaacaaga   7320
tggattgcac gcaggttctc cggcggcttg ggtggagagg ctattcggct atgactgggc   7380
acaacagaca atcggctgct ctgatgccgc cgtgttccgg ctgtcagcgc aggggcgtcc   7440
ggttcttttt gtcaagaccg acctgtccgg tgccctgaat gaactgcaag acgaggcagc   7500
gcggctatcg tggctggcga cgacgggcgt tccttgcgca gctgtgctcg acgttgtcac   7560
tgaagcggga agggactggc tgctattggg cgaagtgccg gggcaggatc tcctgtcatc   7620
tcaccttgct cctgccgaga agtatccat catggctgat gcaatgcggc ggctgcatac   7680
gcttgatccg gctacctgcc cattcgacca ccaagcgaaa catcgcatcg agcgagcacg   7740
tactcggatg gaagccggtc ttgtcgatca ggatgatctg gacgaagagc atcagggggct   7800
cgcgccagcc gaactgttcg ccaggctcaa ggcgtctatg cccgacgcg aggatctcgt   7860
cgtgacccac ggcgatgcct gcttgccgaa tatcatggtg gaaaatggcc gcttttctgg   7920
attcatcgac tgtggccgtc tgggtgtggc ggaccgctat caggacatag cgttggctac   7980
ccgtgatatt gctgaagagc ttggcggcga atgggctgac cgcttcctg tgctttacgg   8040
tatcgccgcg cccgattcgc agcgcatcgc cttctatcgc cttcttgacg agttcttctg   8100
accgattcta ggtgcattgg cgcagaaaaa aatgcctgat gcgacgctgc gcgtcttata   8160
ctcccacata tgccagattc agcaacggat acggcttccc caacttgccc acttccatac   8220
gtgtcctcct taccagaaaat ttatccttaa ggtcgtttaa actcgactct ggctctatcg   8280
aatctccgtc gtttcgagct tacgcgaaca gccgtggcgc tcatttgctc gtcgggcatc   8340
gaatctcgtc agctatcgtc agcttacctt tttggca                             8377
```

```
SEQ ID NO: 87              molype = DNA   length = 8371
FEATURE                    Location/Qualifiers
misc_feature               1..8371
                           note = Synthetic polymer.
source                     1..8371
                           mol_type = other DNA
                           organism = synthetic construct
SEQUENCE: 87
gcgatcgcgg ctcccgacat cttggaccat tagctccaca ggtatcttct tccctctagt     60
ggtcataaca gcagcttcag ctacctctca attcaaaaaa ccccaagaa cccgtttaga    120
ggccccaagg ggttatgcta tcaatcgttg cgttacacac acaaaaaacc aacacacatc    180
catcttcgat ggatagcgat tttattatct aactgctgat cgagtgtagc cagatctata    240
gtaatcaatt acgggtcat tagttcatag cccatatatg gagttccgcg ttacataact    300
tacggtaaat ggcccgcctg gctgaccgcc caacgaccc cgcccattga cgtcaataat    360
gacgtatgtt cccatagtaa cgccaatagg gactttccat tgacgtcaat gggtggacta    420
tttacggtaa actgcccact tggcagtaca tcaagtgtat catatgccaa gtacgccccc    480
tattgacgtc aatgacggta atggcccgc ctggcattat gcccagtaca tgaccttatg    540
ggactttcct acttggcagt acatctacgt attagtcatc gctattacca tgcgtcgagg    600
tgagccccac gttctgcttc actctcccca tctccccccc ctccccaccc ccaatttgtg    660
atttatttat tttttaattta ttttatgcag cgatgggggc ggggggggg ggggcgcgcg    720
ccaggcgggg cggggcgggg cgagggggcgg ggcggggcga ggcggagagg tgcggcggca    780
gccaatcaga gcggcgcgct ccgaaagttt ccttttatgg cgaggcggcg gcggcggcgg    840
ccctataaaa agcgaagcgc gcggcgggcg ggagtcgtcg cgttgccttc gccccgtgcc    900
ccgctccgcg ccgcctcgcg ccgcccgccc cggctctgac tgaccgcgtt actcccacag    960
gtgagcgggc gggacggcccc ttctccctcc gggctgtaat tagcgcttgg tttaatgacg   1020
gctcgttct tttctgtggc tgcgtgaaag ccttaaaggg ctcgggaggg cctttgtgc    1080
ggggggagc ggctcggggg gtgcgtgcgt gtgtgtgtgc gtggggagcc ccgcgtgcgg   1140
cccgcgctgc ccggcggctg tgagcgctgc gggcgcggcc cggggctttg tgcgctccgc   1200
gtgtgcgcga gggagcgcg ggcggggcc ggtgcccgc ggtgcggggg ggctgcgagg    1260
ggaacaaagg ctgcgtgcgg ggtgtgtgcg tggggggtg agcaggggt gtgggcgcgg   1320
cggtcgggct gtaacccccc cctggcaccc ccctccccga gttgctgagc acggcccggc   1380
ttcgggtgcg gggctccgtg ggcgggggctc gcgggggctc cgctgccgg ggggggggtg   1440
gcggcaggtg ggggtgccgg gcggggcggg gccgcctcgg gccggggagg gctcggggga   1500
ggggcgcggc ggcccggag cgccggcggc tgtcgaggcg cggcgagccg cagccattgc   1560
ctttttatggt aatcgtgcga gagggcgcag ggacttcctt tgtcccaaat ctggcggagc   1620
cgaaatctgg gaggcgccgc cgcacccct ctagcggggc cggcgaagc ggtcggggcgc   1680
cggcaggaag gaaatggggcg ggggggcct tcgtgcgtcg ccgcgccgcc gtccccttct   1740
ccatctccag cctcgggct gccgcagggg gacggctgcc ttcggggggg acggggcagg   1800
gcggggttcg gcttctggcg tgtgaccggc ggctttagag cctctgctaa ccatgttcat   1860
gccttcttcc ttttcctaca gctcctgggc aacgtgctgg ttgttgtgct gtctcatcat   1920
tttggcaaag atctttgtcg atcctaccat ccactcgaca cacccgccag cggccgctgc   1980
caagcttccg agctctcgaa ttcaggaggt acccaccatg agggtccccg ctcagctcct   2040
```

```
ggggctcctg ctgctctggc tcccaggcgc gcgatgtcaa gccgtggtga cccaagagtc 2100
cgctctgaca acaagccccg gcgagacagt gacactgaca tgtagaagca gcaccggagc 2160
cgtgaccacc agcaactacg ccaactgggt gcaagagaag cccgaccatc tgtttaccgg 2220
actgatcgga ggcaccaata acagagcccc cggcgtgccc gccagattta gcggctctct 2280
gattggcgac aaggctgctc tgaccatcac cggagcccaa accgaggacg aggccatcta 2340
cttctgcgct ctgtggttca gcaaccactg ggtgtttggc ggcggcacca aactgaccgt 2400
gctcgggcag cctaaaagct cgccgtccgt gaccctcttt ccaccatcat cggaagagct 2460
ggaaaccaac aaggctactc tcgtctgcac catcacggat ttctaccccg agtggtcac 2520
cgtggactgg aaagtggacg ggactccggt gactcaggga atggaaacga cccaaccgtg 2580
aaagcagtcg aacaataagt acatggcctc cagctacctg accttgaccg ccagagcgtg 2640
ggagcggcac agctcctact catgtcaagt cactcacgaa ggccatactg tggagaagag 2700
cctgtcccgc gcagattgct cgtagtgagc ggccgcgtct agacctgcac tgactgactg 2760
atacaatcga tttctggatc cgcaggcctc tgctagcttg actgactgag atacagcgta 2820
ccttcagctc acagacatga taagatacat tgatgagttt gacaaaacca caactagaat 2880
gcagtgaaaa aaatgcttta tttgtgaaat ttgtgatgct attgctttat ttgtaaccat 2940
tataagctgc aataaacaag ttaacaacaa caattgcatt cattttatgt ttcaggttca 3000
gggggaggtg tgggaggttt tttaaagcaa gtaaacctc tacaaatgtg gtattggccc 3060
atctctatcg gtatcgtagc ataacccctt ggggcctcta aacgggtctt gagggggtttt 3120
ttgtgcccct cgggccggat tgctatctac cggcattggc gcagaaaaaa atgcctgatg 3180
cgacgctgcg cgtcttatac tcccacatat gccagattca gcaacggata cggcttcccc 3240
aacttgccca cttccatacg tgtcctcctt accagaaatt tatccttaag gtcgtcagct 3300
atcctgcagg cgatctctcg atttcgatca agacattcct ttaatggtct tttctggaca 3360
ccactagggg tcagaagtag ttcatcaaac tttcttccct ccctaatctc attggttacc 3420
ttgggctatc gaaacttaat taaccagtca agtcagctac ttggcgagat cgacttgtct 3480
gggtttcgac tacgctcaga attgcgtcag tcaagttcga tctggtcctt gctattgcac 3540
ccgttctccg attacgagtt tcatttaaat catgtgagca aaaggccagc aaaaggccag 3600
gaaccgtaaa aaggccgcgt tgctggcgtt tttccatagg ctccgccccc ctgacgagca 3660
tcacaaaaat cgacgctcaa gtcagaggtg gcgaaacccg acaggactat aaagatacca 3720
ggcgtttccc cctggaagct ccctcgtgcg ctctcctgtt ccgaccctgc cgcttaccgg 3780
atacctgtcc gcctttctcc cttcgggaag cgtggcgctt tctcatagct cacgctgtag 3840
gtatctcagt tcggtgtagg tcgttcgctc caagctgggc tgtgtgcacg aaccccccgt 3900
tcagcccgac cgctgcgcct tatccggtaa ctatcgtctt gagtccaacc cggtaagaca 3960
cgacttatcg ccactggcag cagccactgg taacaggatt agcagagcga gtatgtaggg 4020
cggtgctaca gagttcttga agtggtggcc taactacggc tacactagaa gaacagtatt 4080
tggtatctgc gctctgctga agccagttac cttcggaaaa agagttggta gctcttgatc 4140
cggcaaacaa accaccgctg gtagcggtgg ttttttttgtt tgcaagcagc agattacgcg 4200
cagaaaaaaa ggatctcaag aagatccttt gatcttttct acggggtctg acgctcagtg 4260
gaacgaaaac tcacgttaag ggattttggt catgagatta tcaaaaagga tcttcaccta 4320
gatcctttta aattaaaaat gaagttttaa atcaatctaa agtatatatg agtaaacttg 4380
gtctgacagt taccaatgct taatcagtga ggcacctatc tcagcgatct gtctatttcg 4440
ttcatccata gttgcattta aatttccgaa ctctccaagg ccctcgtcgg aaaatcttca 4500
aacctttcgt ccgatccatc ttgcaggcta cctctcgaac gaactatcgc aagtctcttg 4560
gccggccttg cgccttggct attgcttggc agcgcctatc gccaggtatt actccaatcc 4620
cgaatatccg agatcgggat cacccgagag aagttcaacc tacatcctca atcccgatct 4680
atccgagatc gaggaatat cgaaatcggg gcgcgcctgg cctccgcgcc gggttttggc 4740
gcctcccgcg ggcgccccc tcgtcacggc gagcgctgcc acgtcagacg aagggcgcag 4800
gagcgtcctg atccttccgc ccggacgctc aggacagcgg cccgctgctc ataagactcg 4860
gccttagaac cccagtatca gcagaaggac attttaggac gggacttggg tgactctagg 4920
gcactggttt tctttccaga gagcggaaca ggcgaggaaa agtagtccct tctcggcgat 4980
tctgcggagg gatctccgtg gggcggtgaa cgccgatgat tatataagga cgcgccgggt 5040
gtggcacagc tagttccgtc gcagccgtga tttgggtcgc ggttcttgtt tgtggatcgc 5100
tgtgatcgtc acttggtgag tagcgggctg ctgggctggc cggggctttc gtggccgccg 5160
ggccgctcgg tgggacggaa gcgtgtggag agaccgccaa gggctgtagt ctgggtccgc 5220
gagcaaggtt gccctgaact gggggttggg gggagcgcag caaaatgcgc gctgttcccg 5280
agtcttgaat ggaagacgct tgtgaggcgg gctgtgaggt cgttgaaaca aggtgggggg 5340
catggtgggc ggcaagaacc caaggtcttg agcccttcgc taatgcggga aagctcttat 5400
tcgggtgaga tgggctgggc accatctggg gaccctgacg tgaagtttgt cactgactgg 5460
agaactcggt ttgtcgtctg ttgcggggc ggcagttatg gcggtgccgt gggcagtgc 5520
acccgtacct ttgggagcgc gcgccctcgt cgtgtcgtga cgtcacccgt tctgttgcgt 5580
tataatgcag ggtggggcca cctgccgta ggtgtgcggt aggcttttct ccgtcgcagg 5640
acgcagggtt cgggcctagg gtaggctctc ctgaatcgac aggcgccgga cctctggtga 5700
ggggaggat aagtgaggcg tcagtttctt tggtcggttt tatgtaccta tcttcttaag 5760
tagctgaagc tccggttttg aactatcgcg tcggggttgg cgagtgtgtt ttgtgaagtt 5820
ttttaggcac ctttttgaaat gtaatcattt gggtcaatat gtaattttcg ggttagtact 5880
tgtaaattgt ccgctaaatt ctggccgttt ttggcttttt tgttagacaa catgtgtaaa 5940
aagcctgaac tcaccgcgac gtctgtcgag aagtttctga tcgaaagtt cgacagcgtc 6000
tccgacctga tgcagctctc ggagggcgaa gaatctcgtg ctttcagctt cgatgtagga 6060
gggcgtggat atgtcctgcg ggtaaatagc tgcgccgatg gtttctacaa agatcgttat 6120
gtttatcgga acttttgcatc cgccgcgctc ccgattccga agtgcttga cattgggaag 6180
ttcagcgaga gcctgaccta ttgcatctcc cgccgtgcac agggtgtcac gttgcaagac 6240
ctgcctgaaa ccgaactgcc cgctgttctg cagccggtcg cggaggcaat ggatgccatc 6300
gctgccgccg atcttagcca gacgagcggg ttcggcccat tcggaccgca aggaatcggt 6360
caatacacta catggcgtga tttcatatgc gcgattgctg atccccatgt gtatcactgg 6420
caaactgtga tggacgacac cgtcagtgcg tccgtcgcgc aggctctcga tgagctgatg 6480
ctttgggccg aggactgccc cgaagtccgg cacctcgtgc acgcggattt cggctccaac 6540
aatgtcctga cggacaatgg ccgcataaca gcggtcattg actggagcga ggcgatgttc 6600
ggggattccc aatacgaggt cgccaacatc ttcttctgga ggccgtggtt ggcttgtatg 6660
gagcagcaga cgcgctactt cgagcggagg catccggagc ttgcaggatc gccccggctc 6720
cgggcgtata tgctccgcat tggtcttgac caactctatc agagcttggt tgacggcaat 6780
```

```
ttcgatgatg cagcttgggc gcagggtcga tgcgacgcaa tcgtccgatc cggagccggg   6840
actgtcgggc gtacacaaat cgcccgcaga agcgccgccg tctggaccga tggctgtgta   6900
gaagtactcg ccgatagtgg aaaccgacgc cccagcactc gtccgagggc aaaggaataa   6960
gctagtatgt aagcctagtc ttagataata aaatcgctat ccatcgaaga tggatgtgtg   7020
ttggtttttt gtgtgtgtaa cgctaggcgc gcctggtgta ccgagaacga tcctctcagt   7080
gcgagtctcg acgatccata tcgttgcttg gcagtcagcc agtcggaatc cagcttggga   7140
cccaggaagt ccaatcgtca gatattgtac tcaagcctgg tcacggcagc gtaccgatct   7200
gtttaaacct agatattgat agtctgatcg gtcaacgtat aatcgagtcc tagcttttgc   7260
aaacatctat caagagacag gatcagcagg aggctttcgc atgattgaac aagatggatt   7320
gcacgcaggt tctccggcgg cttgggtgga gaggctattc ggctatgact gggcacaaca   7380
gacaatcggc tgctctgatg ccgccgtgtt ccggctgtca gcgcaggggc gtccggttct   7440
ttttgtcaag accgacctgt ccggtgccct gaatgaactg caagacgagg cagcgcggct   7500
atcgtggctg gcgacgacgg gcgttccttg cgcggctgtg ctcgacgttg tcactgaagc   7560
gggaagggac tggctgctat tgggcgaagt gccggggcag gatctcctgt catctcacct   7620
tgctcctgcc gagaaagtat ccatcatggc tgatgcaatg cggcggctgc atacgcttga   7680
tccggctacc tgcccattcg accaccaagc gaaacatcgc atcgagcgag cacgtactcg   7740
gatggaagcc ggtcttgtcg atcaggatga tctggacgaa gagcatcagg ggctcgcgcc   7800
agccgaactg ttcgccaggc tcaaggcgtc tatgcccgac ggcgaggatc tcgtcgtgac   7860
ccacggcgat gcctgcttgc cgaatatcat ggtggaaaat ggccgctttt ctggattcat   7920
cgactgtggc cgtctgggtg tggcggaccg ctatcaggac atagcgttgg ctacccgtga   7980
tattgctgaa gagcttggcg gcgaatgggc tgaccgcttc cttgtgcttt acggtatcgc   8040
cgcgcccgat tcgcagcgca tcgccttcta tcgccttctt gacgagttct tctgaccgat   8100
tctaggtgca ttggcgcaga aaaaaatgcc tgatgcgacg ctgcgcgtct tatactccca   8160
catatgccag attcagcaac ggatacggct tccccaactt gcccacttcc atacgtgtcc   8220
tccttaccag aaatttatcc ttaaggtcgt ttaaactcga ctctggctct atcgaatctc   8280
cgtcgtttcg agcttacgcg aacagccgtg gcgctcattt gctcgtcggg catcgaatct   8340
cgtcagctat cgtcagctta cctttttggc a                                  8371
```

SEQ ID NO: 88          moltype = DNA  length = 11147
FEATURE                Location/Qualifiers
misc_feature           1..11147
                       note = Synthetic polymer.
source                 1..11147
                       mol_type = other DNA
                       organism = synthetic construct
SEQUENCE: 88

```
gcgatcgcgg ctcccgacat cttggaccat tagctccaca ggtatcttct tccctctagt     60
ggtcataaca gcagcttcag ctacctctca attcaaaaaa ccccctcaaga cccgtttaga   120
ggccccaagg ggttatgcta tcaatcgttg cgttacacac acaaaaaacc aacacacatc   180
catcttcgat ggatagcgat tttattatct aactgctgat cgagtgtagc cagatctata   240
gtaatcaatt acggggtcat tagttcatag cccatatatg gagttccgcg ttacataact   300
tacggtaaat ggcccgcctg gctgaccgcc caacgacccc cgcccattga cgtcaataat   360
gacgtatgtt cccatagtaa cgccaatagg gactttccat tgacgtcaat gggtggacta   420
tttacggtaa actgcccact tggcagtaca tcaagtgtat catatgccaa gtacgccccc   480
tattgacgtc aatgacggta aatggcccgc ctggcattat gcccagtaca tgaccttatg   540
ggactttcct acttggcagt acatctacgt attagtcatc gctattacca tcgtcgagg    600
tgagccccac gttctgcttc actctccccca tctccccccc ctccccaccc ccaatttttg   660
atttatttat ttttaatta ttttatgcag cgatggggc ggggggggg gggcgcgcg       720
ccaggcgggg cggggcgggg cgaggggcgg ggcggggcga ggcggagagg tgcggcggca   780
gccaatcaga gcggcgcgct ccgaaagttt ccttttatgg cgaggcggcg gcggcggcgg   840
ccctataaaa agcgaagcgc gcggcggggcg ggagtcgctg cgttgccttc gccccgtgc   900
ccgctccgcg ccgcctcgcg ccgcccgccc cggctctgac tgaccgcgtt actcccacag   960
gtgagcgggc gggacggccc ttctccctcc gggctgtaat tagcgcttgg tttaatgacg  1020
gctcgtttct tttctgtggc tgcgtgaaag ccttaaaggg ctccggggag gccttttgtgc  1080
gggggggagc ggctcggggg gtgcgtgcgt gtgtgtgtgc gtgggggagcg ccgcgtgcgg  1140
cccgcgctgc ccgcggcctg tgagcgctgc gggcgcggcg cggggctttg tgcgctccgc  1200
gtgtgcgcga ggggagcgcg ggcggggc ggtgccccgc ggtgcggggg ggctgcgagg   1260
ggaacaaagg ctgcgtgcgg ggtgtgtgcg tggggggggtg agcaggggt gtgggcgcgg   1320
cggtcgggct gtaacccccc cctggcaccc ccctccccga gttgctgagc acggcccggc   1380
ttccgggtgcg gggctccgtg cgggcgtgg cgcgggcgtc gcgtgccgg gcgggggcg   1440
gcggcaggtg ggggtgccgg gcgggcggg gccgcctcgg gccgggggag gctcggggga   1500
ggggcgcggc ggcccggag cgccggcggc tgtcgaggcg cggcgagccg cagccattgc   1560
cttttatggt aatcgtgcga gagggcgcag ggacttcctt tgtcccaaat ctggcggagc   1620
cgaaatctgg gaggcgccgc cgcaccccct ctagcggggg cgaaagc ggtgcggcgc   1680
cggcaggaag gaaatgggcg gggagggcct tcgtgcgtcg ccgcgccgcc gtcccctcct   1740
ccatctccag cctcggggct gccgcagggg gacggctgcc ttggggggg acggggcagg   1800
gcggggttcg gcttctggcg tgtgaccggc ggctttagag cctctgctaa ccatgttcat   1860
gccttcttct ttttccctaca gctccttggc aacgtgctgg ttgttgtgct gtctcatcat   1920
tttggcaaag atctttgtcg atcctaccat ccactcgaca cccgccag cggccgctgc   1980
caagcttccg agctctcgaa ttcaggaggt acccaccatg agggtccccg ctcagctcct   2040
ggggctcctg ctgctctggc tcccaggcgc gcgatgtcaa gccgtggtga cccaagagtc   2100
cgctctgaca caagccccg gcgagacagt gacactgaca tgtagaagca gcaccggagc   2160
cgtgaccacc agcaactacg ccaactgggt gcaagagaag cccgaccatc tgtttaccgg   2220
actgatcgga ggcaccaata acagagcccc cggcagtcca gcagatttag gcggctctca   2280
gattggcgac aaggctgctc tgaccatcac cggagcccag accgaggacg aggcatctca   2340
cttctcgcgct ctgtggttca gcaacctg ggtgtttggc gcggcacca aactgaccgt   2400
gctcgggcag cctaaaagct cgccgtcgt gaccctcttt ccaccatcat cggaagagct   2460
ggaaccaac aaggctactc tcgtctgcac catcacggat ttctaccccg gagtggtcac   2520
cgtggactgg aaagtggacg ggactccggt gactcaggga atgaaacga cccaaccgtc   2580
```

```
aaagcagtcg aacaataagt acatggcctc cagctacctg accttgaccg ccagagcgtg 2640
ggagcggcac agctcctact catgtcaagt cactcacgaa ggccatactg tggagaagag 2700
cctgtcccgc gcagattgct cgtagtgagc ggccgcgtct agacctgcac tgactgactg 2760
atacaatcga tttctggatc cgcaggcctc tgctagcttg actgactgag atacagcgta 2820
ccttcagctc acagacatga taagatacat tgatgagttt ggacaaacca caactagaat 2880
gcagtgaaaa aaatgcttta tttgtgaaat ttgtgatgct attgctttat ttgtaaccat 2940
tataagctgc aataaacaag ttaacaacaa caattgcatt cattttatgt ttcaggttca 3000
gggggaggtg tgggaggttt tttaaagcaa gtaaaacctc tacaaatgtg gtattggccc 3060
atctctatcg gtatcgtagc ataacccctt ggggcctcta aacgggtctt gagggggttt 3120
ttgtgcccct cgggccggat tgctatctac cggcattggc gcagaaaaaa atgcctgatg 3180
cgacgctgcg cgtcttatac tcccacatat gccagattca gcaacggata cggcttcccc 3240
aacttgccca cttccatacg tgtcctcctt accagaaatt tatccttaag gtcgtcagct 3300
atcctgcagg atagtaatca attacggggt cattagttca tagcccatat atggagttcc 3360
gcgttacata acttacggta aatggcccgc ctggctgacc caacgacccc cgcccat 3420
tgacgtcaat aatgacgtat gttcccatag taacgccaat agggactttc cattgacgtc 3480
aatgggtgga ctatttacgg taaactgccc acttggcagt acatcaagtg tatcatatgc 3540
caagtacgcc ccctattgac gtcaatgacg gtaaatggcc cgcctggcat tatgcccagt 3600
acatgacctt atgggacttt cctacttggc agtacatcta cgtattagtc atcgctatta 3660
ccatgcgtcg aggtgagccc cacgttctgc ttcactctcc ccatctcccc ccctcccca 3720
cccccaattt tgtatttatt tattttttaa ttatttatg cagcgatggg ggcgggggg 3780
gggggggcgc gcgccaggcg gggcggggcg gggcgagggg cggggcgggg cgaggcggag 3840
aggtgcgggg gcagccaatc agagcgggcg gctccgaaag tttcctttta tggcgaggcg 3900
gcggcggcgg cggccctata aaaagcgaag cgcgcggcgg gcgggagtcg ctgcgttgcc 3960
ttcgccccgt gccccgctcc gcgccgcctc gcgccgcccg ccccggctct gactgaccgc 4020
gttactccca caggtgagcg ggcgggacgg cccttctccc tccgggctgt aattagcgct 4080
tggttaaatg acggctcgtt tcttttctgt ggctgcgtga aagccttaaa gggctccggg 4140
agggcctttg tgcggggggg agccgctcgg ggggtgcgtg cgtgtgtgtg tgcgtgggga 4200
gcgccgcgtg cggcccgcgc tgcccggcgg ctgtgagcgc tgcggcgcg gcgcgggct 4260
ttgtgcgctc cgcgtgtgcg cgaggggagc gcgggccggg ggcggtgccc cgcggtgcgg 4320
gggggctgcg aggggaacaa aggctgcgtg cggggtgtgt gcgtgggggg gtgagcaggg 4380
ggtgtgggcg cggcggtcgg gctgtaaccc ccccctggca cccccctccc cgagttgctg 4440
agcacggccc ggcttcgggt gcgggctcc gtgcggggcg tggcgcgggg ctcgccgtgc 4500
cgggcggggg gtggcggcag gtgggggtgc cgggcggggc ggggccgcct cgggccgggg 4560
agggctcggg ggaggggcgc ggcggccccg gagcgaggcg ggctgtcgag gcgcggcgag 4620
ccgcagccat tgccttttat ggtaatcgtg cgagagggcg cagggacttc ctttgtccca 4680
aatctggcgc agccgaaatc tgggaggcgc cgccgcaccc cctctagcgg gcgcgggcga 4740
agcggtgcgg cgccggcagg aaggaaatgg gcggggaggg ccttcgtgcg tcgccgcgcc 4800
gccgtcccct tctccatctc cagcctcggg gctgccgcag gggacggct gccttcgggg 4860
gggacgggca agggcgggt tcggcttctg gcgtgtgacc ggcggcttta gagcctctgc 4920
taaccatgtt catgccttct tctttttcct acagctcctg gcaacgtgc tggttgttgt 4980
gctgtctcat cattttggca aattcgacca accttccttc gacacgggc ccaaagtact 5040
aaagtcgaca ggaggtaccc accatgggtt ggagcctcat cttgctcttc cttgtcgctg 5100
ttgctacgcg tgtccactcc caagtgcagc tgcagcagga ggagccgaa ctggctagac 5160
ccggagcctc cgtgaagctg agctgtaagg cctccggcta caccttcacc agctacggca 5220
tcagctgggt gaggcaaagg accggccaag gactggaatg gatcggcgag atctacccta 5280
ggaggggcaa cacctactac aacgagaagt tcaagggcaa ggccacactg acagcctaca 5340
agtccagcgg cacagcctac atggagctga gatctctgac agccgaggat agcgccgtgt 5400
tcttttgcgc cagaggcggc atctactacg gcaatctgtt cgactactgg ggccaagca 5460
ccacactgac cgtctcgagc gctaagacga ctccaccgtc cgtgtacccg ctcgcgccag 5520
gttcggccgc tcagacgaac agcatggtga ccctcggctg cctcgtgaag ggttatttcc 5580
cagagccggt gaccgtgacg tggaactccg gctcactgtc atcgggcgtg cacacttgtg 5640
cagcagtgct gcagtcggac ctttacaccc tcagctcgtc cgtcaccgtc ccttcatcaa 5700
cttggcctag ccagaccgtg acttgcaatg tcgcccaccc ggcgtccagc actaaggtgg 5760
acaagaagat ccaccaccat caccatcacc atcaccatca ctagagagcg gccgcgtcta 5820
gacctgcact gactgactga tacactagtt agcctgtgcc ttctagttgc cagccatctg 5880
ttgtttgccc ctcccccgtg ccttccttga ccctggaagg tgccactccc actgtccttt 5940
cctaataaaa tgaggaaatt gcatcgcatt gtctgagtag gtgtcattct attctgggg 6000
gtggggtggg gcaggacagc aagggggagg attgggaaga caatagcagg catgctgggg 6060
atgcggtggg ctctatggcc tgcacgcgat ctctcgattt cgatcaagac attcctttaa 6120
tggtctttc tggacaccac taggggtcag aagtagttca tcaaactttc ttccctccct 6180
aatctcattg gttaccttgg gctatcgaaa cttaattaac cagtcaagtc agctacttgg 6240
cgagatcgac ttgtctgggt ttcgactacg ctcagaattg cgtcagtcaa gttcgatctg 6300
gtccttgcta ttgcacccgt tctccgatta cgagtttcat ttaaatcatg tgagcaaaag 6360
gccagcaaaa ggccaggaac cgtaaaaagg ccgcgttgct gcgttttttc catagctccg 6420
gcccccctga cgagcatcac aaaaatcgac gctcaagtca gaggtggcga acccgacag 6480
gactataaag ataccaggcg tttccccctg gaagctccct cgtgcgctct cctgttccga 6540
ccctgccgct taccggatac ctgtccgcct ttctcccttc gggaagcgtg gcgctttctc 6600
atagctcacg ctgtaggtat ctcagttcgg tgtaggtcgt tcgctccaag ctgggctgtg 6660
tgcacgaacc cccgttcag cccgaccgct gcgccttatc cggtaactat cgtcttgagt 6720
ccaacccggt aagacacgac ttatcgccac tggcagcagc cactggtaac aggattagca 6780
gagcgaggta tgtaggcggt gctacagagt tcttgaagtg gtggcctaac tacggctaca 6840
ctagaagaac agtatttggt atctgcgctc tgctgaagcc agttaccttc ggaaaaagag 6900
ttggtagctc ttgatccggc aaacaaacca ccgctggtag cggtggtttt tttgtttgca 6960
agcagcagat tacgcgcaga aaaaaaggat ctcaagaaga tcctttgatc ttttctacgg 7020
ggtctgacgc tcagtggaac gaaaactcac gttaagggat tttggtcatg agattatcaa 7080
aaaggatctt cacctagatc ctttaaatt aaaaatgaag ttttaaatca atctaaagta 7140
tatatgagta aacttggtct gacagttacc aatgcttaat cagtgaggca cctatctcag 7200
cgatctgtct atttcgttca tccatagttg catttaaatt tccgaactct caaggccct 7260
cgtcggaaaa tcttcaaacc tttcgtccga tccatcttgc aggctacctc tcgaacgaac 7320
```

```
tatcgcaagt ctcttggccg gccttgcgcc ttggctattg cttggcagcg cctatcgcca    7380
ggtattactc caatcccgaa tatccgagat cgggatcacc cgagagaagt tcaacctaca    7440
tcctcaatcc cgatctatcc gagatccgag gaatatcgaa atcggggcgc gcctggcctc    7500
cgcgccgggt tttggcgcct cccgcgggcg ccccctcgt cacggcgagc gctgccacgt     7560
cagacgaagg gcgcaggagc gtcctgatcc ttccgcccgg acgctcagga cagcggcccg    7620
ctgctcataa gactcggcct tagaacccca gtatcagcag aaggacattt taggacggga    7680
cttgggtgac tctagggcac tggttttctt tccagagagc ggaacaggcg aggaaaagta    7740
gtcccttctc ggcgattctg cggagggatc tccgtggggc ggtgaacgcc gatgattata    7800
taaggacgcg ccgggtgtgg cacagctagt tccgtcgcag ccgggatttg ggtcgcggtt    7860
cttgttttgtg gatcgctgtg atcgtcactt ggtgagtagc ggcggtgctgg gctggccggg    7920
gctttcgtgg ccgccgggcc gctcggtggg acggaagcgt gtggagagac cgccaagggc    7980
tgtagtctgg gtccgcgagc aaggttgccc tgaactgggg gttgggggga gcgcagcaaa    8040
atggcggctg ttcccgagtc ttgaatggaa gacgcttgtg aggcgggctg tgaggtcgtt    8100
gaaacaaggt ggggggcatg gtgggcggca agaacccaag gtcttgagcc cttcgctaat    8160
gcgggaaagc tcttattcgg gtgagatggg ctgggcacca tctgggaccc ctgacgtgaa    8220
gtttgtcact gactggagaa ctcggtttgt cgtctgttgc ggggcggca gttatggcgg     8280
tgccgttggg cagtgcaccc gtaccttgg gagcgcgcgc cctcgtcgtg tcgtgacgtc     8340
acccgttctg ttggcttata atgcagggtg gggccacctg ccggtaggtg tgcggtaggc    8400
ttttctccgt cgcaggacgc agggttcggg cctagggtag gctctcctga atcgacaggc    8460
gccggacctc tggtgagggg agggataagt gaggcgtcag tttctttggt cggttttatg    8520
tacctatctt cttaagtagc tgaagctccg gttttgaact atgcgctcgg ggttggcgag    8580
tgtgttttgt gaagttttt aggcacctt tgaaatgtaa tcatttgggt caatatgtaa     8640
ttttcagtgt tagacttgta aattgtccgc taaattctgg ccgttttggg cttttttgtt    8700
agacaacatg ggtaaaaagc ctgaactcac cgcgacgtct gtcgagaagt ttctgatcga    8760
aaagttcgac agcgtctccg acctgatgca gctctcggag ggcgaagaat ctcgtgcttt    8820
cagcttcgat gtaggagggc gtggatatgt cctgcgggta aatagctgcg ccgatggttt    8880
ctacaaagat cgttatgttt atcggcactt tgcatccgcc gcgctcccga ttccggaagt    8940
gcttgacatt ggggagttca gcgagagcct gacctattgc atctcccgcc gtgcacaggg    9000
tgtcacgttg caagacctgc ctgaaaccga actgcccgct gttctgcagc cggtcgcgga    9060
ggcaatggat gccatcgctg ccgccgatct tagccagacg agcgggttcg gcccattcgg    9120
accgcaagga atcggtcaat acactacatg gcgtgatttc atatgcgcga ttgctgatcc    9180
ccatgtgtat cactggcaaa ctgtgatgga cgacaccgtc agtgcgtccg tcgcgcaggc    9240
tctcgatgag ctgatgcttt gggccgagga ctgccccgaa gtccggcacc tcgtgcacgc    9300
ggatttcggc tccaacaatg tcctgacgga caatggccgc ataacagcgg tcattgactg    9360
gagcgaggcg atgttcgggg attcccaata cgaggtcgcc aacatcttct tctggaggcc    9420
gtggttggct tgtatggagc agcagacgcg ctacttcgag cggaggcatc cggagcttgc    9480
aggatcgccc cggctccggg cgtatatgct ccgcattggt cttgaccaac tctatcagag    9540
cttggttgac ggcaatttcg atgatgcagc ttgggcgcag ggtcgatgcg acgcaatcgt    9600
ccgatcccgga gccggactg tcgggcgtac acaaatcgcc cgcagaagcg ccgccgtcgtg   9660
gaccgatggc tgtgtagaag tactcgccga tagtggaaac cgacgcccca gcactcgtcc    9720
gagggcaaag gaataagcta gtatgtaagc ctagtcttag ataataaaat cgctatccat    9780
cgaagatgga tgtgtgttgg ttttttgtgt gtgtaacgct aggcgcgcct ggtgtaccga    9840
gaacgatcct ctcagtgcga gtctcgacga tccatatcgt tgcttggcag tcagccagtc    9900
ggaatccagc ttgggaccca ggaagtccaa tcgtcagata ttgtactcaa gcctggtcac    9960
ggcagcgtac cgatcgtgtt taaacctagat attgatagtc tgatcggtca acgtataatc   10020
gagtcctagc ttttgcaaac atctatcaag agacaggatc agcaggaggc tttcgcatga   10080
ttgaacaaga tggattgcac gcaggttctc cggccggcttg ggtggagagg ctattcggct   10140
atgactgggc acaacagaca atcggctgct ctgatgccgc cgtgttccgg ctgtcagcgc   10200
aggggcgtcc ggttctttttt gtcaagaccg acctgtccgg tgccctgaat gaactgcaag   10260
acgaggcagc gcggctatcg tggctggcga cgacgggcgt tccttgcgcg gctgtgctcg   10320
acgttgtcac tgaagcggga aagggactgg ctgctattgg cgaagtgccg gggcaggatc   10380
tcctgtcatc tcaccttgct cctgccgaga aagtatccat catggctgat gcaatgcggc   10440
ggctgcatac gcttgatccg gctacctgcc cattcgacca ccaagcgaaa catcgcatcg   10500
agcgagcacg tactcggatg gaagccggtc ttgtcgatca ggatgatctg gacgaagagc   10560
atcaggggct cgcgccagcc gaactgttcg ccaggctcaa ggcgtctatg cccgacggcg   10620
aggatctcgt cgtgacccac ggcgatgcct gcttgccgaa tatcatggtg gaaaatggcc   10680
gcttttctgg attcatcgac tgtggccgtc tgggtgtggc ggaccgctat caggacatag   10740
cgttggctac ccgtgatatt gctgaagagc ttggcggcga atgggctgac cgcttccttg   10800
tgctttacgg tatcgccgcg cccgattcgc agcgcatcgc cttctatcgc cttcttgacg   10860
agttcttctg accgattcta ggtgcattgg cgcagaaaaa atgcctgat gcgacgctgc    10920
gcgtcttata ctcccacata tgccagattc agcaacggat acggcttccc caacttgccc   10980
acttccatac gtgtcctcct taccagaaat ttatccttaa ggtcgtttaa actcgactct   11040
ggctctatcg aatctccgtc gtttcgagct tacgcgaaca gccgtggcgc tcatttgctc   11100
gtcgggcatc gaatctcgtc agctatcgtc agcttaccct tttggca                11147
SEQ ID NO: 89         moltype = DNA   length = 4997
FEATURE               Location/Qualifiers
misc_feature          1..4997
                      note = Synthetic polymer.
source                1..4997
                      mol_type = other DNA
                      organism = synthetic construct
SEQUENCE: 89
gcgatcgcgg ctcccgacat cttggaccat tagctccaca ggtatcttct tccctctagt      60
ggtcataaca gcagcttcag ctacctctca attcaaaaaa cccctcaaga cccgtttaga    120
ggccccaagg ggttatgcta tcaatcgttt cgttacacac acaaaaaacc aacacacatc    180
catcttcgat ggatagcgat tttattatct aactgctgat cgagtgtagc cagatctagt    240
aatcaattac ggggtcatta gttcatagcc catatatgga gttccgcgtt acataactta    300
cggtaaatgg cccgcctggc tgaccgccca acgacccccg cccattgacg tcaataatga    360
```

```
cgtatgttcc catagtaacg ccaataggga ctttccattg acgtcaatgg gtggagtatt    420
tacggtaaac tgcccacttg gcagtacatc aagtgtatca tatgccaagt acgcccccta    480
ttgacgtcaa tgacggtaaa tggcccgcct ggcattatgc ccagtacatg acctatggg     540
actttcctac ttggcagtac atctacgtat tagtcatcgc tattaccatg ctgatgcggt    600
tttggcagta catcaatggg cgtggatagc ggtttgactc acggggattt ccaagtctcc    660
accccattga cgtcaatggg agtttgtttt ggcaccaaaa tcaacgggac tttccaaaat    720
gtcgtaacaa ctccgcccca ttgacgcaaa tgggcggtag gcgtgtacgg tgggaggtct    780
atataagcag agctggttta gtgaaccgtc agatcagatc tttgtcgatc ctaccatcca    840
ctcgacacac ccgccagcag ccgctgccaa gcttccgagc tctcgaattc aaaggaggta    900
cccaccatgc cgctgctgct actgctgccc ctgctgtgtg caggggcgct agctcaagtg    960
cagctgcagc agagcggagc cgagctggtg aagcccggag ccagcgtgaa gatcagctgc   1020
aaggccagcg gctacgcctt ctccaactac tggatgaact gggtgaagca gagacccggc   1080
aagggactgg aatggatcgg ccagatctac cccggcgacg agacaccaa ctacaacggc    1140
aagttcaagg gcaaagccac actgaccgcc gacaagagct ccagcaccgc ctacatgcag   1200
ctgagctctc tgaccagcga ggatagcgcc gtgtacttct gcgccagagg agactactgg   1260
ggccaaggca ccacactgac cgtctcgagc gctaagacga ctccaccgtc cgtgtacccg   1320
ctcgcgccag gttcggccgc tcagacgaac agcatggtga ccctcggctg cctcgtgaag   1380
ggttatttcc cagagccggt gaccgtgacg tggaactccg gctcactgtc atcgggcgtg   1440
cacacttttc cagcagtgct gcagtcggac ctttacaccc tcagctcgtc cgtcaccgtc   1500
ccttcatcaa cttggcctag ccagaccgtg acttgcaatg tcgcccaccc ggcgtccagc   1560
actaaggtgg acaagaagat ccaccaccat caccatcacc atcaccatca ctagtgagcg   1620
gccgcgtcta gacctgcact gactgactga tacaatcgat ttctgatcc gcaggcctct   1680
cctagcttga ctgactgaga tacagcgtac cttcagctca cagacatgat aagatacatt   1740
gatgagtttg gacaaaccac aactagaatg cagtgaaaaa aatgctttat ttgtgaaatt   1800
tgtgatgcta ttgcttattt tgtaaccatt ataagctgca ataacaagt taacaacaac    1860
aattgcattc attttatgtt tcaggttcag ggggaggtgt gggaggtttt tttaaagcaag   1920
taaaacctct acaaatgtgg tattggccca tctctatcgg tatcgtagca taacccttg    1980
gggcctctaa acgggtcttg aggggttttt tgtgccctc cggccggatt gctatctacc    2040
ggcattggcg cagaaaaaaa tgcctgatgc gacgctgcgc gtcttatact cccacatatg   2100
ccagattcag caacggatac ggcttcccca acttgcccac ttccatacgt gtcctcctta   2160
ccagaaattt atccttaagg tcgtcagcta tcctgcagge gatctctcga tttcgatcaa   2220
gacattcctt taatggtctt ttctggacac cactagggt cagaagtagt tcatcaaact    2280
ttcttccctc cctaatctca ttggttacct tgggctatcg aaacttaatt aaccagtcaa   2340
gtcagctact tggcgagatc gacttgtctg ggtttcgact acgctcagaa ttgcgtcagt   2400
caagttcgat ctggtccttg ctattgcacc cgttctccga ttacgagttt catttaaatc    2460
atgtgagcaa aaggccagca aaaggccagg aaccgtaaaa aggccgcgtt gctggcgttt   2520
ttccataggc tccgcccccc tgacgagcat cacaaaaatc gacgctcaag tcagaggtgg   2580
cgaaacccga caggactata agataccag gcgtttcccc ctggaagctc cctcgtgcgc    2640
tctcctgttc cgaccctgcc gcttaccgga tacctgtccg cctttctccc ttcgggaagc   2700
gtggcgcttt ctcatagctc acgctgtagg tatctcagtt cggtgtaggt cgttcgctcc   2760
aagctgggct gtgtgcacga accccccgtt cagcccgacc gctgcgcctt atccggtaac   2820
tatcgtcttg agtccaaccc ggtaagacac gacttatcgc cactggcagc agccactggt   2880
aacaggatta gcagagcgag gtatgtaggc ggtgctacag agttcttgaa gtggtggcct   2940
aactacggct acactagaag aacagtattt ggtatctgcg ctctgctgaa gccagttacc   3000
ttcggaaaaa gagttggtag ctcttgatcc ggcaaacaaa ccaccgctgg tagcggtggt   3060
tttttgttt gcaagcagca gattacgcgc agaaaaaaag gatctcaaga agatcctttg    3120
atctttcta cgggtctga cgctcagtgg aacgaaaact cacgttaagg gattttggtc     3180
atgagattat caaaaaggat cttcacctag atccttttaa attaaaaatg aagttttaaa   3240
tcaatctaaa gtatatatga gtaaacttgg tctgacagtt accaatgctt aatcagtgag   3300
gcacctatct cagcgatctg tctatttcgt tcatccatag ttgcctttaa atttccgaac   3360
tctccaaggc cctcgtcgga aaatcttcaa acctttcgtc cgatccatct tgcaggctac   3420
ctctcgaacg aactatcgca agtctcttgg ccggccttgc gccttggcta ttgcttggca   3480
gcgcctatcg ccaggtatta ctccaatccc gaatatccga gatcgggatc acccagaga    3540
agttcaacct acatcctcaa tcccgatcta tccgagatcc gaggaatatc gaaatcgggg   3600
cgcgctggt gtaccgagaa cgatcctctc agtgcgagtc tcgacgatcc atatcgttgc    3660
ttggcagtca gccagtcgga atccagcttg ggaccagga agtccaatcg tcagatattg    3720
tactcaagcc tggtcacggc agcgtaccga tctgtttaaa cctagatatt gatagtctga   3780
tcggtcaacg tataatcgag tcctagcttt tgcaaacatc tatcaagaga caggatcagc   3840
aggaggcttt cgcatgagta ttcaaacattt ccgtgtcgcc cttattccct ttttttgcgg  3900
attttgcctt cctgtttttg ctcacccaga aacgctggtg aaagtaaaag atgctgaaga   3960
tcagttgggt gcgcgagtgg gttacatcga actggatctc aacagcggta agatccttga   4020
gagttttcgc cccgaagaac gctttccaat gatgagcact tttaaagttc tgctatgtgg   4080
cgcggtatta tcccgtattg acgccgggca agagcaactc ggtcgccgca tacactattc   4140
tcagaatgac ttggttgagt attcaccagt cacagaaaag catcttacgg atggcatgac   4200
agtaagagaa ttatgcagtg ctgccataac catgagtgat aacactgcgg ccaacttact   4260
tctgacaacg attggaggac cgaaggagct aaccgctttt ttgcacaaca tgggggatca   4320
tgtaactcgc cttgatcgtt gggaaccgga gctgaatgaa gccataccaa acgacgagcg   4380
tgacaccacg atgcctgtag caatggcaac aaccttgcgt aaactattaa ctggcgaact   4440
acttactcta gcttcccggc aacagttgat agactggatg gaggcggata agttgcagg    4500
accacttctg cgctcggccc ttccggctgg ctggtttatt gctgataaat ctggagccgg   4560
tgagcgtggg tctcgcggta tcattgcagc actggggcca gatggtaagc cctcccgtat   4620
cgtagttatc tacacgacgg ggagtcaggc aactatggat gaacgaaata gacagatcgc   4680
tgagataggt gcctcactga ttaagcattg gtaaccgatt ctaggtgcat ggcgcagaa    4740
aaaaatgcct gatgcgacga tgcgcgtctt atactcccac atatgccac ttcagcaacg    4800
gatacggctt ccccaacttg cccacttcca tacgtgtcct ccttaccaga aatttatcct   4860
taagatcccg aatcgtttaa actgcgactct ggctctatcg aatctccgtc gtttcgagct  4920
tacgcgaaca gccgtggcgc tcatttgctc gtcgggcatc gaatctcgtc agctatcgtc   4980
agcttaccctt tttggca                                                 4997
```

| SEQ ID NO: 90 | moltype = DNA length = 5000 |
|---|---|
| FEATURE | Location/Qualifiers |
| misc_feature | 1..5000 |
| | note = Synthetic polymer. |
| source | 1..5000 |
| | mol_type = other DNA |
| | organism = synthetic construct |

SEQUENCE: 90

```
gcgatcgcgg ctcccgacat cttggaccat tagctccaca ggtatcttct tccctctagt   60
ggtcataaca gcagcttcag ctacctctca attcaaaaaa cccctcaaga cccgtttaga  120
ggccccaagg ggttatgcta tcaatcgttg cgttacacac acaaaaaacc aacacacatc  180
catcttcgat ggatagcgat tttattatct aactgctgat cgagtgtagc cagatctagt  240
aatcaattac ggggtcatta gttcatagcc catatatgga gttccgcgtt acataactta  300
cggtaaatgg cccgcctggc tgaccgccca acgaccccg cccattgacg tcaataatga  360
cgtatgttcc catagtaacg ccaataggga ctttccattg acgtcaatgg gtggagtatt  420
tacggtaaac tgcccacttg gcagtacatc aagtgtatca tatgccaagt acgccccta  480
ttgacgtcaa tgacggtaaa tggcccgcct ggcattatgc ccagtacatg accttatggg  540
actttcctac ttggcagtac atctacgtat tagtcatcgc tattaccatg ctgatgcggt  600
tttggcagta catcaatggg cgtggatagc ggtttgactc acggggattt ccaagtctcc  660
accccattga cgtcaatggg agtttgtttt ggcaccaaaa tcaacgggac tttccaaaat  720
gtcgtaacaa ctccgcccca ttgacgcaaa tgggcggtag cgtgtacgg tgggaggtct  780
atataagcag agctggttta gtgaaccgtc agatcagatc tttgtcgatc ctaccatcca  840
ctcgacacac ccgccagcag ccgctgccaa gcttccgagc tctcgaattc aaaggaggta  900
cccaccatgc cgctgctgct actgctgccc ctgctgtggg caggggcgct agctgacatc  960
gtgatgacac agagccctag ctctctggcc atgtccgtgg gccagaaggt gaccatgagc 1020
tgcaagtcca gccagtctct gctgaactcc agcaaccaga agaactatct ggcttggtac 1080
cagcagaagc ccggccagag ccccaagctg ctcgtgtact cgccagcac cagagagagc 1140
ggcgtgcccg acagattcat cggcagcggc agcggaaccg acttcacact gaccatctcc 1200
tccgtgcaag ccgaggatct ggccgactat ttctgccagc agcactacaa cacccctctg 1260
acctttggag ccggcaccaa gctcgagatc aagcgcgaa atgctgctcc taccgtgga 1320
atcttcccgc cgtccagcga acaactcact agcggaggcg cgtcagtggt ctgcttcctt 1380
aacaatttct accctaagga catcaacgtc aagtggaaga ttgacggatc ggaacgccag 1440
aacggagtgc tgaactcatg gactgatcag gattccaaag actcgactta ctccatgtcc 1500
agcaccctga ccctgaccaa agacgagtac gaaaggcaca agtgctacac gtgcgaagcc 1560
acccacaaga cttccacctc gccatcgtg aagtccttca atcgcaatga gtgctagtga 1620
gcggccgcgt ctagacctgc actgactgac tgatacaatc gatttctgga tccgcaggcc 1680
tctcctagct tgactgactg agatacagcg taccttcagc tcacagacat gataagatac 1740
attgatgagt ttggacaaac cacaactaga atgcagtgaa aaaaatgctt tatttgtgaa 1800
atttgtgatg ctattgcttt atttgtaacc attataagct gcaataaaca agttaacaac 1860
aacaattgca ttcattttat gtttcaggtt cagggggagg tgtgggaggt tttttaaagc 1920
aagtaaaacc tctacaaatg tggtattggc ccatctctat cggtatcgta gcataacccc 1980
ttggggcctc taaacgggtc ttgaggggtt ttttgtgccc ctcggccgg attgctatct 2040
accggcattg gcgcagaaaa aaatgcctga tgcgacgctg cgcgtcttat actcccacat 2100
atgccagatt cagcaacgga tacgcttcc ccaacttgcc cacttccata cgtgtcctcc 2160
ttaccagaaa tttatcctta aggtcgtcag ctatcctgca ggcgatctct cgatttcgat 2220
caagacattc ctttaatggt ctttctgga caccactagg ggtcagaagt agttcatcaa 2280
acttctctc ctccctaatc tcattggtta ccttgggcta tcgaaactta attaaccagt 2340
caagtcagct acttggcgag atcgacttgt ctgggtttcg actacgctca gaattcgctc 2400
agtcaagttc gatctggtcc ttgctattgc accgttctc cgattacgag tttcatttaa 2460
atcatgtgag caaaaggcca gcaaaaggcc aggaaccgta aaaaggccgc gttgctggcg 2520
ttttccata ggctccgccc ccctgacgag catcacaaaa atcgacgctc aagtcagagg 2580
tggcgaaacc cgacaggact ataaagatac caggcgttt cccctggaag ctccctcgtg 2640
cgctctcctg ttccgaccct gccgcttacc ggataccttg tccgcctttct cccttcggga 2700
agcgtggcgc tttctcatag ctcacgctgt aggtatctca gttcggtgta ggtcgttcgc 2760
tccaagctgg gctgtgtgca cgaacccccc gttcagccg accgctgcgc cttatccggt 2820
aactatcgtc ttgagtccaa cccggtaaga cacgacttat cgccactggc agcagccact 2880
ggtaacagga ttagcagagc gaggtatgta ggcggtgcta cagagttctt gaagtggtgg 2940
cctaactacg gctacactag aagaacagta tttggtatct gcgctctgct gaagccagtt 3000
accttcggaa aaagagttgg tagctcttga tccggcaaca aaccaccgc tggtagcggt 3060
ggttttttg tttgcaagca gcagattacg cgcagaaaaa aaggatctca agaagatcct 3120
ttgatctttt ctacggggtc tgacgctcag tggaacgaaa actcacgtta agggattttg 3180
gtcatgagat tatcaaaaag gatcttcacc tagatccttt taaattaaaa atgaagtttt 3240
aaatcaatct aaagtatata tgagtaaact tggtctgaca gttaccaatg cttaatcagt 3300
gaggcaccta tctcagcgat ctgtctattt cgttcatcca tagttgcatt taaatttccg 3360
aactctccaa ggcccctcgtc ggaaaatctt caaaccttc gtccgatcca tcttgcaggc 3420
tacctctcga acgaactatc gcaagtctct tggccggcct tgcgccttgg ctattgcttg 3480
gcagcgccta tcgccaggta ttactccaat cccgaatatc cgagatcggg atcacccag  3540
agaagttcaa cctacatcct caatcccgat ctatccgaga tccgaggaat atcgaaatcg 3600
gggcgcgcct ggtgtaccga gaacgatcct ctcagtgcga gtctcgacga tccatatcg 3660
tgcttggcag tcagccagtc ggaatccagc ttgggaccca ggaagtccaa tcgtcagata 3720
ttgtactcaa gcctggtcac ggcagcgtac cgatctgttt aaacctagat attgatagtc 3780
tgatcggtca acgtataatc gagtcctagc ttttgcaaac atctatcaag agacaggatc 3840
agcaggaggc tttcgcatga gtattcaaca ttttccgtgt cgcccttatt ccttttttgc 3900
ggcattttgc cttcctgttt ttgctcaccc agaaacgctg gtgaaagtaa aagatgctga 3960
agatcagttg ggtgcgcgag tgggttacat cgaactggat ctcaacagcg gtaagatcct 4020
tgagagtttt cgccccgaag aacgctttcc aatgatgagc acttttaaag ttctgctatg 4080
tggcgcggta ttatcccgta ttgacgccgg gcaagagcaa ctcggtcgcc gcatacacta 4140
ttctcagaat gacttggttg agtattcacc agtcacagaa aagcatctta cggatggcat 4200
gacagtaaga gaattatgca gtgctgccat aaccatgagt gataacactg cggccaactt 4260
```

```
acttctgaca acgattggag gaccgaagga gctaaccgct tttttgcaca acatgggggga    4320
tcatgtaact cgccttgatc gttgggaacc ggagctgaat gaagccatac caaacgacga    4380
gcgtgacacc acgatgcctg tagcaatggc aacaaccttg cgtaaactat taactggcga    4440
actacttact ctagcttccc ggcaacagtt gatagactgg atggaggcgg ataaagttgc    4500
aggaccactt ctgcgctcgg ccttccggc tggctggttt attgctgata aatctggagc     4560
cggtgagcgt gggtctcgcg gtatcattgc agcactgggg ccagatggta agccctcccg    4620
tatcgtagtt atctacacga cggggagtca ggcaactatg gatgaacgaa atagacagat    4680
cgctgagata ggtgcctcac tgattaagca ttggtaaccg attctaggtg cattggcgca    4740
gaaaaaaatg cctgatgcga cgctgcgcgt cttatactcc cacatatgcc agattcagca    4800
acggatacgg cttccccaac ttgcccactt ccatacgtgt cctccttacc agaaatttat    4860
ccttaagatc ccgaatcgtt taaactcgac tctggctcta tcgaatcccc gtcgtttcga    4920
gcttacgcga acagccgtgg cgctcatttg ctcgtcgggc atcgaatctc gtcagctatc    4980
gtcagcttac cttttttggca                                               5000
```

SEQ ID NO: 91          moltype = DNA   length = 8353
FEATURE                Location/Qualifiers
misc_feature           1..8353
                       note = Synthetic polymer.
source                 1..8353
                       mol_type = other DNA
                       organism = synthetic construct
SEQUENCE: 91
```
gcgatcgcgg ctcccgacat cttggaccat tagctccaca ggtatcttct tccctctagt     60
ggtcataaca gcagcttcag ctacctctca attcaaaaaa cccctcaaga cccgtttaga    120
ggccccaagg ggttatgcta tcaatcgttg cgttacacac acaaaaaacc aacacacatc    180
catcttcgat ggatagcgat tttattatct aactgctgat cgagtgtagc cagatctata    240
gtaatcaatt acgggtcat tagttcatag cccatatatg gagttccgcg ttacataact     300
tacggtaaat ggcccgcctg gctgaccgcc caacgacccc cgcccattga cgtcaataat    360
gacgtatgtt cccatagtaa cgccaatagg gactttccat tgacgtcaat gggtggacta    420
tttacggtaa actgcccact tggcagtaca tcaagtgtat catatgccaa gtacgcccsc    480
tattgacgtc aatgacggta aatggcccgc ctggcattat gcccagtaca tgaccttatg    540
ggactttcct acttggcagt acatctacgt attagtcatc gctattacca tgcgtcgagg    600
tgagccccac gttctgcttc actctcccca tctcccccc ctcccaccc caatttgt       660
atttatttat tttttaatta tttatgcag cgatggggcg ggggggggg ggggcgcgcg     720
ccaggcgggg cggggcgggg cgaggggcga ggcgagagg tgcggcggca                780
gccaatcaga gcggcgcgct ccgaaagttt ccttttatgg cgaggcggcg gcggcggcgg    840
ccctataaaa agcgaagcgc gcggcgggcg ggagtcgctg cgttgccttc gccccgtgcc    900
ccgctccgcg ccgcctcgcg ccgcccgccc cggctctgac tgaccgcgtt actcccacag    960
gtgagcgggc gggacgggcc ttctccctcc gggctgtaat tagcgcttgg tttaatgacg   1020
gctcgttttct tttctgtggc tgcgtgaaag ccttaaaggg ctccgggagg gcctttgtgt   1080
gggggggagc ggctcggggg gtgcgtgcgt gtgtgtgtgc gtggggagcg ccgcgtgcgg   1140
cccgcgctgc ccggcggctg tgagcgctgc gggcgcggcg cggggctttg tgcgctccgc   1200
gtgtgcgcga gggagcgcg gccgggggc ggtgccccgc ggtgcccggc ggctgcgagg    1260
ggaacaaagg ctgcgtgcgg ggtgtgtgcg tgggggggtg agcagggggt gtgggcgcgg   1320
cggtcgggct gtaaccccc cctggcaccc ccctccccga gttgctgagc acggcccggc    1380
ttcgggtgcg gggctccgtg cggggcgtgg cgcggggctc gccgtgccgg gcggggggtg    1440
gcggcaggtg ggggtgccgg gcggggcggg gccgcctcgg gcggggggga gctcgggga    1500
ggggcgcggc ggcccggag cgccggcggc tgtcgaggcg cggcgagccg cagccattgc    1560
cttttatggt aatcgtgcga gagggcgcag ggacttcctt tgtcccaaat ctggcggagc   1620
cgaaatctgg gaggcgccgc cgcacccct ctagcgggcg cgggcgaagc ggtgcggcgc     1680
cggcaggaag gaaatgggcg gggagggcct tcgtgcgtcg ccgcgccgcc gtccccttct    1740
ccatctccag cctcggggct gccgcagggg gacggctgcc ttcgggggg acggggcagg    1800
gcggggttcg gcttctggcg tgtgaccggg ggctttagag cctctgctaa ccatgttcat    1860
gccttcttct ttttcctaca gctcctgggc aacgtgctgg ttgttgtgct gtctcatcat    1920
tttggcaaag atctttgtcg atcctaccat ccactcgaca cacccgccag ggccgcgtc    1980
caagcttccg agctctcgaa ttcaggaggt acccaccatg ggttggagcc tcatcttgct    2040
cttccttgtc gctgttgcta cgcgtgtcca ctcccaagtg cagctgcagc agagcggagc   2100
cgagctggtg aagcccggag ccagcgtgaa gatcagctgc aaggcagcg gctacgcctt    2160
ctccaactac tggatgaact gggtgaagca gaggccggag aagggactgg aatggatcgg    2220
ccagatctac cccggcgacg gagacaccaa ctacaacgag aagttcaagg gcaaagccac   2280
actgaccgcc gacaagagct ccagcaccgc ctacatgcag ctgagctctc tgaccagcga    2340
ggatagcgcc gtgtacttct gcgccagagg agactactgg ggccaaggca ccacactgac    2400
cgtctcgagc gctaagacga ctccaccgtc cgtgtacccg ctcgcgccag ttcggccgc    2460
tcagacgaac agcatggtga ccctcggctg cctcgtgaag ggttatttcc cagagcggt     2520
gaccgtgacg tggaactccg gctcactgtc atcgggcgtg cacacttttc cagcagtgct    2580
gcagtcggac ctttacaccc tcagctcgtc cgtcaccgtc ccttcatcaa cttggcctag    2640
ccagaccgtg acttgcaatg tcgccacccc ggcgtccagc actaaggtgg acaagaagat    2700
ccaccaccat caccatcacc atcaccatca ctagagagcg gccgcgtca gacctgcact    2760
gactgactga tacgctagct tgactgactg agatacagcg taccttcagc tcacagacat    2820
gataagatac attgatgagt ttggacaaac cacaactaga atgcagtgaa aaaaatgctt    2880
tatttgtgaa atttgtgatg ctattgcttt atttgtaacc attataagct gcaataaaca    2940
agttaacaac aacaattgca ttcattttat gtttcaggtt caggggggagg tgtggaggt    3000
tttttaaagc aagtaaaacc tctacaaatg tggtattggc ccatctctat cggtatcgta    3060
gcataaccc ttggggcctc taaacgggtc ttgagggggtt tttttgccc ctcgggccgg    3120
attgctatct accggcattg gcgcagaaaa aaatgcctga tgcgacgctg cgcgtcttat    3180
actcccacat atgccagatt cagcaacgga tacggcttcc ccaacttgcc cacttccata    3240
cgtgtcctcc ttaccagaaa tttatccta aggtcgtcag ctatcctgca ggcgatctct   3300
cgatttcgat caagacattc cttaatggt cttttctgga caccactagg ggtcagaagt    3360
agttcatcaa actttcttcc ctccctaatc tcattggtta ccttgggcta tcgaaactta    3420
```

```
attaaccagt caagtcagct acttggcgag atcgacttgt ctgggtttcg actacgctca 3480
gaattgcgtc agtcaagttc gatctggtcc ttgctattgc acccgttctc cgattacgag 3540
tttcatttaa atcatgtgag caaaaggcca gcaaaaggcc aggaaccgta aaaaggccgc 3600
gttgctggcg ttttttccata ggctccgccc ccctgacgag catcacaaaa atcgacgctc 3660
aagtcagagg tggcgaaacc cgacaggact ataaagatac caggcgtttc ccctggaag 3720
ctccctcgtg cgctctcctg ttccgaccct gccgcttacc ggatacctgt ccgcctttct 3780
cccttcggga agcgtggcgc tttctcatag ctcacgctgt aggtatctca gttcggtgta 3840
ggtcgttcgc tccaagctgg gctgtgtgca cgaaccccc gttcagcccg accgctgcgc 3900
cttatccggt aactatcgtc ttgagtccaa cccggtaaga cacgacttat cgccactggc 3960
agcagccact ggtaacagga ttagcagagc gaggtatgta ggcggtgcta cagagttctt 4020
gaagtggtgg cctaactacg gctacactag aagaacagta tttggtatct gcgctctgct 4080
gaagccagtt accttcggaa aaagagttgg tagctcttga tccggcaaac aaaccaccgc 4140
tggtagcggt ggtttttttg tttgcaagca gcagattacg cgcagaaaaa aaggatctca 4200
agaagatcct ttgatctttt ctacgggtc tgacgctcag tggaacgaaa actcacgtta 4260
agggattttg gtcatgagat tatcaaaaag gatcttcacc tagatccttt taaattaaaa 4320
atgaagtttt aaatcaatct aaagtatata tgagtaaact tggtctgaca gttaccaatg 4380
cttaatcagt gaggcaccta tctcagcgat ctgtctattt cgttcatcca tagttgcatt 4440
taaatttccg aactctccaa ggccctcgtc ggaaaatct caaaccttc gtccgatcca 4500
tcttgcaggc tacctctcga acgaactatc gcaagtctct tggccggcct tgcgccttgg 4560
ctattgcttg gcagcgccta tcgccaggta ttactccaat cccgaatatc cgagatcggg 4620
atcacccgag agaagttcaa cctacatcct caatcccgat ctatccgaga tccgaggaat 4680
atcgaaatcg gggcggcgcct ggcctccgcg ccggttttg ccgcctcccg cgggcgcccc 4740
cctcgtcacg gcgagcgctg ccacgtcaga cgaagggcgc aggagcgtcc tgatccttcc 4800
gcccggacgc tcaggacagc ggcccgctgc tcataagact cggccttaga accccagtat 4860
cagcagaagg acatttttagg acgggacttg ggtgactcta gggcactggt tttcttcca 4920
gagagcggaa caggcgagga aaagtagtcc cttctgcgga attctgcgga gggatctccg 4980
tggggcggtg aacgccgatg attatataag gacgcgccgg gtgtggcaca gctagttccg 5040
tcgcagccgg gatttgggtc gcggttcttg tttgtggatc gctgtgatcg tcacttggtg 5100
agtagcgggc tgctgggctg gccggggctt tcgtggccgc cgggccgctc ggtgggacgg 5160
aagcgtgtgg agagaccgcc aagggctgta tctgggtcc gcgagcaagg ttgccctgaa 5220
ctgggggttg gggggagcgc agcaaaatgg cggctgttcc cgagtcttga atggaagacg 5280
cttgtgaggc gggctgtgag gtcgttgaaa caaggtgggg ggcatggtgg gcggcaagaa 5340
cccaaggtct tgagcccttc gctaatgcgg gaaagctctt attcgggtga gatgggctgg 5400
gcaccatctg gggacccctga cgtgaagttt gtcactgact ggagaactcg gtttgtcgtc 5460
tgttgcgggg gcggcagtta tggcggtgcc gttgggcagt gcaccccgtac ctttgggagc 5520
gcgcgccctc gtcgtgtcgt gacgtcaccc gttctgttgg cttataatgc agggtgggc 5580
cacctgccgg taggtgtgcg gtaggctttt ctccgtcgca ggacgcaggg ttcgggccta 5640
gggtaggctc tcctgaatcg acaggcgccg gacctctggt gagggaggg ataagtgagg 5700
cgtcagtttc tttggtcggt tttatgtacc tatcttctta agtagctgaa gctccggttt 5760
tgaactatgc gctcggggtt ggcgagtgtg ttttgtgaag ttttttaggc accttttgaa 5820
atgtaatcat ttgggtcaat atgtaatttt cagtgttaga cttgtaaatt gtccgctaaa 5880
ttctggccgt ttttggcttt tttgttagac aacatgggta aaaagcctga actcaccgcg 5940
acgtctgtcg agaagtttct gatcgaaaag ttcgacagcg tctccgacct gatgcagctc 6000
tcggagggcg aagaatctcg tgctttcagc ttcgatgtag gagggcgtgg atatgtcctg 6060
cgggtaaata gctgcgccga tggtttctac aaagatcgtt atgtttatcg gcactttgca 6120
tccgccgcgc tcccgattcc ggaagtgctt gacattgggg agttcagcga gagcctgacc 6180
tattcatct cccgccgtgc acagggtgtc acgttgcaag acctgcctga aaccgaactg 6240
cccgctgttc tgcagccggt cgcggaggca atggatgcca tcgctgccgc cgatcttagc 6300
cagacgagcg ggttcggccc attcggaccg caaggaatcg gtcaatacac tacatggcgt 6360
gatttcatat gcgcgattgc tgatccccat gtgtatcact ggcaaactgt gatggacgac 6420
accgtcagtg cgtccgtcgc gcaggctctc gatgagctga tgctttgggc cgaggactgc 6480
cccgaagtcc ggcacctcgt gcacgcggat ttcggctcca acaatgtcct gacgacaat 6540
ggccgcataa cagcggtcat tgactggagc gaggcgatgt tcggggattc caatacgag 6600
gtcgccaaca tcttcttctg gaggccgtgg ttggcttgta tggagcagca gacgcgctac 6660
ttcgagcgga ggcatccgga gcttgcagga tcgccccggc tccgggcgta tatgctccgc 6720
attggtcttg accaactcta tcagagcttg gttgacgga atttcgatga tgcagcttgg 6780
gcgcagggtc gatgcgacgc aatcgtccga tccggagccg gactgtcgg gcgtacacaa 6840
atcgcccgca gaagcgccgc cgtctggacc gatggctgtg tagaagtact cgccgatagt 6900
ggaaaccgac gccccagcac tcgtccgagg gcaaaggaat aagtagtag gtaagcctaa 6960
tcttagataa taaaatcgct atccatcgaa gatgatgtg tgttggtttt ttgtgtgtgt 7020
aacgctaggc gcgcctggtg taccgagaac gatcctctca gtgcgagtct cgacgatcca 7080
tatcgttgct tggcagtcag ccagtcggaa tccagcttgg gacccaggaa gtccaatcgt 7140
cagatattgt actcaagcct ggtcacggca gcgtaccgat ctgtttaaac ctagatattg 7200
atagtctgat cggtcaacgt ataatcagt cctagctctt gcaaacatct atcaagagac 7260
aggatcagca ggaggctttc gcatgattga acaagatgga ttgcacgcag gttctccggc 7320
ggcttggtg gagaggctat tcggctatga ctgggcacaa cagacaatcg gctgctctga 7380
tgccgccgtg ttccggctgt cagcgcaggg gcgtccggtt cttttttgtca agaccgacct 7440
gtccggtgcc ctgaatgaac tgcaagacga ggcagcgcgg ctatcgtggc tggcgacgac 7500
gggcgttcct tgcgcgctg tgctcgacgt tgtcactgaa gcgggaaggg actggctgct 7560
attgggcgaa gtgccgggc aggatctcct gtcatctcac cttgctcctg ccgagaaagt 7620
atccatcatg gctgatgcaa tgcggcggct gcatacgctt gatccggcta cctgcccatt 7680
cgaccaccaa gcgaaacatc gcatcgagcg agcacgtact cggatggaag ccggtcttgt 7740
cgatcaggat gatctggacg aagagcatca ggggctcgcg ccagccgaac tgttcgccag 7800
gctcaaggcg tctatgccg acggcgagga tctcgtcgtg acccacggcg atgcctgctt 7860
gccgaatatc atggtggaaa atggccgctt ttctggattc atcgactgtg gccgctgggg 7920
tgtggcggac cgctatcagg acatagcgtt ggctacccgt gatattgctg aagagcttgg 7980
cggcgaatgg gctgaccgct tcctcgtgct ttacggtatc gccgcccg attcgcagcg 8040
catcgccttc tatcgccttc ttgacgagtt cttctgaccg attctaggtg cattggcgca 8100
gaaaaaatg cctgatgcga cgctgcgcgt cttatactcc cacatatgcc agattcagca 8160
```

```
acggatacgg cttccccaac ttgcccactt ccatacgtgt cctccttacc agaaatttat   8220
ccttaaggtc gtttaaactc gactctggct ctatcgaatc tccgtcgttt cgagcttacg   8280
cgaacagccg tggcgctcat ttgctcgtcg ggcatcgaat ctcgtcagct atcgtcagct   8340
tacctttttg gca                                                     8353

SEQ ID NO: 92         moltype = DNA   length = 8386
FEATURE               Location/Qualifiers
misc_feature          1..8386
                      note = Synthetic polymer.
source                1..8386
                      mol_type = other DNA
                      organism = synthetic construct
SEQUENCE: 92
gcgatcgcgg ctcccgacat cttggaccat tagctccaca ggtatcttct tccctctagt    60
ggtcataaca gcagcttcag ctacctctca attcaaaaaa cccctcaaga cccgtttaga   120
ggccccaagg ggttatgcta tcaatcgttg cgttacacac acaaaaaacc aacacacatc   180
catcttcgat ggatagcgat tttattatct aactgctgat cgagtgtagc cagatctata   240
gtaatcaatt acggggtcat tagttcatag cccatatatg gagttccgcg ttacataact   300
tacggtaaat ggcccgcctg gctgaccgcc caacgacccc cgcccattga cgtcaataat   360
gacgtatgtt cccatagtaa cgccaatagg gactttccat tgacgtcaat gggtggacta   420
tttacggtaa actgcccact tggcagtaca tcaagtgtat catatgccaa gtacgccccc   480
tattgacgtc aatgacggta aatggcccgc ctggcattat gcccagtaca tgaccttatg   540
ggactttcct acttggcagt acatctacgt attagtcatc gctattacca tgcgtcgagg   600
tgagccccac gttctgcttc actctcccca tctcccccac ctcccaccc caatttttgt    660
atttatttat ttttttaatta ttttatgcag cgatggggc ggggggggg ggggcgcgcg   720
ccaggcgggg cggggcgggg cgagggcggg ggcggggcgg ggcggagagg tgcggcggca   780
gccaatcaga gcggcgcgct ccgaaagttt cctttttatgg cgaggcggcg cggcggcggcg   840
ccctataaaa agcgaagcgc gcggcgggcg ggagtcgctg cgttgccttc gccccgtgcc   900
ccgctccgcg ccgcctcgcg ccgcccgccc cggctctgac tgaccgcgtt actcccacag   960
gtgagcgggc gggacgggcc ttctccctcc gggctgtaat tagcgcttgg tttaatgacg  1020
gctcgttttct tttctgtggc tgcgtgaaag ccttaaaggg ctccggggagg gcctttgtgc  1080
ggggggggagc ggctcgggg gtgcgtgcgt gtgtgtgtgc gtggggagcg ccgcgtgcgg  1140
cccgcgctgc ccggcggctg tgagcgctgc gggcgcggcg cggggcttg tgcgctccgc  1200
gtgtgcgcga ggggagcgcg ggccggggc ggtgccccgc ggtgcggggg ggctgcgagg  1260
ggaacaaagg ctgcgtgcgg ggtgtgtgcg tggggggtg agcagggggt gtggggcggg  1320
cggtcgggct gtaaccccc cctggcaccc ccctcccga gttgctgagc acggcccggc  1380
ttcgggtgcg gggctccgtg cggggcgtgg cgcggggctc gccgtgccgg gcggggggtg  1440
gcggcaggtg ggggtgccgg gcgggcggg gccgcctcgg gccggggagg gctcgggga  1500
ggggcgcggc ggccccggag cgccgcggc tgtcgagggg cggcgagccg cagccattgc  1560
cttttatggt aatcgtgcga gagggcgcag ggacttcctt tgtcccaaat ctggcggagc  1620
cgaaatctgg gaggcgccgc cgcacccct ctagcgggcg cgggcgaagc ggtgcggcgc  1680
cggcaggaag gaaatgggcg gggagggcct tcgtgcgtcg ccgcgccgcc gtccccttct  1740
ccatctccag cctcggggct gccgcagggg gacggctgcc ttcgggggg acggggcagg  1800
gcggggttcg gcttctgcgc tgtgaccggc ggctttagag cctctgctaa ccatgttcat  1860
gccttcttct ttttcctaca gctcctgggc aacgtgctgg ttgttgtgct gtctcatcat  1920
tttggcaaag atctttgtcg atcctaccat ccactcgaca caccccgccag cggccgctgc  1980
caagcttccg agctctgaa ttcaggaggt acccaccatg agggtccccg ctcagctcct  2040
ggggctcctg ctgctctggc tcccaggcgc gcgatgtgac atcgtgatga cacagagccc  2100
tagctctctg gccatgtccg tgggccagaa ggtgaccatg agctgcaagt ccagccagtc  2160
tctgctgaac tccagcaacc agaagaacta tctggcttgg taccagcaga agcccggcca  2220
gagccccaag ctgctcgtgt acttcgccaa caccagagag agcggcgtgc cagacagatt  2280
catcggcagc ggcagcggaa ccgacttcac actgaccatc tcctccgtgc aagccgagga  2340
tctgccgac tatttctgcc agcagcacta caacacccct ctgacctttg gagccggcac  2400
caagctcgag atcaagcgcg cagatgctgc tcctaccgtg agcatcttcc cgccgtccac  2460
cgaacaactc actagcggag gcgcgtcagt ggtctgcttc cttaacaatt tctaccctaa  2520
ggacatcaac gtcaagtgga agattgacgg atcggaacgc cagaacggag tgctgaactc  2580
atggactgat caggattcca aagactcgac ttactccatg tccagcaccc tgaccctgac  2640
caaagacgag tacgaaaggc acaactcgta cacgtgcgaa gccacccaca agacttccac  2700
ctcgcccatc gtgaagtcct tcaatcgcaa tgagtgctag tgagcggccg cgtctagacc  2760
tgcactgact gactgataca atcgatttct ggatccgcag gcctctgcta gttgactga  2820
ctgagataca gcgtaccttc agctcacaga catgataaga tacattgatg agtttggaca  2880
aaccacaact agaatgcagt gaaaaaaatg ctttatttgt gaaatttgtg atgctattgc  2940
tttatttgta accattataa gctgcaataa acaagttaac aacaacaatt gcattcattt  3000
tatgtttcag gttcaggggg aggtgtggga ggttttttaa agcaagtaaa acctcctacaa  3060
atgtggtatt ggcccatctc tatcggtatc gtagcataac cctgggggc ctctaaacgg  3120
gtcttgaggg gtttttgtg ccctcgggc cggattgcta tctaccggca ttggcgcaga  3180
aaaaatgcc tgatgcgacg ctgcgcgtct tatactccca catatgccag attcagcaac  3240
ggatacggct tccccaactt gcccacttcc atacgtgtcc tccttaccag aaattatcc  3300
ttaaggtcgt cagctatcct gcagcgatc tctgcgattc gatcaagaca ttcctttaat  3360
ggtcttttct ggacaccact aggggtcaga agtagttcat caaactttct tccctcccta  3420
atctcattgg ttaccttggg ctatcgaac ttaattaacc agtcaagtca gctacttggc  3480
gagatcgact tgtctgggtt tcgactacgc tcagaattgc gtcagtcaag ttcgatctgg  3540
tccttgctat tgcacccgtt ctccgattac gagtttcatt taaatcatgt gagcaaaagg  3600
ccagcaaaag gccaggaacc gtaaaaaggc cgcgttgctg gcgtttttcc ataggctccg  3660
cccccctgac gagcatcaca aaaatcgacg ctcaagtcag aggtggcgaa acccgacagg  3720
actataaaga taccaggcgt ttccccctgg aagctccctc gtgcgctctc ctgttccgac  3780
cctgccgctt accggatacc tgtccgcctt tctcccttcg ggaagcgtgg cgctttctca  3840
tagctcacgc tgtaggtatc tcagttcggt gtaggtcgtt cgctccaagc tgggctgtgt  3900
gcacgaaccc cccgttcagc ccgaccgctg cgccttatcc ggtaactatc gtcttgagtc  3960
```

```
caacccggta agacacgact tatcgccact ggcagcagcc actggtaaca ggattagcag  4020
agcgaggtat gtaggcggtg ctacagagtt cttgaagtgg tggcctaact acggctacac  4080
tagaagaaca gtatttggta tctgcgctct gctgaagcca gttaccttcg gaaaaagagt  4140
tggtagctct tgatccggca aacaaaccac cgctggtagc ggtggttttt ttgtttgcaa  4200
gcagcagatt acgcgcagaa aaaaaggatc tcaagaagat cctttgatct tttctacggg  4260
gtctgacgct cagtggaacg aaaactcacg ttaagggatt ttggtcatga gattatcaaa  4320
aaggatcttc acctagatcc ttttaaatta aaaatgaagt tttaaatcaa tctaaagtat  4380
atatgagtaa acttggtctg acagttacca atgcttaatc agtgaggcac ctatctcagc  4440
gatctgtcta tttcgttcat ccatagttgc atttaaattt ccgaactctc caaggcccctc  4500
gtcggaaaat cttcaaacct ttcgtccgat ccatcttgca ggctacctct cgaacgaact  4560
atcgcaagtc tcttggccgg ccttgcgcct tggctattgc ttggcagcgc ctatcgccag  4620
gtattactcc aatcccgaat atccgagatc gggatcaccc gagagaagtt caacctacat  4680
cctcaatccc gatctatccg agatccgagg aatatcgaaa tcgggcgcg cctgcctcc    4740
gcgccgggtt ttggcgcctc ccgcgggcgc cccctcgtc acggcgagcg ctgccacgtc    4800
agacgaaggg cgcaggagcg tcctgatcct tccgcccgga cgctcaggac agcggcccgc  4860
tgctcataag actcggcctt agaacccag tatcagcaga aggacattttt aggacgggac  4920
ttgggtgact ctagggcact ggttttcttt ccagagagcg aacaggcga ggaaaagtag   4980
tcccttctcg gcgattctgc ggagggatct ccgtggggcg gtgaacgccg atgattatat  5040
aaggacgcgc cgggtgtggc acagctagtt ccgtcgcagc cgggatttgg gtcgcggttc  5100
ttgtttgtgg atcgctgtga tcgtcacttg gtgagtagcg ggctgctggg ctggccgggg  5160
cttttcgtggc cgccgggccg ctcggtggga cggaagcgtg tggagagacc gccaagggct  5220
gtagtctggg tccgcgagca aggttgccct gaactggtgg gcagcaaaa                5280
tggcggctgt tccgagtct tgaatgaag acgcttgtga ggcgggctgt gaggtcgttg     5340
aaacaaggtg gggggcatgg tgggcggcaa gaacccaagg tcttgagccc ttcgctaatg    5400
cgggaaagct cttattcggg tgagatgggc tgggcaccat ctgggacccc tgacgtgaag    5460
tttgtcactg actggagaac tcggtttgtc gtctgttggg ggcggcag ttatggcggt    5520
gccgttgggc agtgcacccg tacctttggg agcgcgcgcc ctcgtcgtgt cgtgacgtca    5580
cccgttctgt tggcttataa tgcagggtgg ggccaccctgc cggtaggtgt gcggtaggct    5640
tttctccgtc gcaggacgca gggttcgggc ctagggtagg ctctcctgaa tcgacaggcg    5700
ccggacctct ggtgagggga gggataagtg aggcgtcagt ttctttggtc ggttttatgt    5760
acctatcttc ttaagtagct gaagctccgg ttttgaacta tgcgctcggg gttggcgagt    5820
gtgttttgtg aagttttta ggcacccttt gaaatgtaat catttgggtc aatatgtaat    5880
tttcagtgtt agacttgtaa attgtccgct aaattctggc cgttttggc tttttttgtta   5940
gacaacatgg gtaaaaagcc tgaactcacc gcgacgtctg tcgagaagtt tctgatcgaa    6000
aagttcgaca gcgtctccga cctgatgcag ctctcggagg gcgaagaatc tcgtgctttc    6060
agcttcgatg taggagggcg tggatatgtc ctgcgggtaa atagctcgcg cgatggtttc    6120
tacaaagatc gttatgttta tcggcacttt gcatccgccg cgctcccgat tccggaagtg    6180
cttgacattg gggagttcag cgagagcctg acctattgca tctcccgccg tgcacagggt    6240
gtcacgttgc aagacctgcc tgaaaccgaa ctgcccgctg ttctgcagcc ggtcgcggag    6300
gcaatggatg ccatcgctgc cgccgatctt agccagacga cgggttcgg cccattcgga    6360
ccgcaaggaa tcggtcaata cactacatgg cgtgatttca tatgcgcgat tgctgatccc    6420
catgtgtatc actggcaaac tgtgatggac gacaccgtca gtgcgtccgt cgcgcaggct    6480
ctcgatgagc tgatgctttg ggccgatgac tgccccgaag tccggcacct cgtgcacgcg    6540
gatttcggct ccaacaatgt cctgacggac aatggccgca taacagcggt cattgactgg    6600
agcgaggcga tgttcgggga ttcccaatac gaggtcgcca acatcttctt ctggaggccg    6660
tggttggctt gtatggagca gcagacgcgc tacttcgagc ggaggcatcc ggagcttgca    6720
ggatcgcccc ggctccggc gtatatgctc cgcattggtc ttgaccaact ctatcagagc    6780
ttggttgacg gcaatttcga tgatgcagct tgggcgcagg gtcgatgcga cgcaatcgtc    6840
cgatccggag ccgggactgt cgggcgtaca caaatcgccc gcagaagcgc cgccgtctgg    6900
accgatggct gtgtagaagt actcgccgat agtggaaacc gacgccccag cactcgtccg    6960
agggcaaagg aataagctag tatgtaagcc tagtcttaga taataaaatc gctatccatt    7020
gaagatggat gtgtgttggt ttttttgtgtg tgtaacgcta ggcgcgcctg gtgtaccgag    7080
aacgatcctc tcagtgcgag tctcgacgat ccatatcgtt gcttggcagt cagccagtcg    7140
gaatccagct tgggacccag gaagtccaat cgtcagatat tgtactcaag cctggtcacg    7200
gcagcgtacc gatctgttta aacctagata ttgatagtct gatcggtcaa cgtataatcg    7260
agtcctagct tttgcaaaca tctatcaaga gacaggatca gcaggaggct ttcgcatgat    7320
tgaacaagat ggattgcacg caggttctcc ggccgcttgg gtggagaggc tattcggcta    7380
tgactgggca caacagacaa tcggctgctc tgatgccgcc gtgttccggc tgtcagcgca    7440
ggggcgtccg gttcttttg tcaagaccga cctgtccggt gccctgaatg aactgcaaga    7500
cgaggcagcg cggctatcgt ggctggcgac gacgggcgtt ccttgcgcgg ctgtgctcga    7560
cgttgtcact gaagcgggaa gggactggct gctattgggc gaagtgccgg gcaggatct    7620
cctgtcatct caccttgctc ctgccagaaa gtatccatc atggctgatg caatgcggcg    7680
gctgcatacg cttgatccgg ctacctgccc attcgaccac caagcgaaac atcgcatcga    7740
gcgagcacgt actcggatgg aagccggtct tgtcgatcag gatgatctgg acgaagagca    7800
tcagggctc gcgccagccg aactgttcgc caggctcaag gcgtctatgc ccgacgcgga    7860
ggatctgtc gtgacccacg gcgatgcctg cttgccgaat atcatggtgg aaaatggccg    7920
cttttctgga ttcatcgact gtggccgtct gggtgtggcg gaccgctatc aggacatagc    7980
gttggctacc cgtgatattg ctgaagagct tggcggcgaa tgggctgacc gcttcctgt    8040
gctttacggt atcgccgctc ccgattcgca gcgcatcgcc ttctatcgcc ttcttgacga    8100
gttcttctga ccgattctag gtgcattggc gcagaaaaaa atgcctgatg cgacgctgcg    8160
cgtcttatac tcccacatat gccagattca gcaacggata cggcttcccc aacttgccca    8220
cttccatacg tgtcctcctt accagaaatt tatccttaag gtcgtttaaa ctcgactctg    8280
gctctatcga atctccgtcg tttcgagctt acgcgaacag ccgtgcgct catttgctcg    8340
tcgggcatcg aatctcgtca gctatcgtca gcttaccttt ttggca                   8386
```

| | | |
|---|---|---|
| SEQ ID NO: 93 | moltype = DNA length = 11138 | |
| FEATURE | Location/Qualifiers | |
| misc_feature | 1..11138 | |
| | note = Synthetic polymer. | |

| source | 1..11138 |
| --- | --- |
| | mol_type = other DNA |
| | organism = synthetic construct |

SEQUENCE: 93

```
gcgatcgcgg ctcccgacat cttggaccat tagctccaca ggtatcttct tccctctagt   60
ggtcataaca gcagcttcag ctacctctca attcaaaaaa cccctcaaga cccgtttaga  120
ggccccaagg ggttatgcta tcaatcgttg cgttacacac acaaaaaacc aacacacatc  180
catcttcgat ggatagcgat tttattatct aactgctgat cgagtgtagc cagatctata  240
gtaatcaatt acggggtcat tagttcatag cccatatatg gagttccgcg ttacataact  300
tacggtaaat ggcccgcctg gctgaccgcc caacgacccc cgcccattga cgtcaataat  360
gacgtatgtt cccatagtaa cgccaatagg gactttccat tgacgtcaat gggtggacta  420
tttacggtaa actgcccact tggcagtaca tcaagtgtat catatgccaa gtacgccccc  480
tattgacgtc aatgacggta aatggcccgc ctggcattat gcccagtaca tgaccttatg  540
ggactttcct acttggcagt acatctacgt attagtcatc gctattacca tgctgatgc  600
tgagccccac gttctgcttc actctcccca tctcccccc ctcccacc caattttgt  660
atttatttat tttttaatta ttttatgcag cgatggggc gggggggggg ggggcgcgcg  720
ccaggcgggg cggggcgggg cgaggggcgg ggcggggcga ggcggagagg tgcggcggca  780
gccaatcaga gcggcgcgct ccgaaagttt cctttatgg cgaggcggcg gcggcggcgc  840
ccctataaaa agcgaagcgc gcggcgggcg ggagtcgctg cgttgccttc gccccgtgcc  900
ccgctccgcg ccgcctcgcg ccgcccgcc cggctctgac tgaccgcgtt actcccacag  960
gtgagcgggg gggacggccc ttctccctcc gggctgtaat tagcgcttgg tttaatgacg 1020
gctcgtttct tttctgtggc tgcgtgaaag ccttaaaggg ctccgggagg gccttttgtc 1080
gggggggage ggctcggggg gtgcgtgcgt gtgtgtgtgc gtgggagcc ccgcgtgcgg 1140
cccgcgctgc ccggcggctg tgagcgctgc gggcgcggcg cggggctttg tgcgctccgc 1200
gtgtgcgcga ggggagcgcg ggccggggc ggtgccccgc ggtgcggggg ggctgcgagg 1260
ggaacaaagg ctgcgtcgg ggtgtgtgcg tggggggtg agcagggggt gtgggcgcgg 1320
cggtcgggct gtaacccccc cctggcaccc ccctccccga gttgctgagc acggccggc 1380
ttcgggtgcg gggctccgtg cggggcgtgg cgcggggctc gccgtgccgg gcggggggtg 1440
gcggcaggtg ggggtgccgg gcggggcggg gccgcctcgg gccggggagg gctcggggga 1500
gggggcggcg ggccccggag gccggcggc tgtcgagggg cggcgagccg cagccattgc 1560
ctttatggt aatcgtgcga gaggggcgcag ggacttcctt tgtcccaaat ctggcggagc 1620
cgaaatctgg gaggcgccgc cgcacccct ctagcgggcg cgggcgaagc ggtgcggcgc 1680
cggcaggaag gaaatgggcg gggagggcct tcgtgcgtcg ccgcgccgcc gtccccttct 1740
ccatctccag cctcgggggct gccgcagggg gacggctgcc ttcggggggg acggggcagg 1800
gcggggttcg gcttctggcg tgtgaccggc ggctttagag cctctgctaa ccatgttcat 1860
gccttcttct ttttcctaca gctcctgggc aacgtgctgg ttgttgtgct gtctcatcat 1920
tttggcaaag atctttgtcg atcctaccat ccactgcaca cacccgccag cggccgctgc 1980
caagcttccg agctctcgaa ttcaggaggt acccaccatg agggtcccc ctcagctcct 2040
ggggctcctg ctgctctggc tcccaggcgc gcgatgtgac atcgtgatga cacagagccc 2100
tagctctctg gccatgtccg tgggccagaa ggtgaccatg agctgcaagt ccagccagtc 2160
tctgctgaac tccagcaacc agaagaacta tctggcttgg taccagcaga agcccggcca 2220
gagccccaag ctgctcgtgt acttcgccag caccagagag agcggcgtgc ccgacagatt 2280
catccgcagc ggcagcggaa ccgacttcac actgaccatc tcctccgtgc aagccgagga 2340
tctggccgac tatttctgcc agcagcacta caacacccct ctgacctttg agcggcac  2400
caagctcgag atcaagcgcg cagatgctgc tcctaccgtg agcatcttcc cgccgtccag 2460
cgaacaactc actagcggag gcgcgtcagt ggtctgcttc cttaacaatt tctacccctaa 2520
ggacatcaac gtcaagtgga agattgacgg atccgaactg tgctgaactc 2580
atggactgat caggattcca aagactcgac ttactccatg tccagcaccc tgaccctgac 2640
caaagacgag tacgaaaggc acaactcgta cacgtgcgaa gccacccaca agacttccac 2700
ctcgcccatc gtgaagtcct tcaatcgcaa tgagtgctag tgagcggccg cgtctagacc 2760
tgcactgact gactgataca atcgatttct ggatccgcag gcctctgcta gcttgactga 2820
ctgagataca gcgtaccttc agctcacaga catgataaga tacattgatg agtttggaca 2880
aaccacaact agaatgcagt gaaaaaaatg ctttatttgt gaaatttgtg atgctattgc 2940
tttatttgta accattataa gctgcaataa acaagttaac aacaacaatt gcattcattt 3000
tatgtttcag gttcagggggga aggtgtggga gtttttttaa agcaagtaaa acctctacaa 3060
atgtggtatt ggcccatctc tatcggtatc gtagcataac cccttgggggc ctctaaacgg 3120
gtcttgaggg gttttttgtg cccctcgggc cggattgcta tctaccggca ttggcgcaga 3180
aaaaaatgcc tgatgcgacg ctgcgcgtct tatactccca catatgccag attcagcaac 3240
ggatacggct tccccaactt gcccacttcc atacgtgtcc tccttaccag aaatttatcc 3300
ttaaggtcgt cagctatcct gcaggatagt aatcaattac gggggtcatta gttcatagcc 3360
catatatgga gttccgcgtt acataactta cggtaaatgg cccgcctggc tgaccgccca 3420
acgaccccgg cccattgacg tcaataatga cgtatgttcc catagtaacg ccaataggga 3480
cttttccattg acgtcaatgg ggtggactatt tacggtaaac tgcccacttg gcagtacatc 3540
aagtgtatca tatgccaagt acgcccccta ttgacgtcaa tggcgcgtaaa tggcccgcct 3600
ggcattatgc ccagtacatg accttatggg actttcctac ttggcagtac atctacgtat 3660
tagtcatcgc tattaccatg cgtcgaggtg agccccacgt tctgcttcac tctccccatc 3720
tccccccct cccacccc aattttgtat ttattttattt tttaattatt ttatgcagcg 3780
atgggggcgg gggggggggg ggcgcgcgcc aggcggggcg gggcggggcg aggggcgggg 3840
cggggcgagg cggagaggtg cggcggcagc caatcagagc ggcgcgctcc gaaagtttcc 3900
ttttatggcg aggcggcggc ggcggcggcc ctataaaaag cgaagcgcgc gcgggcgggg 3960
agtcgctgcg ttgccttcgc cccgtgcccc gctccgcgcc gcctcgcgcc gcccgcccg 4020
gctctgactg accgcgttac tcccacaggt gagcggggg gacggccctt ctccctcggg 4080
gctgtaatta gcgcttggtt taatgacggc tcgtttcttt tctgtggctg cgtgaaagcc 4140
ttaaagggct ccgggagggc ctttgtgcgg ggggggcggt gctggtgcg 4200
gtgtgtgcgt ggggagcgcc gcgtgcggcc cgcgctgccc ggcggctgtg agcgctgcgg 4260
gcgcggcgcg ggctttgtg cgctccgcgt gtgcgaggg agcgcggg ccggggcgg 4320
tgccccgcgc tgcggggggg ctgcgagggg aacaaaggct gcgtcggggg tgtgtgcgtg 4380
ggggggtgag caggggggtg tgggcgcgcg gtcgggctgt aacccccccc tggcacccc 4440
ctccccgagt tgctgagcac ggcccggctt cgggtgcggg gctccgtgcg gggcgtgcg 4500
```

```
cggggctcgc cgtgccgggc ggggggtggc ggcaggtggg ggtgccgggc ggggcggggc   4560
cgcctcgggc cggggagggc tcggggagg ggcgcggcgg ccccggagcg ccggcggctg    4620
tcgaggcgcg gcgagccgca gccattgcct tttatggtaa tcgtgcgaga gggcgcaggg   4680
acttcctttg tcccaaatct ggcggagccg aaatctggga ggcgccgccg cacccctct    4740
agcgggcgg ggcgaagcgg tgcggcgccg gcaggaagga aatgggcgg gagggccttc     4800
gtgcgtcgcc gcgccgccgt ccccttctcc atctccagcc tcggggctgc cgcagggga    4860
cggctgcctt cggggggac ggggcagggc ggggttcggc ttctggcgtg tgaccggcgg    4920
cttttagagc tctgctaacc atgttcatgc cttcttcttt ttcctacagc tcctgggcaa   4980
cgtgctggtt gttgtgctgt ctcatcattt tggcaaattc gaccaacctt ccttcgacac   5040
ggggcccaaa gtactaaagt cgacaggagg tacccaccat gggttggagc ctcatcttgc   5100
tcttccttgt cgctgttgct acgcgtgtcc actcccaagt gcagctgcag cagagcggag   5160
ccgagctggt gaagcccgga gccagcgtga agatcagctg caaggccagc ggctacgcct   5220
tctccaacta ctggatgaac tgggtgaagc agagacccgg caagggactg aatggatcg    5280
gccagatcta ccccggcgac ggagacacca actacacgg caagttcaag ggcaaagcca   5340
cactgaccgc cgacaagagc tccagcaccg cctacatgca gctgagctct ctgaccagcg   5400
aggatagcgc cgtgtacttc tgcgccagag gagactactg gggccaaggc accacactga   5460
ccgtctcgag cgctaagacg actccaccgt ccgtgtaccc gctcgcgcca ggttcggccg   5520
ctcagacgaa cagcatggtg accctcggct gcctcgtgaa gggttattc cagagccgga   5580
tgaccgtgac gtggaactcc ggctcactgt catcgggcgt gcacactttt ccagcagtgc   5640
tgcagtcgga ccttacacc ctcagctcgt ccgtcaccgt cccttcatca acttggccta   5700
gccagaccgt gacttgcaat gtcgcccacc cggcgtccag cactaaggtg gacaagaaga   5760
tccaccacca tcaccatcac catcaccatc actagagcgc accgcgtct agacctgcac   5820
tgactgactg atacactagt tagcctgtgc cttctagttg ccagccatct gttgtttgcc   5880
cctccccgt gccttccttg accctggaag gtgccactcc cactgtcctt tcctaataaa    5940
atgaggaaat tgcatcgcat tgtctgagta ggtgtcattc tattctgggg ggtggggtgg   6000
ggcaggacag caaggggag gattgggaag acaatagcag gcatgctggg gatgcggtgg    6060
gctctatggc ctgcaggcga tctctcgatt tcgatcaaga cattcccttta atggtctttt   6120
ctggacacca ctagggtca gaagtagttc atcaaacttt cttccctccc taatctcatt   6180
ggttaccttg ggctatcgaa acttaattaa ccagtcaagt cagctacttg gcgagatcga   6240
cttgtctggg tttcgactac gctcagaatt gcgtcagtca agttcgatct ggtccttgct   6300
attgcacccg ttctccgatt acgagtttca tttaaatcat gtgagcaaaa ggccagcaaa   6360
aggcaggaa ccgtaaaaag gccgcgttgc tggcgttttt ccataggctc cgccccctg     6420
acgagcatca caaaaatcga cgctcaagtc agaggtggcg aaacccgaca ggactataaa   6480
gataccaggc gtttccccct ggaagctccc tcgtgcgctc tcctgttccg accctgccgc   6540
ttaccggata cctgtccgcc tttctccctt cgggaagcgt ggcgctttct catgctcgc    6600
gctgtaggta tctcagttcg gtgtaggtcg ttcgctccaa gctgggctgt gtgcacgaac   6660
cccccgttca gcccgaccgc tgcgccttat ccggtaacta tcgtcttgag tccaacccgg   6720
taagacacga cttatcgcca ctggcagcag ccactggtaa caggattagc agagcgaggt   6780
atgtaggcgg tgctacagag ttcttgaagt ggtggcctaa ctacggctac actagaagaa   6840
cagtatttgg tatctgcgct ctgctgaagc cagttacctt cggaaaaaga gttggtagct   6900
cttgatccgg caaacaaacc accgctgta gcggtggttt ttttgtttgc aagcagcaga    6960
ttacgcgcag aaaaaaagga tctcaagaag atcctttgat cttttctacg ggtctgacg    7020
ctcagtggaa cgaaaactca cgttaaggga ttttggtcat gagattatca aaaaggatct   7080
tcacctagat ccttttaaat taaaatgaa gttttaaatc aatctaaagt atatatgagt    7140
aaacttggtc tgacagttac caatgcttaa tcagtgaggc acctatctca gcgatctgtc   7200
tatttcgttc atccatagtt gcatttaaat ttccgaactc tccaaggccc tcgtcggaaa   7260
atcttcaaac ctttctccg atccatcttg caggctacct ctcgaacgaa ctatcgcaag   7320
tctcttggcc ggccttgcgc cttggctatt gcttggcagc gcctatcgcc aggtattact   7380
ccaatcccga atatccgaga tcgggatcac ccgagagaag ttcaacctac atcctcaatc   7440
ccgatctatc cgagatccga ggaatatcga aatcggggcg cgcctggcct ccgcgccggg   7500
ttttggcgcc tcccgcgggc gccccctccg tcacggcgag cgctgccacg tcagacgaag   7560
ggcgcaggag cgtcctgatc cttccgcccg gacgctcagg acagcggccc gctgctcata   7620
agactcggcc ttagaacccc agtatcagca aaggacatt ttaggacggg acttgggtga    7680
ctctagggca ctggtttct ttccagagag cggaacaggc gaggaaaagt agtcccttct    7740
cggcgattct gcgcgagggat ctccgtgggg cggtgaacgc cgatgattat ataaggacgc   7800
gccgggtgtg gcacagctag ttccgtcgca gccgggattt gggtcgcggt tcttgttttgt   7860
ggatcgctgt gatcgtcact tggtgagtag ccggctgctg ggctggcgg ggctttcgtg    7920
gccgccgggc cgctcggtgg gacggaagcg tgtggagaga ccgccaaggg ctgtagtctg   7980
ggtccgcgag caaggttgcc ctgaactggg ggttgggggg agcgcagcaa aatggcgagt   8040
gttcccgagt cttgaatgga agacgcttgt gaggcgggcg gtgagtcgt tgaaacaagg    8100
tgggggcat ggtgggcggc aagaacccaa ggtcttgagc ccttcgctaa tgcgggaaag    8160
ctcttattcg ggtgagatgg gctgggcacc atctggggac cctgacgtga agtttgtcac   8220
tgactggaga actcggtttg tcgtctgttc cggggcggg agttatgcg gtgccgttgg    8280
gcagtcgcacc cgtaccttg ggagcgcgcg ccctcgtcgt gtcgtgacgt caccgtcgt    8340
gttggcttat aatgcagggt ggggccacct gccgtaggt gtgcgtagg cttttctccg    8400
tcgcaggacg caggggtcgg gcctagggta ggctctcctg aatcgacagg cgccggacct   8460
ctggtgaggg gagggataag tgaggcgtca gtttctttgg tcggttttat gtacctatct   8520
tcttaagtag ctgaagctcc ggttttgaac tatgcgctcg gggttggcga gtgtgttttg   8580
tgaagttttt taggcacctt ttgaaatgta tcaatatgta attttcagtg               8640
ttagacttgt aaattgtccg ctaaattctg gccgttttg gctttttgt tagacaacat     8700
gggtaaaaag cctgaactca ccgcgacgtc tgtcagaag tttctgatcg aaaagttcga   8760
cagcgtctcc gacctgatgc agctctcgga gggcgaagaa tctcgtgctt tcagcttcga   8820
tgtaggaggg cgtggataty tcctgcgggt aaatagctgc gccgatggtt tctacaaaga   8880
tcgttatgtt tatcggcact ttgcatccgg agttccggaag tgcttgacat               8940
tggggagttc agcgagagcc tgacctattg catctcccgc cgtgcacagg gtgtcacgtt   9000
gcaagacctg cctgaaaccg aactgcccgc tgttctgcag ccggtcgcgg aggcaatgga   9060
tgccatcgct gccgccgatc ttagccgac gagcgggttc ggcccattcg accgcaagg    9120
aatcggtcaa tacactacat ggcgtgattt catatgcgcg attgctgatc cccatgtgta   9180
tcactggcaa actgtgatgg acgacaccgt cagtgcgtcc gtcgcgcagg ctctcgatga   9240
```

```
gctgatgctt tgggccgagg actgccccga agtccggcac ctcgtgcacg cggatttcgg  9300
ctccaacaat gtcctgacgg acaatggccg cataacagcg gtcattgact ggagcgaggc  9360
gatgttcggg gattcccaat acgaggtcgc caacatcttc ttctggaggc cgtggttggc  9420
ttgtatggag cagcagacgc gctacttcga gcggaggcat ccggagcttg caggatcgcc  9480
ccggctccgg gcgtatatgc tccgcattgg tcttgaccaa ctctatcaga gcttggttga  9540
cggcaatttc gatgatgcag cttgggcgca gggtcgatgc gacgcaatcg tccgatccgg  9600
agccgggact gtcgggcgta cacaaatcgc ccgcagaagc gccgccgtct ggaccgatgg  9660
ctgtgtagaa gtactcgccg atagtggaaa ccgacgcccc agcactcgtc cgagggcaaa  9720
ggaataagct agtatgtaag cctagtctta gataataaaa tcgctatcca tcgaagatgg  9780
atgtgtgttg gttttttgtg tgtgtaacgc taggcgcgcc tggtgtaccg agaacgatcc  9840
tctcagtgcg agtctcgacg atccatatcg ttgcttggca gtcagccagt cggaatccag  9900
cttgggaccc aggaagtcca atcgtcagat attgtactca agcctggtca cggcagcgta  9960
ccgatctgtt taaacctaga tattgatagt ctgatcggtc aacgtataat cgagtcctag 10020
cttttgcaaa catctatcaa gagacaggat cagcaggagg ctttcgcatg attgaacaag 10080
atggattgca cgcaggttct ccggcggctt gggtggagag gctattcggc tatgactggg 10140
cacaacagac aatcggctgc tctgatgccg ccgtgttccg gctgtcagcg cagggcgtc  10200
cggttctttt tgtcaagacc gacctgtccg gtgccctgaa tgaactgcaa gacgaggcag 10260
cgcggctatc gtggctggcg acgacgggcg ttccttgcgc ggctgtgctc gacgttgtca 10320
ctgaagcggg aagggactgg ctgctattgg gcgaagtgcc ggggcaggat ctcctgtcat 10380
ctcaccttgc tcctgccgag aaagtatcca tcatggctga tgcaatgcgg cggctgcata 10440
cgcttgatcc ggctacctgc ccattcgacc accaagcgaa acatcgcatc gagcgagcac 10500
gtactcggat ggaagccggt cttgtcgatc aggatgatct ggacgaagag catcaggggc 10560
tcgcgccagc cgaactgttc gccaggctca aggcgtctat gcccgacggc gaggatctcg 10620
tcgtgaccca cggcgatgcc tgcttgccga atatcatggt ggaaaatggc cgcttttctg 10680
gattcatcga ctgtggccgt ctgggtgtgg cggaccgcta tcaggacata gcgttggcta 10740
cccgtgatat tgctgaagag cttggcggcg aatgggctga ccgcttcctt gtgctttacg 10800
gtatcgccgc gcccgattcg cagcgcatcg ccttctatcg ccttcttgac gagttcttct 10860
gaccgattct aggtgcattg gcgcagaaaa aaatgcctga tgcgacgctg cgcgtcttat 10920
actcccacat atgccagatt cagcaacgga tacggcttcc ccaacttgcc cacttccata 10980
cgtgtcctcc ttaccagaaa tttatcctta aggtcgttta aactcgactc tggctctatc 11040
gaatctccgt cgtttcgagc ttacgccgaac agccgtggcg ctcatttgct cgtcgggcat 11100
cgaatctcgt cagctatcgt cagcttacct ttttggca                         11138
SEQ ID NO: 94          moltype = AA  length = 112
FEATURE                Location/Qualifiers
REGION                 1..112
                       note = Synthetic polymer.
source                 1..112
                       mol_type = protein
                       organism = synthetic construct
SEQUENCE: 94
QVQLQQSGAE LVKPGASVKI SCKASGYAFS NYWMNWVKQR PGKGLEWIGQ IYPGDGDTNY  60
NGKFKGKATL TADKSSSTAY MQLSSLTSED SAVYFCARGD YWGQGTTLTV SS         112
```